(12) United States Patent
Lei et al.

(10) Patent No.: US 11,339,171 B2
(45) Date of Patent: May 24, 2022

(54) MDM2 INHIBITORS

(71) Applicant: Gan & Lee Pharmaceuticals, Beijing (CN)

(72) Inventors: Yin Lei, Beijing (CN); Yao Zhenglin, Beijing (CN); Li Heng, Beijing (CN)

(73) Assignee: Gan & Lee Pharmaceuticals, Beijing (CN)

( * ) Notice: Subject to any disclaimer, the term of this patent is extended or adjusted under 35 U.S.C. 154(b) by 66 days.

(21) Appl. No.: 16/954,380

(22) PCT Filed: Dec. 21, 2018

(86) PCT No.: PCT/CN2018/122796
§ 371 (c)(1),
(2) Date: Jun. 16, 2020

(87) PCT Pub. No.: WO2019/128877
PCT Pub. Date: Jul. 4, 2019

(65) Prior Publication Data
US 2021/0079007 A1 Mar. 18, 2021

(30) Foreign Application Priority Data

Dec. 29, 2017 (CN) .......................... 201711484280.8

(51) Int. Cl.
| C07D 487/20 | (2006.01) |
| A61K 31/4188 | (2006.01) |
| A61P 35/00 | (2006.01) |
| A61K 45/06 | (2006.01) |

(52) U.S. Cl.
CPC ............ *C07D 487/20* (2013.01); *A61P 35/00* (2018.01); *A61K 45/06* (2013.01)

(58) Field of Classification Search
CPC .... C07D 487/20; A61K 31/4188; A61P 35/00
See application file for complete search history.

*Primary Examiner* — Bruck Kifle
(74) *Attorney, Agent, or Firm* — Burke Patent Law Group, LLC

(57) ABSTRACT

A compound capable of being used as a tumor inhibitor, a preparation method therefor, and application thereof. The compound has a structure represented by general formula I; a stereoisomer, an enantiomer, a raceme, a cis/trans isomer, a tautomer, and an isotopic variant of the compound are comprised; the compound can be used separately or in combination with other drugs for treating tumors or inflammatory diseases, or for treating other disorders or diseases mediated by the activity of MDM2 and/or MDM4, and shows prominent curative activity.

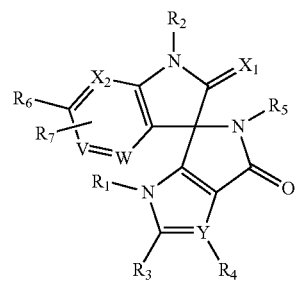

(I)

19 Claims, No Drawings

MDM2 INHIBITORS

CROSS REFERENCE TO RELATED APPLICATIONS

This is a U.S. national stage application of the International Patent Application No. PCT/CN2018/122796, filed Dec. 21, 2018, which claims priority to Chinese Patent Application No. 20171 1484280.8, filed Dec. 29, 2017, each of which is incorporated herein by reference in its entirety.

TECHNICAL FIELD

The present invention relates to the field of pharmaceutical preparations, in particular to a compound useful as a tumor inhibitor, and a preparation method therefor and use thereof.

BACKGROUND ART

P53 is a known tumor inhibition protein that plays an important role in growth inhibition and apoptosis of tumor cells. As a transcription factor, P53 can control the response of cells to DNA damage and prevent the proliferation of permanently damaged cells (controlled cell death) by triggering growth arrest, apoptosis, and senescence to maintain the normal function of cells.

However, in approximately 50% of tumors, P53 is inactivated due to gene mutation or deletion. In the remaining 50% of tumors, the function of P53 is regulated through a series of complex mechanisms, in which MDM2 acts as a negative regulator of P53, and has an important regulatory effect on the function of P53. In tumor cells, P53 is often inactivated due to overexpression of MDM2. Studies have found that about 10% of tumors have MDM2 amplification or overexpression phenomenon. In some specific tumors, this proportion is higher, for example, about 44% of liver cancers, 20% of osteosarcomas, and 31% of soft tissue sarcomas have MDM2 amplification or overexpression phenomenon. Therefore, inhibiting the negative regulatory effect of MDM2 in tumor cells on P53 can activate the P53 pathway, thereby inhibiting the proliferation of tumor cells and playing an antitumor role. MDM2 inhibitors that have been reported include RG7388, MI-773, HDM201 and the like.

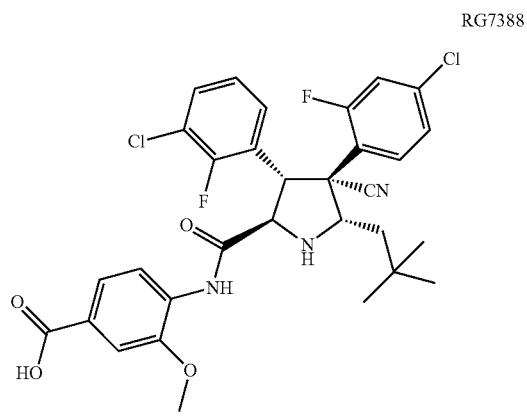

RG7388

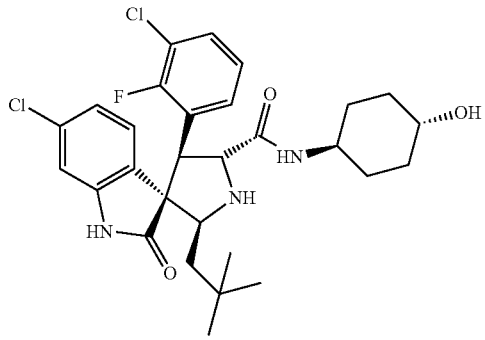

MI-773

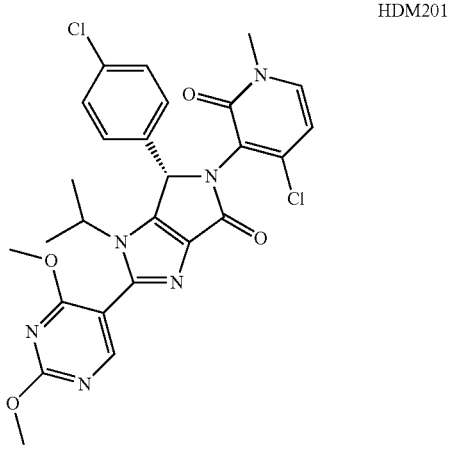

HDM201

However, considering the actual clinical needs, there is still an urgent need to develop other new compounds that can be used as tumor inhibitors.

SUMMARY OF THE INVENTION

Therefore, the purpose of the present invention is to overcome the defects in the prior art, to provide a compound that can be used as a tumor inhibitor, and a preparation method thereof and use thereof.

In a first aspect, the present invention provides a compound of structural formula I; or a stereoisomer, an enantiomer, a diastereomer, a racemate, a mesomer, a cis/trans isomer, a tautomer, an isotopic variant of the compound of structural formula I, or any combination thereof, or a pharmaceutical salt, a solvate, a hydrate, a polymorph or a prodrug of the compound of structural formula I, the stereoisomer, the enantiomer, the diastereomer, the racemate, the mesomer, the cis/trans isomer, the tautomer, the isotopic variant or their combination; or a hydrate of the pharmaceutical salt,

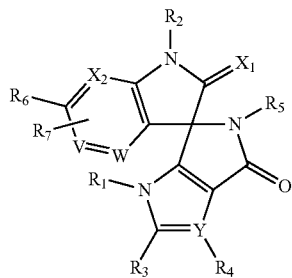

(I)

wherein, $R_1$ is selected from linear or branched alkyl or cycloalkyl having 1 to 5 carbon atoms, or

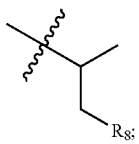

$R_2$ is selected from H, —($C_1$-$C_6$ alkyl), wherein the alkyl is optionally substituted by 0 to 3 substituents, wherein the 0 to 3 substituents are independently selected from alkoxy having 1 to 4 carbon atoms, hydroxyl, sulfhydryl, halogen, —C(O)OH, —C(O)O—($C_1$-$C_4$)alkyl, —C(O)N$R_9$$R_{10}$, —N$R_9$$R_{10}$, or methanesulfonyl;

$R_3$ is selected from a 5- or 6-membered aromatic ring or aromatic heterocycle which is unsubstituted or substituted by 1 to 3 substituents, and the 1 to 3 substituents are independently selected from H, ($C_1$-$C_6$)alkyl, ($C_3$-$C_6$)cycloalkyl, —O—($C_1$-$C_6$)alkyl, —O—($C_3$-$C_6$)cycloalkyl, —S—($C_1$-$C_6$)alkyl, halogen, haloalkyl, haloalkoxy, hydroxyalkoxy, —CN, —C(O)N$R_9$$R_{10}$, —C(O)-morpholin-4-yl, hydroxy-azetidin-1-yl-carbonyl, —CH$_2$N$R_9$$R_{10}$, —CH$_2$N$R_9$—C(O)$R_{10}$, methyl-imidazolyl-, —CH$_2$C(O)N$R_9$$R_{10}$, —CH$_2$C(O)OH, —C(O)OH, —CH$_2$C(O)O—($C_1$-$C_4$)alkyl, —N($R_9$)—C(O)—($C_1$-$C_4$)alkyl, —N$R_9$$R_{10}$, —CH$_2$N$R_9$$R_{10}$, —C(O)O—($C_1$-$C_4$)alkyl, —CH$_2$CN, tetrahydropyrrol-1-yl, azetidin-1-yl, or azetidin-1-yl substituted by one or more —OH or by both —CH$_3$ and —OH; wherein the alkyl or cycloalkyl is optionally substituted by 0 to 3 substituents independently selected from alkoxy having 1 to 4 carbon atoms, hydroxyl, sulfhydryl, halogen, —C(O)OH, —C(O)O—($C_1$-$C_4$)alkyl, —C(O)N$R_9$$R_{10}$, —N$R_9$$R_{10}$, or methanesulfonyl; preferably, $R_3$ is selected from a 5- or 6-membered aromatic ring or aromatic heterocycle which is unsubstituted or substituted by 1 to 3 substituents, and the 1 to 3 substituents are independently selected from H, ($C_1$-$C_6$)alkyl, —O—($C_1$-$C_6$)alkyl, —S—($C_1$-$C_6$)alkyl, halogen, haloalkyl, haloalkoxy, —CN, —C(O)N$R_9$$R_{10}$, —C(O)-morpholin-4-yl, hydroxy-azetidin-1-yl-carbonyl, —CH$_2$N$R_9$$R_{10}$, —CH$_2$N$R_9$—C(O)$R_{10}$, methyl-imidazolyl-, —CH$_2$C(O)N$R_9$$R_{10}$, —CH$_2$C(O)OH, —C(O)OH, —CH$_2$C(O)O—($C_1$-$C_4$)alkyl, —N($R_9$)—C(O)—($C_1$-$C_4$)alkyl, —N$R_9$$R_{10}$, —CH$_2$N$R_9$$R_{10}$, —C(O)O—($C_1$-$C_4$)alkyl, —CH$_2$CN, azetidin-1-yl, or azetidin-1-yl substituted by one or more —OH or by both —CH$_3$ and —OH; wherein the alkyl is optionally substituted by 0 to 3 substituents independently selected from alkoxy having 1 to 4 carbon atoms, hydroxyl, sulfhydryl, halogen, —C(O)OH, —C(O)O—($C_1$-$C_4$)alkyl, —C(O)N$R_9$$R_{10}$, —N$R_9$$R_{10}$, or methanesulfonyl;

or $R_3$ is selected from:

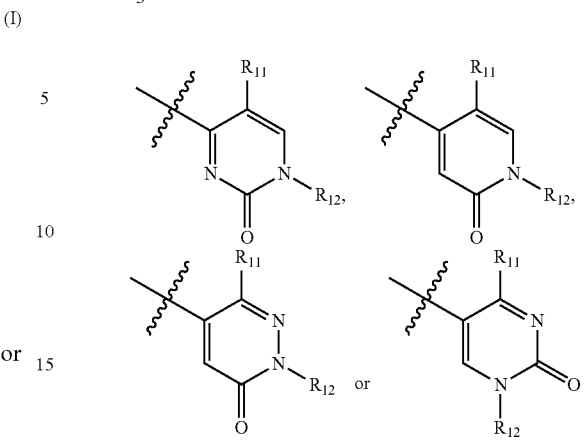

$R_5$ is selected from a 5- or 6-membered aromatic ring or aromatic heterocycle which is unsubstituted or substituted by 1 to 3 substituents, and the 1 to 3 substituents are independently selected from H, ($C_1$-$C_6$)alkyl, ($C_3$-$C_6$)cycloalkyl, —O—($C_1$-$C_6$)alkyl, —O—($C_3$-$C_6$)cycloalkyl, —S—($C_1$-$C_6$)alkyl, halogen, haloalkyl, haloalkoxy, hydroxyalkoxy, —CN, —C(O)N$R_9$$R_{10}$, —C(O)-morpholin-4-yl, hydroxy-azetidin-1-yl-carbonyl, —CH$_2$N$R_9$$R_{10}$, —CH$_2$N$R_9$—C(O)$R_{10}$, methyl-imidazolyl-, —CH$_2$C(O)N$R_9$$R_{10}$, —CH$_2$C(O)OH, —C(O)OH, —CH$_2$C(O)O—($C_1$-$C_4$)alkyl, —N($R_9$)—C(O)—($C_1$-$C_4$)alkyl, —N$R_9$$R_{10}$, —CH$_2$N$R_9$$R_{10}$, —C(O)OCH$_3$, —CH$_2$CN, tetrahydropyrrol-1-yl, azetidin-1-yl, or azetidin-1-yl substituted by one or more —OH or by both —CH$_3$ and —OH; wherein the alkyl or cycloalkyl is optionally substituted by 0 to 3 substituents independently selected from alkoxy having 1 to 4 carbon atoms, hydroxyl, sulfhydryl, halogen, —C(O)OH, —C(O)O—($C_1$-$C_4$)alkyl, —C(O)N$R_9$$R_{10}$, —N$R_9$$R_{10}$, or methanesulfonyl; preferably, $R_5$ is selected from a 5- or 6-membered aromatic ring or aromatic heterocycle which is unsubstituted or substituted by 1 to 3 substituents, and the 1 to 3 substituents are independently selected from H, ($C_1$-$C_6$)alkyl, —O—($C_1$-$C_6$)alkyl, —S—($C_1$-$C_6$)alkyl, halogen, haloalkyl, haloalkoxy, —CN, —C(O)N$R_9$$R_{10}$, —C(O)-morpholin-4-yl, hydroxy-azetidin-1-yl-carbonyl, —CH$_2$N$R_9$$R_{10}$, —CH$_2$N$R_9$—C(O)$R_{10}$, —CH$_2$CN, methyl-imidazolyl-, —CH$_2$C(O)N$R_9$$R_{10}$, —CH$_2$C(O)OH, —C(O)OH, —CH$_2$C(O)O—($C_1$-$C_4$)alkyl, —N($R_9$)—C(O)—($C_1$-$C_4$)alkyl, —N$R_9$$R_{10}$, —CH$_2$N$R_9$$R_{10}$, —C(O)OCH$_3$, —CH$_2$CN, azetidin-1-yl, or azetidin-1-yl substituted by one or more —OH or by both —CH$_3$ and —OH; wherein the alkyl is optionally substituted by 0 to 3 substituents independently selected from alkoxy having 1 to 4 carbon atoms, hydroxyl, sulfhydryl, halogen, —C(O)OH, —C(O)O—($C_1$-$C_4$)alkyl, —C(O)N$R_9$$R_{10}$, —N$R_9$$R_{10}$, or methanesulfonyl;

or $R_5$ is selected from:

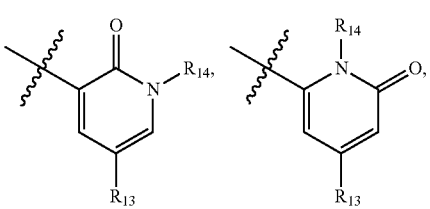

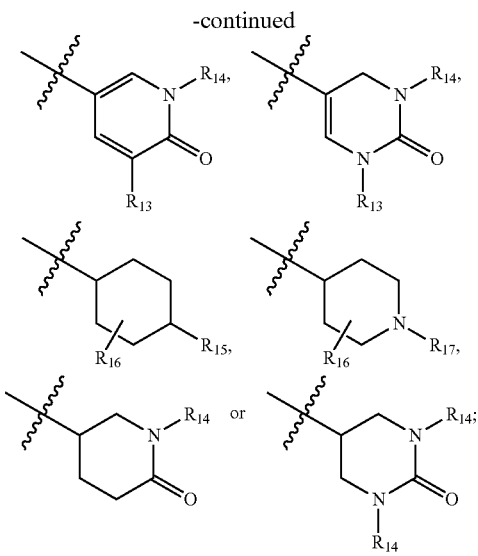

$R_6$ is selected from halogen, halomethyl, methyl or cyano;

$R_7$ is selected from H, $(C_1-C_6)$ alkyl, or halogen; wherein the alkyl is optionally substituted by 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)NR$_9$R$_{10}$, —NR$_9$R$_{10}$ or methanesulfonyl;

wherein:

$R_8$ is selected from —OH, —OCH$_3$, —NH$_2$, —NHMe, —NMe$_2$, —NHCOMe, —NHCOH or methanesulfonyl;

$R_9$ is selected from H or alkyl having 1 to 4 carbon atoms;

$R_{10}$ is selected from H or $(C_1-C_6)$ alkyl, wherein the alkyl is optionally substituted by 0 to 3 substituents independently selected from alkoxy having 1 to 4 carbon atoms, hydroxyl, sulfhydryl, halogen, —C(O)OH, —C(O)O—$(C_1-C_4)$alkyl or methanesulfonyl;

$R_{11}$ is selected from —OCH$_3$, —CH$_2$CH$_3$, —OH, halomethoxy or H;

$R_{12}$ is selected from H or $(C_1-C_6)$ alkyl, wherein the alkyl is optionally substituted by 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)NR$_9$R$_{10}$, —NR$_9$R$_{10}$, or methanesulfonyl;

$R_{13}$ is selected from halogen or alkyl having 1 to 4 carbon atoms;

$R_{14}$ is selected from H or $(C_1-C_6)$ alkyl, wherein the alkyl is optionally substituted by 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)NR$_9$R$_{10}$, —NR$_9$R$_{10}$ or methanesulfonyl;

$R_{15}$ is selected from NH$_2$, —C(O)OH, —NH(C(O)—CH$_3$) or —C(O)—NH(CH$_3$);

$R_{16}$ is selected from H, $(C_1-C_6)$ alkyl or halogen; wherein the alkyl is optionally substituted by 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)NR$_9$R$_{10}$, —NR$_9$R$_{10}$, or methanesulfonyl;

$R_{17}$ is selected from —C(O)—NR$_9$(R$_{10}$), $(C_1-C_6)$alkyl, —C(O)$(C_1-C_6)$alkyl, and —C(O)O$(C_1-C_6)$alkyl; wherein the alkyl is optionally substituted by 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)NR$_9$R$_{10}$, —NR$_9$R$_{10}$, or methanesulfonyl; and/or $X_1$ is selected from oxygen or sulfur; Y, $X_2$, V and W are each independently selected from carbon or nitrogen; when Y is carbon, $R_4$ is selected from H, hydroxyl, —O—$(C_1-C_6)$alkyl, —CN, halogen, —$(C_1-C_6)$alkyl, —C(O)OH, —CH$_2$C(O)OH, —CH$_2$C(O)NR$_9$R$_{10}$, or —C(O)O—$(C_1-C_6)$alkyl, wherein the alkyl is optionally substituted by 0 to 3 substituents independently selected from alkoxy having 1 to 4 carbon atoms, hydroxyl, sulfhydryl, halogen, —C(O)OH, —C(O)O—$(C_1-C_4)$alkyl or methanesulfonyl.

Preferably, the linear or branched alkyl or cycloalkyl having 1 to 5 carbon atoms in $R_1$ is selected from methyl, ethyl, isopropyl, cyclopropyl, isobutyl, cyclobutyl or cyclopentyl;

the alkoxy in $R_2$ is selected from methoxy or ethoxy;

the haloalkyl in $R_3$ is halomethyl, preferably —CF$_3$, —CHF$_2$ or —CH$_2$F; the haloalkoxy in $R_3$ is selected from —OCF$_3$, —OCHF$_2$, —OCH$_2$F, —OCH$_2$CF$_3$, —OCH$_2$CHF$_2$ or —OCH$_2$CH$_2$F, and is preferably selected from —OCF$_3$, —OCHF$_2$, or —OCH$_2$F; and/or the alkoxy in $R_3$ is selected from methoxy or ethoxy;

the haloalkyl in $R_5$ is halomethyl, preferably —CF$_3$, —CHF$_2$, or —CH$_2$F; the haloalkoxy in $R_5$ is selected from —OCF$_3$, —OCHF$_2$, —OCH$_2$F, —OCH$_2$CF$_3$, —OCH$_2$CHF$_2$, or —OCH$_2$CH$_2$F, and is preferably selected from —OCF$_3$, —OCHF$_2$, or —OCH$_2$F; and/or the alkoxy in $R_5$ is selected from methoxy or ethoxy;

the halogen in $R_6$ is selected from chlorine, fluorine or bromine; and/or the halomethyl in $R_6$ is selected from trifluoromethyl, difluoromethyl or monofluoromethyl;

the alkoxy in $R_7$ is selected from methoxy or ethoxy;

the alkyl in $R_9$ is selected from methyl or ethyl;

the alkoxy in $R_{10}$ is selected from methoxy or ethoxy;

the halomethoxy in $R_{11}$ is selected from —OCF$_3$, —OCHF$_2$ or —OCH$_2$F;

the alkoxy in $R_{12}$ is selected from methoxy or ethoxy;

the alkyl in $R_{13}$ is selected from methyl or ethyl;

the alkoxy in $R_{14}$ is selected from methoxy or ethoxy;

the alkoxy in $R_{16}$ is selected from methoxy or ethoxy;

the alkoxy in $R_{17}$ is selected from methoxy or ethoxy; and the alkoxy in $R_4$ is selected from methoxy or ethoxy.

Furthermore, in the compound of the present invention, preferably, $R_1$ is selected from methyl, ethyl, isopropyl, cyclopropyl, isobutyl, cyclobutyl, cyclopentyl or is:

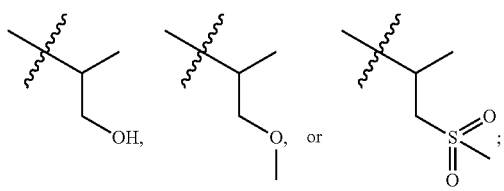

$R_2$ is selected from H or methyl; preferably H;

$R_3$ is selected from a 6-membered aromatic ring or aromatic heterocycle substituted by 1 to 3 substituents independently selected from H, —$(C_1-C_6)$alkyl, $(C_3-C_6)$cycloalkyl, —O—$(C_1-C_6)$alkyl, —O—$(C_3-C_6)$cycloalkyl, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, hydroxyalkoxy, —CN, —C(O)NR$_9$R$_{10}$, —CH$_2$NR$_9$R$_{10}$, —CH$_2$NR$_9$—C(O)R$_{10}$, —CH$_2$C(O)NR$_9$R$_{10}$, —CH$_2$C(O)OH, —C(O)OH, —CH$_2$C(O)O—$(C_1-C_4)$alkyl, —N(R$_9$)—C(O)—$(C_1-C_4)$alkyl, —NR$_9$R$_{10}$, —CH$_2$NR$_9$R$_{10}$, —C(O)O—$(C_1-C_4)$alkyl, —CH$_2$CN, and tetrahydropyrrol-1-yl, wherein the alkyl or cycloalkyl is optionally substituted by 0 to 3 substituents independently selected from methoxy, ethoxy, hydroxyl, sulfhydryl, halogen, —C(O)OH, —C(O)O—($C_1$-$C_4$)alkyl, —C(O)N$R_9R_{10}$, —N$R_9R_{10}$, or methanesulfonyl; preferably, $R_3$ is selected from a 6-membered aromatic ring or aromatic heterocycle substituted by 1 to 3 substituents independently selected from H, ($C_1$-$C_6$)alkyl, —O—($C_1$-$C_6$)alkyl, halogen, —$CF_3$, —$CHF_2$, —$CH_2F$, —$OCF_3$, —$OCHF_2$, —$OCH_2F$, —CN, —C(O)N$R_9R_{10}$, —$CH_2$N$R_9R_{10}$, —$CH_2$N$R_9$—C(O)$R_{10}$, —$CH_2$CN, —$CH_2$C(O)N$R_9R_{10}$, —$CH_2$C(O)OH, —C(O)OH, —$CH_2$C(O)O—($C_1$-$C_4$)alkyl, —N($R_9$)—C(O)—($C_1$-$C_4$)alkyl, —N$R_9R_{10}$, —$CH_2$N$R_9R_{10}$, —C(O)O—($C_1$-$C_4$)alkyl, and —$CH_2$CN, wherein the alkyl is optionally substituted by 0 to 3 substituents independently selected from methoxy, ethoxy, hydroxyl, sulfhydryl, halogen, —C(O)OH, —C(O)O—($C_1$-$C_4$)alkyl, —C(O)N$R_9R_{10}$, —N$R_9R_{10}$, or methanesulfonyl; preferably, $R_3$ is selected from a 6-membered aromatic ring or aromatic heterocycle substituted by 1 to 3 substituents independently selected from H, methyl, ethyl, isopropyl, tert-butyl, cyclopropyl, methoxy, ethoxy, isopropoxy, —O-cyclopropyl, hydroxyethoxy, halogen, —$CF_3$, —$CHF_2$, —$CH_2F$, —$OCF_3$, —$OCHF_2$, —$OCH_2F$, —$OCH_2CF_3$, —$OCH_2CHF_2$, —$OCH_2CH_2F$, —CN, —C(O)N$R_9R_{10}$, —$CH_2$N$R_9R_{10}$, —$CH_2$N$R_9$—C(O)$R_{10}$, —$CH_2$CN, —$CH_2$C(O)N$R_9R_{10}$, —$CH_2$C(O)OH, —C(O)OH, —$CH_2$C(O)O—($C_1$-$C_4$)alkyl, —N($R_9$)—C(O)—($C_1$-$C_4$)alkyl, —N$R_9R_{10}$, —$CH_2$N$R_9R_{10}$, —C(O)O—($C_1$-$C_4$)alkyl, and tetrahydropyrrol-1-yl;

$R_5$ is selected from a 6-membered aromatic ring or aromatic heterocycle substituted by 1 to 3 substituents independently preferably selected from H, —($C_1$-$C_6$)alkyl, ($C_3$-$C_6$)cycloalkyl, —O—($C_1$-$C_6$)alkyl, —S—($C_1$-$C_6$)alkyl, —O—($C_3$-$C_6$)cycloalkyl, halogen, —$CF_3$, —$CHF_2$, —$CH_2F$, —$OCF_3$, —$OCHF_2$, —$OCH_2F$, —$OCH_2CF_3$, —$OCH_2CHF_2$, —$OCH_2CH_2F$, hydroxyalkoxy, —CN, —C(O)N$R_9R_{10}$, —$CH_2$N$R_9R_{10}$, —$CH_2$N$R_9$—C(O)$R_{10}$, —$CH_2$C(O)N$R_9R_{10}$, —$CH_2$C(O)OH, —C(O)OH, —$CH_2$C(O)O—($C_1$-$C_4$)alkyl, —N($R_9$)—C(O)—($C_1$-$C_4$)alkyl, —N$R_9R_{10}$, —$CH_2$N$R_9R_{10}$, —C(O)O$CH_3$, —$CH_2$CN, and tetrahydropyrrol-1-yl, wherein the alkyl or cycloalkyl is optionally substituted by 0 to 3 substituents independently selected from methoxy, ethoxy, hydroxyl, sulfhydryl, halogen, —C(O)OH, —C(O)O—($C_1$-$C_4$)alkyl, —C(O)N$R_9R_{10}$, —N$R_9R_{10}$, or methanesulfonyl; preferably, $R_5$ is selected from a 6-membered aromatic ring or aromatic heterocycle substituted by 1 to 3 substituents independently preferably selected from H, ($C_1$-$C_6$)alkyl, —O—($C_1$-$C_6$)alkyl, halogen, —$CF_3$, —$CHF_2$, —$CH_2F$, —$OCF_3$, —$OCHF_2$, —$OCH_2F$, —CN, —C(O)N$R_9R_{10}$, —$CH_2$N$R_9R_{10}$, —$CH_2$N$R_9$—C(O)$R_{10}$, —$CH_2$CN, —$CH_2$C(O)N$R_9R_{10}$, —$CH_2$C(O)OH, —C(O)OH, —$CH_2$C(O)O—($C_1$-$C_4$)alkyl, —N($R_9$)—C(O)—($C_1$-$C_4$)alkyl, —N$R_9R_{10}$, —$CH_2$N$R_9R_{10}$, —C(O)O$CH_3$, and —$CH_2$CN, wherein the alkyl is optionally substituted by 0 to 3 substituents independently selected from methoxy, ethoxy, hydroxyl, sulfhydryl, halogen, —C(O)OH, —C(O)O—($C_1$-$C_4$)alkyl, —C(O)N$R_9R_{10}$, —N$R_9R_{10}$, or methanesulfonyl; preferably, $R_5$ is selected from a 6-membered aromatic ring or aromatic heterocycle substituted by 1 to 3 substituents independently selected from H, methyl, ethyl, isopropyl, tert-butyl, cyclopropyl, methoxy, ethoxy, isopropoxy, —O-cyclopropyl, hydroxyethoxy, halogen, —$CF_3$, —$CHF_2$, —$CH_2F$, —$OCF_3$, —$OCHF_2$, —$OCH_2F$, —$OCH_2CF_3$, —$OCH_2CHF_2$, —$OCH_2CH_2F$, —CN, —C(O)N$R_9R_{10}$, —$CH_2$N$R_9R_{10}$, —$CH_2$N$R_9$—C(O)$R_{10}$, —$CH_2$CN, —$CH_2$C(O)N$R_9R_{10}$, —$CH_2$C(O)OH, —C(O)OH, —$CH_2$C(O)O—($C_1$-$C_4$)alkyl, —N($R_9$)—C(O)—($C_1$-$C_4$)alkyl, —N$R_9R_{10}$, —$CH_2$N$R_9R_{10}$, —C(O)O$CH_3$, and tetrahydropyrrol-1-yl;

$R_6$ is selected from chlorine or cyano; preferably chlorine;

$R_7$ is hydrogen;

$X_1$ is oxygen; $X_2$, V and W are all carbon; and/or

Y is nitrogen or carbon; when Y is carbon, $R_4$ is selected from H, hydroxyl, —O—($C_1$-$C_6$)alkyl, —C(O)OH, —$CH_2$C(O)OH, —$CH_2$C(O)N$R_9R_{10}$ or —C(O)O—($C_1$-$C_6$) alkyl, wherein the alkyl is optionally substituted by 0 to 3 substituents independently selected from methoxy, ethoxy, hydroxyl, sulfhydryl, halogen, —C(O)OH, —C(O)O—($C_1$-$C_4$) alkyl, —C(O)N$R_9R_{10}$, —N$R_9R_{10}$, or methanesulfonyl;

wherein, $R_9$ is selected from H, methyl or ethyl;

$R_{10}$ is selected from H or ($C_1$-$C_6$)alkyl, wherein the alkyl is optionally substituted by 0 to 3 substituents independently selected from methoxy, ethoxy, hydroxyl, sulfhydryl, halogen, —C(O)OH, —C(O)O—($C_1$-$C_4$) alkyl or methanesulfonyl.

In addition, as one of the preferred embodiments of the present invention: when Y is nitrogen, $R_4$ is not present; when Y is carbon, $R_4$ is selected from H, hydroxyl, —O—($C_1$-$C_6$)alkyl, —C(O)OH, —$CH_2$C(O)OH, —$CH_2$C(O)N$R_9R_{10}$ or —C(O)O—($C_1$-$C_6$)alkyl, wherein the alkyl is optionally substituted by 0 to 3 substituents independently selected from methoxy, ethoxy, hydroxyl, sulfhydryl, halogen, —C(O)OH, —C(O)O—($C_1$-$C_4$)alkyl, —C(O)N$R_9R_{10}$, —N$R_9R_{10}$, or methanesulfonyl;

$R_1$ is selected from methyl, ethyl, isopropyl, cyclopropyl, cyclobutyl, or cyclopentyl;

$R_2$ is H;

$R_3$ is a 6-membered aromatic ring or aromatic heterocycle substituted by 1 to 3 substituents, the aromatic heterocycle is preferably pyridine ring, pyridone ring, pyrimidine ring, pyrazine ring, or pyridazine ring, and the substituent is independently selected from H, —($C_1$-$C_6$)alkyl, ($C_3$-$C_6$)cycloalkyl, —O—($C_1$-$C_6$)alkyl, —S—($C_1$-$C_6$)alkyl, —O—($C_3$-$C_6$)cycloalkyl, halogen, —$CF_3$, —$CHF_2$, —$CH_2F$, —$OCF_3$, —$OCHF_2$, —$OCH_2F$, —$OCH_2CF_3$, —$OCH_2CHF_2$, —$OCH_2CH_2F$, hydroxyalkoxy, —CN, —C(O)N$R_9R_{10}$, —$CH_2$N$R_9R_{10}$, —$CH_2$N$R_9$—C(O)$R_{10}$, —C(O)OH, —$CH_2$N$R_9R_{10}$, tetrahydropyrrol-1-yl or —N$R_9R_{10}$; wherein the alkyl or cycloalkyl is optionally substituted by 0 to 3 substituents independently selected from methoxy, ethoxy, hydroxyl, sulfhydryl, halogen, —C(O)OH, —C(O)O—($C_1$-$C_4$)alkyl, —C(O)N$R_9R_{10}$, —N$R_9R_{10}$, or methanesulfonyl; preferably, $R_3$ is a 6-membered aromatic ring or aromatic heterocycle substituted by 1 to 3 substituents, the aromatic heterocycle is preferably pyridine ring, pyridone ring, pyrimidine ring, pyrazine ring, or pyridazine ring, and the substituent is independently selected from H, ($C_1$-$C_6$)alkyl, —O—($C_1$-$C_6$)alkyl, —S—($C_1$-$C_6$)alkyl, halogen, —$CF_3$, —$CHF_2$, —$CH_2F$, —$OCF_3$, —$OCHF_2$, —$OCH_2F$, —CN, —C(O)N$R_9R_{10}$, —$CH_2$N$R_9R_{10}$, —$CH_2$N$R_9$—C(O)$R_{10}$, —C(O)OH, —$CH_2$N$R_9R_{10}$, or —N$R_9R_{10}$; wherein the alkyl is optionally substituted by 0 to 3 substituents independently selected from methoxy, ethoxy, hydroxyl, sulfhydryl, halogen, —C(O)OH, —C(O)O—($C_1$-$C_4$)alkyl, —C(O)N$R_9R_{10}$, —N$R_9R_{10}$, or methanesulfonyl; preferably, $R_3$ is selected from a 6-membered aromatic ring or aromatic heterocycle substituted by 1 to 3 substituents, the aromatic heterocycle is preferably pyridine ring, pyridone ring, pyrimidine ring, pyrazine ring or pyridazine ring, and the substituent is independently selected from H, methyl, ethyl, isopropyl, tert-butyl, cyclopropyl, methoxy, ethoxy, isopropoxy, —O-cyclopropyl, hydroxyethoxy, halogen, —$CF_3$, —$CHF_2$, —CH$_2$F, —OCF$_3$, —OCHF$_2$, —OCH$_2$F, —OCH$_2$CF$_3$, —OCH$_2$CHF$_2$, —OCH$_2$CH$_2$F, —CN, —C(O)NR$_9$R$_{10}$, —CH$_2$NR$_9$R$_{10}$, —CH$_2$NR$_9$—C(O)R$_{10}$, —C(O)OH, —CH$_2$NR$_9$R$_{10}$, tetrahydropyrrol-1-yl or —NR$_9$R$_{10}$;

R$_5$ is a 6-membered aromatic ring or aromatic heterocycle substituted by 1 to 3 substituents, and the aromatic heterocycle is preferably pyridine ring, pyridone ring, pyrimidine ring, pyrazine ring, or pyridazine ring; the substituent is independently selected from H, —(C$_1$-C$_6$)alkyl, (C$_3$-C$_6$)cycloalkyl, —O—(C$_1$-C$_6$)alkyl, —S—(C$_1$-C$_6$)alkyl, —O—(C$_3$-C$_6$)cycloalkyl, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, hydroxyalkoxy, —CN, —C(O)NR$_9$R$_{10}$, —CH$_2$NR$_9$R$_{10}$, —CH$_2$NR$_9$—C(O)R$_{10}$, —C(O)OH, —CH$_2$NR$_9$R$_{10}$, tetrahydropyrrol-1-yl or —NR$_9$R$_{10}$; wherein the alkyl is optionally substituted by 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$, or methanesulfonyl; preferably, R$_5$ is a 6-membered aromatic ring or aromatic heterocycle substituted by 1 to 3 substituents, and the aromatic heterocycle is preferably pyridine ring, pyridone ring, pyrimidine ring, pyrazine ring, or pyridazine ring; the substituent is independently selected from H, (C$_1$-C$_6$)alkyl, —O—(C$_1$-C$_6$)alkyl, —S—(C$_1$-C$_6$)alkyl, halogen, —CF$_3$, —CHF$_2$, —CH$_2$F, —OCF$_3$, —OCHF$_2$, —OCH$_2$F, —CN, —C(O)NR$_9$R$_{10}$, —CH$_2$NR$_9$R$_{10}$, —CH$_2$NR$_9$—C(O)R$_{10}$, —C(O)OH, —CH$_2$NR$_9$R$_{10}$, or —NR$_9$R$_{10}$; wherein the alkyl is optionally substituted by 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$, or methanesulfonyl; preferably, R$_5$ is selected from a 6-membered aromatic ring or aromatic heterocycle substituted by 1 to 3 substituents, the aromatic heterocycle is preferably pyridine ring, pyridone ring, pyrimidine ring, pyrazine ring, or pyridazine ring, and the substituent is independently selected from H, methyl, ethyl, isopropyl, tert-butyl, cyclopropyl, methoxy, ethoxy, isopropoxy, —O-cyclopropyl, hydroxyethoxy, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, —CN, —C(O)NR$_9$R$_{10}$, —CH$_2$NR$_9$R$_{10}$, —CH$_2$NR$_9$—C(O)R$_{10}$, —C(O)OH, —CH$_2$NR$_9$R$_{10}$, tetrahydropyrrol-1-yl or —NR$_9$R$_{10}$;

R$_6$ is chlorine; R$_7$ is hydrogen; X$_1$ is oxygen; and/or X$_2$, V and W are all carbon;

wherein R$_9$ is selected from H, methyl or ethyl, and R$_{10}$ is selected from H, and —(C$_1$-C$_6$)alkyl, wherein the alkyl is optionally substituted by 0 to 3 substituents independently selected from methoxy, ethoxy, hydroxyl, sulfhydryl, halogen, —C(O)OH, —C(O)O—(C$_1$-C$_4$)alkyl, or methanesulfonyl; and R$_{10}$ is preferably H, methyl, ethyl, or 1-hydroxyethyl, more preferably H, methyl or ethyl.

Furthermore, as the most preferred embodiment of the present invention:

R$_1$ is selected from ethyl or isopropyl;
R$_2$ is H;
R$_3$ is a 6-membered aromatic ring or aromatic heterocycle substituted by 1 to 3 substituents, the aromatic heterocycle is preferably pyridine ring, pyridone ring, pyrimidine ring, pyrazine ring, or pyridazine ring, and the substituent is independently selected from H, —(C$_1$-C$_6$)alkyl, —O—(C$_1$-C$_6$)alkyl, —S—(C$_1$-C$_6$)alkyl, halogen, —CF$_3$, —CHF$_2$, —CH$_2$F, —OCF$_3$, —OCHF$_2$, —OCH$_2$F, —CN, —C(O)NR$_9$R$_{10}$, or —NR$_9$R$_{10}$;

when Y is nitrogen, R$_4$ is not present;
R$_5$ is a 6-membered aromatic ring or aromatic heterocycle substituted by 1 to 3 substituents, the aromatic heterocycle is preferably pyridine ring, pyridone ring, pyrimidine ring, pyrazine ring, or pyridazine ring, and the substituent is independently selected from H, —(C$_1$-C$_6$)alkyl, —O—(C$_1$-C$_6$)alkyl, —S—(C$_1$-C$_6$)alkyl, halogen, —CF$_3$, —CHF$_2$, —CH$_2$F, —OCF$_3$, —OCHF$_2$, —OCH$_2$F, —CN, or —C(O)NH$_2$;

R$_6$ is chlorine; R$_7$ is hydrogen;
X$_1$ is oxygen; Y is nitrogen; X$_2$, V, and W are all carbon;
wherein, R$_9$ is selected from H, methyl or ethyl, and R$_{10}$ is selected from H, methyl or ethyl.

More preferably, the compound according to the first aspect is one selected from the following structures:

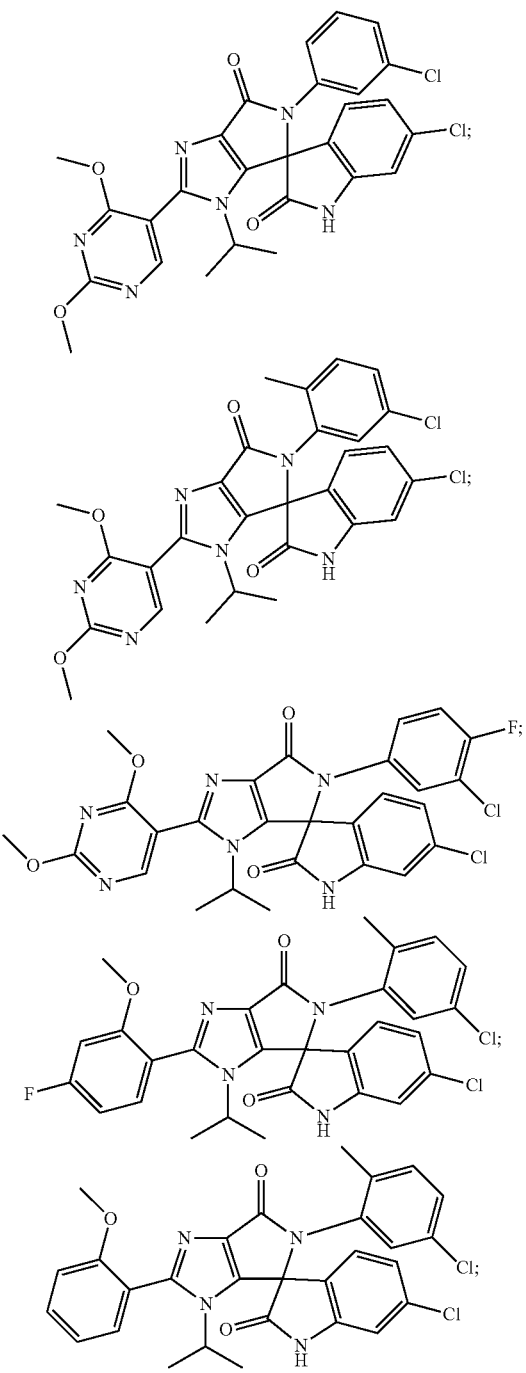

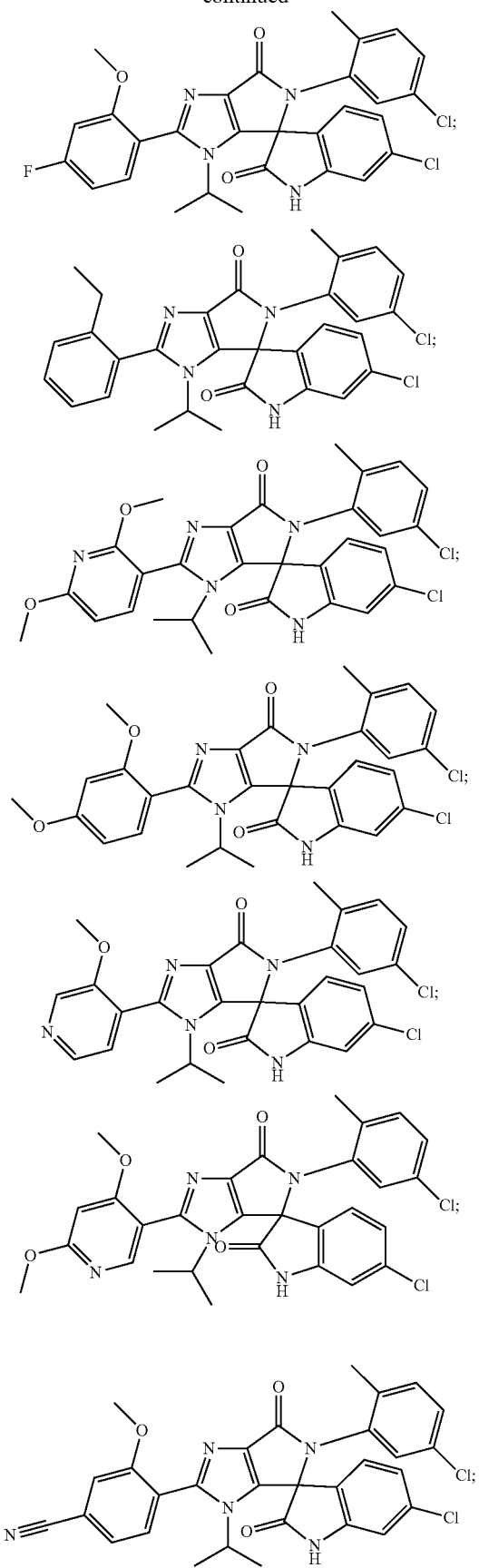
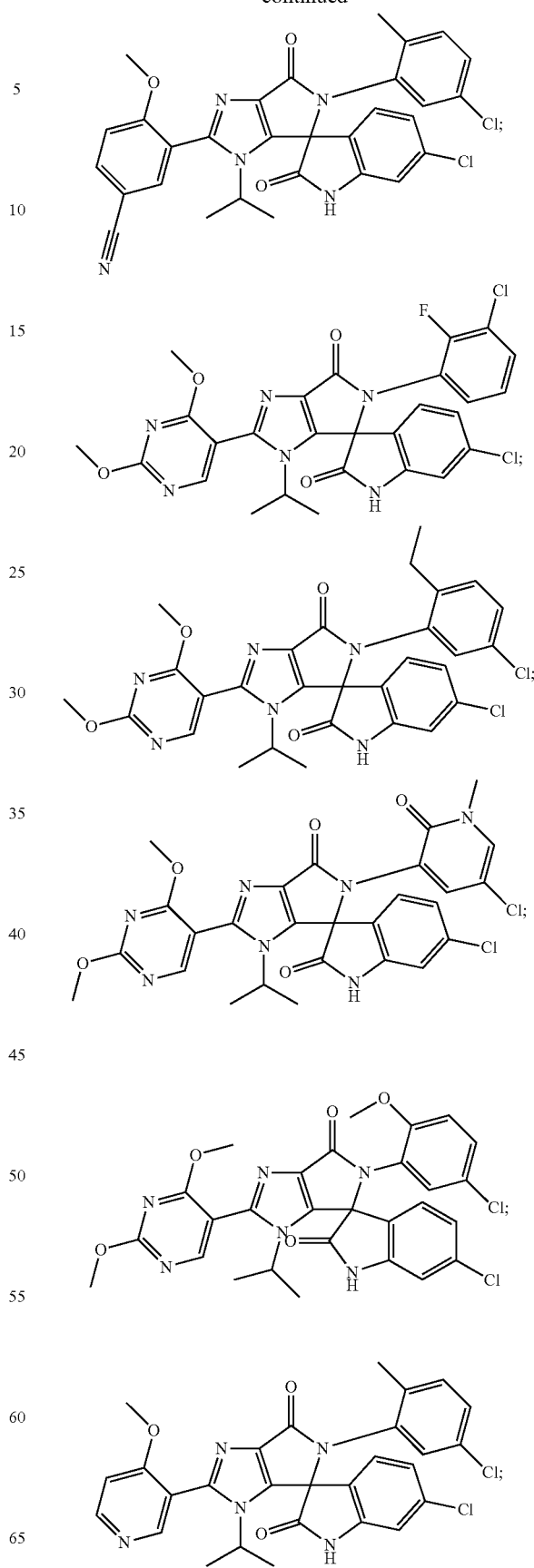

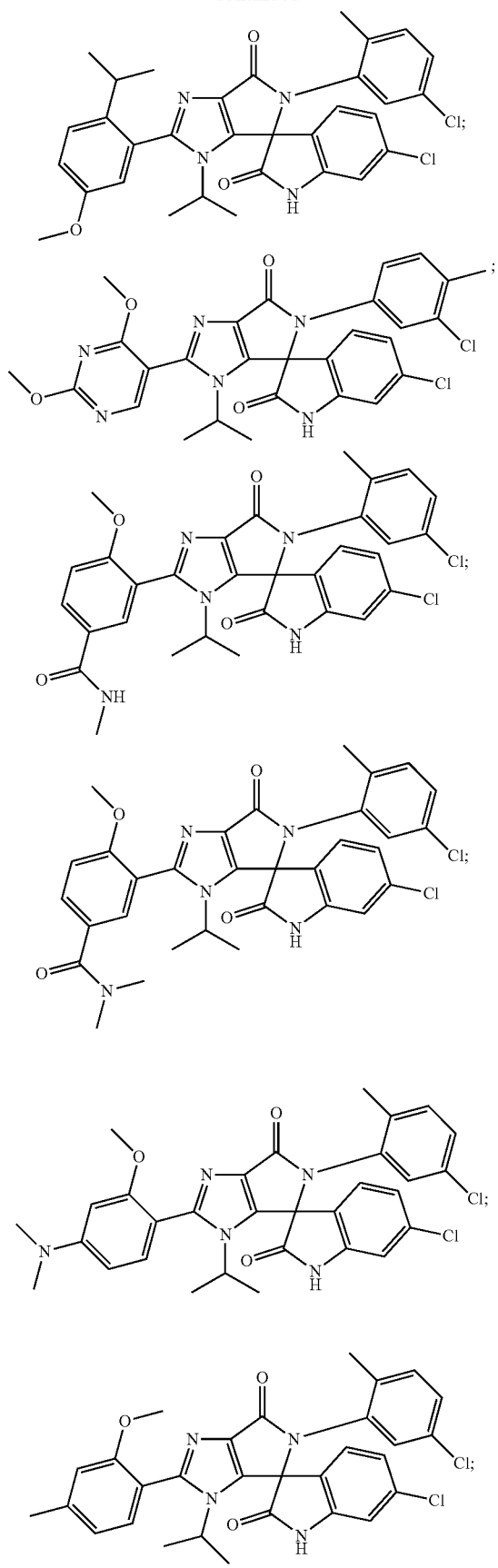
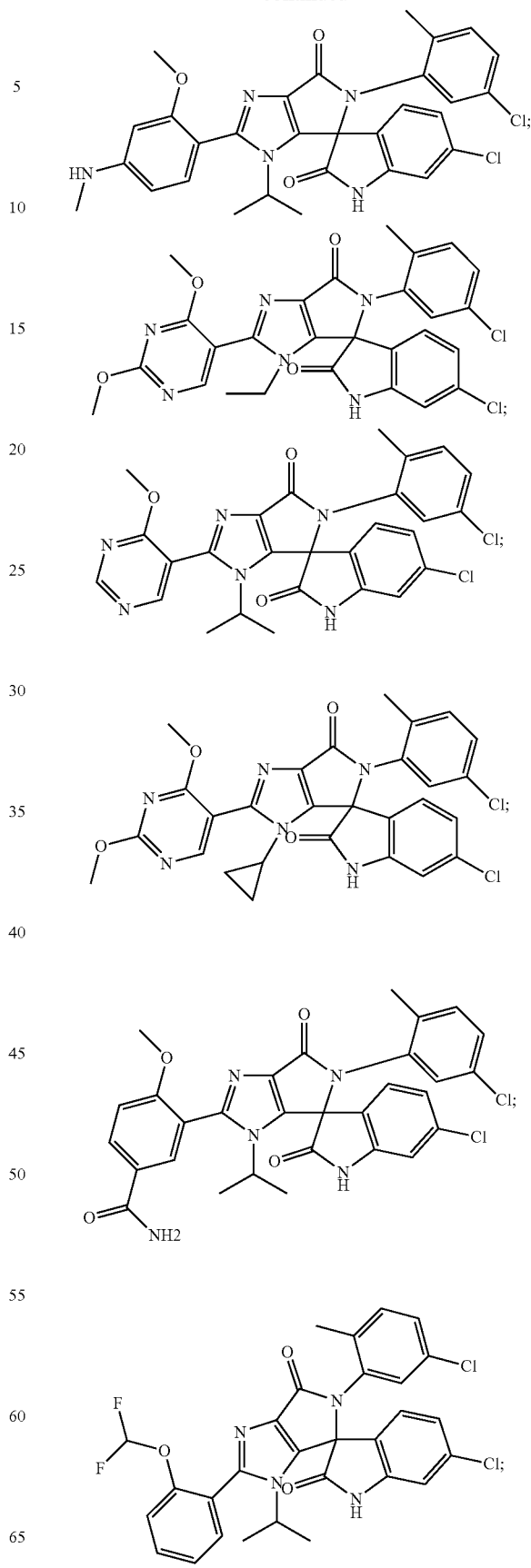

-continued
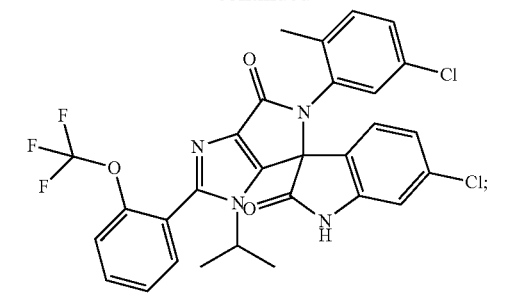
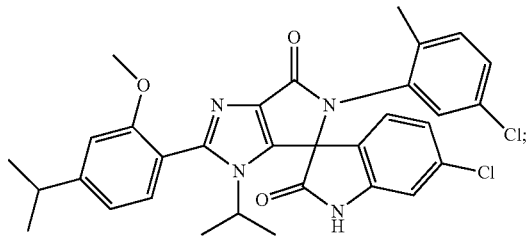
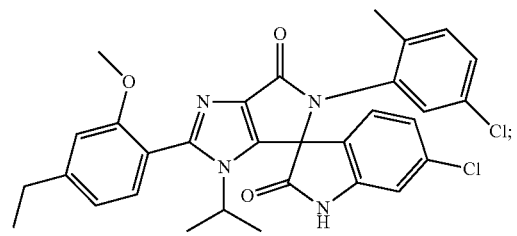
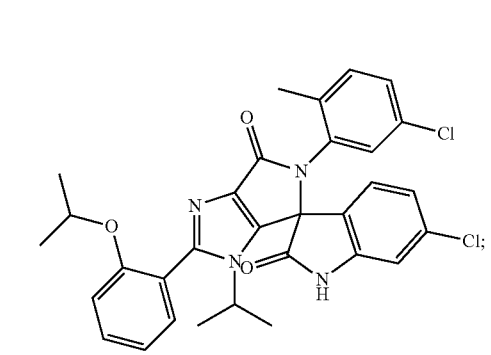
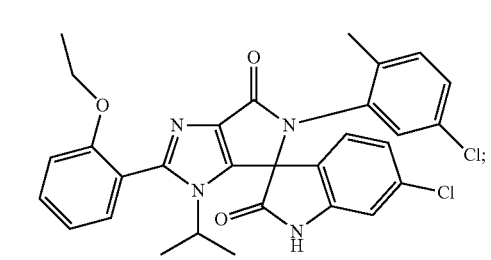
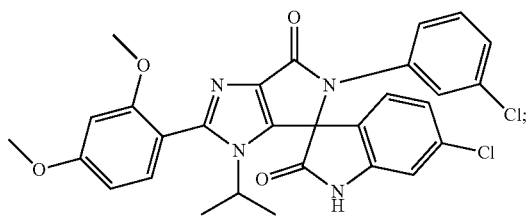
-continued
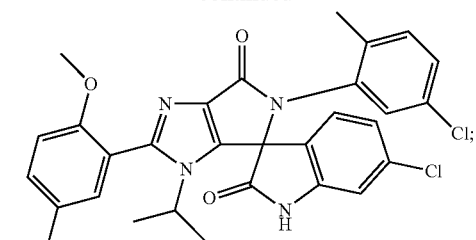
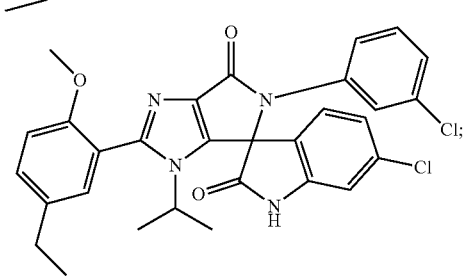
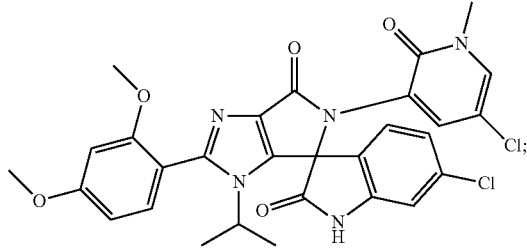
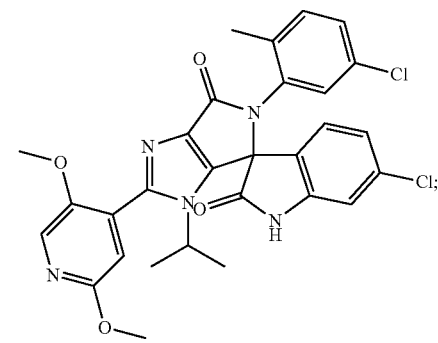
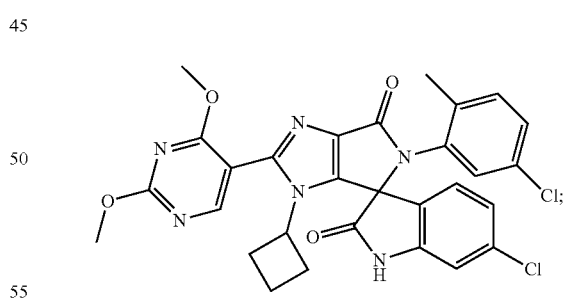
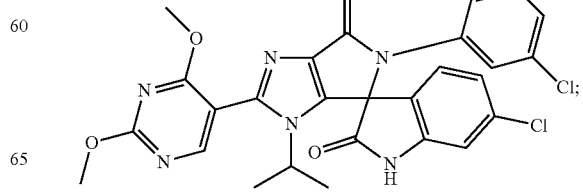

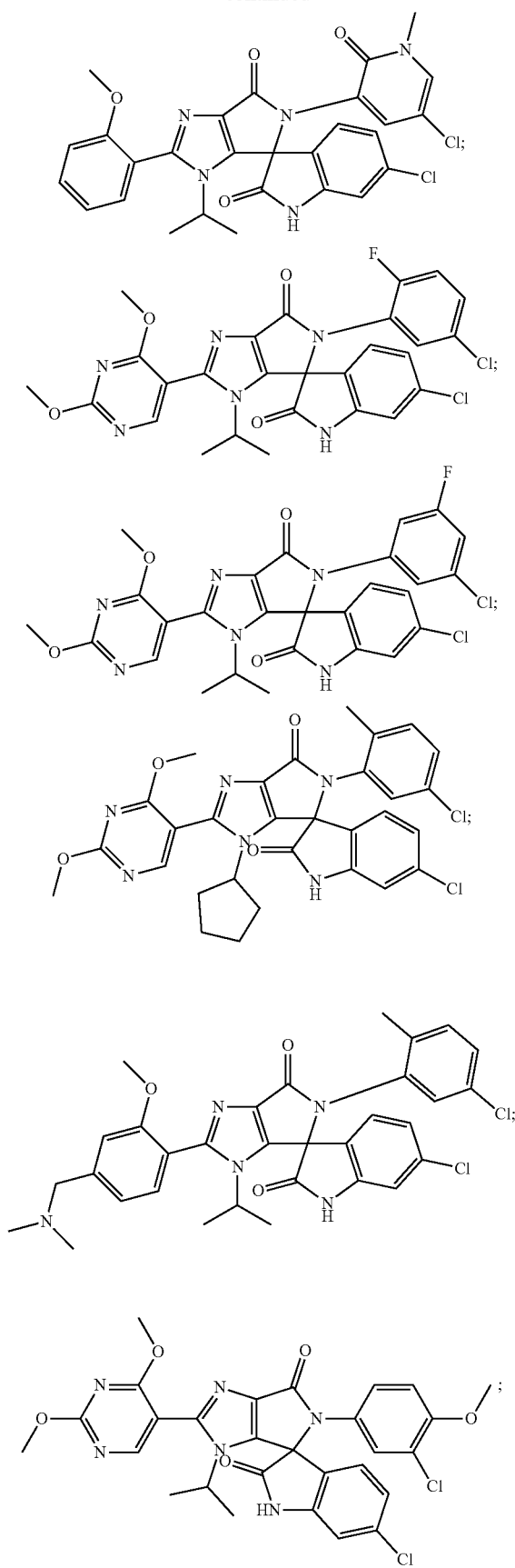
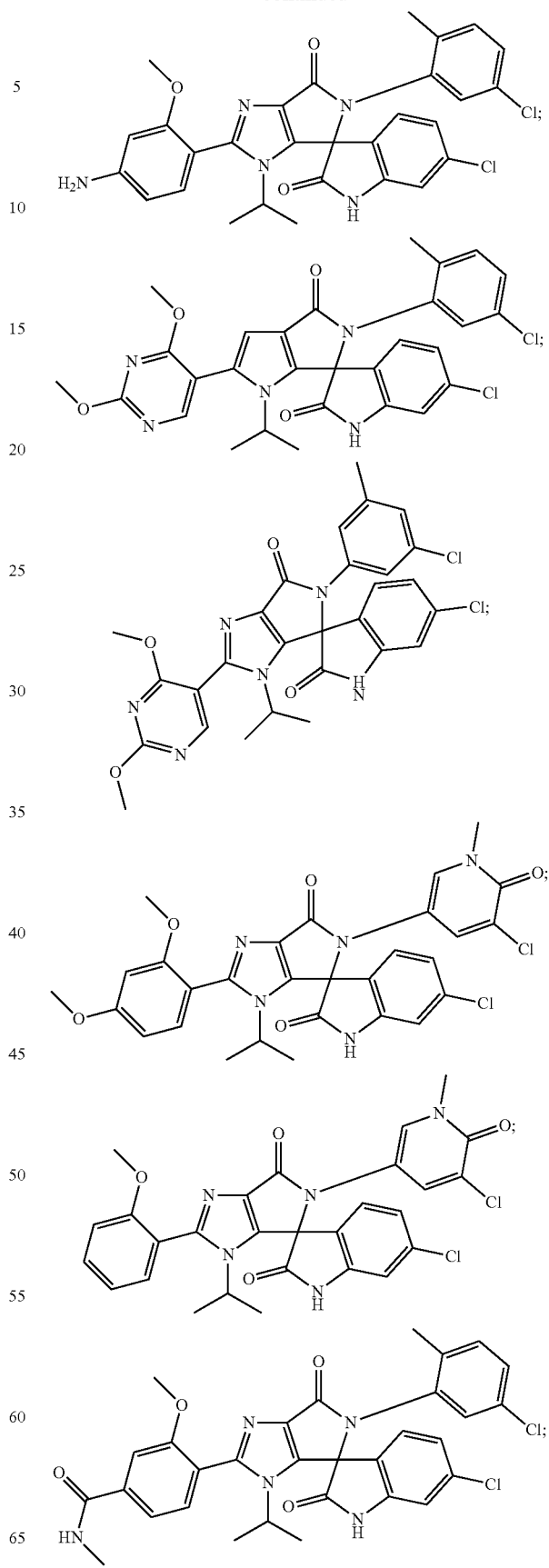

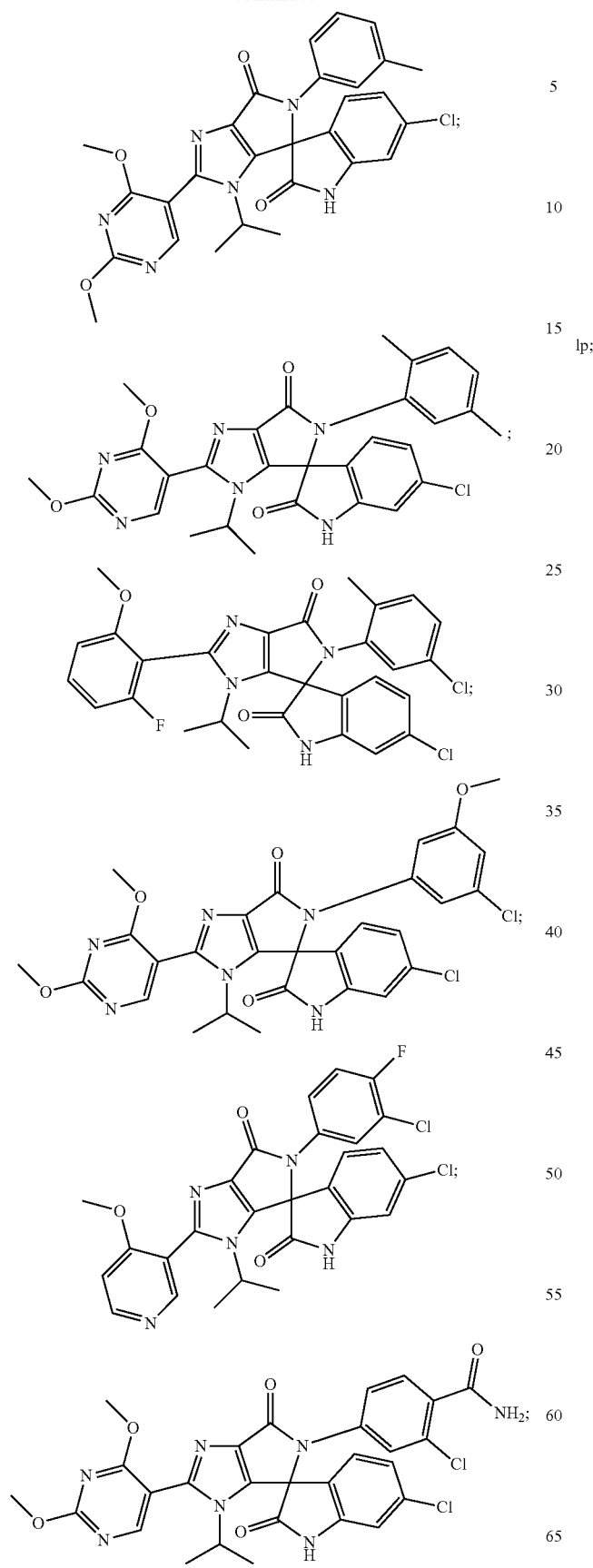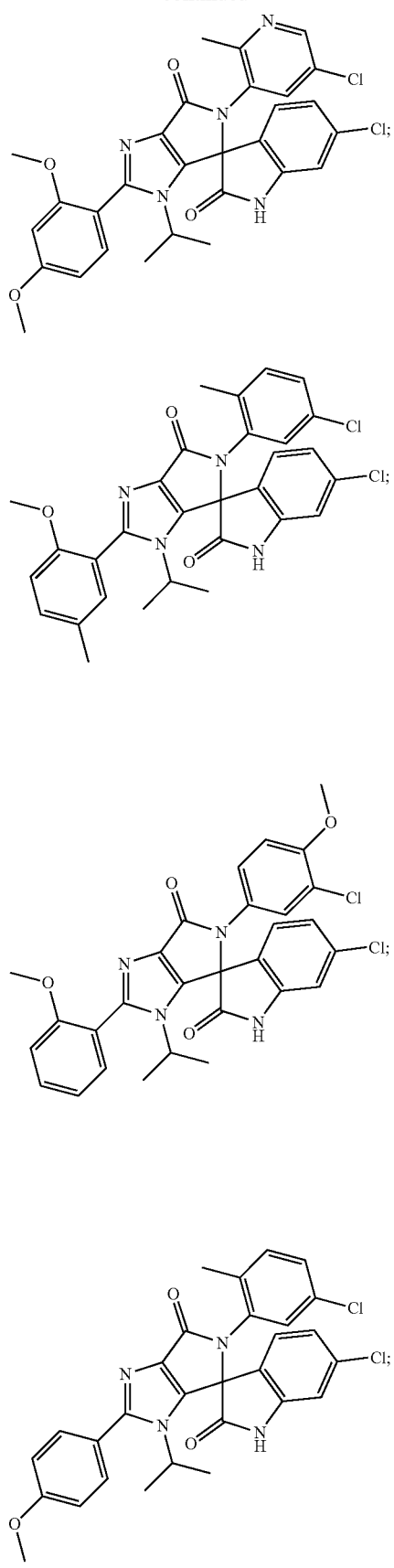
lp;4p

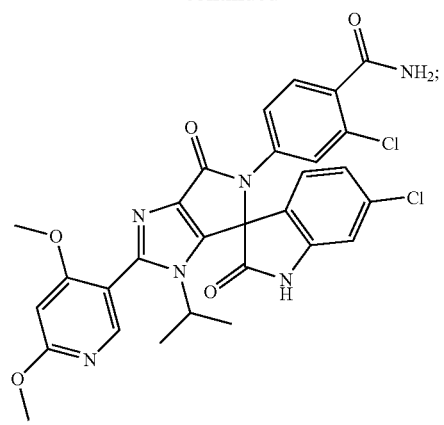
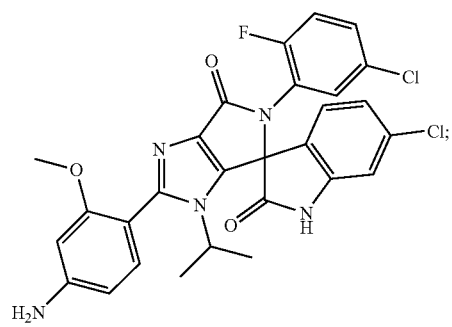
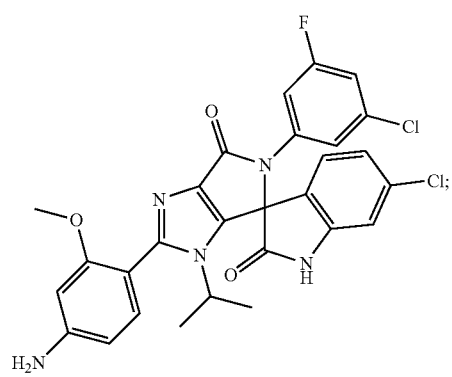
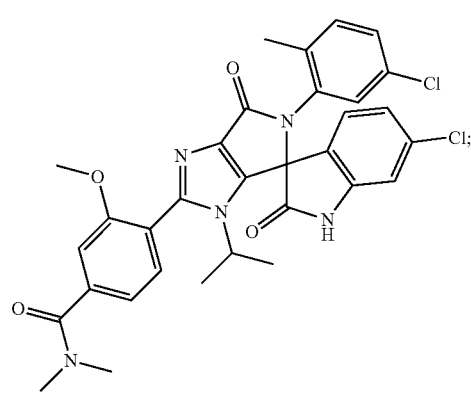
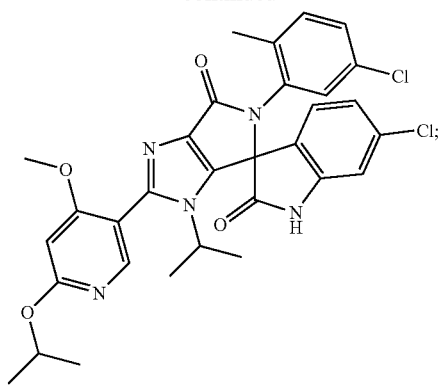
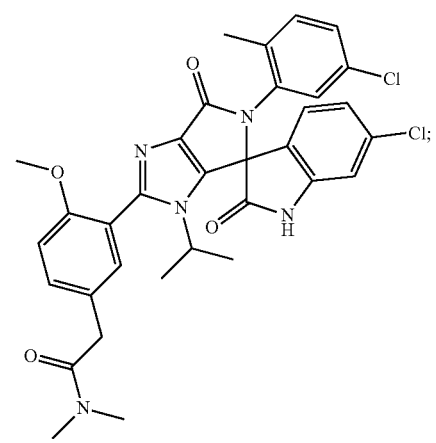
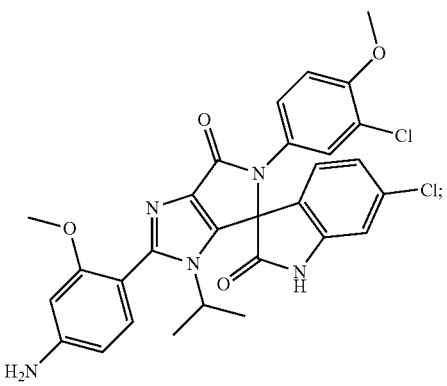
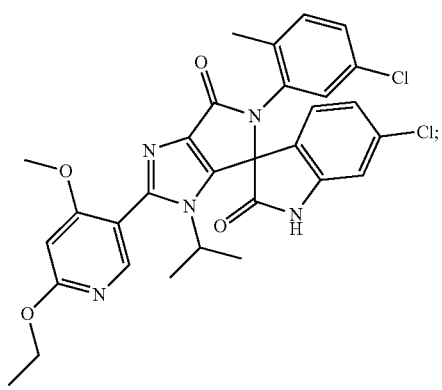

-continued
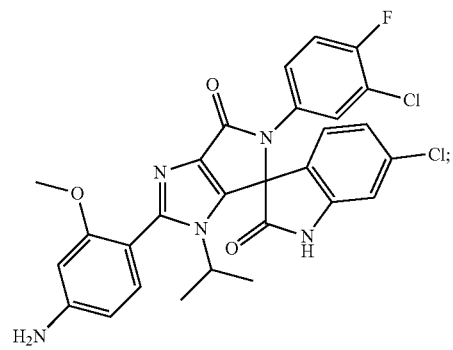
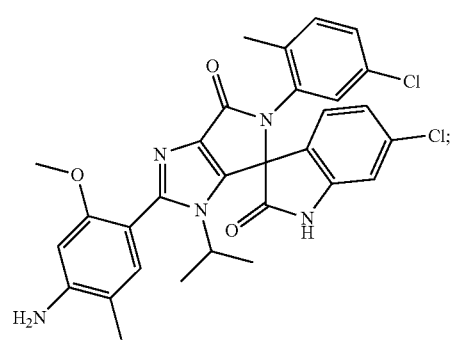
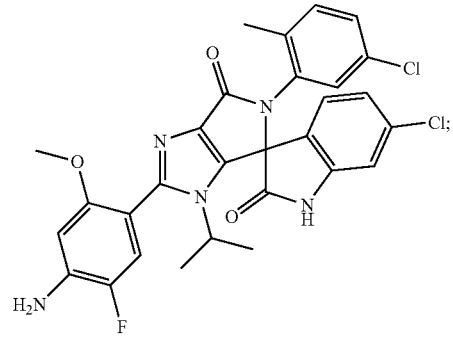
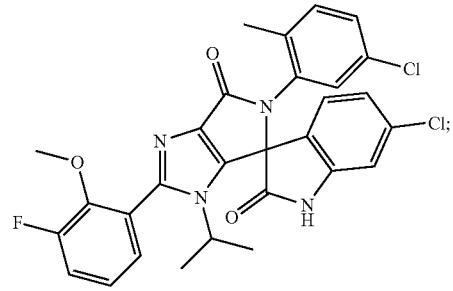
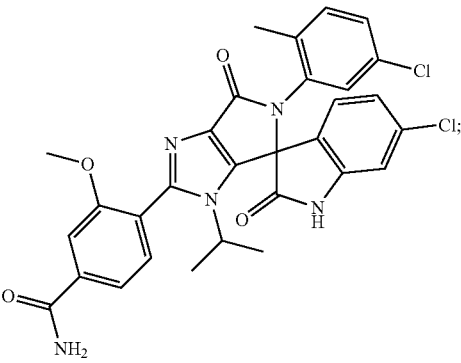
-continued
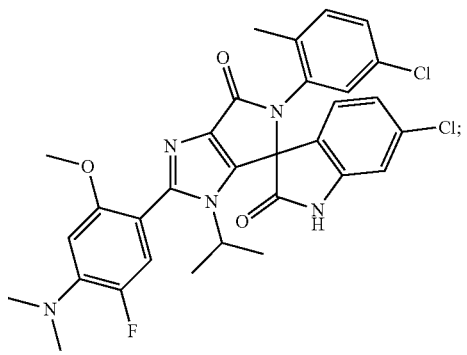
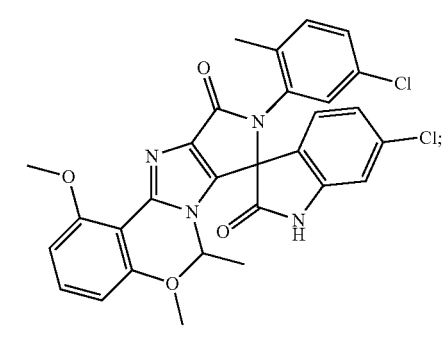
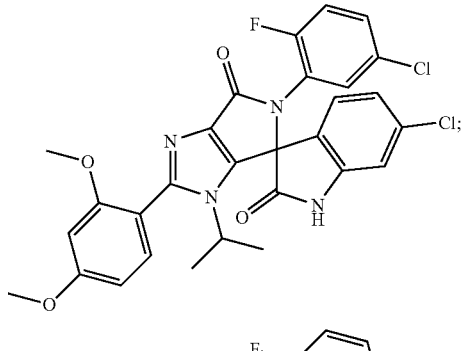
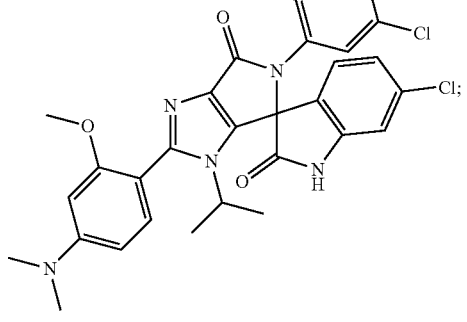
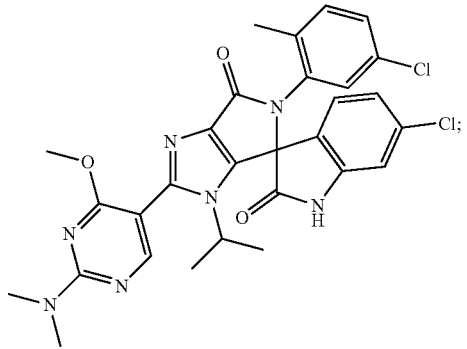

-continued
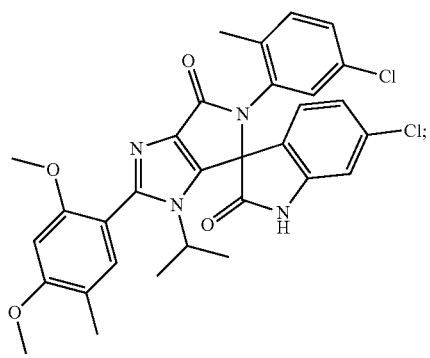
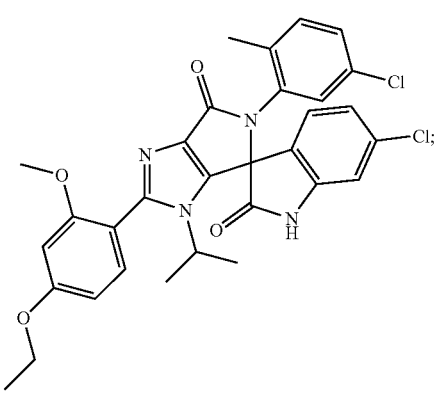
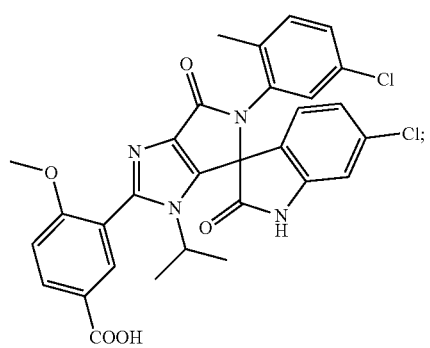
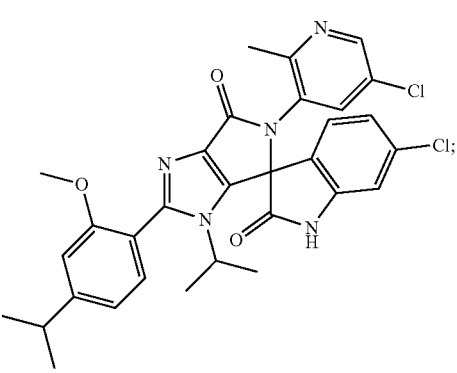
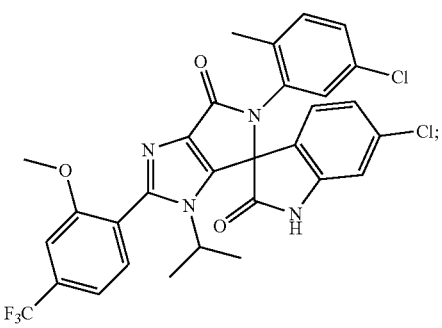

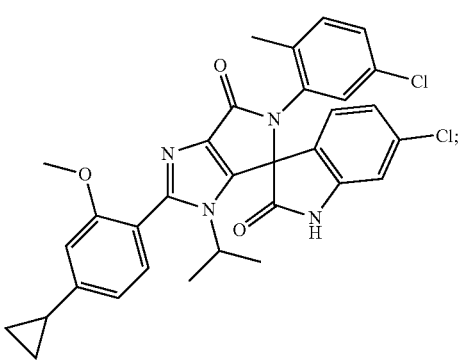
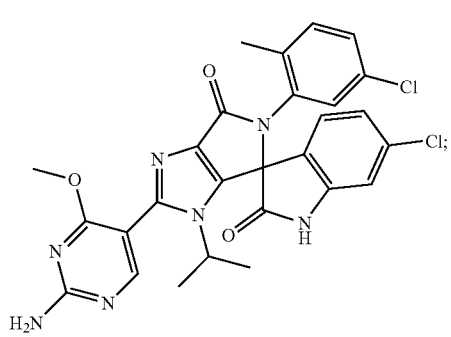

-continued
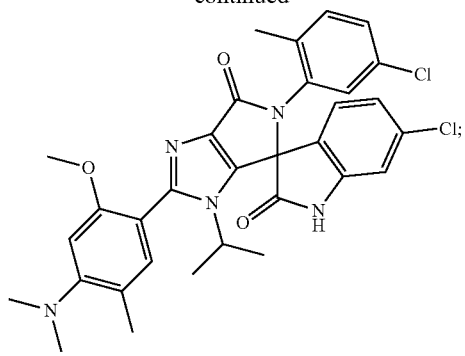
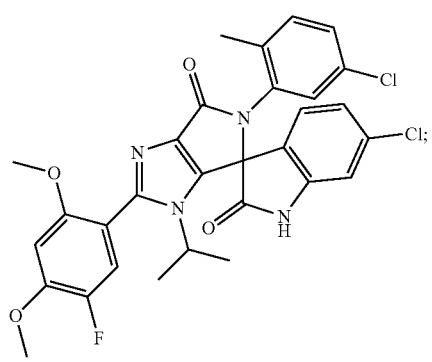
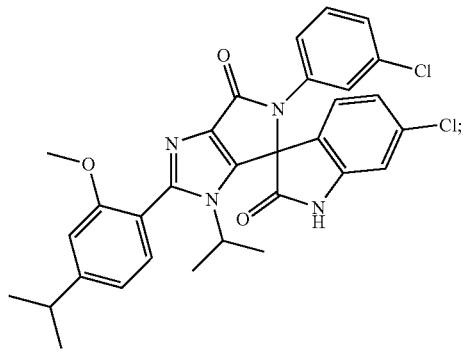
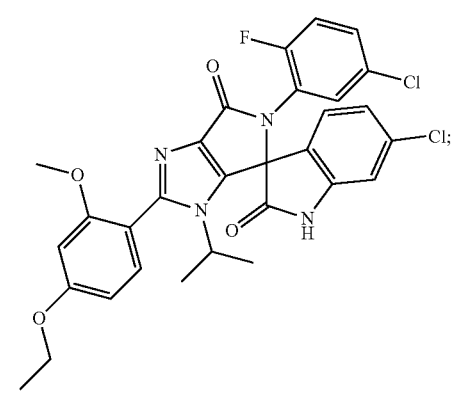
-continued
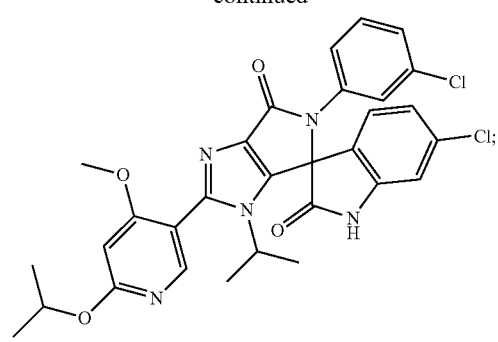
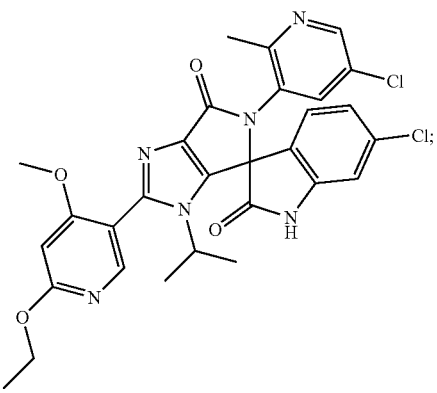
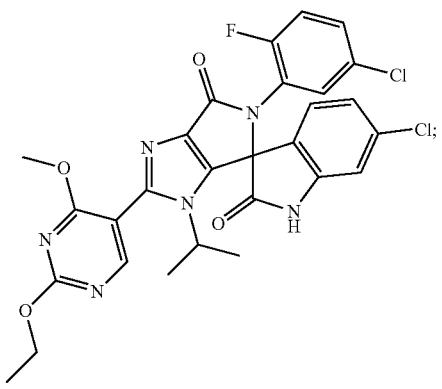
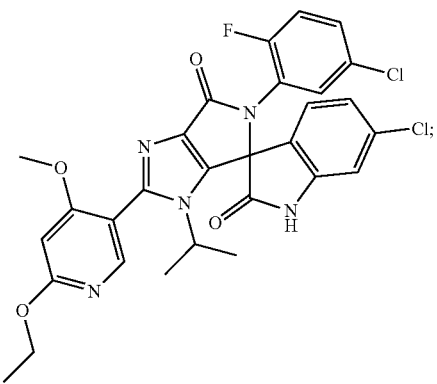

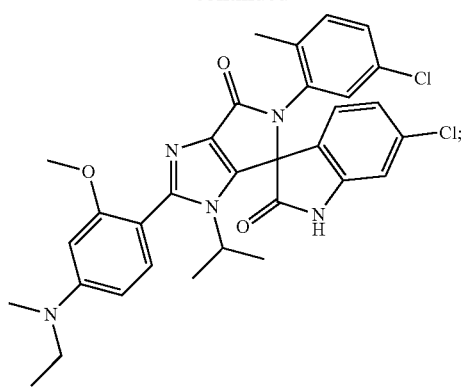
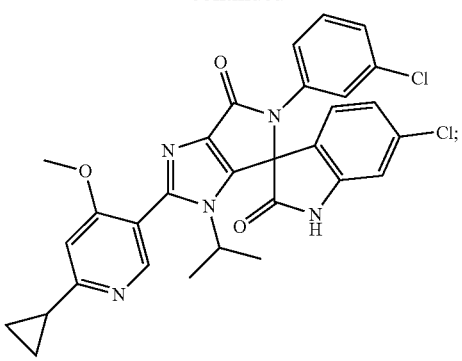
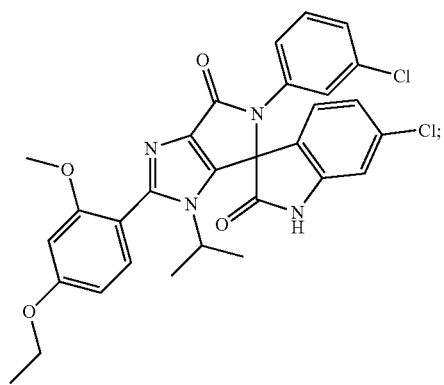
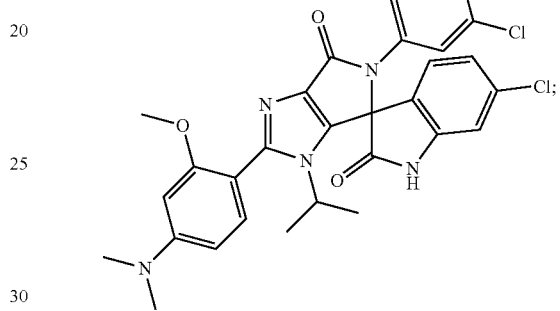
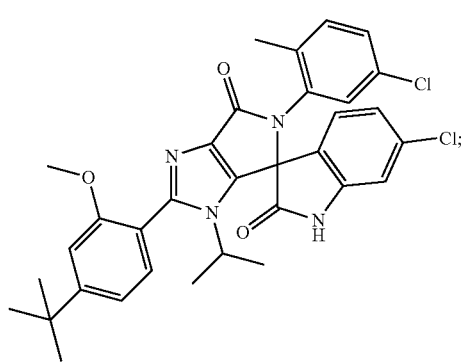
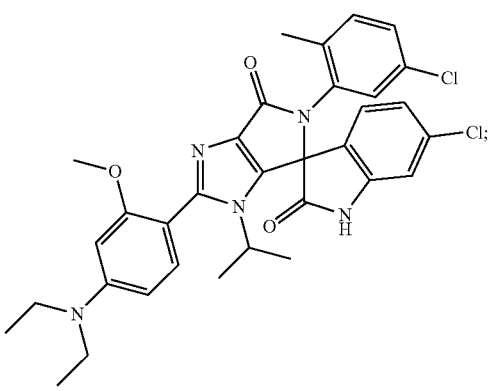
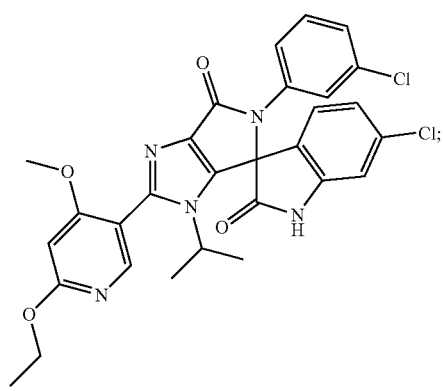
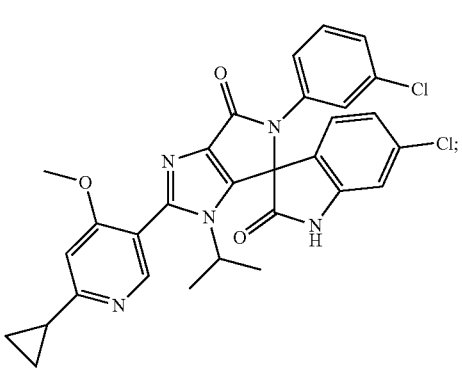

-continued
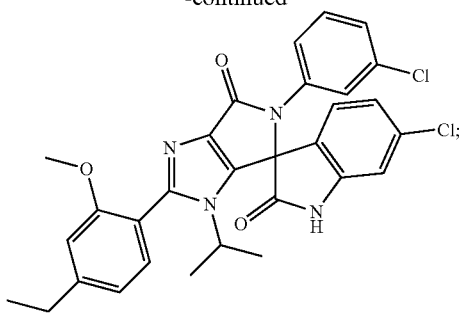
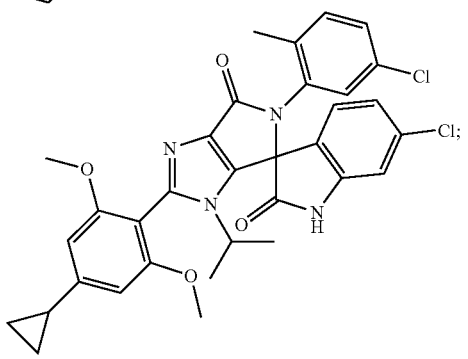
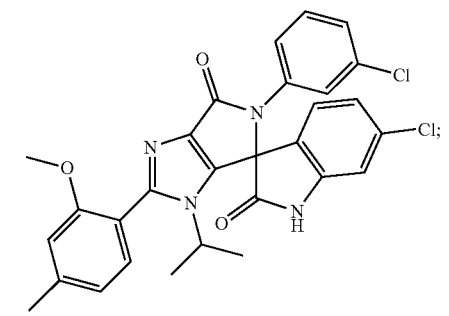
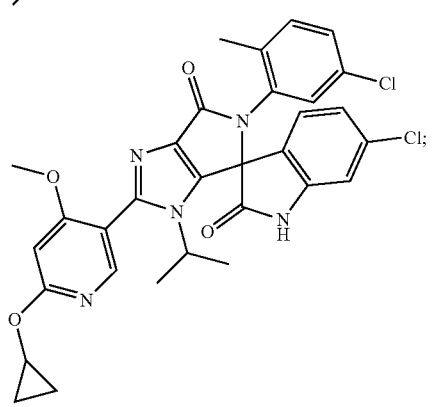
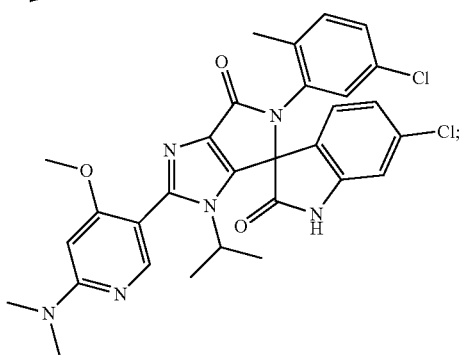
-continued
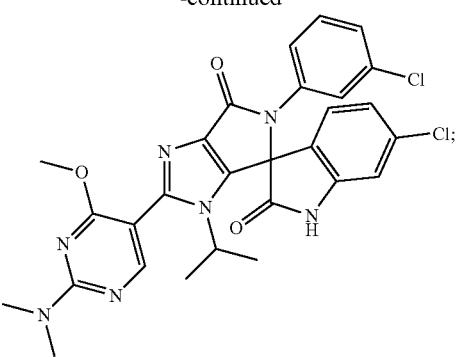
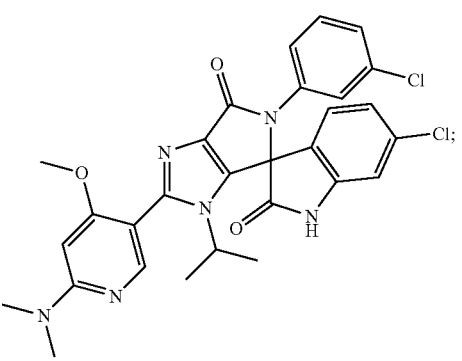
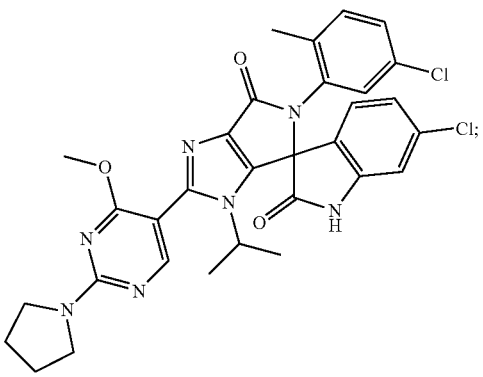
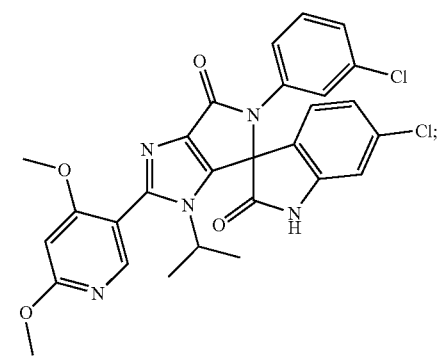

33
-continued
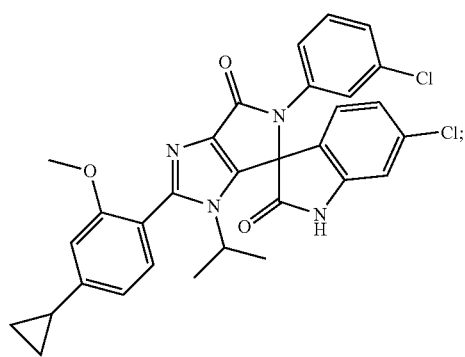
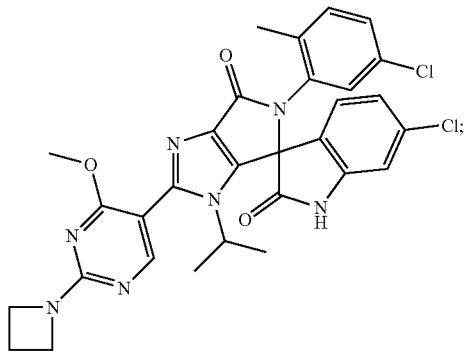
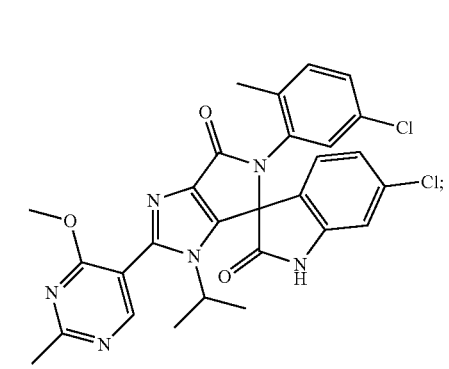
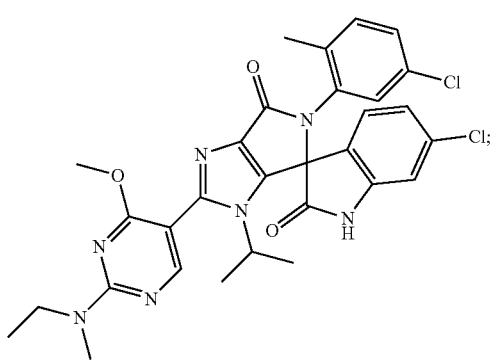
34
-continued
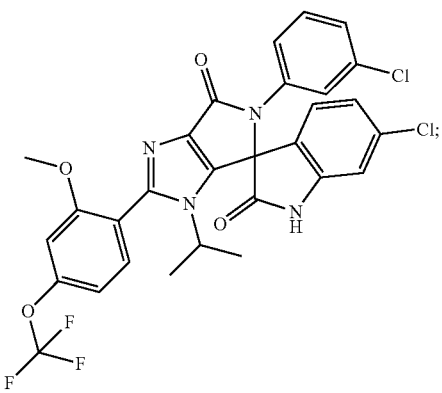
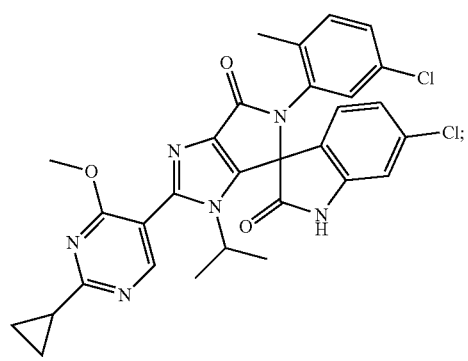
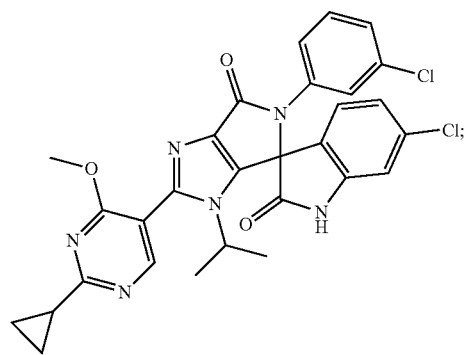
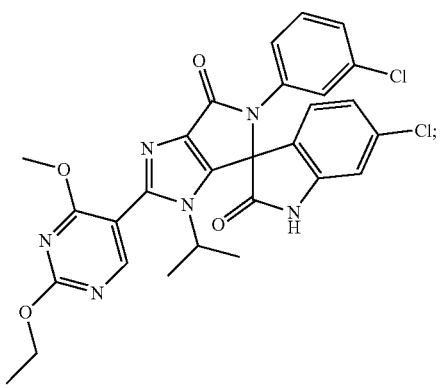

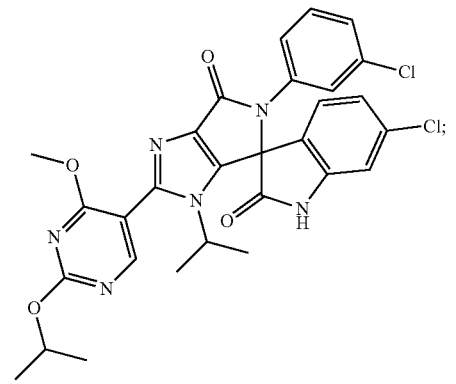
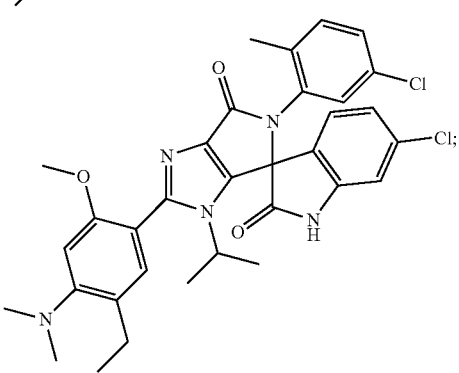
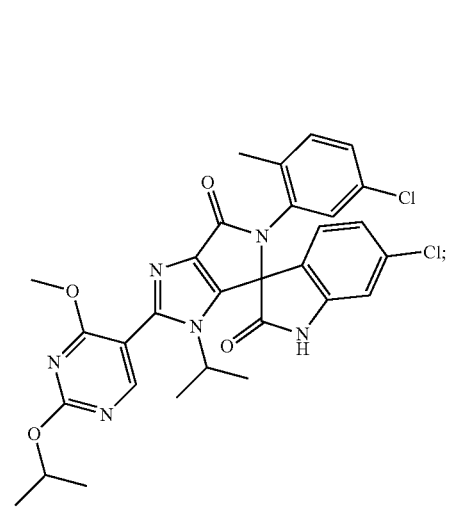
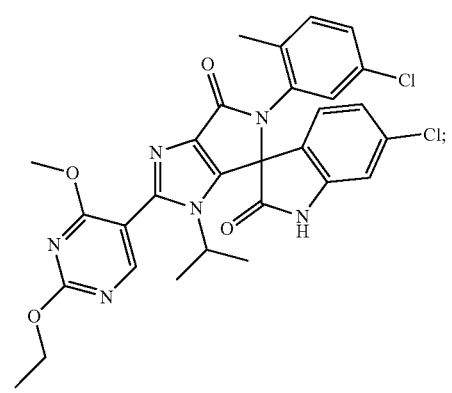
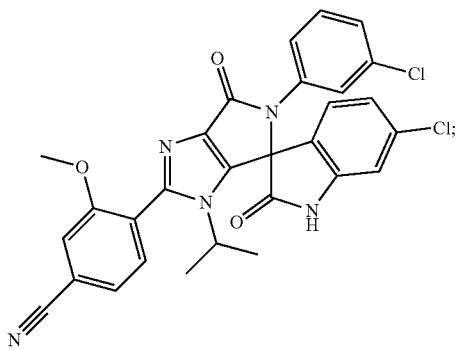
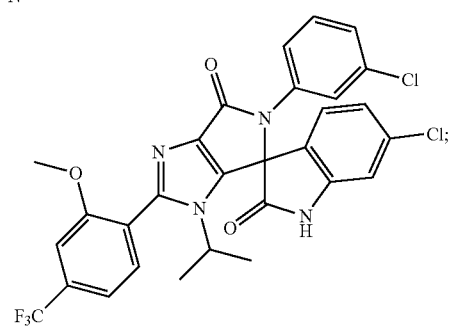
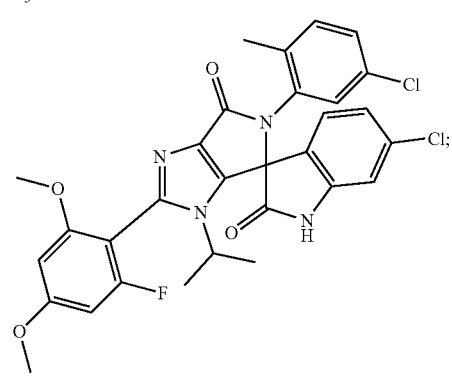
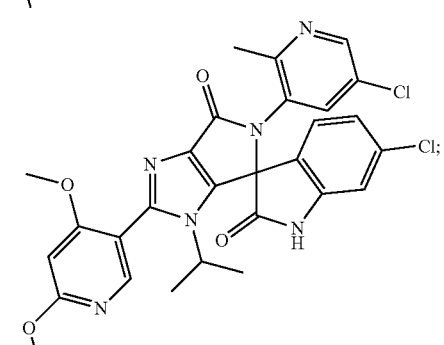
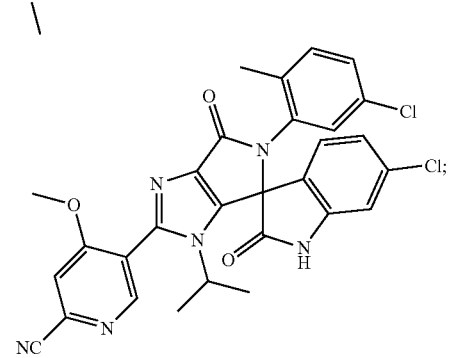

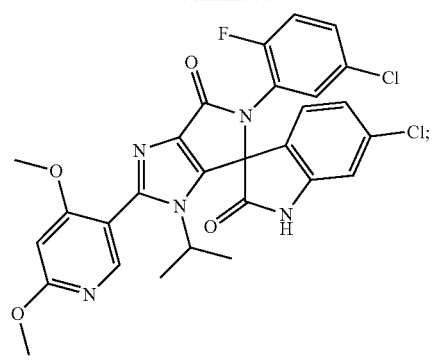
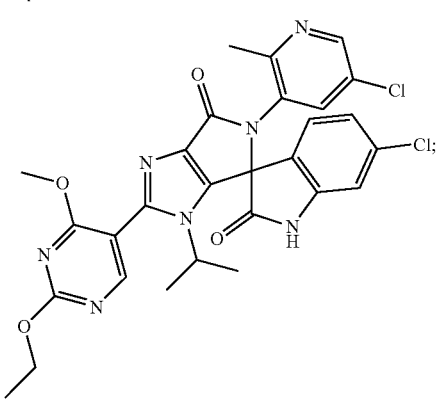
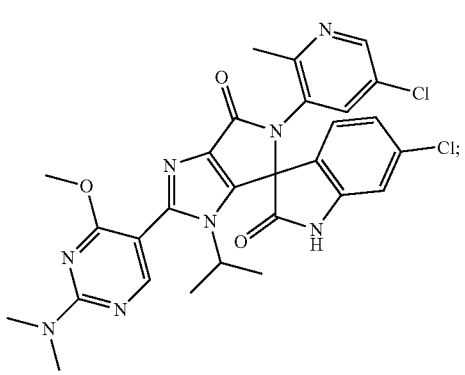
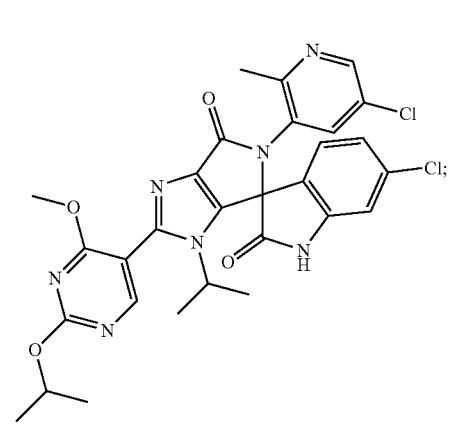
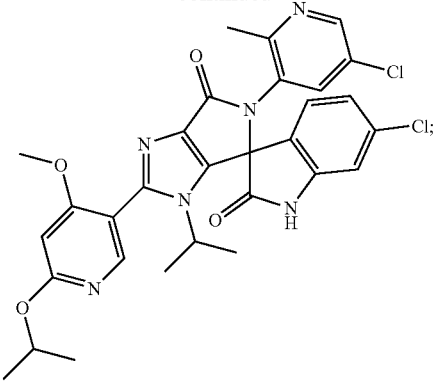
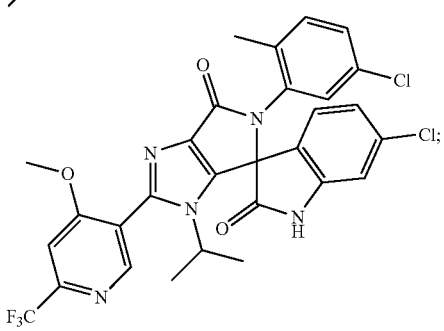
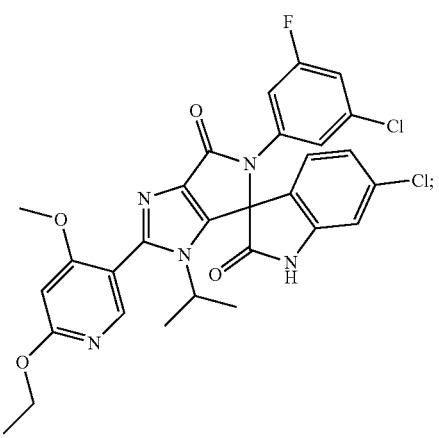
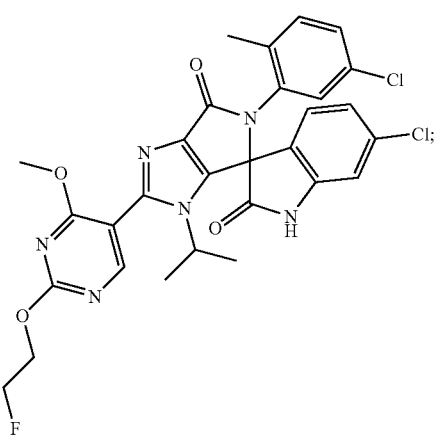

-continued
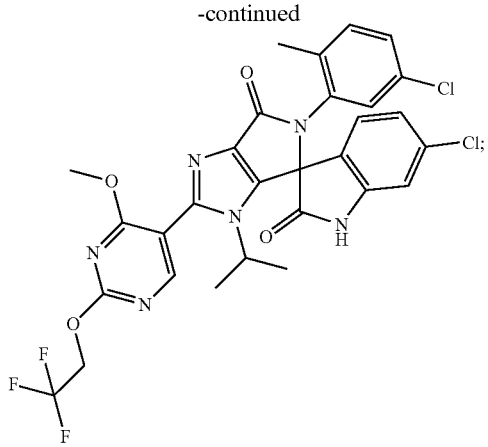
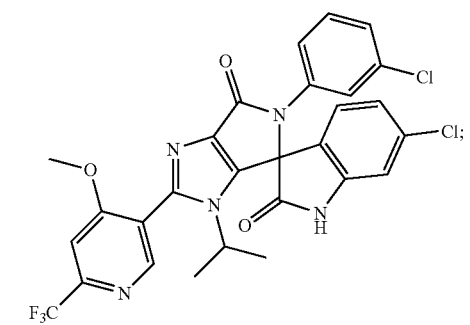
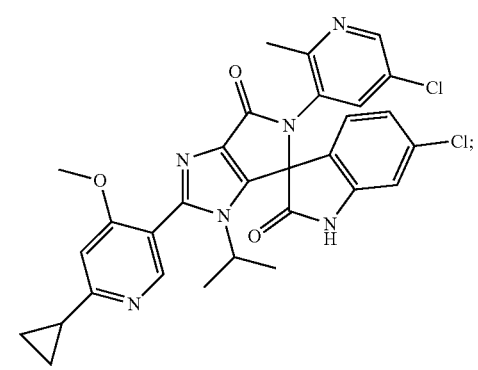
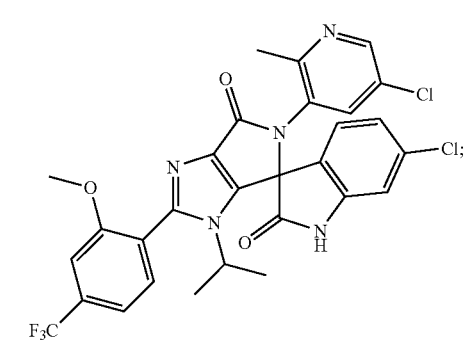
-continued
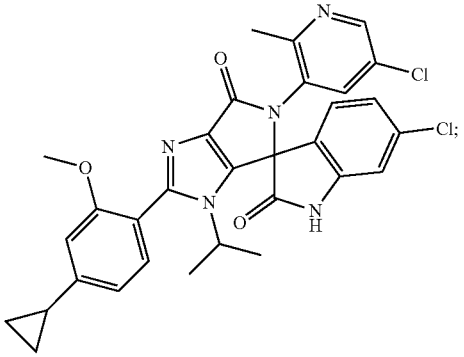
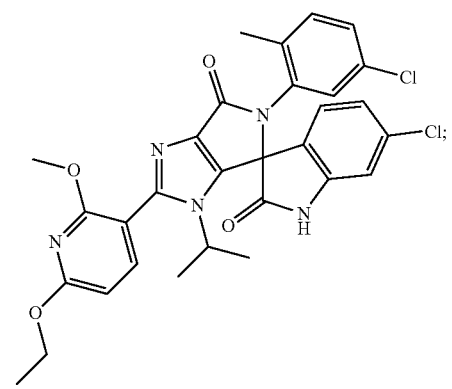
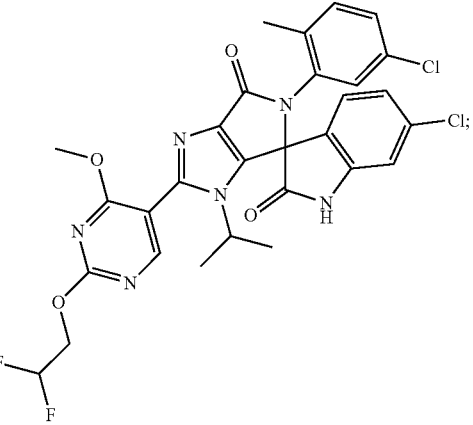
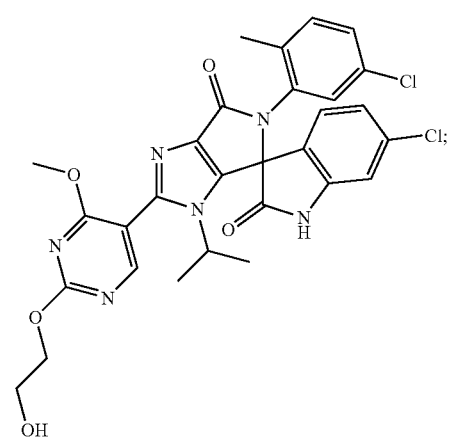

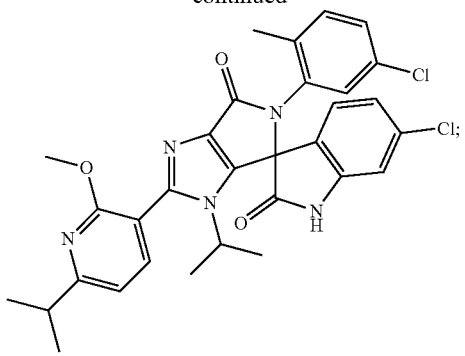
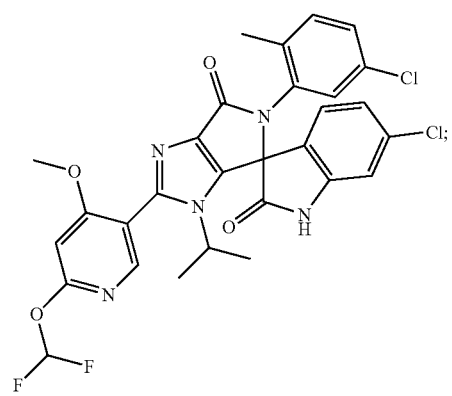
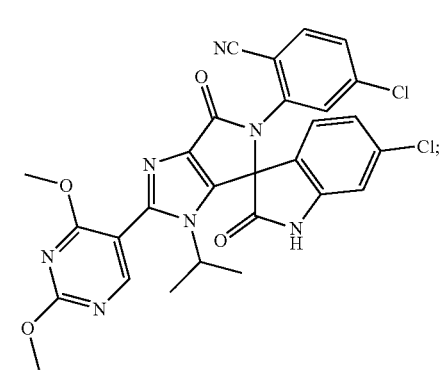
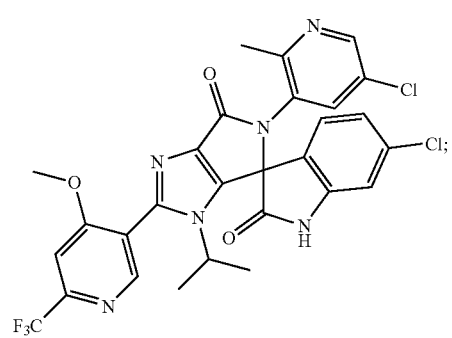
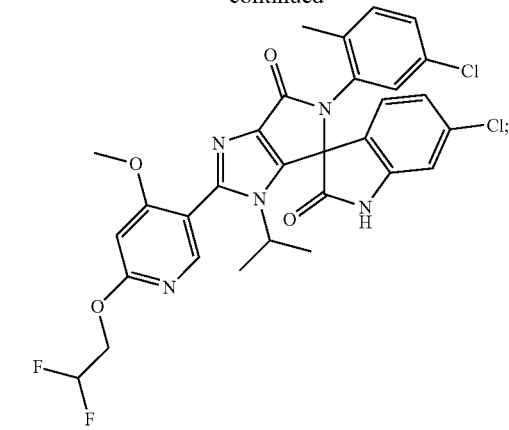
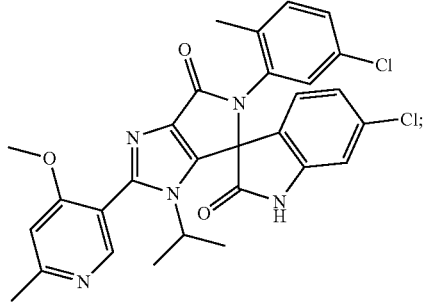
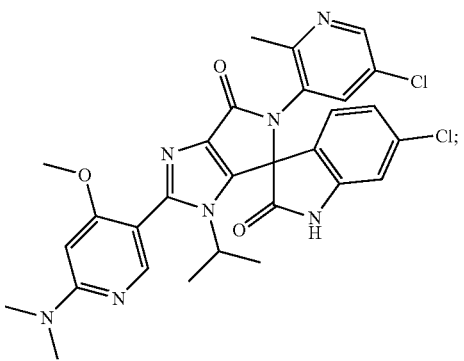
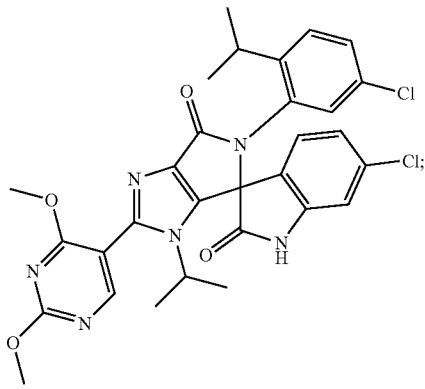

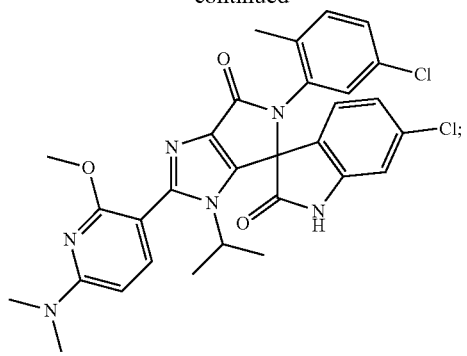
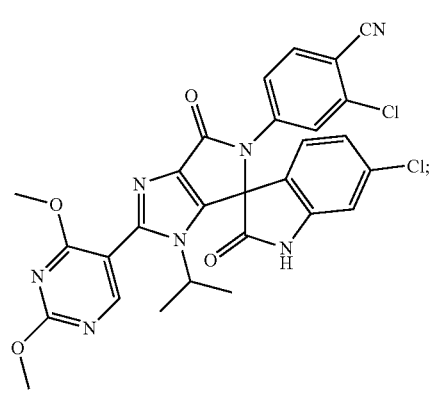
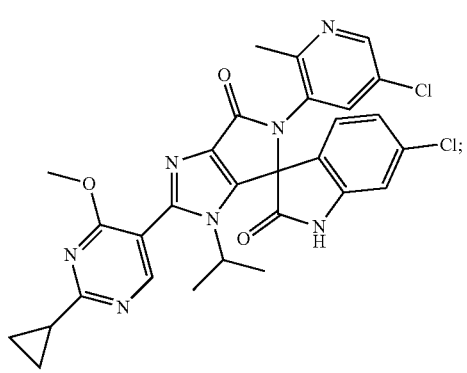
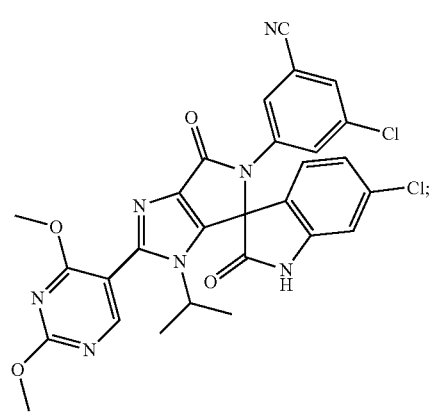
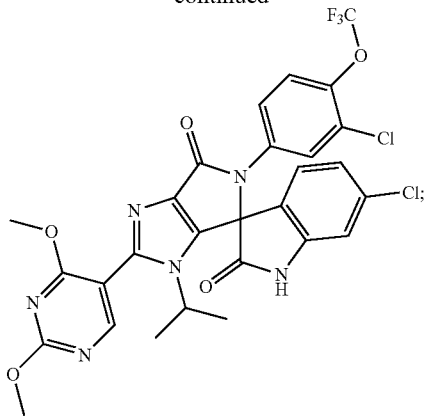
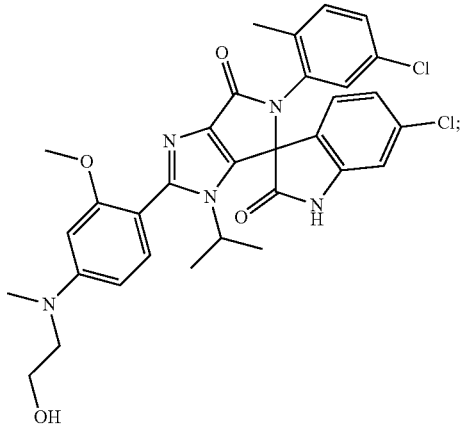
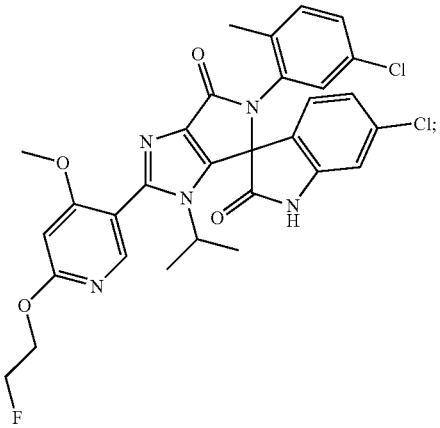
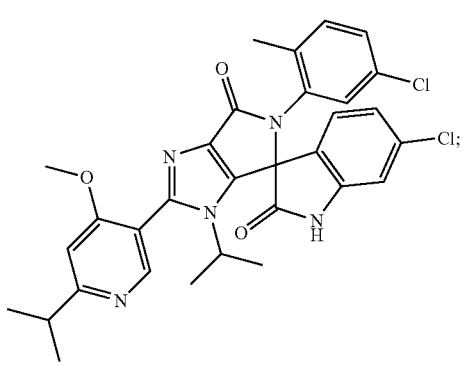

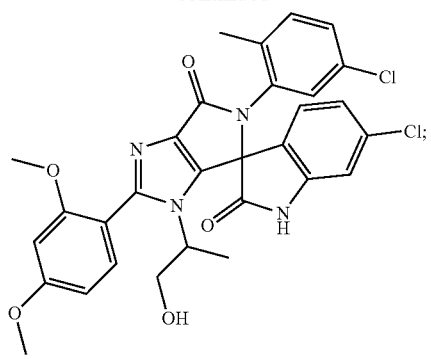
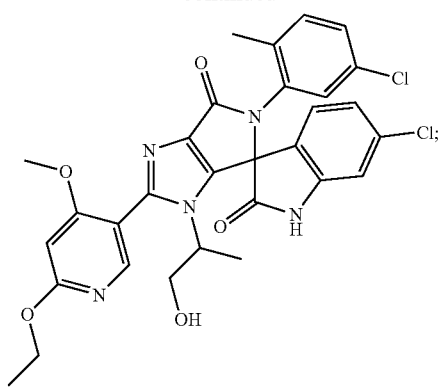
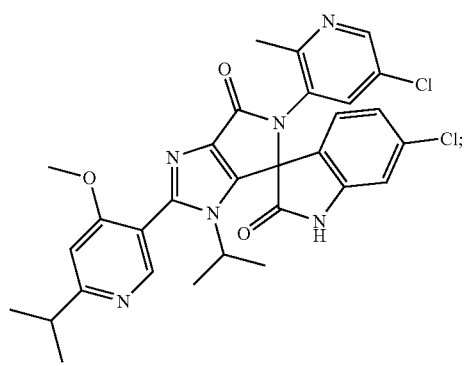
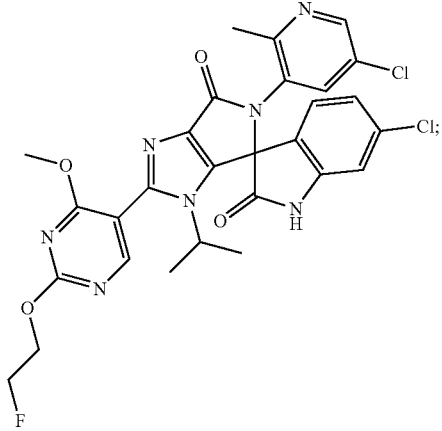
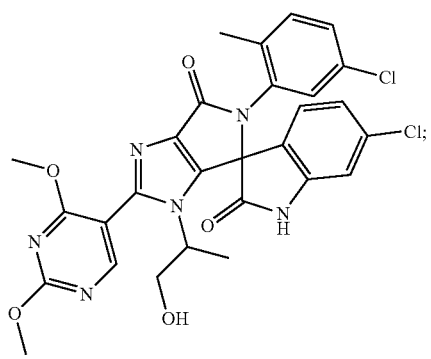
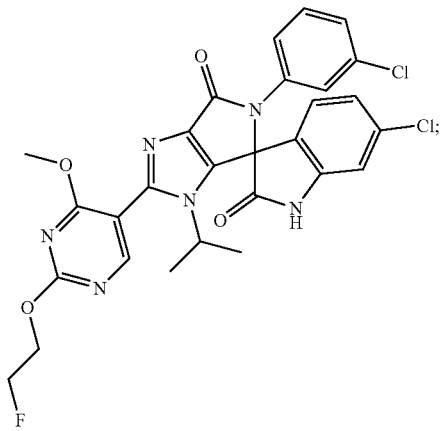
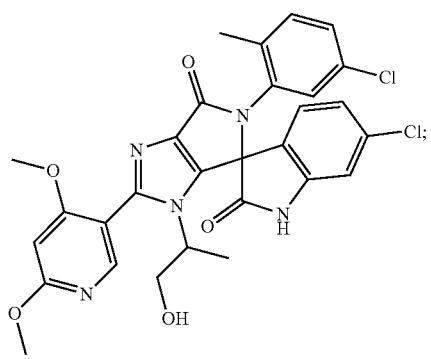

-continued

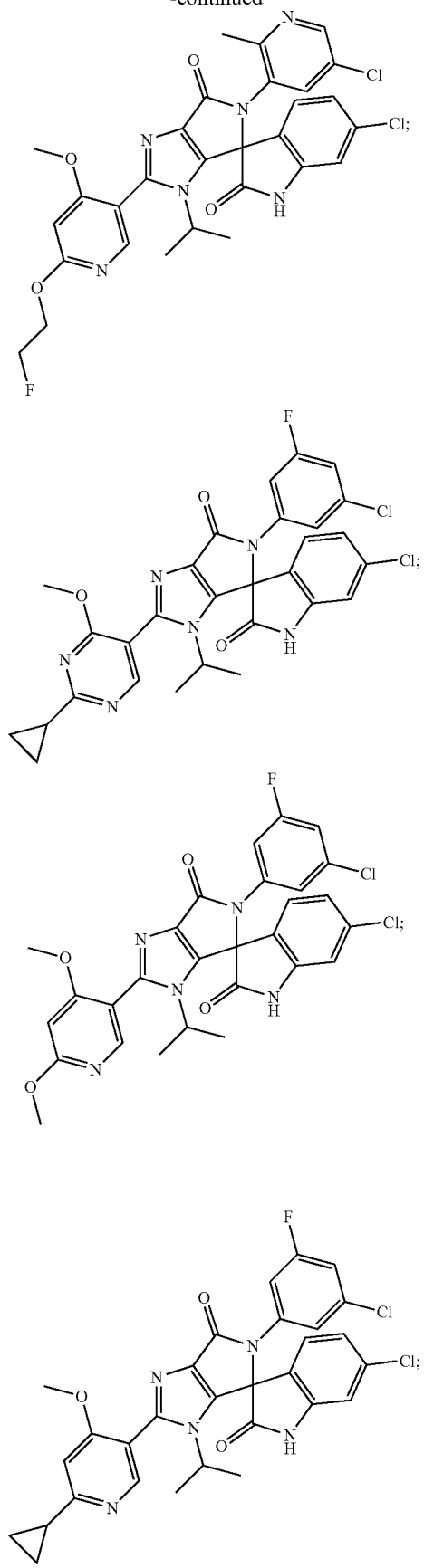

-continued

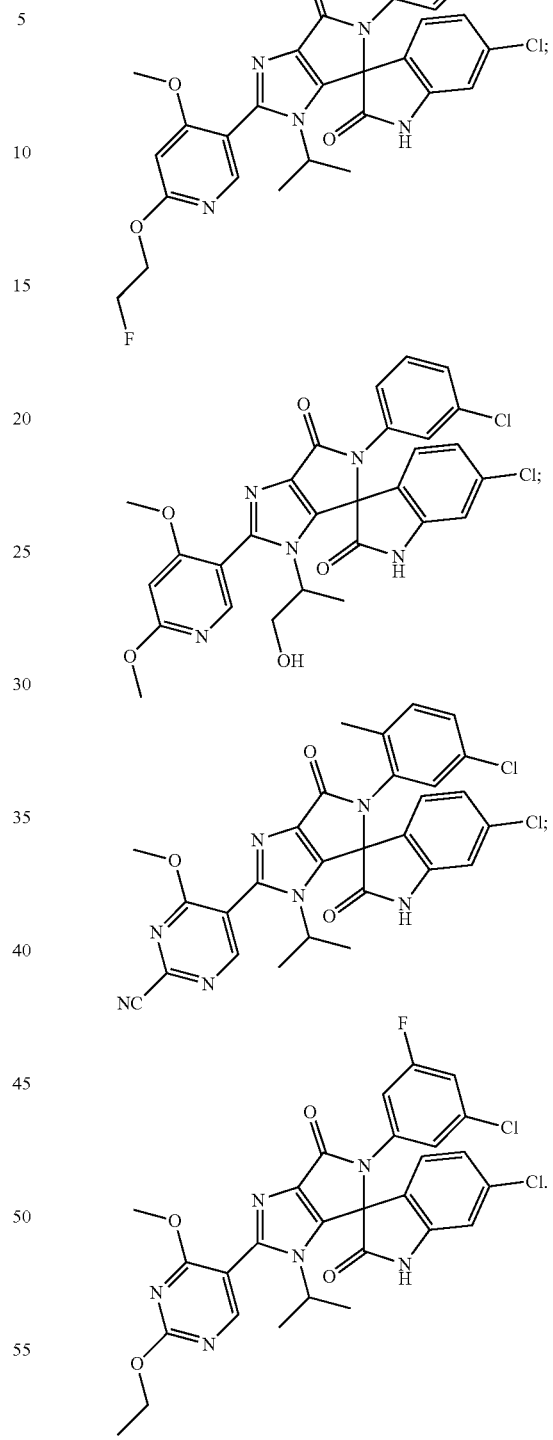

Depending on the type or combination of substituents, the compounds represented by the general formula (I) of the present invention may have various isomers, for example, the isomers include, but are not limited to, stereoisomers (for example, "cis" and "trans" forms, enantiomers), tautomers and optical isomers (for example, dextrorotary and levorotary forms). Preferably, the compound of the present invention is in the S configuration to obtain a more ideal application activity. The compounds of the present invention also include all of these isomers, and mixtures of these isomers at any ratio, unless otherwise specified.

In addition, the present invention also includes a compound which is converted into compound (I) as an active ingredient of the pharmaceutical composition of the present invention due to reactions induced by enzymes, gastric acid and the like under physiological conditions in the body, that is, a compound which is converted into compound (I) by enzymatic oxidation, reduction, hydrolysis and the like, or a "pharmaceutically acceptable prodrug compound" which is converted into compound (I) by hydrolysis induced by gastric acid or the like.

Any structural formula given herein is also intended to represent the unlabeled form and isotope-labeled form of the compounds. An isotope-labeled compound or isotopic variant has the structure depicted by the structural formula given herein, except that one or more atoms are replaced by atom(s) having selected atomic mass or mass number. For example, the compound represented by the general formula (I) of the present invention may contain isotope(s) in an unnatural proportion as one or more constituent atom(s). Examples of isotopes include, but are not limited to, for example, deuterium ($^2$H), tritium ($^3$H), iodine-125 ($^{125}$I), and carbon-14 ($^{14}$C). These compounds are useful therapeutic or preventive agents, research reagents (for example, test reagents), and diagnostic agents (for example, in vivo diagnostic imaging agents). Regardless of the presence or absence of radioactivity, all isotopic variants of the compound represented by the general formula (I) are also included in the scope of the present invention.

The "pharmaceutically acceptable salt" in the present invention refers to an acid addition salt or a base addition salt of the compound of the present invention. "Salt" specifically includes "pharmaceutical salt". The term "pharmaceutical salt" means a salt that retains the biological effectiveness and properties of the compound of the present invention, which is generally not biologically or otherwise undesirable. In many cases, the compound of the present invention can form acid and/or base salt(s) through the present amino and/or carboxyl or similar groups, for example, pharmaceutical acid addition salts can form the following salts with inorganic and organic acids, such as acetate, aspartate, benzoate, benzenesulfonate, bromide/hydrobromide, bicarbonate/carbonate, bisulfate/sulfate, camphor sulfonate, chloride/hydrochloride, chlortheophyllonate, citrate, ethanedisulfonate, fumarate, glucoheptanoate, gluconate, glucuronate, hippurate, hydroiodate/iodide, hydroxyl ethyl sulfonate, lactate, lactobionate, dodecyl sulfate, malate, maleate, malonate, mandelate, mesylate, methyl sulfate, naphthalene formate, naphthalenesulfonate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate.

The pharmaceutical solvates of the present invention include those in which the crystalline solvent may be isotopically substituted, such as $D_2O$, $d_6$-acetone, and $d_6$-DMSO.

In addition, the compounds of the present invention, including their salts, can also be obtained in the form of their hydrates, or contain other solvents for their crystallization. The compounds of the invention may form solvates inherently or by design with pharmaceutical solvents (including water); therefore, it means that the present invention includes both solvated and unsolvated forms. The term "solvate" means a molecular complex of the compound of the present invention (including a pharmaceutical salt thereof) with one or more solvent molecules. These solvent molecules are those commonly used in the pharmaceutical field and are known to be harmless to recipients, such as water, ethanol, and the like. The term "hydrate" refers to a complex in which the solvent molecule is water. The compounds of the present invention, including their salts, hydrates, and solvates, can form polymorphs inherently or by design. Solvates or hydrates can be used to prepare crystalline forms of the compounds of formula (I).

In a second aspect, the present invention provides a preparation method of a plurality of the compounds of the first aspect as a preferred embodiment:

As a first parallel embodiment, when Y is N, the preparation method of the compound of the general formula I of the present invention comprises at least the following steps:

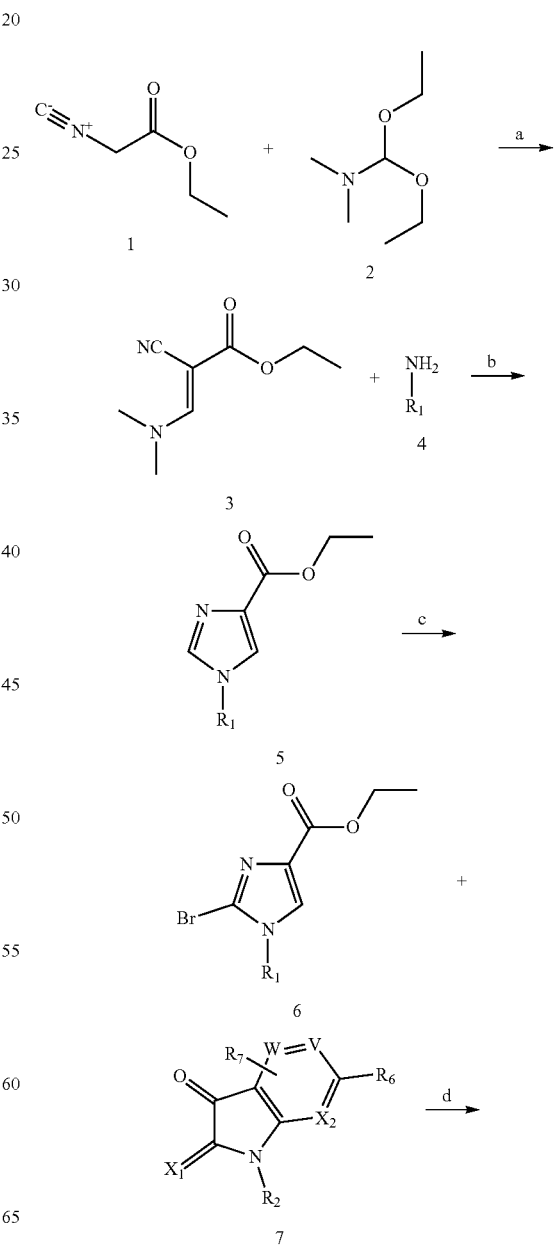

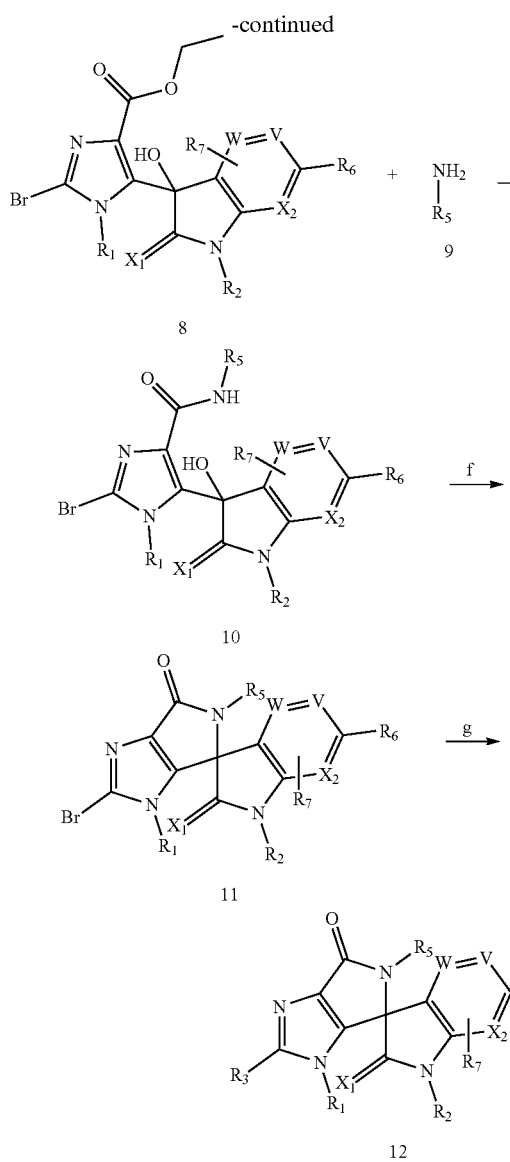

(1) compound 1 and compound 2 are subjected to a substitution and rearrangement reaction to synthesize compound 3;

(2) compound 3 and compound 4 are subjected to a cyclization reaction to construct an imidazole ring to obtain compound 5;

(3) compound 5 is brominated by NBS to obtain compound 6;

(4) compound 6 and compound 7 are subjected to low-temperature lithiation with LDA to obtain compound 8;

(5) compound 8 and compound 9 are subjected to an ammonolysis reaction to obtain compound 10;

(6) compound 10 is subjected to an acidification and dehydration reaction to obtain compound 11; and (7) compound 11 and aryl or heteroaryl borate or boronic acid are subjected to a Suzuki coupling reaction to obtain product 12 (corresponding to the compound represented by the general formula (I));

wherein, $R_1$, $R_2$, $R_3$, $R_5$, $R_6$, $R_7$, $X_1$, $X_2$, V and W are as defined for the general formula I.

In the above-mentioned preparation method provided by the present invention, each step can be implemented by using various known reaction conditions. As a preferred embodiment, the present invention further defines each step as follows:

Step 1: preferably, the compound 2 is added dropwise to the compound 1 at 0±2° C., to react overnight at room temperature;

Step 2: preferably, cyclization reaction is performed at 70±2° C.;

Step 3: preferably, tetrahydrofuran is used as a solvent, and more preferably, NBS is added in batches at 0±2° C., followed by stirring overnight at room temperature;

Step 4: preferably, tetrahydrofuran is used as a solvent, and more preferably, the reaction is performed at −78±2° C. for 2 h;

Step 5: preferably, toluene is used as a solvent, more preferably, $AlMe_3$ and the compound 9 are added dropwise at 0±2° C., to react overnight at 90±2° C.;

Step 6: preferably, glacial acetic acid is used as a solvent, and reaction is performed under the action of concentrated sulfuric acid at 110±5° C. for 2 h;

Step 7: preferably, 1,4-dioxane and water are used as solvents, more preferably, $Pd(PPh_3)_4$ is used as a catalyst, sodium carbonate or potassium phosphate is used as a base, and a microwave reaction is performed at 100±2° C. for 1±0.5 h.

As a second parallel embodiment, when Y is C, the preparation method of the compound of the general formula I of the present invention comprises at least the following steps:

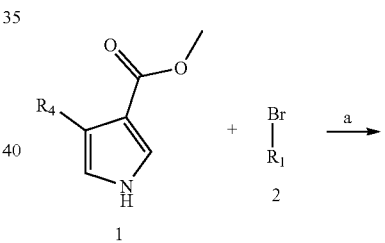

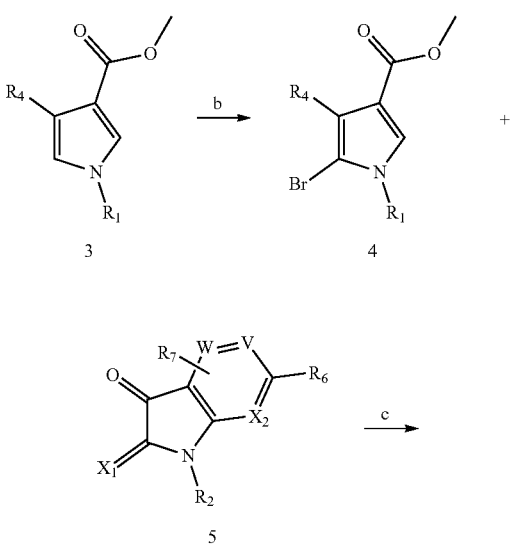

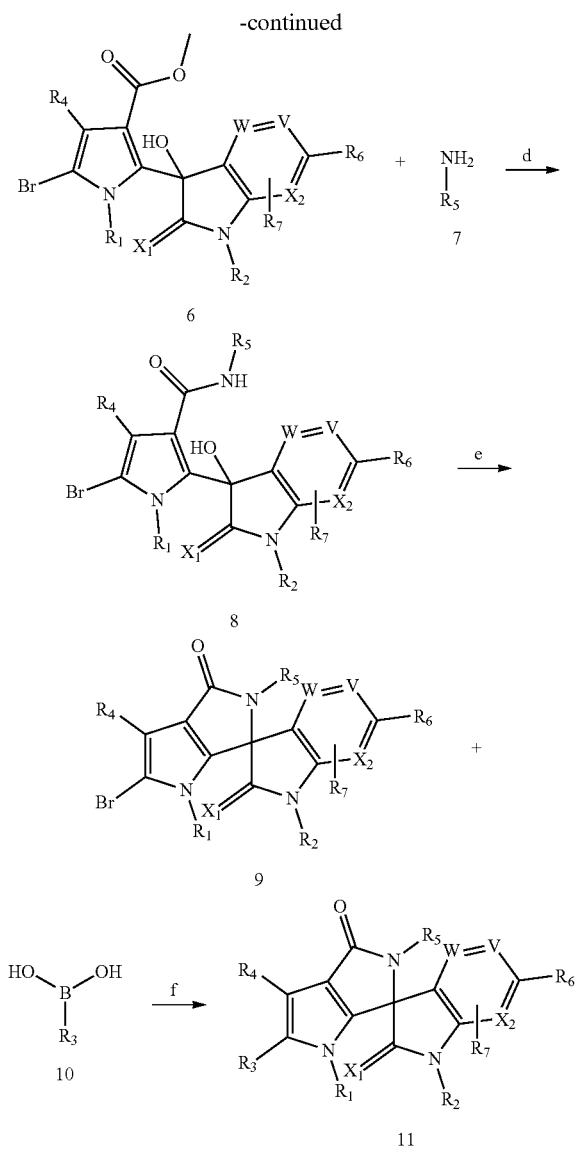

(1) compound 1 and compound 2 are subjected to a substitution reaction to synthesize compound 3;

(2) compound 3 is brominated by NBS to obtain compound 4;

(3) compound 4 and compound 5 are subjected to low-temperature lithiation with LDA to obtain compound 6;

(4) compound 6 and compound 7 are subjected to an ammonolysis reaction to obtain compound 8;

(5) compound 8 is subjected to an acidification and dehydration reaction to obtain compound 9; and (6) compound 9 and aryl or heteroaryl boronic acid are subjected to a Suzuki coupling reaction to obtain product 11 (corresponding to the compound represented by the general formula (I));

wherein, $R_1$, $R_2$, $R_3$, $R_4$, $R_5$, $R_6$, $R_7$, $X_1$, $X_2$, V and W are as defined for the general formula I.; preferably $X_1$ is O.

In the above-mentioned preparation method provided by the present invention, each step can be implemented by using various known reaction conditions. As a preferred embodiment, the present invention further defines each step as follows:

wherein, step 1: preferably, at 0±2° C., DMF is used as a solvent, and the compound 2 is slowly added to the compound 1, to react overnight at room temperature;

Step 2: preferably, tetrahydrofuran is used as a solvent, NBS is added in batches at 0±2° C., followed by stirring overnight at room temperature;

Step 3: preferably, tetrahydrofuran is used as a solvent, and reaction is performed at −78±2° C. for 2±1 h;

Step 4: preferably, toluene is used as a solvent, AlMe$_3$ and compound 7 are added dropwise at 0±2° C., to react overnight at 90±2° C.;

Step 5: preferably, glacial acetic acid is used as a solvent, and reaction is performed under the action of concentrated sulfuric acid at 110±5° C. for 2±1 h;

Step 6: preferably, 1,4-dioxane and water are used as solvents, Pd(PPh$_3$)$_4$ is used as a catalyst, sodium carbonate or potassium phosphate is used as a base, and a microwave reaction is performed at 100±5° C. for 1±0.5 h.

Conventional conditions in the art can be used to carry out the reactions described in the above steps, which are not particularly limited in the present invention.

In a third aspect, the present invention provides a pharmaceutical composition comprising at least one compound as described in the first aspect above as an active ingredient.

The compounds described in the first aspect of the present invention may also be advantageously combined with one or more therapeutically active agents, preferably with one or more other antiproliferative compounds. Such antiproliferative compounds include, but are not limited to, aromatase inhibitors; antiestrogen; topoisomerase I inhibitor; topoisomerase II inhibitor; microtubule active compounds; alkylating compounds; histone deacetylase inhibitor; compounds that induce cell differentiation processes; cyclooxygenase inhibitor; MMP inhibitor; mTOR inhibitors such as RAD001; antitumor antimetabolites; platinum compounds; compounds that target/reduce protein or lipid kinase activity; and further anti-angiogenic compounds; compounds that target, reduce or inhibit protein or lipid phosphatase activity; gonadorelin agonists; antiandrogens; methionine aminopeptidase inhibitors; bisphosphonates; biological response modifiers; antiproliferative antibodies such as HCD122; heparanase inhibitors; inhibitors of Ras oncogenic isoforms; telomerase inhibitors; proteasome inhibitors; compounds for treating blood cancer such as fludarabine; compounds that target, reduce or inhibit Flt-3 activity, such as PKC412; Hsp90 inhibitors, such as 17-AAG (17-allylaminogeldanamycin, NSC330507), 17-DMAG (17-dimethylaminoethyl-amino-17-demethoxy-geldanamycin, NSC707545), IPI-504, CNF1010, CNF2024, and CNF1010 and AUY922 of Conforma Therapeutics; temozolomide (TEMODAL™); kinesin spindle protein inhibitors such as SB715992 or SB743921 of GlaxoSmithKline, or pentamidine/chlorpromazine of CombinatoRx; PI3K inhibitors such as BEZ235; RAF inhibitors such as RAF265; MEK inhibitors such as ARRY142886 of Array PioPharma, AZD6244 of AstraZeneca, PD181461 of Pfizer, calcium folinate, EDG binding agents, anti-leukemic drug compounds, nucleotide reductase inhibitors, S-adenosylmethionine decarboxylase inhibitors, apoptosis regulators, antiproliferative antibodies, or other chemotherapeutic compounds. In addition, they may alternatively or additionally be used in combination with other tumor treatment methods including surgery, ionizing radiation, photodynamic therapy, implants, for example, with corticosteroids and hormones, or they may be used as radio sensitization agents. Moreover, in anti-inflammatory and/or anti-proliferative treatment, combinations with anti-inflammatory drugs are included. Combinations with antihistamines, bronchodilators, NSAID or chemokine receptor antagonists are also possible.

In addition to the active ingredient, the pharmaceutical composition of the present invention may further include a pharmaceutically acceptable carrier, and may be administered as various injections (such as intravenous injection, intramuscular injection, subcutaneous injection and the like), or administered by various methods (such as oral administration and transdermal administration). A pharmaceutically acceptable carrier refers to a pharmacologically acceptable material (for example, excipient, diluent, additive, solvent and the like) that involves transporting a compound of the present invention or a composition comprising a compound of the present invention from a given organ to another organ.

A formulation can be prepared by selecting an appropriate dosage form (for example, an oral formulation or an injection) according to the method of administration and using various methods for preparing the formulation. Examples of oral formulations include tablets, powders, granules, capsules, pills, lozenges, solutions, syrups, elixirs, emulsions, oily or aqueous suspensions, and the like.

The present invention also provides the use of the compound described in the first aspect in the preparation of a medicament for treating diseases based on dysregulation of cell cycle.

Also provided is a method for treating a disease associated with MDM2 and P53 regulation, comprising administering to the patient an effective amount of the compound according to the first aspect of the present invention.

The compounds of the present invention are believed to be useful in the treatment of diseases based on dysregulation of cell cycle, such as proliferative disorders or diseases, such as cancers or tumor diseases. In particular, these diseases or disorders include benign or malignant tumors, soft tissue sarcomas or sarcomas such as a liposarcoma, a rhabdomyosarcoma or a bone cancer such as osteosarcoma, a brain cancer, kidney cancer, liver cancer, adrenal cancer, bladder cancer, breast cancer, gastric cancer, ovarian cancer, colon cancer, rectal cancer, prostate cancer, pancreatic cancer, lung cancer, vaginal cancer or thyroid cancer, a glioblastoma, a meningioma, a glioma, a mesothelioma, a multiple myeloma, a gastrointestinal cancer, especially colon cancer or colorectal adenoma, head and neck tumors, a melanoma, a prostate hyperplasia, neoplasia, a neoplasia of epithelial character, a leukemia such as acute myeloid leukemia or B-cell chronic lymphocytic leukemia, lymphomas such as lymphoma of B- or T-cell origin, and other organ metastases, viral infections (such as herpes, papilloma, HIV, Kaposi's, viral hepatitis), and nephritis. Specific uses are for the treatment of benign or malignant tumors, soft tissue sarcomas or sarcomas such as a liposarcoma, a rhabdomyosarcoma or a bone cancer such as osteosarcoma, cancers such as a kidney cancer, liver cancer, adrenal cancer, bladder cancer, breast cancer, gastric cancer, ovarian cancer, colon cancer, rectal cancer, prostate cancer, pancreatic cancer, lung cancer, vaginal cancer or thyroid cancer, a mesothelioma, a multiple myeloma, a gastrointestinal cancer, especially colon cancer or colorectal adenoma, head and neck tumors, a melanoma, a prostate hyperplasia, a neoplasia, a neoplasia of epithelial character, leukemias such as acute myeloid leukemia or B-cell chronic lymphocytic leukemia, lymphomas such as lymphoma of B- or T-cell origin, and other organ metastases and nephritis.

Preferably, it can be used to treat a leukemia, a myeloma and a nephritis.

The present invention also provides a method for treating diseases based on dysregulation of cell cycle, the method comprising administering an effective dose of the compound described in the first aspect or the composition described in the third aspect to a subject in need thereof by an oral or non-oral route.

The disease is preferably a tumor or nephritis disease; more preferably a disorder or disease mediated by the activity of MDM2 and/or MDM4.

The present invention also provides a method for treating diseases based on dysregulation of cell cycle, the method comprising administering an effective dose of the compound described in the first aspect or the composition described in the third aspect to a subject in need thereof by an oral or non-oral route.

The diseases based on dysregulation of cell cycle include cancer or tumor diseases. The tumor diseases include benign or malignant tumors.

Preferably:

the tumor disease include a soft tissue sarcoma or sarcoma, a leukemia or a bone cancer; preferably, the sarcoma is liposarcoma or rhabdomyosarcoma; the leukemia is acute myeloid leukemia, chronic myeloid leukemia, or B-cell chronic lymphocytic leukemia; and the bone cancer is osteosarcoma.

The cancers include a brain cancer, kidney cancer, liver cancer, adrenal cancer, bladder cancer, breast cancer, gastric cancer, ovarian cancer, colon cancer, rectal cancer, prostate cancer, pancreatic cancer, lung cancer, vaginal cancer or thyroid cancer, a glioblastoma, a meningioma, a glioma, a mesothelioma, a multiple myeloma, a gastrointestinal cancer; a especially colon cancer or colorectal adenomas, head and neck tumors, a melanoma, a prostate hyperplasia, a neoplasia, a neoplasia of epithelial character, a leukemia, a lymphoma, and other organ metastases and viral infections.

More preferably, the leukemia is acute myeloid leukemia or B-cell chronic lymphocytic leukemia; the lymphoma is a lymphoma of B- or T-cell origin; the viral infection is herpes, papilloma, HIV, Kaposi's, or viral hepatitis.

Or, the disease of dysregulation of cell cycle is a disorder or disease involving immune system, preferably an autoimmune disease or immune disease caused by transplantation, a chronic inflammatory condition or an inflammatory or allergic condition of skin, or other skin inflammatory or allergic conditions or a hyperproliferativedisorder.

Preferably:

the autoimmune disease or immune disease caused by transplantation is rheumatoid arthritis, graft-versus-host disease, systemic lupus erythematosus, Sjogren's syndrome, multiple sclerosis, Hashimoto's thyroiditis, polymyositis.

The chronic inflammatory condition is asthma, osteoarthritis, nephritis, atherosclerosis or Morbus Crohn.

The inflammatory or allergic condition of skin is psoriasis, contact dermatitis, atopic dermatitis, alopecia areata, erythema multiforme, herpes-like dermatitis, scleroderma, vitiligo, allergic vasculitis, urticaria, bullous pemphigoid, pemphigus, acquired epidermolysis bullosa.

The hyperproliferative disorder is Li-Fraumeni syndrome.

The present invention further provides a compound or composition for treating diseases based on dysregulation of cell cycle, the compound is the compound described in the first aspect.

The disease is preferably a tumor or nephritis disease; more preferably a disorder or disease mediated by the activity of MDM2 and/or MDM4.

The present invention further provides a compound or composition for treating diseases base on dysregulation of cell cycle, the compound is the compound described in the first aspect.

The diseases based on dysregulation of cell cycle include cancer or tumor diseases. The tumor diseases include benign or malignant tumors.

Preferably:
the tumor diseases include soft tissue sarcoma or sarcoma, leukemia or bone cancer; preferably, the sarcoma is liposarcoma or rhabdomyosarcoma; the leukemia is acute myeloid leukemia, chronic myeloid leukemia, or B-cell chronic lymphocytic leukemia; and the bone cancer is osteosarcoma.

The cancers include a brain cancer, kidney cancer, liver cancer, adrenal cancer, bladder cancer, breast cancer, gastric cancer, ovarian cancer, colon cancer, rectal cancer, prostate cancer, pancreatic cancer, lung cancer, vaginal cancer or thyroid cancer, a glioblastoma, a meningioma, a glioma, a mesothelioma, a multiple myeloma, a gastrointestinal cancer; especially colon cancer or colorectal adenomas, head and neck tumors, a melanoma, a prostate hyperplasia, a neoplasia, a neoplasia of epithelial character, a leukemia, a lymphoma, and other organ metastases and viral infections.

More preferably, the leukemia is acute myeloid leukemia or B-cell chronic lymphocytic leukemia; the lymphoma is lymphoma of B- or T-cell origin; and the viral infection is herpes, papilloma, HIV, Kaposi's, or viral hepatitis.

Or, the disease of dysregulation of cell cycle is a disorder or disease involving immune system, preferably an autoimmune disease or immune disease caused by transplantation, a chronic inflammatory condition or an inflammatory or allergic condition of skin, or other skin inflammatory or allergic conditions or a hyperproliferativedisorder.

Preferably:
the autoimmune disease or immune disease caused by transplantation is rheumatoid arthritis, graft-versus-host disease, systemic lupus erythematosus, Sjogren's syndrome, multiple sclerosis, Hashimoto's thyroiditis, or polymyositis.

The chronic inflammatory condition is asthma, osteoarthritis, nephritis, atherosclerosis or Morbus Crohn.

The inflammatory or allergic condition of skin is psoriasis, contact dermatitis, atopic dermatitis, alopecia areata, erythema multiforme, herpes-like dermatitis, scleroderma, vitiligo, allergic vasculitis, urticaria, bullous pemphigoid, pemphigus, or acquired epidermolysis bullosa.

The hyperproliferative disorder is Li-Fraumeni syndrome.

In specific applications, the dosage and the interval of administration can be appropriately selected based on the judgment of a doctor and according to the location of the disease and the height, weight, sex, or medical history of the patient. When the compound of the present invention is administered to a human, the daily dose is about 0.01 to 500 mg/kg body weight, preferably about 0.1 to 100 mg/kg body weight. Preferably, the compound of the present invention is administered to a human once a day, or the dose is administrated in 2 to 4 divided doses at appropriate intervals. In addition, if necessary, the daily dose may exceed the above-mentioned dose based on the judgment of the doctor.

SPECIFIC MODES FOR CARRYING OUT THE EMBODIMENTS

The following Examples are used to illustrate the present invention, but not to limit the scope of the present invention.

All raw materials used in the present invention are known commercial products.

In the present invention, "Mdm2" refers to a protein encoded by the murine double minute 2 gene. "Mdm2" includes Mdm2 protein encoded by the full-length Mdm2 gene, Mdm2 protein encoded by mutated Mdm2 gene (including deletion mutants, substitution mutants, and addition mutants) and the like. In the present invention, "Mdm2" also includes homologs derived from different animal species, such as human Mdm2 homolog (HDM2).

The abbreviations and their meanings in the Examples of the present invention are as follows:
NBS: N-bromosuccinimide
EA: ethyl acetate
PE: petroleum ether
THF: tetrahydrofuran
LDA: lithium diisopropylamide
Pd(PPh$_3$)$_4$: tetrakis(triphenylphosphine)palladium

Example 1

6-chloro-5'-(3-chlorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

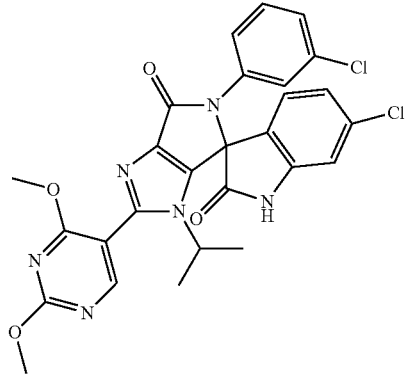 [SMILES: COc1ncc(-c2nc3c(n2C(C)C)C2(C(=O)Nc4cc(Cl)ccc42)N(c2cccc(Cl)c2)C3=O)c(OC)n1]

Step 1: Preparation of Ethyl (E)-2-cyano-3-(dimethylamino)acrylate

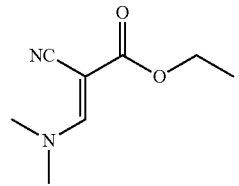

Under nitrogen atmosphere, ethyl isocyanoacetate (500.0 g, 4.425 mol) and 1000 mL of ethanol were added to a 2000 mL three-necked flask, and cooled to −5° C., 1,1-diethoxy-N,N-dimethylmethanamine (845.6 g, 5.752 mol) was added dropwise. During the dropwise addition, the reaction solution was maintained at about 0° C., and then naturally raised to room temperature, stirred overnight, and concentrated under vacuum. The crude product was dissolved in 5 L of tert-butyl methyl ether, and the resultant mixture was added with 1 Kg of silica gel, stirred for 30 min and filtered. The filtrate was washed with 500 mL of tert-butyl methyl ether for 5 times, and concentrated under vacuum to obtain 678.2 g of ethyl (R)-2-cyano-3-(dimethylamino)acrylate (yield 91.25%, yellow oil). MS (ESI): mass calcd. For $C_8H_{12}N_2O_2$ 168.2, m/z found 169.3 [M+H]$^+$.

Step 2: Preparation of Ethyl 1-isopropyl-1H-imidazole-4-carboxylate

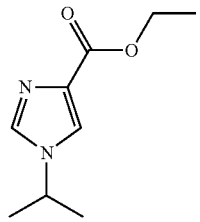

Under nitrogen atmosphere, ethyl (E)-2-cyano-3-(dimethylamino)acrylate (120.0 g, 0.714 mol), 100 mL of N-butanol and propyl-2-amine (126.4 g, 2.14 mol) were added to a 500 ml three-necked flask. The mixture was heated to 70° C. for overnight reaction and concentrated under vacuum. The resultant mixture was added with 1000 mL of ethyl acetate, and washed with 500 mL of saturated sodium chloride aqueous solution for three times. The organic layers were combined, dried over anhydrous sodium sulfate, filtered, and concentrated to obtain 119.3 g of ethyl 1-isopropyl-1H-imidazole-4-carboxylate (yield 91.76%, brown oil). MS (ESI): mass calcd. For $C_9H_{14}N_2O_2$ 182.2, m/z found 183.4 [M+H]$^+$.

Step 3: Preparation of Ethyl 2-bromo-1-isopropyl-1H-imidazole-4-carboxylate

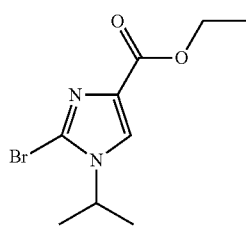

Under nitrogen atmosphere, ethyl 1-isopropyl-1H-imidazole-4-carboxylate (60.0 g, 0.328 mol) and 500 mL of tetrahydrofuran were added to a 1000 mL three-necked flask, and cooled to 0° C., and NBS (87.0 g, 0.492 mol) was added in batches. The resultant was naturally raised to room temperature for overnight reaction, concentrated under vacuum, added with 500 mL of ethyl acetate, washed with 500 mL of saturated sodium carbonate aqueous solution for three times, then washed once with 45 mL of saturated sodium chloride aqueous solution, dried over anhydrous sodium sulfate, filtered, concentrated under vacuum, and separated by column chromatography (EA:PE=1:10 to 1:2) to obtain 21.2 g of ethyl 2-bromo-1-isopropyl-H-imidazole-4-carboxylate (yield 24.7%, yellow oil). MS (ESI): mass calcd. for $C_9H_{13}BrN_2O_2$ 260.0, m/z found 261.5 [M+H]$^+$.

Step 4: Preparation of Ethyl 2-bromo-5-(6-chloro-3-hydroxy-2-oxoindolin 3-yl)-1-isopropyl-1H-imidazole-4-carboxylate

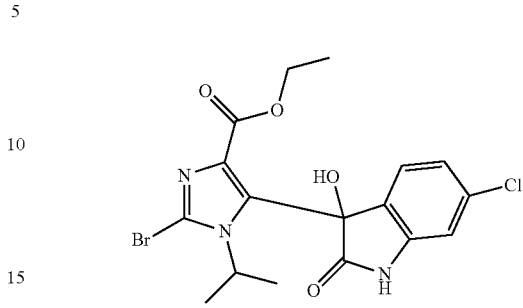

Under nitrogen atmosphere, ethyl 2-bromo-1-isopropyl-1H-imidazole-4-carboxylate (5.0 g, 19.15 mmol) and 10 mL of anhydrous THF were added to a 50 mL three-necked flask, and cooled to −78° C. LDA (40 ml, 2 M) was slowly added dropwise, and the resultant mixture was maintained at −78° C. to react for 1.5 h. Then an anhydrous tetrahydrofuran solution (100 ml) of 6-chlorodihydroindole-2,3-dione (3.46 g, 19.15 mmol) was slowly added dropwise. After the dropwise addition was completed, the mixture was maintained at −78° C. to react for 2 h, followed by quenching with 100 ml of saturated ammonium chloride aqueous solution, and extraction with 200 mL of ethyl acetate for three times. The organic layers were combined, washed once with 45 mL of saturated sodium chloride aqueous solution, dried over anhydrous sodium sulfate, filtered, concentrated under vacuum, and separated by column chromatography (EA:PE=1:10 to 1:2) to obtain 1.4 g of ethyl 2-bromo-5-(6-chloro-3-hydroxy-2-oxoindolin 3-yl)-1-isopropyl-1H-imidazole-4-carboxylate (yield 17.0%, yellow solid) as a yellow solid. MS (ESI): mass calcd. For $C_{17}H_{17}BrClN_3O_4$ 441.0, m/z found 442.0 [M+H]$^+$.

Step 5: Preparation of 2-bromo-5-(6-chloro-3-hydroxy-2-oxoindolin-3-yl)-N-(3-chlorobenzene)-1-isopropyl-1H-imidazole-4-amide

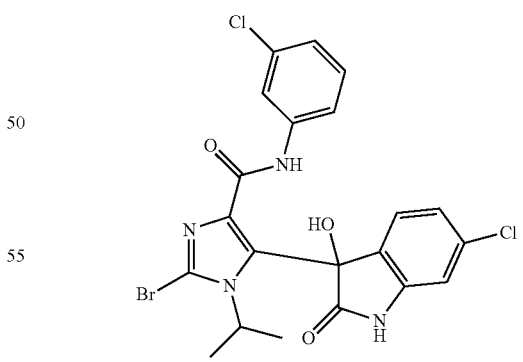

Under nitrogen atmosphere, 3-chloroaniline (503.3 mg, 2.94 mmol) and 5 mL of anhydrous toluene were added to a 25 mL three-necked flask, and cooled to 0° C. AlMe$_3$ (1.2 ml, 25% w/w) was slowly added dropwise to the reaction solution, then 5 mL of anhydrous toluene solution of ethyl 2-bromo-5-(6-chloro-3-hydroxy-2-oxoindolin-3-yl)-1-isopropyl-1H-imidazole-4-carboxylate (600 mg, 1.36 mmol)

was slowly added dropwise into the reaction solution. The resultant mixture was raised to 90° C. for overnight reaction, then naturally lowered to room temperature, and added with 50 mL of ice water and 15 mL of saturated aqueous solution of sodium potassium tartrate, extracted with 100 mL of dichloromethane for two times. The organic layers were combined, washed once with 50 mL of saturated sodium chloride aqueous solution, dried over anhydrous sodium sulfate, filtered, concentrated under vacuum, and separated by column chromatography to obtain 401.2 mg of 2-bromo-5-(6-chloro-3-hydroxy-2-oxoindolin-3-yl)-N-(3-chlorobenzene)-1-isopropyl-1H-imidazole-4-amide (yield 56.47%, yellow solid). MS (ESI): mass calcd. For $C_{21}H_{17}BrCl_2N_4O_3$ 522.0, m/z found 523.4 $[M+H]^+$.

Step 6: Preparation of 2'-bromo-6-chloro-5'-(3-chlorophenyl)-3'-isopropyl-3'H-spiro[dihydroindole-3,4'pyrrolo[3,4-d]imidazole]-2,6'(5'H)-dione

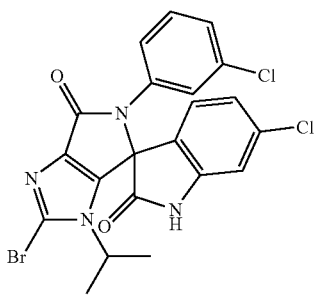 [SMILES: CC(C)n1c(Br)nc2c1C1(C(=O)Nc3cc(Cl)ccc31)N(c1cccc(Cl)c1)C2=O]

2-bromo-5-(6-chloro-3-hydroxy-2-oxoindolin-3-yl)-N-(3-chlorobenzene)-1-isopropyl-1H-imidazole-4-amide (400.0 mg, 0.766 mmol) and acetic acid (5 mL) were added to a 25 mL three-necked flask, concentrated sulfuric acid (0.75 g, 7.66 mmol) was added in batches, and the temperature was raised to 110° C. for reaction overnight, then the temperature was naturally lowered to room temperature, and 20 mL of ice water was added. The pH value was adjusted to 7.0 with saturated sodium carbonate aqueous solution, followed by extraction with 200 mL of dichloromethane for two times. The organic layers were combined, washed once with 50 mL of saturated sodium chloride aqueous solution, dried over anhydrous sodium sulfate, filtered, concentrated under vacuum and separated by column chromatography (EA:PE=1:5 to 1:1) to obtain 130.2 mg of 2'-bromo-6-chloro-5'-(3-chlorophenyl)-3'-isopropyl-3'H-spiro[dihydroindole-3,4'pyrrolo[3,4-d]imidazole]-2,6'(5'H)-dione (33.67% yield, yellow solid). MS (ESI): mass calcd. For $C_{21}H_{15}BrCl_2N_4O_2$ 504.0, m/z found 505.3 $[M+H]^+$.

Step 7: Preparation of 6-chloro-5'-(3-chlorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

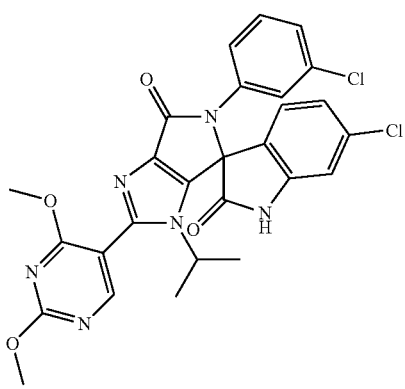 [SMILES: COc1ncc(-c2nc3c(n2C(C)C)C2(C(=O)Nc4cc(Cl)ccc42)N(c2cccc(Cl)c2)C3=O)c(OC)n1]

Under nitrogen atmosphere, 2'-bromo-6-chloro-5'-(3-chlorophenyl)-3'-isopropyl-3'H-spiro[dihydroindole-3,4'pyrrolo[3,4-d]imidazole]-2,6'(5'H)-dione (90.0 mg, 0.178 mmol), (2,4-dimethoxypyrimidin-5-yl)boronic acid (33.0 mg, 0.178 mmol), Pd(PPh$_3$)$_4$ (20.7 mg, 0.0178 mmol), anhydrous Na$_2$CO$_3$ (57.0 mg, 0.535 mmol), 1,4-dioxane (4 mL) and water (1 ml) were added into a microwave reaction flask, and then the temperature was raised to 100° C. to perform a microwave reaction for 1 h. The reaction solution was cooled to room temperature and filtered, and 10 mL of water was added, followed by extraction with 10 mL of dichloromethane for three times. The organic layers were combined, washed once with 10 mL of saturated sodium chloride aqueous solution, dried over anhydrous sodium sulfate, separated by column chromatography, and supercritical high-pressure preparative chromatography to obtain 7.8 mg of (S)-6-chloro-5'-(3-chlorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-1); and 8.8 mg of (R)-6-chloro-5'-(3-chlorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-1). MS (ESI): mass calcd. for $C_{27}H_{22}Cl_2N_6O_4$ 564.1, m/z found 565.3 $[M+H]^+$. $^1$H-NMR (400 MHz, DMSO-d$_6$) δ 11.54 (brs, 1H), 8.51 (s, 1H), 7.48 (d, 1H, J=8.0 Hz), 7.38-7.32 (m, 2H), 7.15-7.12 (m, 2H), 7.01-6.97 (m, 1H), 6.96-6.95 (m, 1H), 4.19-4.12 (m, 1H), 3.99 (s, 3H), 3.94 (s, 3H), 1.12 (d, 3H, J=6.8 Hz), 0.64 (d, 3H, J=6.8 Hz).

Example 2

6-chloro-5'-(5-chloro-2-methylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

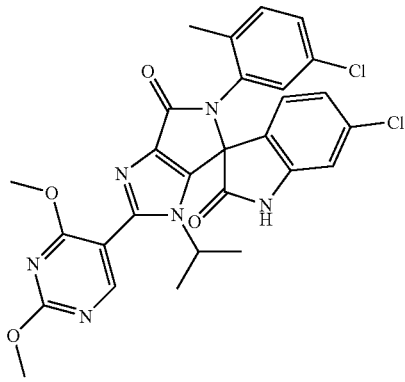 [SMILES: COc1ncc(-c2nc3c(n2C(C)C)C2(C(=O)Nc4cc(Cl)ccc42)N(c2cc(Cl)ccc2C)C3=O)c(OC)n1]

Title compounds were obtained by steps similar to those in Example 1, and supercritical high-pressure preparative chromatography was performed to obtain 23.1 mg of(S)-6-chloro-5'-(5-chloro-2-methylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-2); and 24.0 mg of (R)-6-chloro-5'-(5-chloro-2-methylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-2).

MS (ESI): mass calcd. for $C_{28}H_{24}Cl_2N_6O_4$ 578.1, m/z found 579.1$[M+H]^+$. $^1$H-NMR (400 MHz, DMSO-d$_6$) δ 11.62 (brs, 1H), 8.53 (m, 1H), 7.51-7.41 (m, 4H), 6.98-6.89

(m, 2H), 4.16-4.13 (m, 1H), 3.99 (s, 3H), 3.95 (s, 3H), 2.22 (s, 3H), 1.10 (d, 3H, J=4.8 Hz), 0.67 (d, 3H, J=4.8 Hz).

Example 3

6-chloro-5'-(3-chloro-4-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

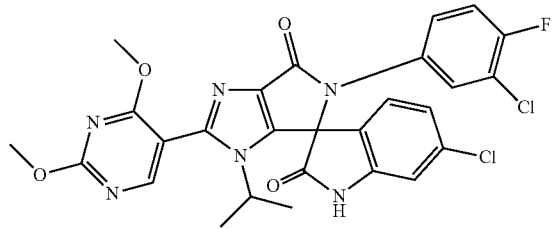 [SMILES: COc1ncc(-c2nc3c(n2C(C)C)C2(C(=O)Nc4cc(Cl)ccc42)N(c2ccc(F)c(Cl)c2)C3=O)c(OC)n1]

Title compounds were obtained by steps similar to those in Example 1, and supercritical high-pressure preparative chromatography was performed to obtain 24.1 mg of (S)-6-chloro-5'-(3-chloro-4-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-3), and 35.8 mg of (R)-6-chloro-5'-(3-chloro-4-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-3). MS (ESI): mass calcd. for $C_{27}H_{21}Cl_2FN_6O_4$ 582.1, m/z found 583.3 [M+H]$^+$. $^1$H-NMR (400 MHz, DMSO-d$_6$) δ 11.55 (brs, 1H), 8.51 (s, 1H), 7.51 (d, 1H, J=8.0 Hz), 7.43-7.39 (m, 1H), 7.27 (dd, 1H, J=9.2 Hz, J$^2$=2.4 Hz), 7.16-7.03 (m, 1H), 7.02-6.99 (m, 1H), 4.19-4.12 (m, 1H), 3.99 (s, 3H), 3.95 (s, 3H), 1.12 (d, 3H, J=6.8 Hz), 0.65 (d, 3H, J=6.8 Hz).

Example 4

6-chloro-5'-(5-chloro-2-methylphenyl)-2'-(4-fluoro-2-methoxyphenyl)-3'-isopropyl-3'H-spiro[dihydroindole-3,4'-pyrrolo[3,4-d]imidazole]-2,6'(5'H)-dione

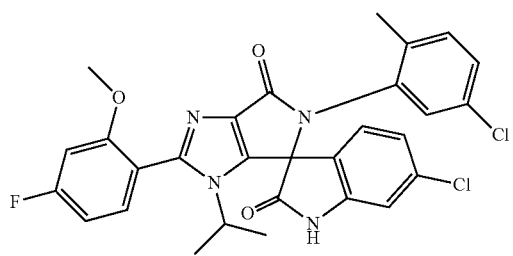 [SMILES: COc1cc(F)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 20.5 mg of(S)-6-chloro-5'-(5-chloro-2-methylphenyl)-2'-(4-fluoro-2-methoxyphenyl)-3'-isopropyl-3'H-spiro[dihydroindole-3,4'-pyrrolo[3,4-d]imidazole]-2,6'(5'H)-dione (S-4); and 22.3 mg of (R)-6-chloro-5'-(5-chloro-2-methylphenyl)-2'-(4-fluoro-2-methoxyphenyl)-3'-isopropyl-3'H-spiro[dihydroindole-3,4'-pyrrolo[3,4-d]imidazole]-2,6'(5'H)-dione (R-4). MS (ESI): mass calcd. for $C_{29}H_{23}Cl_2FN_4O_3$ 564.1, m/z found 565.3 [M+H]$^+$. $^1$H-NMR (400 MHz, DMSO-d$_6$) δ 11.47 (brs, 1H), 7.55-7.49 (m, 2H), 7.48-7.00 (m, 5H), 6.96-6.93 (m, 2H), 4.06-4.02 (m, 1H), 3.81 (s, 3H), 2.32 (s, 3H), 1.06 (d, 3H, J=5.2 Hz), 0.63 (d, 3H, J=5.2 Hz).

Example 5

6-chloro-5'-(5-chloro-2-methylphenyl)-3'-isopropyl-2'-(2-methoxyphenyl)-3'H-spiro[dihydroindole-3,4'-pyrrolo[3,4-d]imidazole]-2,6'(5'H)-dione

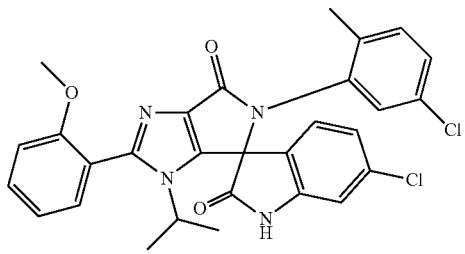 [SMILES: COc1ccccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 15.0 mg of (S)-6-chloro-5'-(5-chloro-2-methylphenyl)-3'-isopropyl-2'-(2-methoxyphenyl)-3'H-spiro[dihydroindole-3,4'-pyrrolo[3,4-d]imidazole]-2,6'(5'H)-dione (S-5); and 13.3 mg of (R)-6-chloro-5'-(5-chloro-2-methylphenyl)-3'-isopropyl-2'-(2-methoxyphenyl)-3'H-spiro[dihydroindole-3,4'-pyrrolo[3,4-d]imidazole]-2,6'(5'H)-dione (R-5). MS (ESI): mass calcd. for $C_{29}H_{24}Cl_2N_4O_3$ 546.1, m/z found 547.3 [M+H]$^+$. $^1$H-NMR (400 MHz, DMSO-d$_6$) δ 11.52 (brs, 1H), 7.57-7.42 (m, 3H), 7.33-7.08 (m, 6H), 7.06-7.00 (m, 1H), 4.08-4.04 (m, 1H), 3.79 (s, 3H), 2.22 (s, 3H), 1.14 (d, 3H, J=5.2 Hz), 0.64 (d, 3H, J=5.2 Hz).

Example 6

6-chloro-5'-(5-chloro-2-methylphenyl)-2'-(5-fluoro-2-methoxyphenyl)-3'-isopropyl-3'H-spiro[dihydroindole-3,4'-pyrrolo[3,4-d]imidazole]-2,6'(5'H)-dione

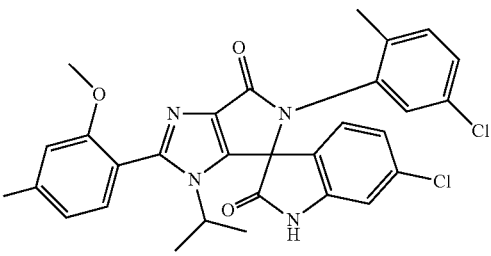

Title compounds were obtained by steps similar to those in Example 1, and supercritical high-pressure preparative chromatography was performed to obtain 17.0 mg of (S)-6-chloro-5'-(5-chloro-2-methylphenyl)-2'-(5-fluoro-2-methoxyphenyl)-3'-isopropyl-3'H-spiro[dihydroindole-3,4'-pyrrolo[3,4-d]imidazole]-2,6'(5'H)-dione (S-6); and 18.5 mg of (R)-6-chloro-5'-(5-chloro-2-methylphenyl)-2'-(5-fluoro-2-methoxyphenyl)-3'-isopropyl-3'H-spiro[dihydroindole-3,4'-pyrrolo[3,4-d]imidazole]-2,6'(5'H)-dione (R-6). MS (ESI): mass calcd. for $C_{29}H_{23}Cl_2FN_4O_3$ 564.1, m/z found 565.4 [M+H]$^+$. $^1$H-NMR (400 MHz, DMSO-d$_6$) δ 11.61 (brs, 1H), 7.54-7.00 (m, 8H), 6.97-6.96 (m, 1H), 4.07-4.04 (m, 1H), 3.78 (s, 3H), 2.49 (s, 3H), 1.08 (d, 3H, J=6.4 Hz), 0.65 (d, 3H, J=6.4 Hz).

Example 7

6-chloro-5'-(5-chloro-2-methylphenyl)-2'-(2-ethylphenyl)-3'-isopropylisopropyl-3'H-spiro[dihydroindole-3,4'-pyrrolo[3,4-d]imidazole]-2,6'(5'H)-dione

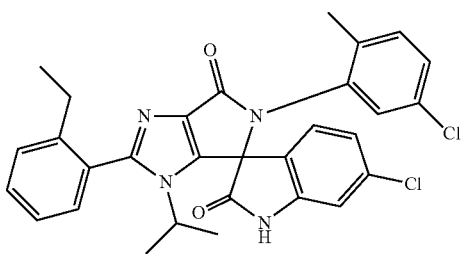 [SMILES: CCc1ccccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 26.3 mg of (S)-6-chloro-5'-(5-chloro-2-methylphenyl)-2'-(2-ethylphenyl)-3'-isopropylisopropyl-3'H-spiro[dihydroindole-3,4'-pyrrolo[3,4-d]imidazole]-2,6'(5'H)-dione (S-7), and 21.5 mg of (R)-6-chloro-5'-(5-chloro-2-methylphenyl)-2'-(2-ethylphenyl)-3'-isopropylisopropyl-3'H-spiro[dihydroindole-3,4'-pyrrolo[3,4-d]imidazole]-2,6'(5'H)-dione (R-7). MS (ESI): mass calcd. for $C_{30}H_{26}Cl_2N_4O_2$ 544.1, m/z found 545.2 [M+H]$^+$. $^1$H-NMR (400 MHz, DMSO-d$_6$) δ 11.70 (brs, 1H), 7.60-6.95 (m, 10H), 6.97-6.96 (m, 1H), 4.07-4.04 (m, 1H), 2.45 (s, 3H), 1.11-1.07 (m, 8H), 0.67 (d, 3H, J=4.8 Hz).

Example 8

6-chloro-5'-(5-chloro-2-methylphenyl)-2'-(2,6-dimethoxypyridin-3-yl)-3'-isopropyl-3'H-spiro[dihydroindole-3,4'-pyrrolo[3,4-d]imidazole]-2,6'(5'H)-dione

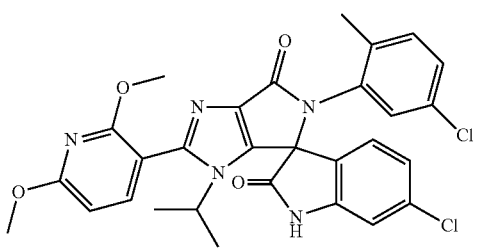 [SMILES: COc1ccc(-c2nc3c(n2C(C)C)C2(C(=O)Nc4cc(Cl)ccc42)N(c2cc(Cl)ccc2C)C3=O)c(OC)n1]

Title compounds were obtained by steps similar to those in Example 1, and supercritical high-pressure preparative chromatography was performed to obtain 22.5 mg of (S)-6-chloro-5'-(5-chloro-2-methylphenyl)-2'-(2,6-dimethoxypyridin-3-yl)-3'-isopropyl-3'H-spiro[dihydroindole-3,4'-pyrrolo[3,4-d]imidazole]-2,6'(5'H)-dione (S-8), and 31.2 mg of (R)-6-chloro-5'-(5-chloro-2-methylphenyl)-2'-(2,6-dimethoxypyridin-3-yl)-3'-isopropyl-3'H-spiro[dihydroindole-3,4'-pyrrolo[3,4-d]imidazole]-2,6'(5'H)-dione (R-8). MS (ESI): mass calcd. for $C_{29}H_{25}Cl_2N_5O_4$ 577.13, m/z found 578.2[M+H]$^+$. $^1$H-NMR (400 MHz, DMSO-d$_6$) δ 7.82-7.80 (m, 1H), 7.79-7.04 (m, 6H), 6.56 (d, 2H, J=8.0 Hz), 4.13-4.10 (m, 1H), 3.94 (s, 3H), 3.91 (s, 3H), 2.21 (s, 3H), 1.08 (d, 3H, J=6.4 Hz), 0.66 (d, 3H, J=6.4 Hz).

Example 9

6-chloro-5'-(5-chloro-2-methylphenyl)-2'-(2,4-dimethoxyphenyl)-3'-isopropyl-3'H-spiro[dihydroindole-3,4'-pyrrolo[3,4-d]imidazole]-2,6'(5'H)-dione

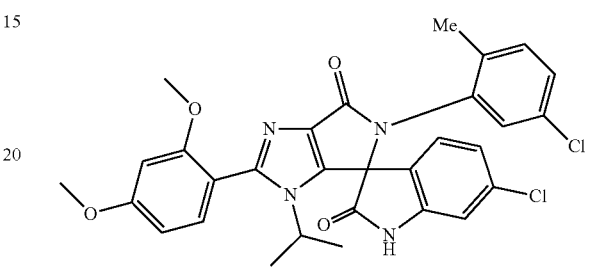

Title compounds were obtained by steps similar to those in Example 1, and supercritical high-pressure preparative chromatography was performed to obtain 19.5 mg of (S)-6-chloro-5'-(5-chloro-2-methylphenyl)-2'-(2,4-dimethoxyphenyl)-3'-isopropyl-3'H-spiro[dihydroindole-3,4'-pyrrolo[3,4-d]imidazole]-2,6'(5'H)-dione (S-9), and 18.3 mg of (R)-6-chloro-5'-(5-chloro-2-methylphenyl)-2'-(2,4-dimethoxyphenyl)-3'-isopropyl-3'H-spiro[dihydroindole-3,4'-pyrrolo[3,4-d]imidazole]-2,6'(5'H)-dione (R-9). MS (ESI): mass calcd. for $C_{30}H_{26}Cl_2N_4O_4$ 576.1 m/z found 577.1 [M+H]$^+$. $^1$H-NMR (400 MHz, DMSO-d$_6$) δ 11.58 (brs, 1H), 7.55-6.67 (m, 9H), 4.08-4.04 (m, 1H), 3.84 (s, 3H), 3.78 (s, 3H), 2.20 (s, 3H), 1.06 (d, 3H, J=4.0 Hz). 0.62 (d, 3H, J=4.0 Hz).

Example 10

6-chloro-5'-(5-chloro-2-methylphenyl)-3'-isopropyl-2'-(3-methoxypyridin-4-yl)-3'H-spiro[dihydroindole-34'-pyrrolo[3,4-d]imidazole]-2,6'(5'H)-dione

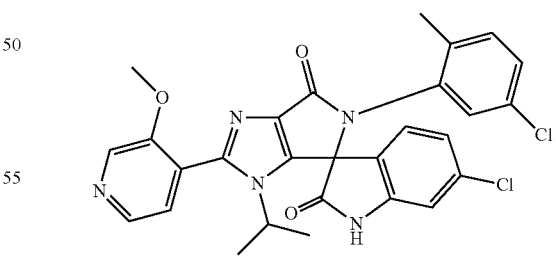

Title compounds were obtained by steps similar to those in Example 1, and supercritical high-pressure preparative chromatography was performed to obtain 25.8 mg of (S)-6-chloro-5'-(5-chloro-2-methylphenyl)-3'-isopropyl-2'-(3-methoxypyridin-4-yl)-3'H-spiro[dihydroindole-3,4'-pyrrolo[3,4-d]imidazole]-2,6'(5'H)-dione (S-10), and 28.0 mg of (R)-6-chloro-5'-(5-chloro-2-methylphenyl)-3'-isopropyl-2'-(3-methoxypyridin-4-yl)-3'H-spiro[dihydroindole-3,4'-pyrrolo[3,4-d]imidazole]-2,6'(5'H)-dione (R-10). MS (ESI): mass calcd. for $C_{28}H_{23}Cl_2N_5O_3$ 547.1, m/z found 548.4 [M+H]$^+$. $^1$H-NMR (400 MHz, DMSO-d$_6$) δ 11.79 (brs, 1H), 8.61 (s, 1H), 8.40 (d, 1H, J=4.8 Hz), 7.62-7.45 (m, 2H), 7.33-6.98 (m, 5H), 4.11-4.10 (m, 1H), 4.08 (s, 3H), 2.22 (s, 3H), 1.10 (d, 3H, J=6.8 Hz), 0.66 (d, 3H, J=6.8 Hz).

Example 11

6-chloro-5'-(5-chloro-2-methylphenyl)-2'-(4,6-dimethoxypyridin-3-yl)-3'-isopropyl-3'H-spiro[dihydroindole-3,4'-pyrrolo[3,4-d]imidazole]-2,6'(5'H)-dione

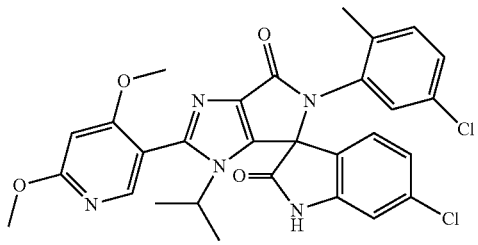 [SMILES: COc1cc(OC)c(-c2nc3c(n2C(C)C)C2(C(=O)Nc4cc(Cl)ccc42)N(c2cc(Cl)ccc2C)C3=O)cn1]

Title compounds were obtained by steps similar to those in Example 1, and supercritical high-pressure preparative chromatography was performed to obtain 18.6 mg of (S)-6-chloro-5'-(5-chloro-2-methylphenyl)-2'-(4,6-dimethoxypyridin-3-yl)-3'-isopropyl-3'H-spiro[dihydroindole-3,4'-pyrrolo[3,4-d]imidazole]-2,6'(5'H)-dione (S-11), and 17.2 mg of (R)-6-chloro-5'-(5-chloro-2-methylphenyl)-2'-(4,6-dimethoxypyridin-3-yl)-3'-isopropyl-3'H-spiro[dihydroindole-3,4'-pyrrolo[3,4-d]imidazole]-2,6'(5'H)-dione (R-11). MS (ESI): mass calcd. for $C_{29}H_{25}Cl_2N_5O_4$ 577.1, m/z found 578.2 [M+H]$^+$. $^1$H-NMR (400 MHz, DMSO-d$_6$) δ 11.61 (brs, 1H), 8.13 (d, 1H, J=4.8 Hz), 7.55 (d, 1H, J=8.4 Hz), 7.43-7.22 (m, 3H), 7.16-6.96 (m, 2H), 6.59 (d, 1H, J=1.6 Hz), 4.10-4.04 (m, 1H), 3.92 (s, 3H), 3.84 (s, 3H), 2.22 (s, 3H), 1.08 (d, 3H, J=6.4 Hz), 0.69 (d, 3H, J=6.4 Hz).

Example 12

4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxybenzonitrile

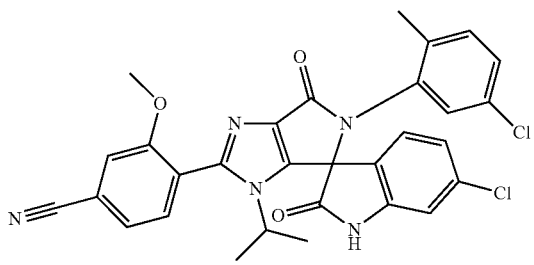 [SMILES: COc1cc(C#N)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 27.1 mg of (S)-4-(6-chloro-5'-(5-chloro-2-methylphenyl)-3'-isopropyl-2,6'-dioxo-5',6'-dihydro-3'H-spiro[dihydroindole-3,4'-pyrrolo[3, 4-d]imidazole]-2'-yl)-3-methoxybenzonitrile (S-12), and 23.5 mg of (R)-4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxybenzonitrile (R-12). MS (ESI): mass calcd. for $C_{27}H_{22}Cl_2N_6O_4$ 564.1, m/z found 565.3[M+H]$^+$. $^1$H-NMR (400 MHz, DMSO-d$_6$) δ 7.73 (s, 1H), 7.68-7.62 (m, 1H), 7.60-7.46 (m, 2H), 7.16-7.09 (m, 2H), 7.01-6.97 (m, 2H), 4.06-4.03 (m, 1H), 3.87 (s, 3H), 2.22 (s, 3H), 1.07 (d, 3H, J=6.4 Hz), 0.64 (d, 3H, J=6.4 Hz).

Example 13

3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxybenzonitrile

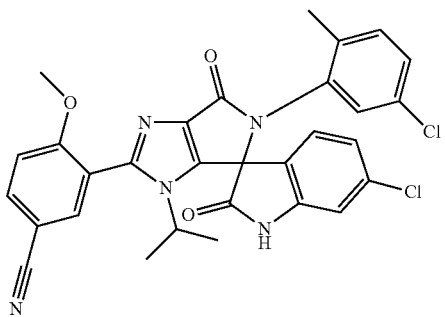 [SMILES: COc1ccc(C#N)cc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 10.1 mg of (S)-3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxybenzonitrile (S-13), and 13.7 mg of (R)-3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxybenzonitrile (R-13). MS (ESI): mass calcd. for $C_{30}H_{23}Cl_2N_5O_3$ 571.1, m/z found 572.4 [M+H]$^+$. $^1$H-NMR (400 MHz, DMSO-d$_6$) δ 8.06-8.04 (m, 2H), 7.97-6.97 (m, 7H), 4.05-4.02 (m, 1H), 3.89 (s, 3H), 2.22 (s, 3H), 1.08 (d, 3H, J=6.4 Hz), 0.65 (d, 3H, J=6.4 Hz).

Example 14

6-chloro-5'-(3-chloro-2-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

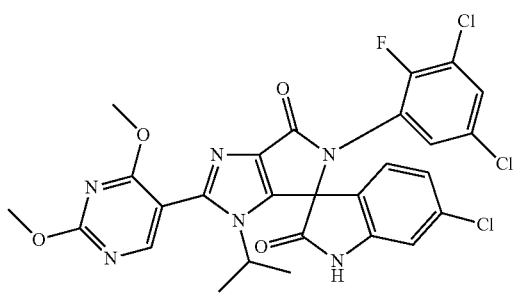 [SMILES: COc1ncc(-c2nc3c(n2C(C)C)C2(C(=O)Nc4cc(Cl)ccc42)N(c2cc(Cl)cc(Cl)c2F)C3=O)c(OC)n1]

Title compounds were obtained by steps similar to those in Example 1, and supercritical high-pressure preparative chromatography was performed to obtain 54.9 mg of (S)-6-chloro-5'-(3-chloro-2-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-14), and 50.8 mg of (R)-6-chloro-5'-(3-chloro-2-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-14). MS (ESI): mass calcd. for $C_{27}H_{21}Cl_2FN_6O_4$ 582.1, m/z found 583.5 [M+H]$^+$. $^1$H-NMR (400 MHz, DMSO-d$_6$) δ 11.52 (brs, 1H), 8.54 (s, 1H), 7.59 (t, 1H, J=6.8 Hz), 7.34 (d, 1H, J=7.6 Hz), 7.23-7.14 (m, 2H), 7.03-6.98 (m, 2H), 4.20-4.13 (m, 1H), 3.99 (s, 3H), 3.95 (s, 3H), 1.12 (d, 3H, J=6.8 Hz), 0.66 (d, 3H, J=6.8 Hz).

Example 15

6-chloro-5'-(5-chloro-2-ethylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

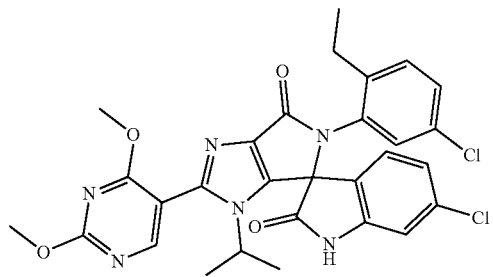 [SMILES: CCc1ccc(Cl)cc1N1C(=O)c2nc(-c3cnc(OC)nc3OC)n(C(C)C)c2C12C(=O)Nc1cc(Cl)ccc12]

Title compounds were obtained by steps similar to those in Example 1, and supercritical high-pressure preparative chromatography was performed to obtain 17.5 mg of (S)-6-chloro-5'-(5-chloro-2-ethylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-15), and 54.6 mg of (R)-6-chloro-5'-(5-chloro-2-ethylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-15). MS (ESI): mass calcd. for $C_{29}H_{26}Cl_2N_6O_4$ 592.1, m/z found 593.2 [M+H]$^+$. $^1$H-NMR (400 MHz, DMSO-d$_6$) δ 11.38 (brs, 1H), 8.53 (d, 1H, J=6.8 Hz), 7.58-7.09 (m, 5H), 7.07-6.95 (m, 1H), 4.17-4.14 (m, 1H), 3.99 (s, 3H), 3.95 (s, 3H), 2.57-2.48 (m, 2H), 1.14-1.02 (m, 6H), 0.67 (d, 3H, J=6.0 Hz).

Example 16

6-chloro-5'-(5-chloro-1-methyl-2-oxo-1,2-dihydropyridin-3-yl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

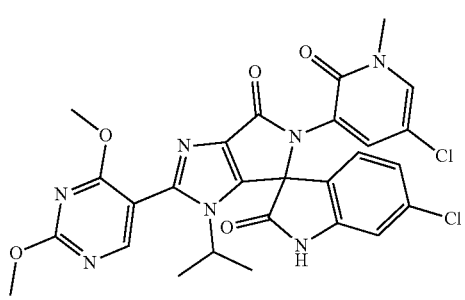 [SMILES: COc1ncc(-c2nc3c(n2C(C)C)C2(C(=O)Nc4cc(Cl)ccc42)N(c2cc(Cl)cn(C)c2=O)C3=O)c(OC)n1]

Title compounds were obtained by steps similar to those in Example 1, and supercritical high-pressure preparative chromatography was performed to obtain 6.3 mg of (S)-6-chloro-5'-(5-chloro-1-methyl-2-oxo-1,2-dihydropyridin-3-yl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-16), and 8.1 mg of (R)-6-chloro-5'-(5-chloro-1-methyl-2-oxo-1,2-dihydropyridin-3-yl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-16). MS (ESI): mass calcd. for $C_{26}H_{21}Cl_2N_7O_5$ 581.1, m/z found 582.1[M+H]$^+$. $^1$H-NMR (400 MHz, DMSO-d$_6$) δ 11.30 (brs, 1H), 8.51 (s, 1H), 7.97 (d, 1H, J=2.4 Hz), 7.31 (d, 1H, J=2.4), 7.21 (d, 1H, J=8.0), 7.04 (d, 1H, J=8.0), 6.99 (s, 1H), 4.13-4.08 (m, 1H), 3.99 (s, 3H), 3.94 (s, 3H), 1.35 (s, 3H), 1.11 (d, 3H, J=6.8 Hz), 0.62 (d, 3H, J=8.0).

Example 17

6-chloro-5'-(5-chloro-2-methoxyphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

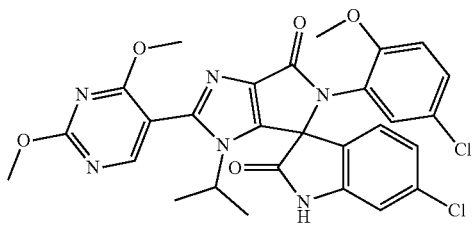 [SMILES: COc1ncc(-c2nc3c(n2C(C)C)C2(C(=O)Nc4cc(Cl)ccc42)N(c2cc(Cl)ccc2OC)C3=O)c(OC)n1]

Title compounds were obtained by steps similar to those in Example 1, and supercritical high-pressure preparative chromatography was performed to obtain 15.1 mg of (S)-6-chloro-5'-(5-chloro-2-methoxyphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-17), and 14.6 mg of (R)-6-chloro-5'-(5-chloro-2-methoxyphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-17). MS (ESI): mass calcd. for $C_{28}H_{24}Cl_2N_6O_5$ 594.1, m/z found 595.2[M+H]$^+$. $^1$H-NMR (400 MHz, DMSO-d$_6$) δ 8.49 (s, 1H), 7.30-7.28 (m, 1H), 7.10 (s, 1H), 7.43-7.22 (m, 3H), 7.98-6.96 (m, 2H), 6.75-6.74 (m, 2H), 4.08-4.03 (m, 1H), 3.98 (s, 3H), 3.94 (s, 3H), 3.63 (s, 3H), 1.12 (d, 3H, J=6.4 Hz), 0.65 (d, 3H, J=6.4 Hz).

Example 18

6-chloro-5'-(5-chloro-2-methylphenyl)-3'-isopropyl-2'-(4-methoxypyridin-3-yl)-3'H-spiro[dihydroindole-3,4'-pyrrolo[3,4-d]imidazole]-2,6'(5'H)-dione

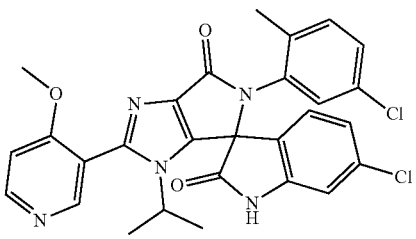 [SMILES: COc1ccncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 23.7 mg of (S)-6-chloro-5'-(5-chloro-2-methylphenyl)-3'-isopropyl-2'-(4-methoxypyridin-3-yl)-3'H-spiro[dihydroindole-3,4'-pyrrolo[3,4-d]imidazole]-2,6'(5'H)-dione (S-18), and 30.9 mg of (R)-6-chloro-5'-(5-chloro-2-methylphenyl)-3'-isopropyl-2'-(4-methoxypyridin-3-yl)-3'H-spiro[dihydroindole-3,4'-pyrrolo[3,4-d]imidazole]-2,6'(5'H)-dione (R-18). MS (ESI): mass calcd. for $C_{28}H_{23}Cl_2N_5O_3$ 547.1, m/z found 548.3 [M+H]$^+$. $^1$H-NMR (400 MHz, DMSO-d$_6$) δ 8.64 (d, 1H, J=5.6 Hz), 8.50 (d, 1H, J=6.0 Hz), 7.56-6.94 (m, 7H), 4.07-4.04 (m, 1H), 3.89 (s, 3H), 2.20 (s, 3H), 1.09 (d, 3H, J=7.2 Hz), 0.66 (d, 3H, J=7.2 Hz).

Example 19

6-chloro-5'-(5-chloro-2-methylphenyl)-3'-isopropyl-2'-(2-isopropyl-5-methoxyphenyl)-3'H-spiro[dihydroindole-3,4'-pyrrolo[3,4-d]imidazole]-2,6'(5'H)-dione

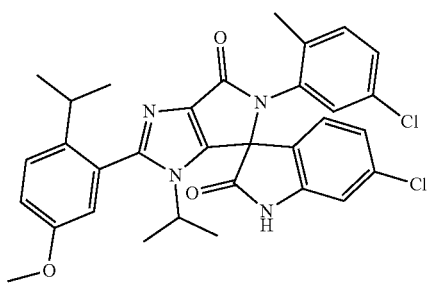 [SMILES: COc1ccc(C(C)C)c(-c2nc3c(n2C(C)C)C2(C(=O)Nc4cc(Cl)ccc42)N(c2cc(Cl)ccc2C)C3=O)c1]

Title compounds were obtained by steps similar to those in Example 1, and supercritical high-pressure preparative chromatography was performed to obtain 24.3 mg of (S)-6-chloro-5'-(5-chloro-2-methylphenyl)-3'-isopropyl-2'-(2-isopropyl-5-methoxyphenyl)-3'H-spiro[dihydroindole-3,4'-pyrrolo[3,4-d]imidazole]-2,6'(5'H)-dione (S-19), and 24.6 mg of (R)-6-chloro-5'-(5-chloro-2-methylphenyl)-3'-isopropyl-2'-(2-isopropyl-5-methoxyphenyl)-3'H-spiro[dihydroindole-3,4'-pyrrolo[3,4-d]imidazole]-2,6'(5'H)-dione (R-19). MS (ESI): mass calcd. for $C_{32}H_{30}Cl_2N_4O_3$ 588.2, m/z found 589.2 [M+H]$^+$. $^1$H-NMR (400 MHz, DMSO-d$_6$) δ 7.59-6.89 (m, 9H), 4.06-4.03 (m, 1H), 3.83 (s, 3H), 2.63-2.59 (m, 1H), 2.22 (s, 3H), 1.23-1.15 (m, 6H), 0.83 (d, 3H, J=6.8 Hz), 0.65 (d.3H, J=6.8 Hz).

Example 20

6-chloro-5'-(3-chloro-4-methylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

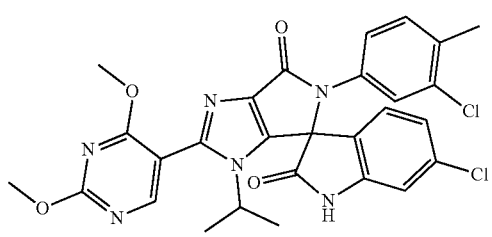

Title compounds were obtained by steps similar to those in Example 1, and supercritical high-pressure preparative chromatography was performed to obtain 24.0 mg of (S)-6-chloro-5'-(3-chloro-4-methylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-20), and 27.9 mg of (R)-6-chloro-5'-(3-chloro-4-methylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-20). MS (ESI): mass calcd. for $C_{28}H_{24}Cl_2N_6O_4$ 578.1, m/z found 579.4 [M+H]$^+$. $^1$H-NMR (400 MHz, DMSO-d$_6$) δ 8.51 (s, 1H), 7.96 (brs, 1H), 7.94 (d, 1H, J=4.8 Hz), 7.47 (d, 1H, J=8.0 Hz), 7.30 (d, 1H, J=8.0 Hz), 7.15 (dd, 1H, J$^1$=8.0 Hz, J$^2$=1.6 Hz), 7.08-7.01 (m, 1H), 6.87 (d, 1H, J=8.0 Hz), 4.18-4.13 (m, 1H), 3.99 (s, 3H), 3.94 (s, 3H), 2.26 (s, 3H), 1.11 (d, 3H, J=6.8 Hz), 0.65 (d, 3H, J=6.8 Hz).

Example 21

3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxy-N-methylbenzamide

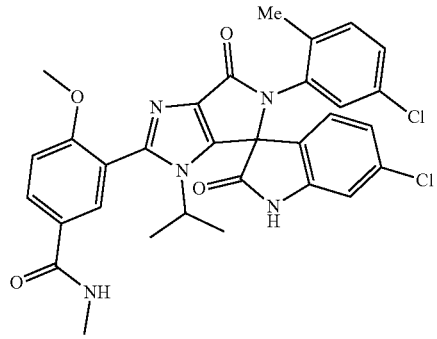 [SMILES: CNC(=O)c1ccc(OC)c(-c2nc3c(n2C(C)C)C2(C(=O)Nc4cc(Cl)ccc42)N(c2cc(Cl)ccc2C)C3=O)c1]

Title compounds were obtained by steps similar to those in Example 1, and supercritical high-pressure preparative chromatography was performed to obtain 26.4 mg of (S)-3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxy-N-methylbenzamide (S-21), and 30.3 mg of (R)-3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxy-N-methylbenzamide (R-21). MS (ESI): mass calcd. for $C_{31}H_{27}Cl_2N_5O_4$, 603.1 m/z found 604.1 [M+H]$^+$. $^1$H-NMR (400 MHz, DMSO-d$_6$) δ 8.46 (d, 1H, J=4.0 Hz), 8.08-8.06 (m, 1H), 7.96 (s, 1H), 7.55-6.99 (m, 6H), 4.08-4.04 (m, 1H), 3.86 (s, 3H), 2.77 (d, 3H, J=4.0 Hz), 2.23 (s, 3H), 1.07 (d, 3H, J=6.0 Hz), 0.65 (d, 3H, J=6.0 Hz).

Example 22

3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxy-N,N-dimethylbenzamide

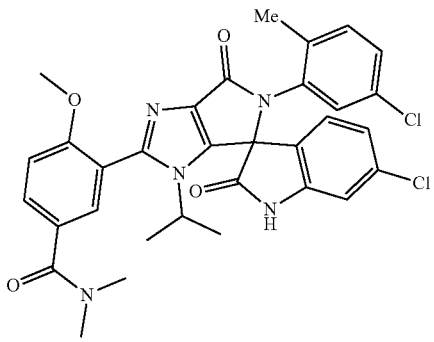 [SMILES: COc1ccc(C(=O)N(C)C)cc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 26.9 mg of (S)-3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxy-N,N-dimethylbenzamide (S-22), and 29.5 mg of (R)-3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxy-N,N-dimethylbenzamide (R-22). MS (ESI): mass calcd. for $C_{31}H_{27}Cl_2N_5O_4$, 617.1 m/z found 618.1 [M+H]$^+$. $^1$H-NMR (400 MHz, DMSO-d$_6$) δ 7.66-6.97 (m, 9H), 4.09-4.06 (m, 1H), 3.85 (s, 3H), 2.98 (s, 6H), 2.22 (s, 3H), 1.08 (s, 3H), 0.65 (s, 3H).

Example 23

6-chloro-5'-(5-chloro-2-methylphenyl)-2'-(4-(dimethylamino)-2-methoxyphenyl)-3'-isopropyl-3'H-spiro[dihydroindole-3,4'-pyrrolo[3,4-d]imidazole]-2,6'(5'H)-dione

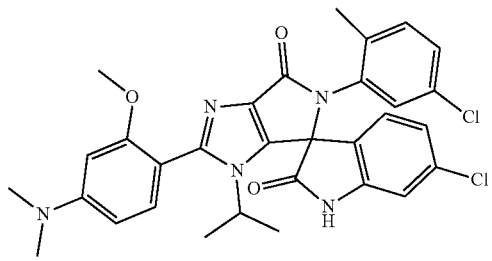 [SMILES: COc1cc(N(C)C)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 23.2 mg of (S)-6-chloro-5'-(5-chloro-2-methylphenyl)-2'-(4-(dimethylamino)-2-methoxyphenyl)-3'-isopropyl-3'H-spiro[dihydroindole-3,4'-pyrrolo[3,4-d]imidazole]-2,6'(5'H)-dione (S-23), and 22.3 mg of (R)-6-chloro-5'-(5-chloro-2-methylphenyl)-2'-(4-(dimethylamino)-2-methoxyphenyl)-3'-isopropyl-3'H-spiro[dihydroindole-3,4'-pyrrolo[3,4-d]imida-zole]-2,6'(5'H)-dione (R-23). MS (ESI): mass calcd. for $C_{31}H_{29}Cl_2N_5O_3$ 589.2, m/z found 590.2 [M+H]$^+$. $^1$H-NMR (400 MHz, DMSO-d$_6$) δ 11.50 (brs, 1H), 7.51-6.38 (m, 9H), 4.12-4.09 (m, 1H), 3.77 (s, 3H), 3.00 (s, 6H), 2.22 (s, 3H), 1.06 (d, 3H, J=6.8 Hz), 0.62 (d, 3H, J=6.8 Hz).

Example 24

6-chloro-5'-(5-chloro-2-methylphenyl)-3'-isopropyl-2'-(2-methoxy-4-methylphenyl)-3'H-spiro[dihydroindole-3,4'-pyrrolo[3,4-d]imidazole]-2,6'(5'H)-dione

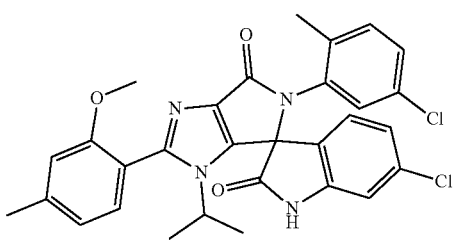 [SMILES: COc1cc(C)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 36.0 mg of (S)-6-chloro-5'-(5-chloro-2-methylphenyl)-3'-isopropyl-2'-(2-methoxy-4-methylphenyl)-3'H-spiro[dihydroindole-3,4'-pyrrolo[3,4-d]imidazole]-2,6'(5'H)-dione (S-24), and 26.2 mg of (R)-6-chloro-5'-(5-chloro-2-methylphenyl)-3'-isopropyl-2'-(2-methoxy-4-methylphenyl)-3'H-spiro[dihydroindole-3,4'-pyrrolo[3,4-d]imidazole]-2,6'(5'H)-dione (R-24). MS (ESI): mass calcd. for $C_{30}H_{26}Cl_2N_4O_3$ 560.1, m/z found 561.1[M+H]$^+$. $^1$H-NMR (400 MHz, DMSO-d$_6$) δ 7.54-6.91 (m, 9H), 4.08-4.04 (m, 1H), 3.77 (s, 3H), 2.39 (s, 3H), 2.22 (s, 3H), 1.06 (d, 3H, J=6.0 Hz), 0.63 (d, 3H, J=6.0 Hz).

Example 25

6-chloro-5'-(5-chloro-2-methylphenyl)-3'-isopropyl-2'-(2-methoxy-4-(methylamine)phenyl)-3'H-spiro[dihydroindole-3,4'-pyrrolo[3,4-d]imidazole]-2,6'(5'H)-dione

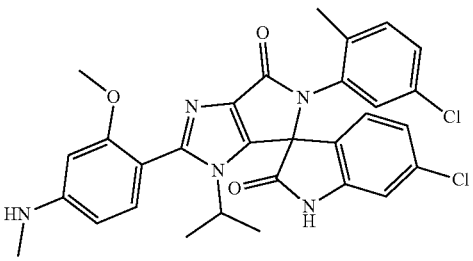 [SMILES: CNc1ccc(-c2nc3c(n2C(C)C)C2(C(=O)Nc4cc(Cl)ccc42)N(c2cc(Cl)ccc2C)C3=O)c(OC)c1]

Title compounds were obtained by steps similar to those in Example 1, and supercritical high-pressure preparative chromatography was performed to obtain 9.0 mg of (S)-6-chloro-5'-(5-chloro-2-methylphenyl)-3'-isopropyl-2'-(2-methoxy-4-(methylamine)phenyl)-3'H-spiro[dihydroindole-3,4'-pyrrolo[3,4-d]imidazole]-2,6'(5'H)-dione (S-25), and 11.6 mg of (R)-6-chloro-5'-(5-chloro-2-methylphenyl)-3'-isopropyl-2'-(2-methoxy-4-(methylamine)phenyl)-3'H-spiro[dihydroindole-3,4'-pyrrolo[3,4-d]imidazole]-2,6'(5'H)-dione (R-25). MS (ESI): mass calcd. for $C_{30}H_{27}Cl_2N_5O_3$ 575.2, m/z found 576.2 [M+H]$^+$. $^1$H-NMR (400 MHz, DMSO-d$_6$) δ 11.69 (brs, 1H), 7.55-6.22 (m, 9H), 4.13-4.09 (m, 1H), 3.72 (s, 3H), 2.74 (s, 3H), 2.22 (s, 3H) 1.05 (d, 3H, J=5.2 Hz), 0.60 (d, 3H, J=5.2 Hz).

Example 26

6-chloro-5'-(5-chloro-2-methylphenyl)-2'-(2,4-dimethoxypyrimidin-5-yl)-3'-ethyl-3'H-spiro[dihydroindole-3,4'-pyrrolo[3,4-d]imidazole]-2,6'(5'H)-dione

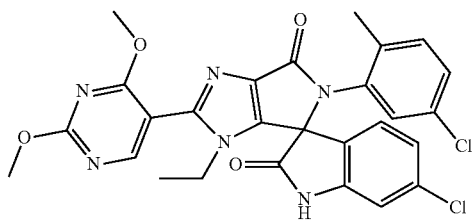 [SMILES: CCn1c(-c2cnc(OC)nc2OC)nc2c1C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 26.2 mg of (S)-6-chloro-5'-(5-chloro-2-methylphenyl)-2'-(2,4-dimethoxypyrimidin-5-yl)-3'-ethyl-3'H-spiro[dihydroindole-3,4'-pyrrolo[3,4-d]imidazole]-2,6'(5'H)-dione (S-26), and 28.3 mg of (R)-6-chloro-5'-(5-chloro-2-methylphenyl)-2'-(2,4-dimethoxypyrimidin-5-yl)-3'-ethyl-3'H-spiro[dihydroindole-3,4'-pyrrolo[3,4-d]imidazole]-2,6'(5'H)-dione (R-26). MS (ESI): mass calcd. for $C_{27}H_{22}Cl_2N_6O_4$ 564.1, m/z found 565.1[M+H]$^+$. $^1$H-NMR (400 MHz, DMSO-d$_6$) δ 8.54 (d, 1H, J=6.0 Hz), 7.64-6.95 (m, 6H), 3.99 (s, 3H), 3.95 (s, 3H), 3.58-3.50 (m, 1H), 2.25 (s, 3H), 1.17 (d, 3H, J=6.0 Hz), 0.85 (d, 3H, J=6.0 Hz).

Example 27

6-chloro-5'-(5-chloro-2-methylphenyl)-3'-isopropyl-2'-(4-methoxypyrimidin-5-yl)-3'H-spiro[dihydroindole-3,4'-pyrrolo[3,4-d]imidazole]-2,6'(5'H)-dione

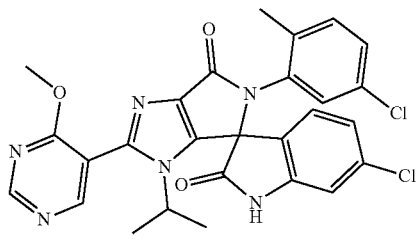 [SMILES: COc1ncncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 2.2 mg of (S)-6-chloro-5'-(5-chloro-2-methylphenyl)-3'-isopropyl-2'-(4-methoxypyrimidin-5-yl)-3'H-spiro[dihydroindole-3,4'-pyrrolo[3,4-d]imidazole]-2,6'(5'H)-dione (S-27), and 3.6 mg of (R)-6-chloro-5'-(5-chloro-2-methylphenyl)-3'-isopropyl-2'-(4-methoxypyrimidin-5-yl)-3'H-spiro[dihydroindole-3,4'-pyrrolo[3,4-d]imidazole]-2,6'(5'H)-dione (R-27). MS (ESI): mass calcd. for $C_{27}H_{22}Cl_2N_6O_3$ 548.1, m/z found 549.4 [M+H]$^+$. $^1$H-NMR (400 MHz, DMSO-d$_6$) δ 11.19 (brs, 1H), 8.99 (s, 1H), 8.76 (d, 1H, J=7.2 Hz), 7.57-6.98 (m, 6H), 4.19-4.12 (m, 1H), 4.00 (s, 3H), 2.22 (s, 3H), 1.11 (d, 3H, J=6.8 Hz), 0.68 (d, 3H, J=6.8 Hz).

Example 28

6-chloro-5'-(5-chloro-2-methylphenyl)-3'-cyclopropane-2'-(2,4-dimethoxypyrimidin-5-yl)-3'H-spiro[dihydroindole-3,4'-pyrrolo[3,4-d]imidazole]-2,6'(5'H)-dione

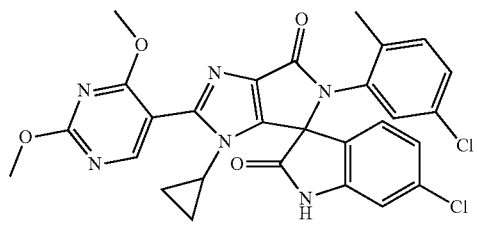 [SMILES: COc1ncc(-c2nc3c(n2C2CC2)C2(C(=O)Nc4cc(Cl)ccc42)N(c2cc(Cl)ccc2C)C3=O)c(OC)n1]

Title compounds were obtained by steps similar to those in Example 1, and supercritical high-pressure preparative chromatography was performed to obtain 10.2 mg of (S)-6-chloro-5'-(5-chloro-2-methylphenyl)-3'-cyclopropane-2'-(2,4-dimethoxypyrimidin-5-yl)-3'H-spiro[dihydroindole-3,4'-pyrrolo[3,4-d]imidazole]-2,6'(5'H)-dione (S-28), and 11.0 mg of (R)-6-chloro-5'-(5-chloro-2-methylphenyl)-3'-cyclopropane-2'-(2,4-dimethoxypyrimidin-5-yl)-3'H-spiro[dihydroindole-3,4'-pyrrolo[3,4-d]imidazole]-2,6'(5'H)-dione (R-28). MS (ESI): mass calcd. for $C_{28}H_{22}Cl_2N_6O_4$ 576.1, m/z found 577.1[M+H]$^+$. $^1$H-NMR (400 MHz, DMSO-d$_6$) δ 11.58 (brs, 1H), 8.55 (d, 1H, J=4.0 Hz), 7.56-6.97 (m, 6H), 3.99 (s, 3H), 3.96 (s, 3H), 3.01-3.00 (m, 1H), 2.23 (s, 3H), 0.85-0.47 (m, 4H).

Example 29

3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxybenzamide

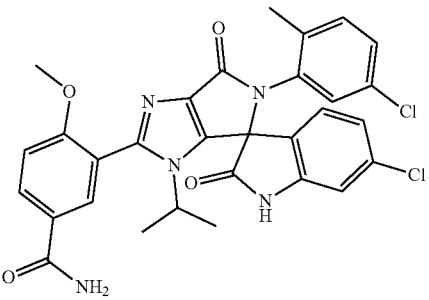 [SMILES: COc1ccc(C(N)=O)cc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 6.1 mg of (S)-3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxybenzamide (S-29), and 6.6 mg of (R)-3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxybenzamide (R-29). MS (ESI): mass calcd. for $C_{30}H_{25}Cl_2N_5O_4$ 589.1, m/z found 590.4 [M+H]$^+$. $^1$H-NMR (400 MHz, DMSO-d$_6$) δ 8.08 (d, 1H, J=6.8 Hz), 7.98 (brs, 2H), 7.37-6.52 (m, 8H), 4.02-3.96 (m, 1H), 3.84 (s, 3H), 2.26 (s, 3H), 1.10 (d, 3H, J=7.2 Hz), 0.66 (d, 3H, J=7.2 Hz).

Example 30

6-chloro-5'-(5-chloro-2-methylphenyl)-2'-(2-(difluoromethoxy)phenyl)-3'-isopropyl-3'H-spiro[dihydroindole-3,4'-pyrrolo[3,4-d]imidazole]-2,6'(5'H)-dione

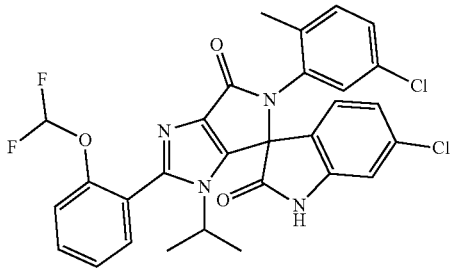

Title compounds were obtained by steps similar to those in Example 1, and supercritical high-pressure preparative chromatography was performed to obtain 36.0 mg of (S)-6-chloro-5'-(5-chloro-2-methylphenyl)-2'-(2-(difluoromethoxy)phenyl)-3'-isopropyl-3'H-spiro[dihydroindole-3,4'-pyrrolo[3,4-d]imidazole]-2,6'(5'H)-dione (S-30), and 36.8 mg of (R)-6-chloro-5'-(5-chloro-2-methylphenyl)-2'-(2-(difluoromethoxy)phenyl)-3'-isopropyl-3'H-spiro[dihydroindole-3,4'-pyrrolo[3,4-d]imidazole]-2,6'(5'H)-dione (R-30). MS (ESI): mass calcd. for $C_{29}H_{22}Cl_2F_2N_4O_3$ 582.1, m/z found 583.4 [M+H]$^+$. $^1$H-NMR (400 MHz, DMSO-d$_6$) δ 11.55 (brs, 1H), 7.69-6.96 (m, 10H), 4.08-4.07 (m, 1H), 2.22 (s, 3H), 1.08 (d, 3H, J=6.0 Hz), 0.67 (d, 3H, J=6.4 Hz).

Example 31

6-chloro-5'-(5-chloro-2-methylphenyl)-3'-isopropyl-2'-(2-(trifluoromethoxy)phenyl)-3'H-spiro[dihydroindole-3,4'-pyrrolo[3,4-d]imidazole]-2,6'(5'H)-dione

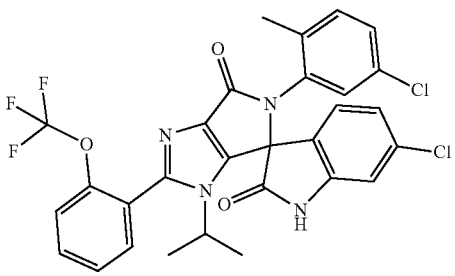 [SMILES: Cc1ccc(Cl)cc1N1C(=O)c2nc(-c3ccccc3OC(F)F)n(C(C)C)c2C12C(=O)Nc1cc(Cl)ccc12]

Title compounds were obtained by steps similar to those in Example 1, and supercritical high-pressure preparative chromatography was performed to obtain 19.9 mg of (S)-6-chloro-5'-(5-chloro-2-methylphenyl)-3'-isopropyl-2'-(2-(trifluoromethoxy)phenyl)-3'H-spiro[dihydroindole-3,4'-pyrrolo[3,4-d]imidazole]-2,6'(5'H)-dione (S-31), and 18.9 mg of (R)-6-chloro-5'-(5-chloro-2-methylphenyl)-3'-isopropyl-2'-(2-(trifluoromethoxy)phenyl)-3'H-spiro[dihydroindole-3,4'-pyrrolo[3,4-d]imidazole]-2,6'(5'H)-dione (R-31). MS (ESI): mass calcd. for $C_{29}H_{21}Cl_2F_3N_4O_3$ 600.1, m/z found 601.4 [M+H]$^+$. $^1$H-NMR (400 MHz, DMSO-d$_6$) δ 11.54 (brs, 1H), 7.77-6.96 (m, 10H), 4.10-4.03 (m, 1H), 2.22 (s, 3H), 1.09 (d, 3H, J=7.2 Hz), 0.70 (d, 3H, J=6.4 Hz).

Example 32

6-chloro-5'-(5-chloro-2-methylphenyl)-3'-isopropyl-2'-(4-isopropyl-2-methoxyphenyl)-3'H-spiro[dihydroindole-3,4'-pyrrolo[3,4-d]imidazole]-2,6'(5'H)-dione

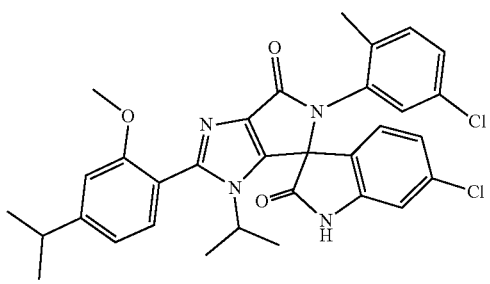 [SMILES: COc1cc(C(C)C)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 27.7 mg of (S)-6-chloro-5'-(5-chloro-2-methylphenyl)-3'-isopropyl-2'-(4-isopropyl-2-methoxyphenyl)-3'H-spiro[dihydroindole-3,4'-pyrrolo[3,4-d]imidazole]-2,6'(5'H)-dione (S-32), and 33.9 mg of (R)-6-chloro-5'-(5-chloro-2-methylphenyl)-3'-isopropyl-2'-(4-isopropyl-2-methoxyphenyl)-3'H-spiro[dihydroindole-3,4'-pyrrolo[3,4-d]imidazole]-2,6'(5'H)-dione (R-32). MS (ESI): mass calcd. for $C_{32}H_{30}Cl_2N_4O_3$ 588.2, m/z found 589.2 [M+H]$^+$. $^1$H-NMR (400 MHz, DMSO-d$_6$) δ 11.71 (brs, 1H), 7.56-6.48 (m, 9H), 4.08-4.05 (m, 1H), 3.79 (s, 3H), 3.01-2.94 (m, 1H), 2.22 (s, 3H) 1.27-1.23 (m, 6H), 1.07 (d, 3H, J=6.8 Hz), 0.63 (d, 3H, J=6.8 Hz).

Example 33

6-chloro-5'-(5-chloro-2-methylphenyl)-2'-(4-ethyl-2-methoxyphenyl)-3'-isopropyl-3'H-spiro[dihydroindole-3,4'-pyrrolo[3,4-d]imidazole]-2,6'(5'H)-dione

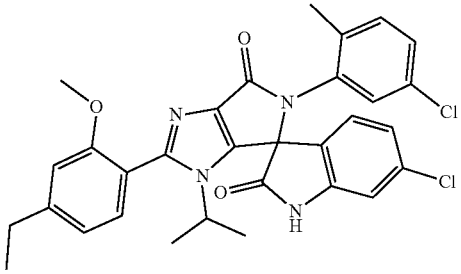 [SMILES: CCc1ccc(-c2nc3c(n2C(C)C)C2(C(=O)Nc4cc(Cl)ccc42)N(c2cc(Cl)ccc2C)C3=O)c(OC)c1]

Title compounds were obtained by steps similar to those in Example 1, and supercritical high-pressure preparative chromatography was performed to obtain 21.8 mg of (S)-6-chloro-5'-(5-chloro-2-methylphenyl)-2'-(4-ethyl-2-methoxyphenyl)-3'-isopropyl-3'H-spiro[dihydroindole-3,4'-pyrrolo[3,4-d]imidazole]-2,6'(5'H)-dione (S-33), and 20.5 mg of (R)-6-chloro-5'-(5-chloro-2-methylphenyl)-2'-(4-ethyl-2-methoxyphenyl)-3'-isopropyl-3'H-spiro[dihydroindole-3,4'-pyrrolo[3,4-d]imidazole]-2,6'(5'H)-dione (R-33). MS (ESI): mass calcd. for $C_{31}H_{28}Cl_2N_4O_3$ 574.2, m/z found 575.2 [M+H]$^+$. $^1$H-NMR (400 MHz, DMSO-d$_6$) δ 11.70 (brs, 1H), 7.55-6.50 (m, 9H), 4.08-4.04 (m, 1H), 3.78 (s, 3H), 2.72-2.50 (m, 2H), 2.22 (s, 3H), 1.27-1.06 (m, 3H), 1.06 (d, 3H, J=6.4 Hz), 0.63 (d, 3H, J=6.4 Hz).

Example 34

6-chloro-5'-(5-chloro-2-methylphenyl)-2'-(2-isopropoxyphenyl)-3'-isopropyl-3'H-spiro[dihydroindole-3,4'-pyrrolo[3,4-d]imidazole]-2,6'(5'H)-dione

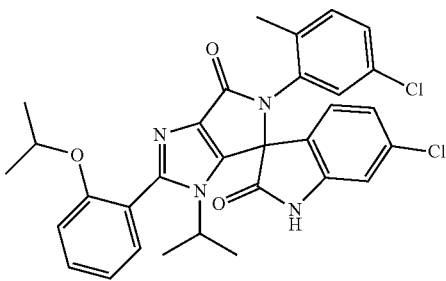 [SMILES: Cc1ccc(Cl)cc1N1C(=O)c2nc(-c3ccccc3OC(C)C)n(C(C)C)c2C12C(=O)Nc1cc(Cl)ccc12]

Title compounds were obtained by steps similar to those in Example 1, and supercritical high-pressure preparative chromatography was performed to obtain 18.8 mg of (S)-6-chloro-5'-(5-chloro-2-methylphenyl)-2'-(2-isopropoxyphenyl)-3'-isopropyl-3'H-spiro[dihydroindole-3,4'-pyrrolo[3,4-d]imidazole]-2,6'(5'H)-dione (S-34), and 21.1 mg of (R)-6-chloro-5'-(5-chloro-2-methylphenyl)-2'-(2-isopropoxyphenyl)-3'-isopropyl-3'H-spiro[dihydroindole-3,4'-pyrrolo[3,4-d]imidazole]-2,6'(5'H)-dione (R-34). MS (ESI): mass calcd. for $C_{31}H_{28}Cl_2N_4O_3$ 574.2, m/z found 575.4 [M+H]$^+$. $^1$H-NMR (400 MHz, DMSO-d$_6$) δ 11.67 (brs, 1H), 7.54-6.95 (m, 10H), 4.65-4.62 (m, 1H), 4.12-4.08 (m, 1H), 2.22 (s, 3H), 1.18 (m, 6H), 1.07 (d, 3H, J=7.2 Hz), 0.65 (d, 3H, J=6.4 Hz).

Example 35

6-chloro-5'-(5-chloro-2-methylphenyl)-2'-(2-ethoxyphenyl)-3'-isopropyl-3'H-spiro[dihydroindole-3,4'-pyrrolo[3,4-d]imidazole]-2,6'(5'H)-dione

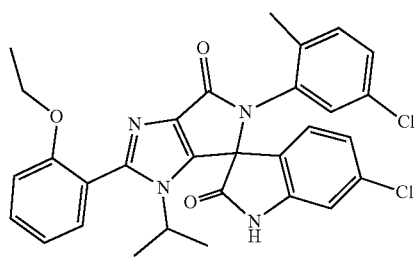 [SMILES: CCOc1ccccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 15.9 mg of (S)-6-chloro-5'-(5-chloro-2-methylphenyl)-2'-(2-ethoxyphenyl)-3'-isopropyl-3'H-spiro[dihydroindole-3,4'-pyrrolo[3,4-d]imidazole]-2,6'(5'H)-dione (S-35), and 23.0 mg of (R)-6-chloro-5'-(5-chloro-2-methylphenyl)-2'-(2-ethoxyphenyl)-3'-isopropyl-3'H-spiro[dihydroindole-3,4'-pyrrolo[3,4-d]imidazole]-2,6'(5'H)-dione (R-35). MS (ESI): mass calcd. for $C_{30}H_{26}Cl_2N_4O_3$ 560.1, m/z found 561.5 [M+H]$^+$. $^1$H-NMR (400 MHz, DMSO-d$_6$) δ 11.68 (brs, 1H), 7.55-6.95 (m, 10H), 4.09-4.08 (m, 3H), 2.22 (s, 3H), 1.24 (t, 3H, J=6.0 Hz), 1.07 (d, 3H, J=6.8 Hz), 0.65 (d, 3H, J=6.8 Hz).

Example 36

6-chloro-5'-(3-chlorophenyl)-2'-(2,4-dimethoxyphenyl)-3'-isopropyl-3'H-spiro[dihydroindole-3,4'-pyrrolo[3,4-d]imidazole]-2,6'(5'H)-dione

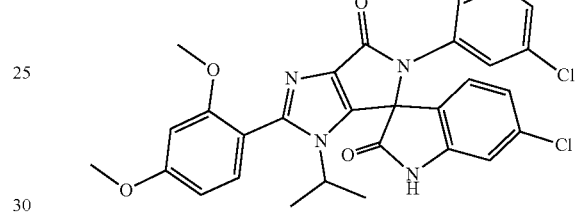

Title compounds were obtained by steps similar to those in Example 1, and supercritical high-pressure preparative chromatography was performed to obtain 29.1 mg of (S)-6-chloro-5'-(3-chlorophenyl)-2'-(2,4-dimethoxyphenyl)-3'-isopropyl-3'H-spiro[dihydroindole-3,4'-pyrrolo[3,4-d]imidazole]-2,6'(5'H)-dione (S-36), and 36.6 mg of (R)-6-chloro-5'-(3-chlorophenyl)-2'-(2,4-dimethoxyphenyl)-3'-isopropyl-3'H-spiro[dihydroindole-3,4'-pyrrolo[3,4-d]imidazole]-2,6'(5'H)-dione (R-36). MS (ESI): mass calcd. for $C_{29}H_{24}C_{12}N_4O_4$ 562.1, m/z found 563.1[M+H]$^+$. $^1$H-NMR (400 MHz, DMSO-d$_6$) δ 7.47-7.45 (m, 1H), 7.38-7.36 (m, 3H), 7.13-7.12 (m, 2H), 7.02 (s, 1H), 6.97 (d, 1H, J=7.2 Hz), 6.72-6.67 (m, 2H), 4.11-4.00 (m, 1H), 3.84 (s, 3H), 3.77 (s, 3H), 1.10 (d, 3H, J=5.2 Hz), 0.60 (d, 3H, J=5.2 Hz).

Example 37

6-chloro-5'-(5-chloro-2-methylphenyl)-2'-(5-ethyl-2-methoxyphenyl)-3'-isopropyl-3'H-spiro[dihydroindole-3,4'-pyrrolo[3,4-d]imidazole]-2,6'(5'H)-dione

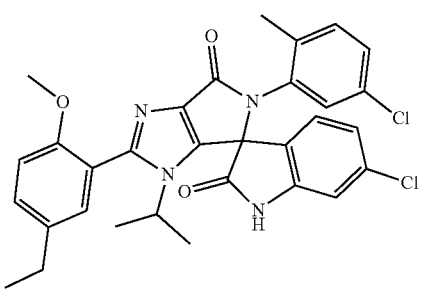 [SMILES: CCc1ccc(OC)c(-c2nc3c(n2C(C)C)C2(C(=O)Nc4cc(Cl)ccc42)N(c2cc(Cl)ccc2C)C3=O)c1]

Title compounds were obtained by steps similar to those in Example 1, and supercritical high-pressure preparative chromatography was performed to obtain 21.5 mg of (S)-6-chloro-5'-(5-chloro-2-methylphenyl)-2'-(5-ethyl-2-methoxyphenyl)-3'-isopropyl-3'H-spiro[dihydroindole-3,4'-pyrrolo[3,4-d]imidazole]-2,6'(5'H)-dione (S-37), and 32.4 mg of (R)-6-chloro-5'-(5-chloro-2-methylphenyl)-2'-(5-ethyl-2-methoxyphenyl)-3'-isopropyl-3'H-spiro[dihydroindole-3,4'-pyrrolo[3,4-d]imidazole]-2,6'(5'H)-dione (R-37). MS (ESI): mass calcd. for $C_{31}H_{28}Cl_2N_4O_3$ 574.1, m/z found 575.2 [M+H]$^+$. $^1$H-NMR (400 MHz, DMSO-d$_6$) δ 7.70-6.98 (m, 9H), 4.08-4.05 (m, 1H), 3.76 (s, 3H), 2.64-2.60 (m, 2H), 2.22 (s, 3H), 1.23-1.17 (m, 3H), 1.07 (d, 3H, J=5.2 Hz), 0.63 (d, 3H, J=5.2 Hz).

Example 38

6-chloro-5'-(3-chlorophenyl)-2'-(5-ethyl-2-methoxyphenyl)-3'-isopropyl-3'H-spiro[dihydroindole-3,4'-pyrrolo[3,4-d]imidazole]-2,6'(5'H)-dione

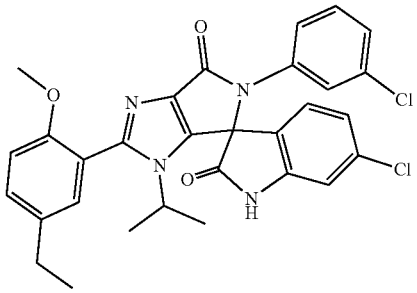 [SMILES: CCc1ccc(OC)c(-c2nc3c(n2C(C)C)C2(C(=O)Nc4cc(Cl)ccc42)N(c2cccc(Cl)c2)C3=O)c1]

Title compounds were obtained by steps similar to those in Example 1, and supercritical high-pressure preparative chromatography was performed to obtain 18.1 mg of (S)-6-chloro-5'-(3-chlorophenyl)-2'-(5-ethyl-2-methoxyphenyl)-3'-isopropyl-3'H-spiro[dihydroindole-3,4'-pyrrolo[3,4-d]imidazole]-2,6'(5'H)-dione (S-38), and 23.1 mg of (R)-6-chloro-5'-(3-chlorophenyl)-2'-(5-ethyl-2-methoxyphenyl)-3'-isopropyl-3'H-spiro[dihydroindole-3,4'-pyrrolo[3,4-d]imidazole]-2,6'(5'H)-dione (R-38). MS (ESI): mass calcd. for $C_{30}H_{26}Cl_2N_4O_3$ 560.1, m/z found 561.1 [M+H]$^+$. $^1$H-NMR (400 MHz, DMSO-d$_6$) δ 11.52 (brs, 1H), 7.48 (d, 1H, J=8.0 Hz), 7.39-7.32 (m, 3H), 7.15-7.10 (m, 3H), 7.01 (s, 1H), 6.98-6.96 (d, 1H, J=7.2 Hz), 4.10-4.04 (m, 1H), 3.75 (s, 3H), 2.64 (q, 2H, J=7.2 Hz), 1.24 (t, 3H, J=7.2 Hz), 1.10 (d, 3H, J=5.2 Hz), 0.61 (d, 3H, J=5.2 Hz).

Example 39

6-chloro-5'-(5-chloro-1-methyl-2-oxo-1,2-dihydropyridin-3-yl)-2'-(2,4-dimethoxyphenyl)-3'-isopropyl-3'H-spiro[dihydroindole-3,4'-pyrrolo[3,4-d]imidazole]-2,6'(5'H)-dione

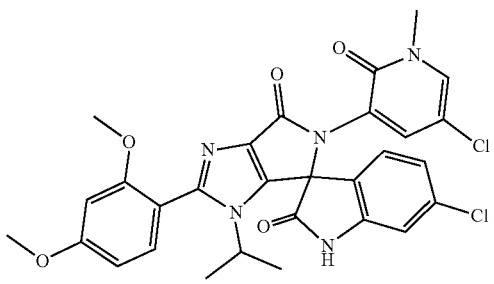 [SMILES: COc1ccc(-c2nc3c(n2C(C)C)C2(C(=O)Nc4cc(Cl)ccc42)N(c2cc(Cl)cn(C)c2=O)C3=O)c(OC)c1]

Title compounds were obtained by steps similar to those in Example 1, and supercritical high-pressure preparative chromatography was performed to obtain 8.0 mg of (S)-6-chloro-5'-(5-chloro-1-methyl-2-oxo-1,2-dihydropyridin-3-yl)-2'-(2,4-dimethoxyphenyl)-3'-isopropyl-3'H-spiro[dihydroindole-3,4'-pyrrolo[3,4-d]imidazole]-2,6'(5'H)-dione (S-39), and 12.7 mg of (R)-6-chloro-5'-(5-chloro-1-methyl-2-oxo-1,2-dihydropyridin-3-yl)-2'-(2,4-dimethoxyphenyl)-3'-isopropyl-3'H-spiro[dihydroindole-3,4'-pyrrolo[3,4-d]imidazole]-2,6'(5'H)-dione (R-39). MS (ESI): mass calcd. for $C_{29}H_{24}Cl_2N_4O_4$ 593.1, m/z found 594.3 [M+H]$^+$. $^1$H-NMR (400 MHz, DMSO-d$_6$) δ 11.44 (brs, 1H), 7.96 (d, 1H, J=2.4 Hz), 7.33-7.31 (m, 2H), 7.22 (d, 1H, J=8.0 Hz), 7.04 (d, 1H, J=8.0 Hz), 6.98 (s, 1H), 6.70-6.66 (m, 2H), 4.07-4.01 (m, 1H), 3.84 (s, 3H), 3.77 (s, 3H), 2.98 (m, 1H), 1.08 (d, 3H, J=6.4 Hz), 0.58 (d, 3H, J=6.4 Hz).

Example 40

6-chloro-5'-(5-chloro-2-methylphenyl)-2'-(2,5-dimethoxypyridin-4-yl)-3'-isopropyl-3'H-spiro[dihydroindole-3,4'-pyrrolo[3,4-d]imidazole]-2,6'(5'H)-dione

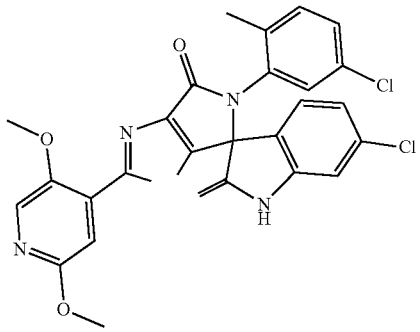 [SMILES: C=C1Nc2cc(Cl)ccc2C12C(C)=C(/N=C(\C)c1cc(OC)ncc1OC)C(=O)N2c1cc(Cl)ccc1C]

Title compounds were obtained by steps similar to those in Example 1, and supercritical high-pressure preparative chromatography was performed to obtain 20.2 mg of (S)-6-chloro-5'-(5-chloro-2-methylphenyl)-2'-(2,5-dimethoxypyridin-4-yl)-3'-isopropyl-3'H-spiro[dihydroindole-3,4'-pyrrolo[3,4-d]imidazole]-2,6'(5'H)-dione (S-40), and 28.2 mg of (R)-6-chloro-5'-(5-chloro-2-methylphenyl)-2'-(2,5-dimethoxypyridin-4-yl)-3'-isopropyl-3'H-spiro[dihydroindole-3,4'-pyrrolo[3,4-d]imidazole]-2,6'(5'H)-dione (R-40). MS (ESI): mass calcd. for $C_{29}H_{25}Cl_2N_5O_4$ 577.1, m/z found 578.3 [M+H]$^+$. $^1$H-NMR (400 MHz, DMSO-d$_6$) δ 11.62 (brs, 1H), 8.10 (s, 1H), 7.56-6.95 (m, 7H), 4.11-4.10 (m, 1H), 3.86 (s, 3H), 3.83 (s, 3H), 2.21 (s, 3H), 1.10 (d, 3H, J=6.4 Hz), 0.66 (d, 3H, J=6.4 Hz).

Example 41

6-chloro-5'-(5-chloro-2-methylphenyl)-3'-cyclobutyl-2'-(2,4-dimethoxypyrimidin-5-yl)-3'H-spiro[dihydroindole-3,4'-pyrrolo[3,4-d]imidazole]-2,6'(5'H)-dione

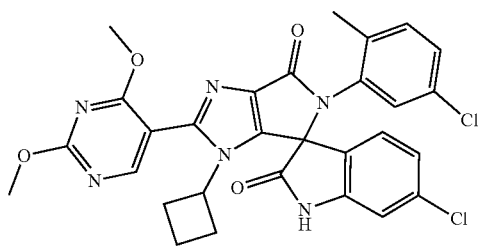 [SMILES: COc1ncc(-c2nc3c(n2C2CCC2)C2(C(=O)Nc4cc(Cl)ccc42)N(c2cc(Cl)ccc2C)C3=O)c(OC)n1]

Title compounds were obtained by steps similar to those in Example 1, and supercritical high-pressure preparative chromatography was performed to obtain 23.5 mg of (S)-6-chloro-5'-(5-chloro-2-methylphenyl)-3'-cyclobutyl-2'-(2,4-dimethoxypyrimidin-5-yl)-3'H-spiro[dihydroindole-3,4'-pyrrolo[3,4-d]imidazole]-2,6'(5'H)-dione (S-41), and 23.3 mg of (R)-6-chloro-5'-(5-chloro-2-methylphenyl)-3'-cyclobutyl-2'-(2,4-dimethoxypyrimidin-5-yl)-3'H-spiro[dihydroindole-3,4'-pyrrolo[3,4-d]imidazole]-2,6'(5'H)-dione (R-41). MS (ESI): mass calcd. for $C_{29}H_{24}Cl_2N_6O_4$ 590.1, m/z found 591.1 [M+H]$^+$. $^1$H-NMR (300 MHz, DMSO-$d_6$) δ 11.38 (brs, 1H), 8.49 (d, 1H, J=5.4 Hz), 7.56-7.47 (m, 1H), 7.45-6.45 (m, 5H), 4.47-4.43 (m, 1H), 3.98-3.94 (m, 6H), 2.21 (s, 3H), 2.01-1.71 (m, 3H), 1.61-1.31 (m, 2H), 1.30-1.29 (m, 1H).

Example 42

6-chloro-5'-(5-chloro-2-methylpyridin-3-yl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

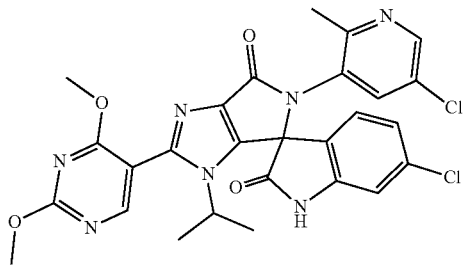 [SMILES: COc1ncc(-c2nc3c(n2C(C)C)C2(C(=O)Nc4cc(Cl)ccc42)N(c2cc(Cl)cnc2C)C3=O)c(OC)n1]

Title compounds were obtained by steps similar to those in Example 1, and supercritical high-pressure preparative chromatography was performed to obtain 8.3 mg of (S)-6-chloro-5'-(5-chloro-2-methylpyridin-3-yl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-42), and 8.9 mg of (R)-6-chloro-5'-(5-chloro-2-methylpyridin-3-yl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-42). MS (ESI): mass calcd. for $C_{27}H_{23}Cl_2N_7O_4$ 579.1, m/z found 580.1 [M+H]$^+$. $^1$H-NMR (400 MHz, DMSO-$d_6$) δ 8.53-8.46 (m, 2H), 7.61-6.96 (m, 4H), 4.17-4.13 (m, 1H), 3.98 (s, 3H), 3.94 (s, 3H), 2.40 (s, 1H), 0.84 (d, 3H, J=6.8 Hz), 0.66 (d, 3H, J=6.8 Hz).

Example 43

6-chloro-5'-(5-chloro-1-methyl-2-oxo-1,2-dihydropyridin-3-yl)-3'-isopropyl-2'-(2-methoxyphenyl)-3'H-spiro[dihydroindole-3,4'-pyrrolo[3,4-d]imidazole]-2,6'(5'H)-dione

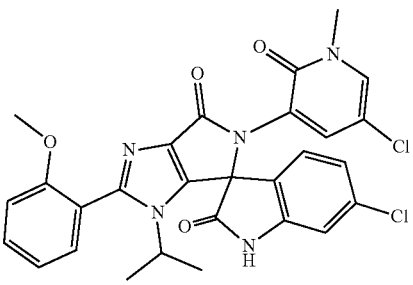 [SMILES: COc1ccccc1-c1nc2c(n1C(C)C)C1(C(=O)Nc3cc(Cl)ccc31)N(c1cc(Cl)cn(C)c1=O)C2=O]

Title compounds were obtained by steps similar to those in Example 1, and supercritical high-pressure preparative chromatography was performed to obtain 26.2 mg of (S)-6-chloro-5'-(5-chloro-1-methyl-2-oxo-1,2-dihydropyridin-3-yl)-3'-isopropyl-2'-(2-methoxyphenyl)-3'H-spiro[dihydroindole-3,4'-pyrrolo[3,4-d]imidazole]-2,6'(5'H)-dione (S-43), and 28.2 mg of (R)-6-chloro-5'-(5-chloro-1-methyl-2-oxo-1,2-dihydropyridin-3-yl)-3'-isopropyl-2'-(2-methoxyphenyl)-3'H-spiro[dihydroindole-3,4'-pyrrolo[3,4-d]imidazole]-2,6'(5'H)-dione (R-43). MS (ESI): mass calcd. for $C_{28}H_{23}Cl_2N_5O_4$ 563.1, m/z found 564.1 [M+H]$^+$. $^1$H-NMR (400 MHz, DMSO-$d_6$) δ 7.95 (d, 1H, J=2.4 Hz), 7.56 (t, 1H, J=7.2 Hz), 7.41 (d, 1H, J=7.2 Hz), 7.31 (d, 1H, J=2.4 Hz), 7.23-7.08 (m, 3H), 6.93 (s, 1H), 4.04-4.01 (m, 1H), 3.98 (s, 3H), 1.10 (d, 3H, J=5.4 Hz), 0.60 (d, 3H, J=5.4 Hz).

Example 44

6-chloro-5'-(5-chloro-2-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

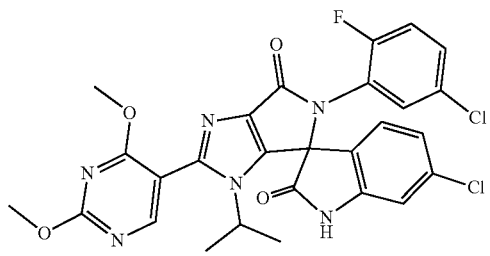 [SMILES: COc1ncc(-c2nc3c(n2C(C)C)C2(C(=O)Nc4cc(Cl)ccc42)N(c2cc(Cl)ccc2F)C3=O)c(OC)n1]

Title compounds were obtained by steps similar to those in Example 1, and supercritical high-pressure preparative chromatography was performed to obtain 15.4 mg of (S)-6-chloro-5'-(5-chloro-2-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-44), and 19.7 mg of (R)-6-chloro-5'-(5-chloro-2-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-44). MS (ESI): mass calcd. for $C_{27}H_{21}Cl_2FN_6O_4$ 582.1, m/z found 583.2 [M+H]$^+$. $^1$H-NMR (400 MHz, DMSO-d$_6$) δ 8.53 (s, 1H), 7.48-7.47 (m, 1H), 7.46-7.36 (m, 2H), 7.21-7.11 (m, 1H), 7.10-7.06 (m, 1H), 7.05-7.01 (m, 1H), 4.20-4.15 (m, 1H), 3.99 (s, 3H), 3.95 (s, 3H), 1.17 (d, 3H, J=6.8 Hz), 0.66 (d, 3H, J=6.8 Hz).

Example 45

6-chloro-5'-(3-chloro-5-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

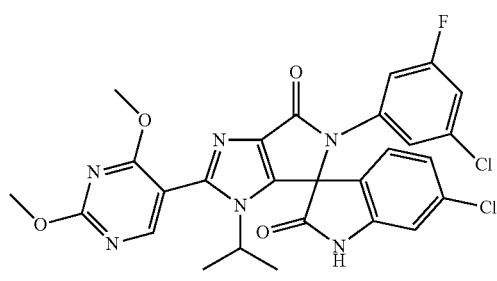 [SMILES: COc1ncc(-c2nc3c(n2C(C)C)C2(C(=O)Nc4cc(Cl)ccc42)N(c2cc(F)cc(Cl)c2)C3=O)c(OC)n1]

Title compounds were obtained by steps similar to those in Example 1, and supercritical high-pressure preparative chromatography was performed to obtain 28.1 mg of (S)-6-chloro-5'-(3-chloro-5-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-45), and 29.8 mg of (R)-6-chloro-5'-(3-chloro-5-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-45). MS (ESI): mass calcd. for $C_{27}H_{21}Cl_2FN_6O_4$ 582.1, m/z found 583.2 [M+H]$^+$. $^1$H-NMR (400 MHz, DMSO-d$_6$) δ 8.51 (s, 1H), 7.49-7.39 (m, 2H), 7.38-7.14 (m, 2H), 7.07-6.85 (m, 2H), 4.19-4.14 (m, 1H), 3.99 (s, 3H), 3.94 (s, 3H), 1.12 (d, 3H, J=6.8 Hz), 0.64 (d, 3H, J=6.8 Hz).

Example 46

6-chloro-5'-(5-chloro-2-methylphenyl)-3'-cyclopropyl-2'-(2,4-dimethoxypyrimidin-5-yl)-3'H-spiro[dihydroindole-3,4'-pyrrolo[3,4-d]imidazole]-2,6'(5'H)-dione

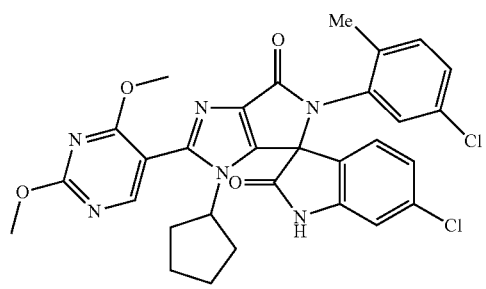 [SMILES: COc1ncc(-c2nc3c(n2C2CCCC2)C2(C(=O)Nc4cc(Cl)ccc42)N(c2cc(Cl)ccc2C)C3=O)c(OC)n1]

Title compounds were obtained by steps similar to those in Example 1, and supercritical high-pressure preparative chromatography was performed to obtain 5.0 mg of (S)-6-chloro-5'-(5-chloro-2-methylphenyl)-3'-cyclopropyl-2'-(2,4-dimethoxypyrimidin-5-yl)-3'H-spiro[dihydroindole-3,4'-pyrrolo[3,4-d]imidazole]-2,6'(5'H)-dione (S-46), and 10.5 mg of (R)-6-chloro-5'-(5-chloro-2-methylphenyl)-3'-cyclopropyl-2'-(2,4-dimethoxypyrimidin-5-yl)-3'H-spiro[dihydroindole-3,4'-pyrrolo[3,4-d]imidazole]-2,6'(5'H)-dione (R-46). MS (ESI): mass calcd. for $C_{30}H_{26}Cl_2N_6O_4$, 604.1 m/z found 605.1 [M+H]$^+$. $^1$H-NMR (400 MHz, DMSO-d$_6$) δ 8.51 (d, 1H, J=6.8 Hz), 7.50-6.48 (m, 7H), 4.32-4.27 (m, 1H), 3.99 (s, 3H), 3.95 (s, 3H), 2.21 (s, 3H), 1.92-1.91 (m, 1H), 1.69-1.67 (m, 1H), 1.37-1.23 (m, 4H), 0.91-0.80 (m, 2H).

Example 47

6-chloro-5'-(5-chloro-2-methylphenyl)-2'-(4-((dimethylamino)methyl)-2-methoxyphenyl)-3'-isopropyl-3'H-spiro[dihydroindole-3,4'-pyrrolo[3,4-d]imidazole]-2,6'(5'H)-dione

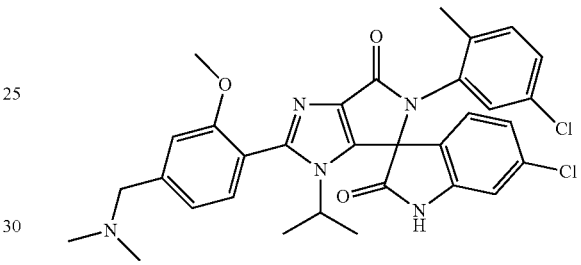

Title compounds were obtained by steps similar to those in Example 1, and supercritical high-pressure preparative chromatography was performed to obtain 9.7 mg of (S)-6-chloro-5'-(5-chloro-2-methylphenyl)-2'-(4-((dimethylamino)methyl)-2-methoxyphenyl)-3'-isopropyl-3'H-spiro[dihydroindole-3,4'-pyrrolo[3,4-d]imidazole]-2,6'(5'H)-dione (S-47), and 9.4 mg of (R)-6-chloro-5'-(5-chloro-2-methylphenyl)-2'-(4-((dimethylamino)methyl)-2-methoxyphenyl)-3'-isopropyl-3'H-spiro[dihydroindole-3,4'-pyrrolo[3,4-d]imidazole]-2,6'(5'H)-dione (R-47). MS (ESI): mass calcd. for $C_{32}H_{31}Cl_2N_5O_3$ 603.2, m/z found 604.4 [M+H]$^+$. $^1$H-NMR (400 MHz, DMSO-d$_6$) δ 7.42-6.73 (m, 9H), 4.07-3.98 (m, 1H), 3.77 (s, 3H), 2.14 (s, 6H), 2.08 (s, 2H), 1.08 (d, 3H, J=6.8 Hz), 0.63 (d, 3H, J=6.8 Hz).

Example 48

6-chloro-5'-(3-chloro-4-methoxyphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

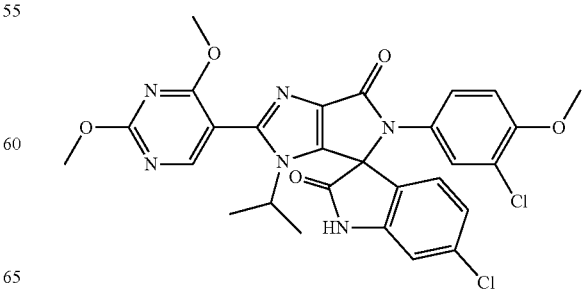

Title compounds were obtained by steps similar to those in Example 1, and supercritical high-pressure preparative chromatography was performed to obtain 32.4 mg of (S)-6-chloro-5'-(3-chloro-4-methoxyphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-48), and 34.4 mg of (R)-6-chloro-5'-(3-chloro-4-methoxyphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-48). MS (ESI): mass calcd. for $C_{28}H_{24}Cl_2N_6O_5$ 594.1, m/z found 595.1 [M+H]$^+$. $^1$H-NMR (400 MHz, DMSO-d$_6$) δ 11.57 (brs, 1H), 8.51 (s, 1H), 7.48 (d, 1H, J=8.0 Hz), 7.14-7.07 (m, 3H), 6.97-6.92 (m, 2H), 4.16-4.11 (m, 1H), 3.99 (s, 3H), 3.95 (s, 3H), 3.81 (s, 3H), 1.11 (d, 3H, J=6.4 Hz), 0.65 (d, 3H, J=6.4 Hz).

Example 49

2'-(4-amino-2-methoxyphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione

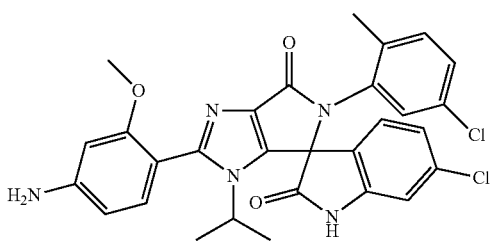 [SMILES: COc1cc(N)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 5.4 mg of (S)-2'-(4-amino-2-methoxyphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (S-49), and 17.1 mg of (R)-2'-(4-amino-2-methoxyphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (R-49). MS (ESI): mass calcd. for $C_{29}H_{25}Cl_2N_5O_3$, 561.1 m/z found 562.1 [M+H]$^+$. $^1$H-NMR (400 MHz, DMSO-d$_6$) δ 7.44-7.15 (m, 4H), 7.02-6.85 (m, 3H), 6.30 (s, 1H), 6.25 (d, 1H, J=8.0 Hz), 5.55 (brs, 2H), 4.24-4.06 (m, 1H), 3.67 (s, 3H), 2.22 (s, 3H), 1.06 (d, 1H, J=6.4 Hz), 0.61 (d, 1H, J=6.4 Hz).

Example 50

6-chloro-5'-(5-chloro-2-methylphenyl)-2'-(2,4-dimethoxypyrimidin-5-yl)-1'-isopropyl-1'H-spiro[dihydroindole-3,6'-pyrrolo[3,4-b]pyrrole]-2,4'(5'H)-dione

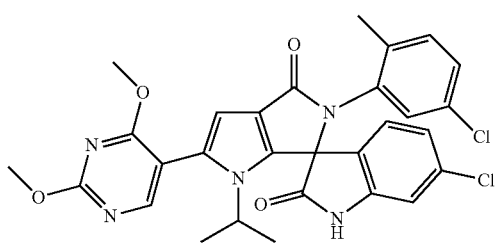 [SMILES: COc1ncc(-c2cc3c(n2C(C)C)C2(C(=O)Nc4cc(Cl)ccc42)N(c2cc(Cl)ccc2C)C3=O)c(OC)n1]

Step 1: Preparation of Methyl 1-isopropyl-1H-pyrrole-3-carboxylate

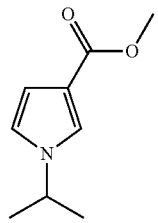

Under nitrogen atmosphere, methyl 1H-pyrrole-3-carboxylate (25 g, 0.1998 mol) and 30 mL of anhydrous tetrahydrofuran were added to a 500 mL three-necked flask, and cooled to 0° C., NaH (7.19 g, 0.2997 mol) was added in batches, and the resultant mixture was maintained at 0° C. to react for 30 min, slowly and dropwise added with 2-bromopropane (49.2 g, 0.3996 mol), then naturally warmed to room temperature, and reacted overnight. The temperature was reduced to 0° C., and 20 mL of water was added dropwise for quenching, the resultant was concentrated under reduced pressure, added with 500 mL of ethyl acetate, and washed with 500 mL of saturated sodium carbonate aqueous solution for three times. The organic layer was dried over anhydrous sodium sulfate, filtered, concentrated under vacuum, and separated by column chromatography (EA:PE=20% to 25%) to obtain 21.1 g of methyl 1-isopropyl-1H-pyrrole-3-carboxylate (yield 63.2%, yellow oil). MS (ESI): mass calcd. for $C_9H_{13}NO_2$ 167.1, m/z found 168.2 [M+H]$^+$.

Step 2 Preparation of Methyl 5-bromo-1-isopropyl-1H-pyrrole-3-carboxylate

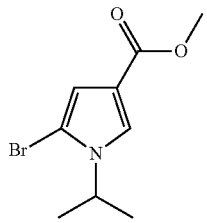

Under nitrogen atmosphere, methyl 1-isopropyl-1H-pyrrole-3-carboxylate (5.0 g, 0.02994 mol) and 30 mL of anhydrous tetrahydrofuran were added to a 100 mL three-necked flask, and cooled to 0° C., and NBS (5.06 g, 0.0284 mol) was added in batches, the resultant was naturally warmed to room temperature to react overnight, concentrated under vacuum, added with 50 mL of ethyl acetate, then washed with 50 mL of saturated sodium carbonate aqueous solution for three times, the organic layer was dried over anhydrous sodium sulfate, and separated by column chromatography (EA:PE=5% to 25%) to obtain 5.8 g of methyl 5-bromo-1-isopropyl-1H-pyrrole-3-carboxylate (93% yield, yellow oil). MS (ESI): mass calcd. for $C_9H_{12}BrNO_2$ 245.0, m/z found 246.1[M+H]$^+$.

Step 3: Preparation of Methyl 5-bromo-2-(6-chloro-3-hydroxy-2-oxoindolin-3-yl)-1-isopropyl-1H-pyrrole-3-carboxylate

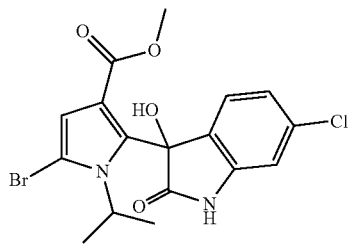 [SMILES: COC(=O)c1cc(Br)n(C(C)C)c1C1(O)C(=O)Nc2cc(Cl)ccc21]

Under nitrogen atmosphere, methyl 5-bromo-1-isopropyl-1H-pyrrole-3-carboxylate (4.8 g, 0.0196 mol) and 20 mL of anhydrous tetrahydrofuran were added to a 100 mL three-necked flask, and cooled to −78° C. LDA (39.2 ml, 2 M) was slowly added dropwise, and the resultant was maintained at −50° C. to react for 1.5 h after completion of the dropwise addition. Then 6-chloroindolin-2,3-dione (3.546 g, 19.6 mmol) was dissolved in 10 mL of anhydrous tetrahydrofuran, and slowly added dropwise into the reaction flask, the resultant was maintained at −50° C. to react for 1 h. 10 mL of saturated ammonium chloride aqueous solution was added dropwise to the reaction flask, the resultant was concentrated under vacuum, added with 100 mL of ethyl acetat and washed once with 50 mL of saturated sodium chloride aqueous solution. The organic layer was dried over anhydrous sodium sulfate, filtered, concentrated and separated by column chromatography (EA:PE=1:10 to 1:2) to obtain 1.2 g of methyl 5-bromo-2-(6-chloro-3-hydroxy-2-oxoindolin-3-yl)-1-isopropyl-1H-pyrrole-3-carboxylate (yield 20%, yellow solid). MS (ESI): mass calcd. For $C_{17}H_{16}BrClN_2O_4$ 426.0, m/z found 409.0 [M+H−18]$^+$.

Step 4: Preparation of 5-bromo-N-(5-chloro-2-methylphenyl)-2-(6-chloro-3-hydroxy-2-oxoindolin-3-yl)-1-isopropyl-1H-pyrrole-3-amide

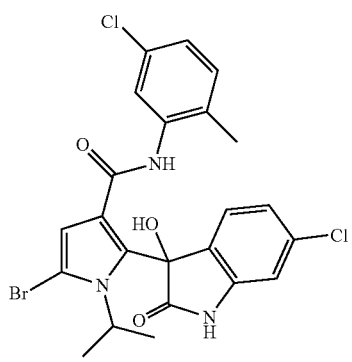 [SMILES: Cc1ccc(Cl)cc1NC(=O)c1cc(Br)n(C(C)C)c1C1(O)C(=O)Nc2cc(Cl)ccc21]

Under nitrogen atmosphere, 5-chloro-2-methylaniline (450 mg, 3.169 mmol) and anhydrous toluene (5 mL) were added to a 50 mL reaction flask, the temperature was reduced to 0° C., and AlMe$_3$ (1.826 g, 25% w/w) was slowly added. Then, methyl 5-bromo-2-(6-chloro-3-hydroxy-2-oxoindolin-3-yl)-1-isopropyl-1H-pyrrole-3-carboxylate (675 mg, 1.585 mmol) was dissolved in 5 mL of toluene, and slowly added dropwise into the reaction flask. The resultant mixture was warmed to 90° C. to react overnight, then cooled to room temperature, added with 20 mL of ice water and 15 mL of saturated aqueous solution of sodium potassium tartrate, then extracted with 50 mL of dichloromethane for two times. The organic phases were combined, washed once with 30 mL of saturated sodium chloride aqueous solution, dried over anhydrous sodium sulfate, filtered, concentrated, and separated by a preparative plate to obtain 795 mg of 5-bromo-N-(5-chloro-2-methylphenyl)-2-(6-chloro-3-hydroxy-2-oxoindolin-3-yl)-1-isopropyl-1H-pyrrole-3-amide (94% yield, yellow solid). MS (ESI): mass calcd. For $C_{23}H_{20}BrCl_2N_3O_3$ 535.0, m/z found 518.0 [M+H−18]$^+$.

Step 5: Preparation of 2'-bromo-6-chloro-5'-(5-chloro-2-methylphenyl)-1'-isopropyl-1'H-spiro[dihydroindole-3,6'-pyrrolo[3,4-b]pyrrole]-2,4'(5'H)-dione

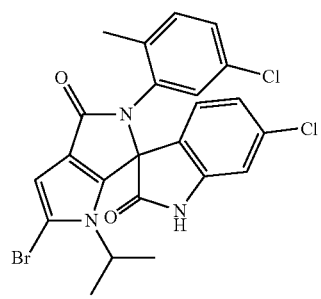 [SMILES: Cc1ccc(Cl)cc1N1C(=O)c2cc(Br)n(C(C)C)c2C12C(=O)Nc1cc(Cl)ccc12]

5-bromo-N-(5-chloro-2-methylphenyl)-2-(6-chloro-3-hydroxy-2-oxoindolin-3-yl)-1-isopropyl-1H-pyrrole-3-amide (1155 mg, 2.155 mmol), H$_2$SO$_4$ (2.112 g, 21.55 mmol) and acetic acid (10 mL) were added to a 50 mL reaction flask, and the temperature was raised to 110° C. for overnight reaction, then the temperature was naturally lowered to room temperature, and 20 mL of ice water was added. The pH value was adjusted to about 7 with saturated sodium carbonate aqueous solution, and the resultant was extracted with 50 mL of dichloromethane for two times. The organic layers were combined, washed once with 20 mL of saturated sodium chloride aqueous solution, dried over anhydrous sodium sulfate, filtered, concentrated, and separated by column chromatography (EA:PE=25%) to obtain 150 mg of 2'-bromo-6-chloro-5'-(5-chloro-2-methylphenyl)-1'-isopropyl-1'H-spiro[dihydroindole-3,6'-pyrrolo[3,4-b]pyrrole]-2,4'(5'H)-dione (13.5% yield, yellow solid). MS (ESI): mass calcd. for $C_{23}HisBrC_2N_{32}$ 517.0, m/z found 518.0 [M+H]$^+$.

Step 6: Preparation of 6-chloro-5'-(5-chloro-2-methylphenyl)-2'-(2,4-dimethoxypyrimidin-5-yl)-1'-isopropyl-1'H-spiro[dihydroindole-3,6'-pyrrolo[3,4-b]pyrrole]-2,4'(5'H)-dione

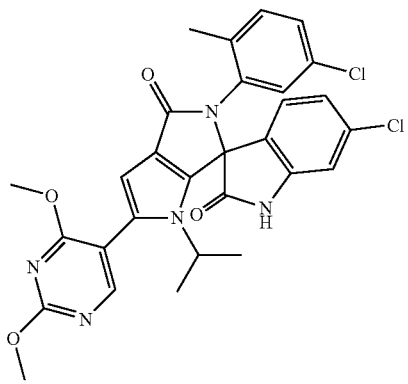 [SMILES: COc1ncc(-c2cc3c(n2C(C)C)C2(C(=O)Nc4cc(Cl)ccc42)N(c2cc(Cl)ccc2C)C3=O)c(OC)n1]

Under nitrogen atmosphere, 2'-bromo-6-chloro-5'-(5-chloro-2-methylphenyl)-1'-isopropyl-1'H-spiro[dihydroindole-3,6'-pyrrolo[3,4-b]pyrrole]-2,4'(5'H)-dione (100 mg, 0.1934 mmol), (2,4-dimethoxypyrimidin-5-yl)boronic acid (36 mg, 0.1934 mmol), Pd(PPh$_3$)$_4$ (45 mg, 0.0387 mmol), Na$_2$CO$_3$ (62 mg, 0.5802 mmol), dioxane (4 mL) and H$_2$O (1 ml) were added into a microwave reaction flask, and the temperature was raised to 100° C. to perform a microwave reaction for 1 h. The resultant was cooled to room temperature, filtered, added with 10 mL of water, and extracted with 10 mL of dichloromethane for three times. The organic layers were combined, washed once with 10 mL of saturated sodium chloride aqueous solution, dried over anhydrous sodium sulfate, filtered, concentrated, and separated by a preparative plate, and then subjected to supercritical high-pressure preparative liquid phase separation to obtain 6.2 mg of (S)-6-chloro-5'-(5-chloro-2-methylphenyl)-2'-(2,4-dimethoxypyrimidin-5-yl)-1'-isopropyl-1'H-spiro[dihydroindole-3,6'-pyrrolo[3,4-b]pyrrole]-2,4'(5'H)-dione (S-50); and 7.8 mg of (R)-6-chloro-5'-(5-chloro-2-methylphenyl)-2'-(2,4-dimethoxypyrimidin-5-yl)-1'-isopropyl-1'H-spiro[dihydroindole-3,6'-pyrrolo[3,4-b]pyrrole]-2,4'(5'H)-dione (R-50). MS (ESI): mass calcd. for C$_{29}$H$_{25}$Cl$_2$N$_5$O$_4$ 577.1, m/z found 578.1 [M+H]$^+$. $^1$H-NMR (400 MHz, DMSO-d$_6$) δ 9.51 (d, 1H, J=8.0 Hz), 7.62-6.55 (m, 8H), 4.07 (s, 3H), 3.94 (s, 3H), 3.62-3.48 (m, 1H), 2.25 (s, 3H), 1.29 (d, 3H, J=6.4 Hz), 1.09 (d, 3H, J=6.4 Hz).

Example 51

6-chloro-5'-(3-chloro-5-methylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

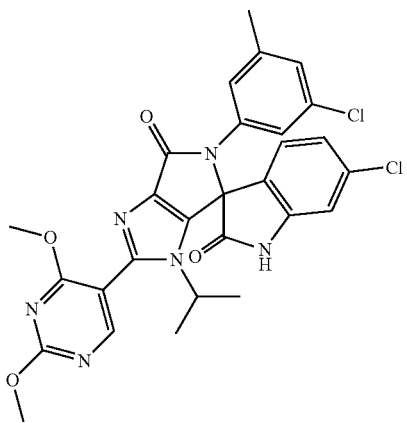 [SMILES: COc1ncc(-c2nc3c(n2C(C)C)C2(C(=O)Nc4cc(Cl)ccc42)N(c2cc(C)cc(Cl)c2)C3=O)c(OC)n1]

Title compounds were obtained by steps similar to those described in Example 1, and supercritical high-pressure preparative chromatography was performed to obtain 18.9 mg of (S)-6-chloro-5'-(3-chloro-5-methylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-51), and 18.4 mg of (R)-6-chloro-5'-(3-chloro-5-methylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-51). MS (ESI): mass calcd. for: C$_{28}$H$_{24}$Cl$_2$N$_6$O$_4$, 579.4 m/z found 580.2 [M+H]$^+$. $^1$H-NMR (400 MHz, DMSO-d$_6$) δ 11.60 (brs, 1H), 8.51 (s, 1H), 7.46 (d, 1H, J=8.0 Hz), 7.18-7.13 (m, 2H), 7.02 (s, 1H), 6.89 (s, 1H), 6.80 (s, 1H), 4.18-4.11 (m, 1H), 3.99 (s, 3H), 3.94 (s, 3H), 2.20 (s, 3H), 1.12 (d, 3H, J=6.8 Hz), 0.64 (d, 3H, J=6.8 Hz).

Example 52

6-chloro-5'-(5-chloro-1-methyl-6-oxo-1,6-dihydropyridin-3-yl)-2'-(2,4-dimethoxyphenyl)-3'-isopropyl-3'H-spiro[dihydroindole-3,4'-pyrrolo[3,4-d]imidazole]-2,6'(5'H)-dione

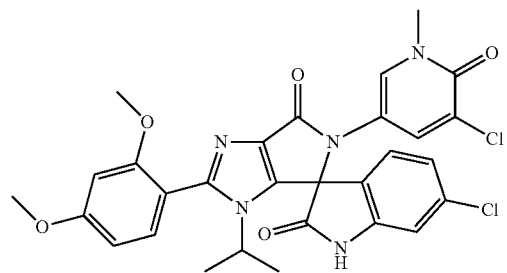 [SMILES: COc1ccc(-c2nc3c(n2C(C)C)C2(C(=O)Nc4cc(Cl)ccc42)N(c2cc(Cl)c(=O)n(C)c2)C3=O)c(OC)c1]

Title compounds were obtained by steps similar to those in Example 1, and supercritical high-pressure preparative chromatography was performed to obtain 17.2 mg of (S)-6-chloro-5'-(5-chloro-1-methyl-6-oxo-1,6-dihydropyridin-3-yl)-2'-(2,4-dimethoxyphenyl)-3'-isopropyl-3'H-spiro[dihydroindole-3,4'-pyrrolo[3,4-d]imidazole]-2,6'(5'H)-dione (S-52), and 14.7 mg of (R)-6-chloro-5'-(5-chloro-1-methyl-6-oxo-1,6-dihydropyridin-3-yl)-2'-(2,4-dimethoxyphenyl)-3'-isopropyl-3'H-spiro[dihydroindole-3,4'-pyrrolo[3,4-d]imidazole]-2,6'(5'H)-dione (R-52). MS (ESI): mass calcd. for C$_{29}$H$_{25}$Cl$_2$N$_5$O$_5$ 593.1, m/z found 594.3[M+H]$^+$. $^1$H-NMR (400 MHz, DMSO-d$_6$) δ 11.51 (s, 1H), 7.55-7.51 (m, 2H), 7.49-7.27 (m, 2H), 7.18-7.14 (m, 1H), 7.02 (s, 1H), 6.71-6.66 (m, 2H), 4.07-4.02 (m, 1H), 3.84 (s, 3H), 3.77 (s, 3H), 3.32 (s, 3H), 1.07 (d, 3H, J=6.8 Hz), 0.62 (d, 3H, J=6.8 Hz).

Example 53

6-chloro-5'-(5-chloro-1-methyl-6-oxo-1,6-dihydropyridin-3-yl)-3'-isopropyl-2'-(2-methoxyphenyl)-3'H-spiro[dihydroindole-3,4'-pyrrolo[3,4-d]imidazole]-2,6'(5'H)-dione

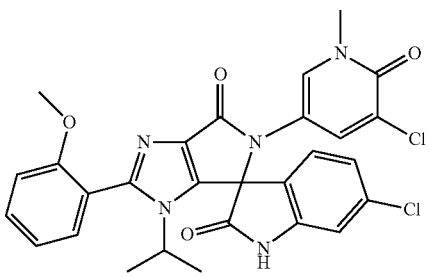 [SMILES: COc1ccccc1-c1nc2c(n1C(C)C)C1(C(=O)Nc3cc(Cl)ccc31)N(c1cc(Cl)c(=O)n(C)c1)C2=O]

Title compounds were obtained by steps similar to those in Example 1, and supercritical high-pressure preparative chromatography was performed to obtain 18.3 mg of (S)-6-chloro-5'-(5-chloro-1-methyl-6-oxo-1,6-dihydropyridin-3-yl)-3'-isopropyl-2'-(2-methoxyphenyl)-3'H-spiro[dihydroindole-3,4'-pyrrolo[3,4-d]imidazole]-2,6'(5'H)-dione (S-53), and 18.2 mg of (R)-6-chloro-5'-(5-chloro-1-methyl-6-oxo-1,6-dihydropyridin-3-yl)-3'-isopropyl-2'-(2-methoxyphenyl)-3'H-spiro[dihydroindole-3,4'-pyrrolo[3,4-d]imidazole]-2,6'(5'H)-dione (R-53). MS (ESI): mass calcd. for $C_{28}H_{23}Cl_2N_5O_4$ 564.1, m/z found 565.3[M+H]$^+$. $^1$H-NMR (400 MHz, DMSO-d$_6$) δ 11.49 (brs, 1H), 7.57-7.52 (m, 3H), 7.52-7.48 (m, 2H), 7.21-7.19 (m, 2H), 7.16-7.12 (m, 1H), 7.10-7.02 (m, 1H), 4.07-4.02 (m, 1H), 3.78 (s, 3H), 3.49 (s, 3H), 1.08 (d, 3H, J=6.8 Hz), 0.62 (d, 3H, J=6.8 Hz).

Example 54

4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxy-N-methylbenzamide

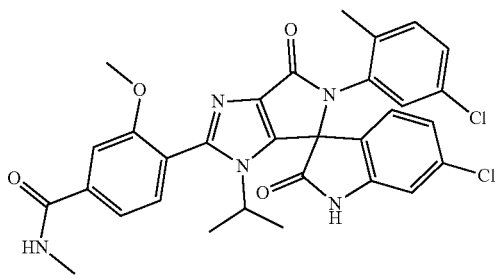 [SMILES: CNC(=O)c1ccc(-c2nc3c(n2C(C)C)C2(C(=O)Nc4cc(Cl)ccc42)N(c2cc(Cl)ccc2C)C3=O)c(OC)c1]

Title compounds were obtained by steps similar to those in Example 1, and supercritical high-pressure preparative chromatography was performed to obtain 7.5 mg of (S)-4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxy-N-methylbenzamide (S-54), and 8.8 mg of (R)-4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxy-N-methylbenzamide (R-54). MS (ESI): mass calcd. for $C_{31}H_{27}Cl_2N_5O_4$, 603.1 m/z found 604.1 [M+H]$^+$. $^1$H-NMR (400 MHz, DMSO-d$_6$) δ 8.59 (d, 1H, J=4.4 Hz), 7.59-6.94 (m, 9H), 4.08-4.04 (m, 1H), 3.85 (s, 3H), 2.83 (d, 3H, J=4.4 Hz), 2.23 (s, 3H), 1.08 (d, 3H, J=5.2 Hz). 0.64 (d, 3H, J=5.2 Hz).

Example 55

6-chloro-2'-(2,4-dimethoxypyrimidin-5-yl)-3'-isopropyl-5'-(m-tolyl)-3'H-spiro[dihydroindole-3,4'-pyrrolo[3,4-d]imidazole]-2,6'(5'H)-dione

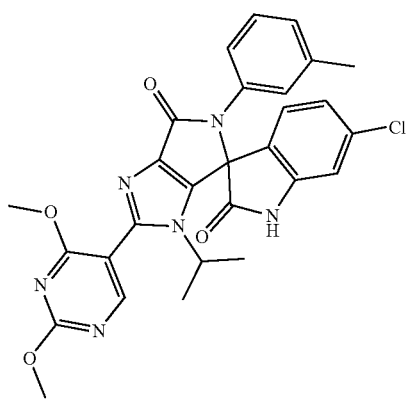 [SMILES: COc1ncc(-c2nc3c(n2C(C)C)C2(C(=O)Nc4cc(Cl)ccc42)N(c2cccc(C)c2)C3=O)c(OC)n1]

Title compounds were obtained by steps similar to those in Example 1, and supercritical high-pressure preparative chromatography was performed to obtain 52.7 mg of (S)-6-chloro-2'-(2,4-dimethoxypyrimidin-5-yl)-3'-isopropyl-5'-(m-tolyl)-3'H-spiro[dihydroindole-3,4'-pyrrolo[3,4-d]imidazole]-2,6'(5'H)-dione (S-55), and 58.7 mg of (R)-6-chloro-2'-(2,4-dimethoxypyrimidin-5-yl)-3'-isopropyl-5'-(m-tolyl)-3'H-spiro[dihydroindole-3,4'-pyrrolo[3,4-d]imidazole]-2,6'(5'H)-dione (R-55). MS (ESI): mass calcd. for $C_{28}H_{25}Cl_1N_6O_4$ 544.2, m/z found 545.2 [M+H]$^+$. $^1$H-NMR (400 MHz, DMSO-d$_6$) δ 8.51 (s, 1H), 7.42 (d, 1H, J=8.0 Hz), 7.20-6.99 (m, 3H), 6.96 (s, 1H), 6.84 (s, 1H), 6.97 (d, 1H, J=8.0 Hz), 4.18-4.11 (m, 1H), 3.99 (s, 3H), 3.95 (s, 3H), 2.20 (s, 3H), 1.10 (d, 3H, J=6.8 Hz), 0.65 (d, 3H, J=6.8 Hz).

Example 56

6-chloro-2'-(2,4-dimethoxypyrimidin-5-yl)-5'-(2,5-dimethylphenyl)-3'-isopropyl-3'H-spiro[dihydroindole-3,4'-pyrrolo[3,4-d]imidazole]-2,6'(5'H)-dione

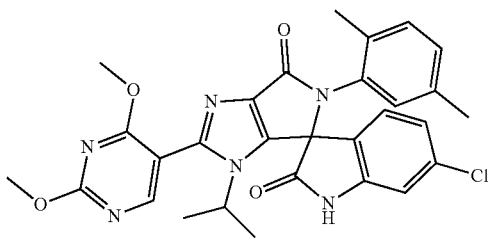 [SMILES: COc1ncc(-c2nc3c(n2C(C)C)C2(C(=O)Nc4cc(Cl)ccc42)N(c2cc(C)ccc2C)C3=O)c(OC)n1]

Title compounds were obtained by steps similar to those in Example 1, and supercritical high-pressure preparative chromatography was performed to obtain 42.4 mg of (S)-6-chloro-2'-(2,4-dimethoxypyrimidin-5-yl)-5'-(2,5-dimethylphenyl)-3'-isopropyl-3'H-spiro[dihydroindole-3,4'-pyrrolo[3,4-d]imidazole]-2,6'(5'H)-dione (S-56), and 48.7 mg of (R)-6-chloro-2'-(2,4-dimethoxypyrimidin-5-yl)-5'-(2,5-dimethylphenyl)-3'-isopropyl-3'H-spiro[dihydroindole-3,4'-pyrrolo[3,4-d]imidazole]-2,6'(5'H)-dione (R-56). MS (ESI): mass calcd. for $C_{29}H_{27}ClN_6O_4$ 558.1, m/z found 559.3 [M+H]$^+$. $^1$H-NMR (400 MHz, DMSO-d$_6$) δ 11.54 (brs, 1H), 8.54 (d, 1H, J=7.6 Hz), 7.62-7.37 (m, 1H), 7.25-7.23 (m, 1H), 7.06-6.93 (m, 4H), 4.16-4.13 (m, 1H), 3.99 (s, 3H), 3.96 (s, 3H), 2.22 (s, 3H), 2.03 (s, 3H), 1.09 (d, 3H, J=6.8 Hz), 0.64 (d, 3H, J=6.8 Hz).

Example 57

6-chloro-5'-(5-chloro-2-methylphenyl)-2'-(2-fluoro-6-methoxyphenyl)-3'-isopropyl-3'H-spiro[dihydroindole-3,4'-pyrrolo[3,4-d]imidazole]-2,6'(5'H)-dione

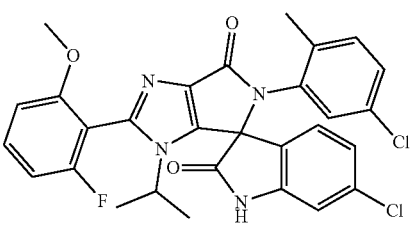

Title compounds were obtained by steps similar to those in Example 1, and supercritical high-pressure preparative chromatography was performed to obtain 19.9 mg of (S)-6-chloro-5'-(5-chloro-2-methylphenyl)-2'-(2-fluoro-6-methoxyphenyl)-3'-isopropyl-3'H-spiro[dihydroindole-3,4'-pyrrolo[3,4-d]imidazole]-2,6'(5'H)-dione (S-57), and 17.9 mg of (R)-6-chloro-5'-(5-chloro-2-methylphenyl)-2'-(2-fluoro-6-methoxyphenyl)-3'-isopropyl-3'H-spiro[dihydroindole-3,4'-pyrrolo[3,4-d]imidazole]-2,6'(5'H)-dione (R-57). MS (ESI): mass calcd. for $C_{29}H_{23}Cl_2FN_4O_3$ 564.1, m/z found 565.1[M+H]$^+$. $^1$H-NMR (300 MHz, DMSO-d$_6$) δ 11.12 (brs, 1H), 7.62-6.97 (m, 9H), 4.01-3.98 (m, 1H), 3.82 (s, 3H), 2.23 (s, 3H), 1.07-1.02 (m, 3H), 0.70-0.63 (m, 3H).

Example 58

6-chloro-5'-(3-chloro-5-methoxyphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

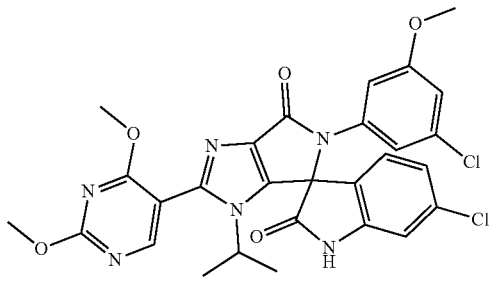 [SMILES: COc1cc(Cl)cc(N2C(=O)c3nc(-c4cnc(OC)nc4OC)n(C(C)C)c3C23C(=O)Nc2cc(Cl)ccc23)c1]

Title compounds were obtained by steps similar to those in Example 1, and supercritical high-pressure preparative chromatography was performed to obtain 26.3 mg of (S)-6-chloro-5'-(3-chloro-5-methoxyphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-58), and 29.9 mg of (R)-6-chloro-5'-(3-chloro-5-methoxyphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-58). MS (ESI): mass calcd. for $C_{28}H_{24}Cl_2N_6O_5$ 594.1, m/z found 595.1 [M+H]$^+$. $^1$H-NMR (400 MHz, DMSO-d$_6$) δ 11.65 (brs, 1H), 8.51 (s, 1H), 7.47 (d, 1H, J=8.4 Hz), 7.16 (d, 1H, J=8.0 Hz), 7.05 (d, 1H, J=1.6 Hz), 6.95 (s, 1H), 6.72 (s, 1H), 6.52 (s, 1H), 4.16-4.13 (m, 1H), 3.99 (s, 3H), 3.94 (s, 3H), 3.67 (s, 3H), 1.12 (d, 3H, J=6.4 Hz), 0.64 (d, 3H, J=6.4 Hz).

Example 59

6-chloro-5'-(3-chloro-4-fluorophenyl)-3'-isopropyl-2'-(4-methoxypyridin-3-yl)-3'H-spiro[dihydroindole-3,4'-pyrrolo[3,4-d]imidazole]-2,6'(5'H)-dione

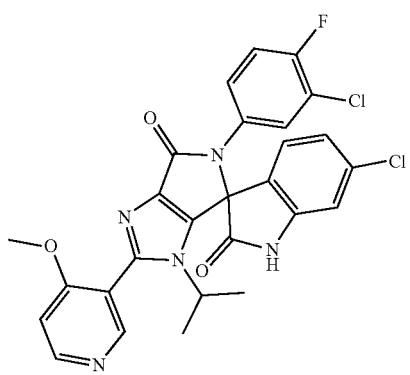 [SMILES: COc1ccncc1-c1nc2c(n1C(C)C)C1(C(=O)Nc3cc(Cl)ccc31)N(c1ccc(F)c(Cl)c1)C2=O]

Title compounds were obtained by steps similar to those in Example 1, and supercritical high-pressure preparative chromatography was performed to obtain 17.9 mg of (S)-6-chloro-5'-(3-chloro-4-fluorophenyl)-3'-isopropyl-2'-(4-methoxypyridin-3-yl)-3'H-spiro[dihydroindole-3,4'-pyrrolo[3,4-d]imidazole]-2,6'(5'H)-dione (S-59), and 22.5 mg of (R)-6-chloro-5'-(3-chloro-4-fluorophenyl)-3'-isopropyl-2'-(4-methoxypyridin-3-yl)-3'H-spiro[dihydroindole-3,4'-pyrrolo[3,4-d]imidazole]-2,6'(5'H)-dione (R-59). MS (ESI): mass calcd. for: $C_{27}H_{20}Cl_2FN_5O_3$ 551.1 m/z found 552.1 [M+H]$^+$. $^1$H-NMR (400 MHz, DMSO-d$_6$) δ 8.64 (d, 1H, J=6.4 Hz), 8.48 (brs, 1H), 7.54 (d, 1H, J=8.0 Hz), 7.44-7.42 (m, 1H), 7.40-7.14 (m, 4H), 7.08-6.97 (m, 2H), 4.09-4.03 (m, 1H), 3.88 (s, 3H), 1.11 (d, 3H, J=6.4 Hz), 0.64 (d, 3H, J=6.4 Hz).

Example 60

2-chloro-4-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzamide

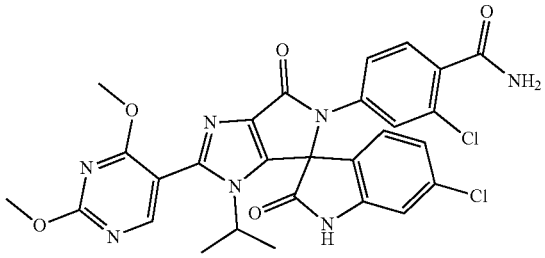 [SMILES: COc1ncc(-c2nc3c(n2C(C)C)C2(C(=O)Nc4cc(Cl)ccc42)N(c2ccc(C(N)=O)c(Cl)c2)C3=O)c(OC)n1]

Title compounds were obtained by steps similar to those in Example 1, and supercritical high-pressure preparative chromatography was performed to obtain 14.0 mg of (S)-2-chloro-4-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzamide (S-60), and 16.3 mg of (R)-2-chloro-4-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzamide (R-60). MS (ESI): mass calcd. for $C_{28}H_{23}Cl_2N_7O_5$ 607.1, m/z found 608.1 [M+H]$^+$. H-NMR (400 MHz, DMSO-d$_6$) δ 11.69 (brs, 1H), 8.51 (s, 1H), 7.91 (s, 1H), 7.59 (s, 1H), 7.50 (d, 1H, J=7.2 Hz), 7.40 (d, 1H, J=8.0 Hz), 7.16-7.14 (m, 2H), 7.06-6.99 (m, 2H), 4.17-4.14 (m, 1H), 3.99 (s, 3H), 3.95 (s, 3H), 1.13 (d, 3H, J=6.4 Hz), 0.63 (d, 3H, J=6.4 Hz).

Example 61

6-chloro-5'-(5-chloro-2-methylpyridin-3-yl)-2'-(2,4-dimethoxyphenyl)-3'-isopropyl-3'H-spiro[dihydroindole-3,4'-pyrrolo[3,4-d]imidazole]-2,6'(5'H)-dione

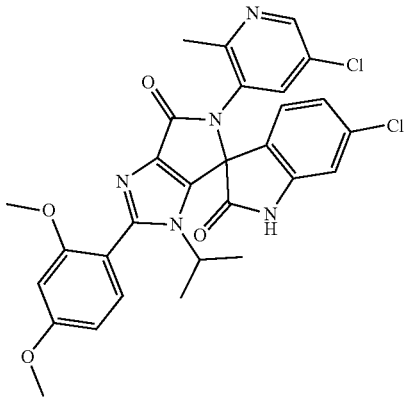 [SMILES: COc1ccc(-c2nc3c(n2C(C)C)C2(C(=O)Nc4cc(Cl)ccc42)N(c2cc(Cl)cnc2C)C3=O)c(OC)c1]

Title compounds were obtained by steps similar to those in Example 1, and supercritical high-pressure preparative chromatography was performed to obtain 29.9 mg of (S)-6-chloro-5'-(5-chloro-2-methylpyridin-3-yl)-2'-(2,4-dimethoxyphenyl)-3'-isopropyl-3'H-spiro[dihydroindole-3,4'-pyrrolo[3,4-d]imidazole]-2,6'(5'H)-dione (S-61), and 26.3 mg of (R)-6-chloro-5'-(5-chloro-2-methylpyridin-3-yl)-2'-(2,4-dimethoxyphenyl)-3'-isopropyl-3'H-spiro[dihydroindole-3,4'-pyrrolo[3,4-d]imidazole]-2,6'(5'H)-dione (R-61). MS (ESI): mass calcd. for C$_{29}$H$_{25}$Cl$_2$N$_5$O$_4$ 577.1, m/z found 578.1 [M+H]$^+$. $^1$H-NMR (400 MHz, DMSO-d$_6$) δ 11.49 (s, 1H), 8.50 (d, 1H, J=8.4 Hz), 7.62 (d, 1H, J=8.4 Hz), 7.54 (d, 1H, J=9.2 Hz), 7.36-7.33 (m, 1H), 7.27 (d, 1H, J=8.0 Hz), 7.04-7.00 (m, 1H), 6.73-6.79 (m, 2H), 4.10 (t, 1H, J=6.8 Hz), 3.84 (s, 3H), 3.79 (s, 3H), 2.42-2.27 (m, 3H), 1.07 (d, 3H, J=4.8 Hz), 0.638 (d, 3H, J=4.8 Hz).

Example 62

6-chloro-5'-(5-chloro-2-methylphenyl)-3'-isopropyl-2'-(2-methoxy-5-methylphenyl)-3'H-spiro[dihydroindole-3,4'-pyrrolo[3,4-d]imidazole]-2,6'(5'H)-dione

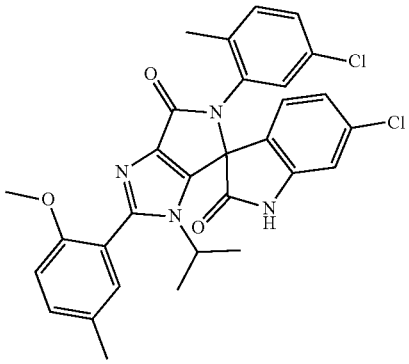 [SMILES: COc1ccc(C)cc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 40.0 mg of (S)-6-chloro-5'-(5-chloro-2-methylphenyl)-3'-isopropyl-2'-(2-methoxy-5-methylphenyl)-3'H-spiro[dihydroindole-3,4'-pyrrolo[3,4-d]imidazole]-2,6'(5'H)-dione (S-62), and 44.0 mg of (R)-6-chloro-5'-(5-chloro-2-methylphenyl)-3'-isopropyl-2'-(2-methoxy-5-methylphenyl)-3'H-spiro[dihydroindole-3,4'-pyrrolo[3,4-d]imidazole]-2,6'(5'H)-dione (R-62). MS (ESI): mass calcd. for C$_{30}$H$_{26}$Cl$_2$N$_4$O$_3$, 560.1 m/z found 561.1 [M+H]$^+$. $^1$H-NMR (400 MHz, DMSO-d$_6$) δ 11.72 (brs, 1H), 7.55-6.97 (m, 10H), 4.09-4.05 (m, 1H), 3.75 (s, 3H), 2.30 (s, 3H), 2.22 (s, 3H), 1.07 (d, 3H, J=5.6 Hz), 0.63 (d, 3H, J=5.6 Hz).

Example 63

6-chloro-5'-(3-chloro-4-methoxyphenyl)-3'-isopropyl-2'-(2-methoxyphenyl)-3'H-spiro[dihydroindole-3,4'-pyrrolo[3,4-d]imidazole]-2,6'(5'H)-dione

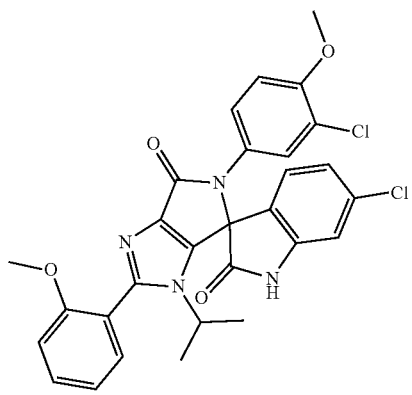 [SMILES: COc1ccc(N2C(=O)c3nc(-c4ccccc4OC)n(C(C)C)c3C23C(=O)Nc2cc(Cl)ccc23)cc1Cl]

Title compounds were obtained by steps similar to those in Example 1, and supercritical high-pressure preparative chromatography was performed to obtain 22.9 mg of (S)-6-chloro-5'-(3-chloro-4-methoxyphenyl)-3'-isopropyl-2'-(2-methoxyphenyl)-3'H-spiro[dihydroindole-3,4'-pyrrolo[3,4-d]imidazole]-2,6'(5'H)-dione (S-63), and 22.9 mg of (R)-6-chloro-5'-(3-chloro-4-methoxyphenyl)-3'-isopropyl-2'-(2-methoxyphenyl)-3'H-spiro[dihydroindole-3,4'-pyrrolo[3,4-d]imidazole]-2,6'(5'H)-dione (R-63). MS (ESI): mass calcd. for C$_{29}$H$_{24}$Cl$_2$N$_4$O$_4$, 563.4 m/z found 564.1 [M+H]$^+$. $^1$H-NMR (400 MHz, DMSO-d$_6$) δ 7.57-6.91 (m, 10H), 4.08-4.00 (m, 1H), 3.81 (s, 3H), 3.78 (s, 3H), 1.08 (m, 3H), 0.75-0.70 (m, 3H).

Example 64

6-chloro-5'-(5-chloro-2-methylphenyl)-3'-isopropyl-2'-(4-methoxyphenyl)-3'H-spiro[dihydroindole-3,4'-pyrrolo[3,4-d]imidazole]-2,6'(5'H)-dione

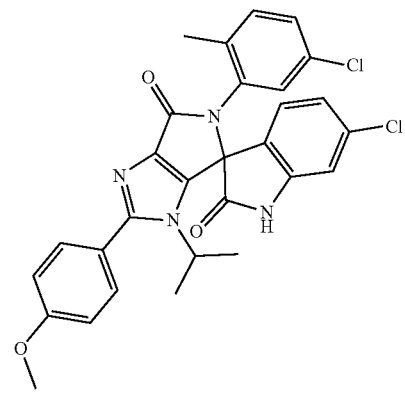 [SMILES: COc1ccc(-c2nc3c(n2C(C)C)C2(C(=O)Nc4cc(Cl)ccc42)N(c2cc(Cl)ccc2C)C3=O)cc1]

Title compounds were obtained by steps similar to those in Example 1, and supercritical high-pressure preparative chromatography was performed to obtain 73.9 mg of (S)-6-chloro-5'-(5-chloro-2-methylphenyl)-3'-isopropyl-2'-(4-methoxyphenyl)-3'H-spiro[dihydroindole-3,4'-pyrrolo[3,4-d]imidazole]-2,6'(5'H)-dione (S-64), and 79.7 mg of (R)-6-chloro-5'-(5-chloro-2-methylphenyl)-3'-isopropyl-2'-(4-methoxyphenyl)-3'H-spiro[dihydroindole-3,4'-pyrrolo[3,4-d]imidazole]-2,6'(5'H)-dione (R-64). MS (ESI): mass calcd. for $C_{29}H_{24}Cl_2N_4O_3$ 546.1, m/z found 547.1 [M+H]$^+$. $^1$H-NMR (400 MHz, DMSO-d$_6$) δ 11.73 (brs, 1H), 7.58-6.45 (m, 10H), 4.46-4.43 (m, 1H), 3.83 (s, 3H), 2.21 (s, 3H), 1.11-1.09 (d, 3H, J=6.4 Hz), 0.75 (d, 3H, J=6.4 Hz).

Example 65

2-chloro-4-(6-chloro-2'-(4,6-dimethoxypyridin-3-yl)-3'-isopropyl-2,6'-dioxo-3',6'-dihydro-5'H-spiro[dihydroindole-3,4'-pyrrolo[3,4-d]imidazole]-5'-yl)benzamide

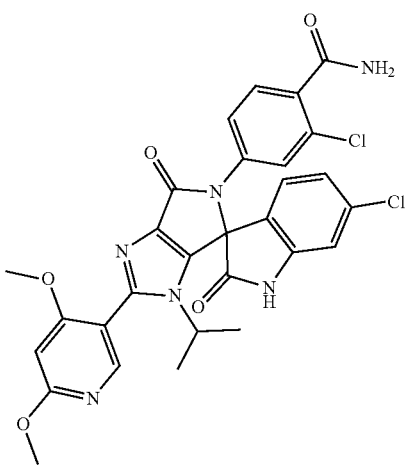 [SMILES: COc1cc(OC)c(-c2nc3c(n2C(C)C)C2(C(=O)Nc4cc(Cl)ccc42)N(c2ccc(C(N)=O)c(Cl)c2)C3=O)cn1]

Title compounds were obtained by steps similar to those in Example 1, and supercritical high-pressure preparative chromatography was performed to obtain 7.3 mg of (S)-2-chloro-4-(6-chloro-2'-(4,6-dimethoxypyridin-3-yl)-3'-isopropyl-2,6'-dioxo-3',6'-dihydro-5'H-spiro[dihydroindole-3,4'-pyrrolo[3,4-d]imidazole]-5'-yl)benzamide (S-65), and 10.3 mg of (R)-2-chloro-4-(6-chloro-2'-(4,6-dimethoxypyridin-3-yl)-3'-isopropyl-2,6'-dioxo-3',6'-dihydro-5'H-spiro[dihydroindole-3,4'-pyrrolo[3,4-d]imidazole]-5'-yl)benzamide (R-65). MS (ESI): mass calcd. for $C_{29}H_{24}Cl_2N_6O_5$ 606.1, m/z found 607.1 [M+H]$^+$. $^1$H-NMR (400 MHz, DMSO-d$_6$) δ 11.63 (brs, 1H), 8.11 (s, 1H), 7.91 (s, 1H), 7.59 (s, 1H), 7.51 (d, 1H, J=8.0 Hz), 7.41 (d, 1H, J=8.4 Hz), 7.16-7.14 (m, 2H), 7.04-7.01 (m, 1H), 7.01-6.99 (m, 1H), 6.59 (s, 1H), 4.07-4.03 (m, 1H), 3.91 (s, 3H), 3.83 (s, 3H), 1.11 (d, 3H, J=6.0 Hz), 0.61 (d, 3H, J=6.0 Hz).

Example 66

2'-(4-amino-2-methoxyphenyl)-6-chloro-5'-(5-chloro-2-fluorophenyl)-3'-isopropyl-3'H-spiro[dihydroindole-3,4'-pyrrolo[3,4-d]imidazole]-2,6'(5'H)-dione

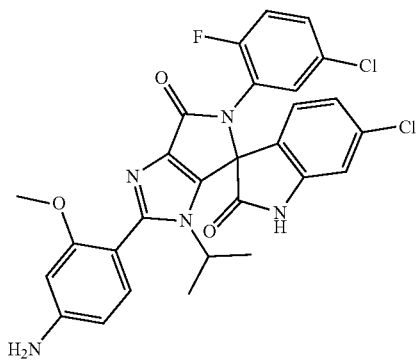 [SMILES: COc1cc(N)ccc1-c1nc2c(n1C(C)C)C1(C(=O)Nc3cc(Cl)ccc31)N(c1cc(Cl)ccc1F)C2=O]

Title compounds were obtained by steps similar to those in Example 1, and supercritical high-pressure preparative chromatography was performed to obtain 12.7 mg of (S)-2'-(4-amino-2-methoxyphenyl)-6-chloro-5'-(5-chloro-2-fluorophenyl)-3'-isopropyl-3'H-spiro[dihydroindole-3,4'-pyrrolo[3,4-d]imidazole]-2,6'(5'H)-dione (S-66), and 10.1 mg of (R)-2'-(4-amino-2-methoxyphenyl)-6-chloro-5'-(5-chloro-2-fluorophenyl)-3'-isopropyl-3'H-spiro[dihydroindole-3,4'-pyrrolo[3,4-d]imidazole]-2,6'(5'H)-dione (R-66). MS (ESI): mass calcd. for $C_{28}H_{22}Cl_2FN_5O_3$ 565.1, m/z found 566.1 [M+H]$^+$. $^1$H-NMR (400 MHz, DMSO-d$_6$) δ 7.70-7.00 (m, 7H), 6.31 (s, 1H), 6.23 (d, 1H, J=9.2 Hz), 5.59 (brs, 2H), 4.12-4.07 (m, 1H), 3.67 (s, 3H), 1.07 (d, 3H, J=5.6 Hz), 0.60 (d, 3H, J=5.6 Hz).

Example 67

2'-(4-amino-2-methoxyphenyl)-6-chloro-5'-(3-chloro-5-fluorophenyl)-3'-isopropyl-3'H-spiro[dihydroindole-3,4'-pyrrolo[3,4-d]imidazole]-2,6'(5'H)-dione

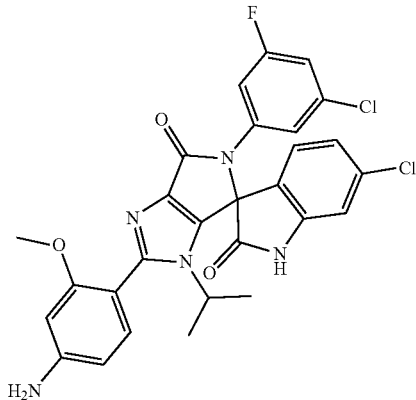 [SMILES: COc1cc(N)ccc1-c1nc2c(n1C(C)C)C1(C(=O)Nc3cc(Cl)ccc31)N(c1cc(F)cc(Cl)c1)C2=O]

Title compounds were obtained by steps similar to those in Example 1, and supercritical high-pressure preparative chromatography was performed to obtain 21.3 mg of (S)-2'-(4-amino-2-methoxyphenyl)-6-chloro-5'-(3-chloro-5-fluorophenyl)-3'-isopropyl-3'H-spiro[dihydroindole-3,4'-pyrrolo[3,4-d]imidazole]-2,6'(5'H)-dione (S-67), and 18.8 mg of (R)-2'-(4-amino-2-methoxyphenyl)-6-chloro-5'-(3-chloro-5-fluorophenyl)-3'-isopropyl-3'H-spiro[dihydroindole-3,4'-pyrrolo[3,4-d]imidazole]-2,6'(5'H)-dione (R-67). MS (ESI): mass calcd. for $C_{28}H_{22}Cl_2FN_5O_3$ 565.1, m/z found 566.1 [M+H]$^+$. $^1$H-NMR (400 MHz, DMSO-d$_6$) δ 7.35-7.28 (m, 2H), 7.02-6.92 (m, 5H), 6.29 (s, 1H), 6.24 (d, 1H, J=8.0 Hz), 5.57 (brs, 2H), 4.10-4.04 (m, 1H), 3.65 (s, 3H), 1.09 (d, 3H, J=6.4 Hz), 0.57 (d, 3H, J=6.4 Hz).

Example 68

4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxy-N,N-dimethylbenzamide

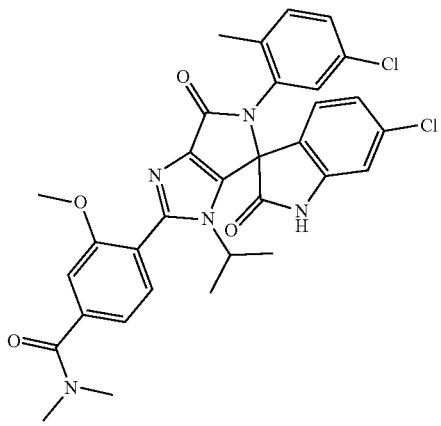 [SMILES: COc1cc(C(=O)N(C)C)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 13.4 mg of (S)-4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxy-N,N-dimethylbenzamide (S-68), and 17.1 mg of (R)-4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxy-N,N-dimethylbenzamide (R-68). MS (ESI): mass calcd. for $C_{32}H_{29}Cl_2N_5O_4$, 617.2 m/z found 618.2 [M+H]$^+$. $^1$H-NMR (400 MHz, DMSO-d$_6$) δ 11.73 (brs, 1H), 7.58-6.97 (m, 9H), 4.10-4.07 (m, 1H), 3.82 (s, 3H), 3.01 (s, 3H), 2.96 (s, 3H), 2.22 (s, 3H), 1.08 (d, 3H, J=6.4 Hz), 0.65 (d, 3H, J=6.4 Hz).

Example 69

6-chloro-5'-(5-chloro-2-methylphenyl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione

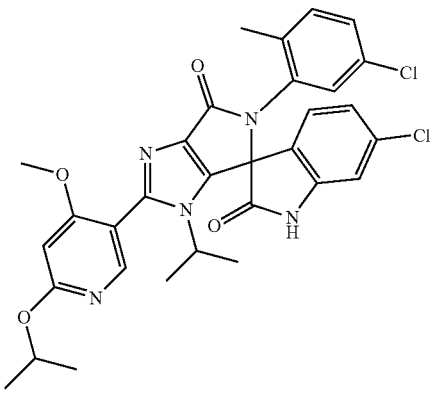 [SMILES: COc1cc(OC(C)C)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 9.6 mg of (S)-6-chloro-5'-(5-chloro-2-methylphenyl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione (S-69), and 28.9 mg of (R)-6-chloro-5'-(5-chloro-2-methylphenyl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione (R-69). MS (ESI): mass calcd. for $C_{31}H_{29}Cl_2N_5O_4$, 605.2 m/z found 606.1 [M+H]$^+$. $^1$H-NMR (400 MHz, DMSO-d$_6$) δ 11.54 (brs, 1H), 8.10 (d, J=4.4 Hz, 1H), 7.56-6.96 (m, 7H), 5.36-5.30 (m, 1H), 4.08-4.05 (m, 1H), 3.83 (s, 3H), 2.21 (s, 3H), 1.33 (d, J=6.4 Hz, 6H), 1.08 (d, J=5.2 Hz, 3H), 0.64 (d, J=5.2 Hz, 3H).

Example 70

2-(3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxyphenyl)-N,N-dimethylacetamide

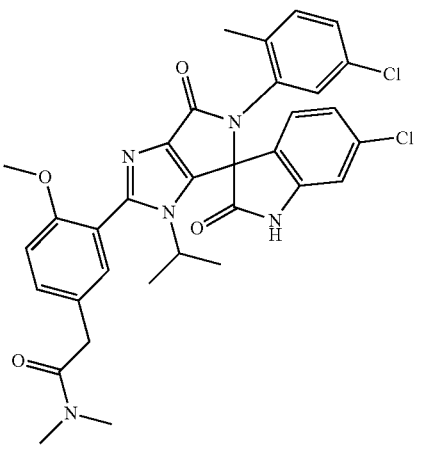 [SMILES: COc1ccc(CC(=O)N(C)C)cc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 25.9 mg of (S)-2-(3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxyphenyl)-N,N-dimethylacetamide (S-70), and 30.7 mg of (R)-2-(3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxyphenyl)-N,N-dimethylacetamide (R-70). MS (ESI): mass calcd. for $C_{33}H_{31}Cl_2N_5O_4$ 631.2, m/z found 632.1 [M+H]$^+$. $^1$H-NMR (400 MHz, DMSO-d$_6$) δ 11.72 (brs, 1H), 7.57-6.96 (m, 9H), 4.09-4.06 (m, 1H), 3.78 (s, 3H), 3.69 (s, 2H), 3.01 (s, 3H), 2.83 (s, 3H), 2.22 (s, 3H), 1.07 (s, 3H), 0.36 (s, 3H).

Example 71

2'-(4-amino-2-methoxyphenyl)-6-chloro-5'-(3-chloro-4-methoxyphenyl)-3'-isopropyl-3'H-spiro[dihydroindole-3,4'-pyrrolo[3,4-d]imidazole]-2,6'(5'H)-dione

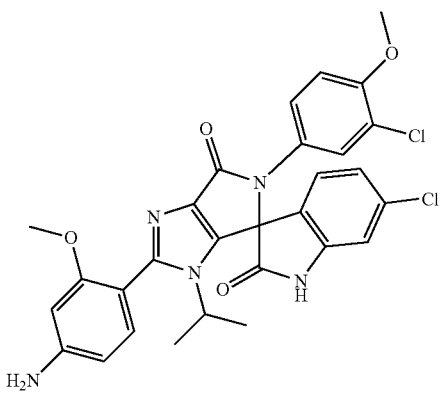 [SMILES: COc1ccc(N2C(=O)c3nc(-c4ccc(N)cc4OC)n(C(C)C)c3C23C(=O)Nc2cc(Cl)ccc23)cc1Cl]

Title compounds were obtained by steps similar to those in Example 1, and supercritical high-pressure preparative chromatography was performed to obtain 17.1 mg of (S)-2'-(4-amino-2-methoxyphenyl)-6-chloro-5'-(3-chloro-4-methoxyphenyl)-3'-isopropyl-3'H-spiro[dihydroindole-3,4'-pyrrolo[3,4-d]imidazole]-2,6'(5'H)-dione (S-71), and 16.1 mg of (R)-2'-(4-amino-2-methoxyphenyl)-6-chloro-5'-(3-chloro-4-methoxyphenyl)-3'-isopropyl-3'H-spiro[dihydroindole-3,4'-pyrrolo[3,4-d]imidazole]-2,6'(5'H)-dione (R-71). MS (ESI): mass calcd. for $C_{29}H_{25}Cl_2N_5O_4$, 577.1 m/z found 578.1 [M+H]$^+$. $^1$H-NMR (400 MHz, DMSO-d$_6$) δ 7.20-6.20 (m, 9H), 5.49 (s, 2H), 3.98 (m, 1H), 3.78 (s, 3H), 3.64 (s, 3H), 1.11-1.05 (m, 3H), 0.60-0.59 (m, 3H).

Example 72

6-chloro-5'-(5-chloro-2-methylphenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione

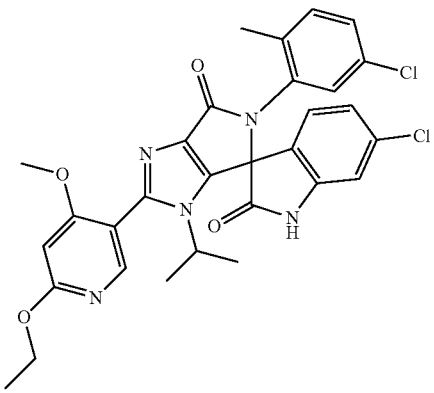 [SMILES: CCOc1cc(OC)c(-c2nc3c(n2C(C)C)C2(C(=O)Nc4cc(Cl)ccc42)N(c2cc(Cl)ccc2C)C3=O)cn1]

Title compounds were obtained by steps similar to those in Example 1, and supercritical high-pressure preparative chromatography was performed to obtain 20.2 mg of (S)-6-chloro-5'-(5-chloro-2-methylphenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione (S-72), and 23.2 mg of (R)-6-chloro-5'-(5-chloro-2-methylphenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione (R-72). MS (ESI): mass calcd. for $C_{30}H_{27}Cl_2N_5O_4$ 591.1, m/z found 592.1 [M+H]$^+$. $^1$H-NMR (400 MHz, DMSO-d$_6$) δ 11.73 (brs, 1H), 8.10 (s, 1H), 7.56-7.44 (m, 1H), 7.31-6.48 (m, 6H), 4.40 (brs, 2H), 4.06-4.02 (m, 1H), 3.84 (s, 3H), 2.21 (s, 3H), 1.36 (t, 3H, J=7.6 Hz), 1.08 (d, 3H, J=6.4 Hz), 0.64 (d, 3H, J=6.4 Hz).

Example 73

2'-(4-amino-2-methoxyphenyl)-6-chloro-5'-(3-chloro-4-fluorophenyl)-3'-isopropyl-3'H-spiro[dihydroindole-3,4'-pyrrolo[3,4-d]imidazole]-2,6'(5'H)-dione

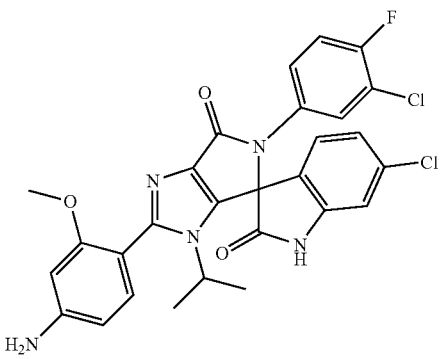 [SMILES: COc1cc(N)ccc1-c1nc2c(n1C(C)C)C1(C(=O)Nc3cc(Cl)ccc31)N(c1ccc(F)c(Cl)c1)C2=O]

Title compounds were obtained by steps similar to those in Example 1, and supercritical high-pressure preparative chromatography was performed to obtain 24.7 mg of (S)-2'-(4-amino-2-methoxyphenyl)-6-chloro-5'-(3-chloro-4- fluorophenyl)-3'-isopropyl-3'H-spiro[dihydroindole-3,4'-pyrrolo[3,4-d]imidazole]-2,6'(5'H)-dione (S-73), and 28.7 mg of (R)-2'-(4-amino-2-methoxyphenyl)-6-chloro-5'-(3-chloro-4-fluorophenyl)-3'-isopropyl-3'H-spiro[dihydroindole-3,4'-pyrrolo[3,4-d]imidazole]-2,6'(5'H)-dione (R-73). MS (ESI): mass calcd. for $C_{28}H_{22}Cl_2FN_5O_3$ 565.1, m/z found 566.1 [M+H]$^+$. $^1$H-NMR (400 MHz, DMSO-d$_6$) δ 7.39-7.34 (m, 1H), 7.27-7.21 (m, 2H), 7.03-6.90 (m, 4H), 6.29 (s, 1H), 6.24 (d, 1H, J=8.0 Hz), 5.56 (brs, 2H), 4.08-4.05 (m, 1H), 3.65 (s, 3H), 1.08 (s, 3H), 0.59 (s, 3H).

Example 74

2'-(4-amino-2-methoxy-5-methylphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione

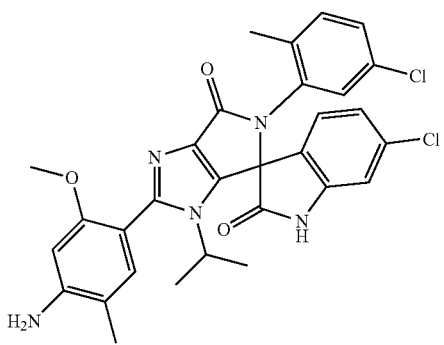 [SMILES: COc1cc(N)c(C)cc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 25.0 mg of (S)-2'-(4-amino-2-methoxy-5-methylphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (S-74), and 26.6 mg of (R)-2'-(4-amino-2-methoxy-5-methylphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (R-74). MS (ESI): mass calcd. for $C_{30}H_{27}Cl_2N_5O_3$ 575.1, m/z found 576.1 [M+H]$^+$. $^1$H-NMR (400 MHz, DMSO-d$_6$) δ 11.68 (brs, 1H), 7.51-6.93 (m, 8H), 5.33 (brs, 2H), 4.12-4.10 (m, 1H), 3.66 (s, 3H), 2.21 (s, 3H), 2.01 (s, 3H), 1.05 (d, 3H, J=6.4 Hz), 0.61 (d, 3H, J=6.4 Hz).

Example 75

2'-(4-amino-5-fluoro-2-methoxyphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione

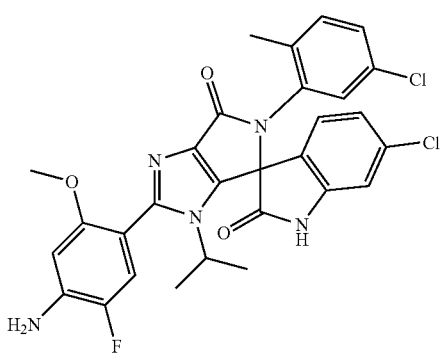 [SMILES: COc1cc(N)c(F)cc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 7.8 mg of (S)-2'-(4-amino-5-fluoro-2-methoxyphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (S-75), and 12.7 mg of (R)-2'-(4-amino-5-fluoro-2-methoxyphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (R-75). MS (ESI): mass calcd. for $C_{29}H_{24}Cl_2FN_5O_3$ 579.1, m/z found 580.1 [M+H]$^+$. $^1$H-NMR (400 MHz, DMSO-d$_6$) δ 11.54 (brs, 1H), 7.49-6.46 (m, 8H), 5.65 (brs, 2H), 4.13-4.11 (m, 1H), 3.67 (s, 3H), 2.21 (s, 3H), 1.06 (s, 3H, J=6.0 Hz), 0.62 (d, 3H, J=6.0 Hz).

Example 76

6-chloro-5'-(5-chloro-2-methylphenyl)-2'-(3-fluoro-2-methoxyphenyl)-3'-isopropyl-3'H-spiro[dihydroindole-3,4'-pyrrolo[3,4-d]imidazole]-2,6'(5'H)-dione

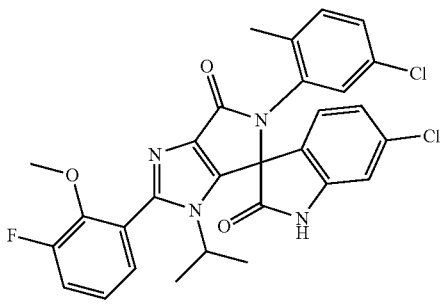 [SMILES: COc1c(F)cccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 22.0 mg of (S)-6-chloro-5'-(5-chloro-2-methylphenyl)-2'-(3-fluoro-2-methoxyphenyl)-3'-isopropyl-3'H-spiro[dihydroindole-3,4'-pyrrolo[3,4-d]imidazole]-2,6'(5'H)-dione (S-76), and 25.1 mg of (R)-6-chloro-5'-(5-chloro-2-methylphenyl)-2'-(3-fluoro-2-methoxyphenyl)-3'-isopropyl-3'H-spiro[dihydroindole-3,4'-pyrrolo[3,4-d]imidazole]-2,6'(5'H)-dione (R-76). MS (ESI): mass calcd. for $C_{29}H_{23}Cl_2FN_4O_3$ 564.1, m/z found 565.3 [M+H]$^+$. $^1$H-NMR (400 MHz, DMSO-d$_6$) δ 11.51 (brs, 1H), 7.57-6.95 (m, 9H), 4.11-4.10 (m, 1H), 3.77 (s, 3H), 2.22 (s, 3H), 1.08 (d, 3H, J=6.0 Hz), 0.66 (d, 3H, J=6.0 Hz).

Example 77

4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxybenzamide

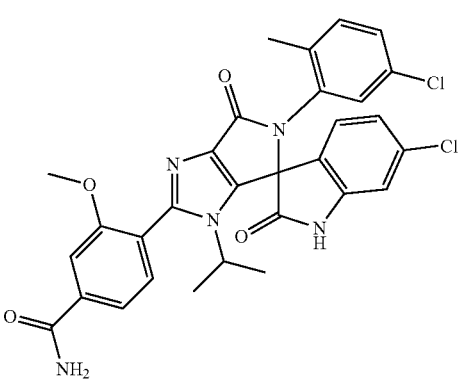 [SMILES: COc1cc(C(N)=O)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 23.6 mg of (S)-4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxybenzamide (S-77), and 21.5 mg of (R)-4-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-3-methoxybenzamide (R-77). MS (ESI): mass calcd. for $C_{30}H_{25}Cl_2N_5O_4$, 589.1 m/z found 590.1 [M+H]$^+$. $^1$H-NMR (400 MHz, DMSO-d$_6$) δ 11.76 (brs, 1H), 8.14 (brs, 2H), 7.64-6.98 (m, 9H), 4.08-4.06 (m, 1H), 3.85 (s, 3H), 2.22 (s, 3H), 1.07 (d, 3H, J=4.8 Hz), 0.64 (d, 3H, J=4.8 Hz).

Example 78

6-chloro-5'-(5-chloro-2-methylphenyl)-2'-(4-dimethylamino)-5-fluoro-2-methoxyphenyl)-3'-isopropyl-3'H-spiro[dihydroindole-3,4'-pyrrolo[3,4-d]imidazole]-2,6'(5'H)-dione

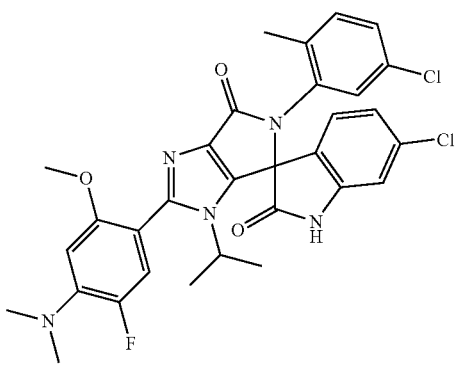 [SMILES: COc1cc(N(C)C)c(F)cc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 19.7 mg of (S)-6-chloro-5'-(5-chloro-2-methylphenyl)-2'-(4-dimethylamino)-5-fluoro-2-methoxyphenyl)-3'-isopropyl-3'H-spiro [dihydroindole-3,4'-pyrrolo[3,4-d]imidazole]-2,6'(5'H)-dione (S-78), and 28.3 mg of (R)-6-chloro-5'-(5-chloro-2-methylphenyl)-2'-(4-dimethylamino)-5-fluoro-2-methoxyphenyl)-3'-isopropyl-3'H-spiro[dihydroindole-3,4'-pyrrolo[3,4-d]imidazole]-2,6'(5'H)-dione (R-78). MS (ESI): mass calcd. for $C_{31}H_{28}Cl_2FN_5O_3$ 607.2, m/z found 608.2 [M+H]$^+$. H-NMR (400 MHz, DMSO-d$_6$) δ 11.54 (brs, 1H), 7.52-6.57 (m, 9H), 4.12-4.10 (m, 1H), 3.78 (s, 3H), 2.91 (s, 6H), 2.21 (s, 3H), 1.06 (d, 3H, J=4.0 Hz), 0.63 (d, 3H, J=4.0 Hz).

Example 79

6-chloro-5'-(5-chloro-2-methylphenyl)-2'-(2,6-dimethoxyphenyl)-3'-isopropyl-3'H-spiro[dihydroindole-3,4'-pyrrolo[3,4-d]imidazole]-2,6'(5'H)-dione

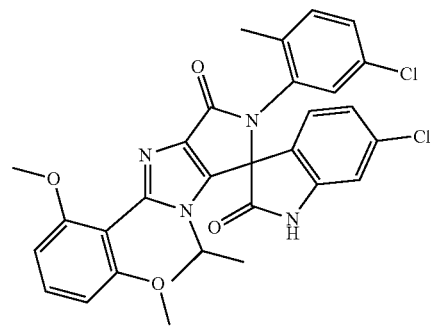 [SMILES: COc1cccc(OC)c1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 23.7 mg of (S)-6-chloro-5'-(5-chloro-2-methylphenyl)-2'-(2,6-dimethoxyphenyl)-3'-isopropyl-3'H-spiro[dihydroindole-3,4'-pyrrolo[3,4-d]imidazole]-2,6'(5'H)-dione (S-79), and 24.7 mg of (R)-6-chloro-5'-(5-chloro-2-methylphenyl)-2'-(2,6-dimethoxyphenyl)-3'-isopropyl-3'H-spiro[dihydroindole-3,4'-pyrrolo[3,4-d]imidazole]-2,6'(5'H)-dione (R-79). MS (ESI): mass calcd. for $C_{30}H_{26}Cl_2N_4O_4$ 576.1, m/z found 577.2 [M+H]$^+$. $^1$H-NMR (400 MHz, DMSO-d$_6$) δ 11.70 (brs, 1H), 7.51-6.78 (m, 9H), 3.90-3.83 (m, 1H), 3.75 (s, 3H), 3.71 (s, 3H), 2.24 (s, 3H), 1.02 (d, 3H, J=6.8 Hz), 0.61 (d, 3H, J=6.8 Hz).

Example 80

6-chloro-5'-(5-chloro-2-fluorophenyl)-2'-(2,4-dimethoxyphenyl)-3'-isopropyl-3'H-spiro[dihydroindole-3,4'-pyrrolo[3,4-d]imidazole]-2,6'(5'H)-dione

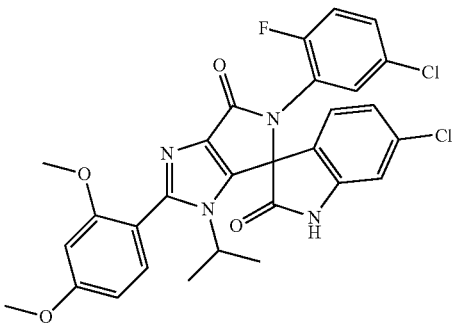 [SMILES: COc1ccc(-c2nc3c(n2C(C)C)C2(C(=O)Nc4cc(Cl)ccc42)N(c2cc(Cl)ccc2F)C3=O)c(OC)c1]

Title compounds were obtained by steps similar to those in Example 1, and supercritical high-pressure preparative chromatography was performed to obtain 32.0 mg of (S)-6-chloro-5'-(5-chloro-2-fluorophenyl)-2'-(2,4-dimethoxyphenyl)-3'-isopropyl-3'H-spiro[dihydroindole-3,4'-pyrrolo[3,4-d]imidazole]-2,6'(5'H)-dione (S-80), and 35.4 mg of (R)-6-chloro-5'-(5-chloro-2-fluorophenyl)-2'-(2,4-dimethoxyphenyl)-3'-isopropyl-3'H-spiro[dihydroindole-3,4'-pyrrolo[3,4-d]imidazole]-2,6'(5'H)-dione (R-80). MS (ESI):

mass calcd. for $C_{29}H_{23}Cl_2FN_4O_4$ 580.1, m/z found 581.2 [M+H]$^+$. 1H-NMR (400 MHz, DMSO-d$_6$) δ 11.85 (brs, 1H), 7.48-6.66 (m, 9H), 4.09-4.03 (m, 1H), 3.84 (s, 3H), 3.77 (s, 3H), 1.04 (d, 3H, J=6.0 Hz), 0.61 (d, 3H, J=6.0 Hz).

Example 81

6-chloro-5'-(5-chloro-2-fluorophenyl)-2'-(4-(dimethylamino)-2-methoxyphenyl)-3'-isopropyl-3'H-spiro[dihydroindole-3,4'-pyrrolo[3,4-d]imidazole]-2,6'(5'H)-dione

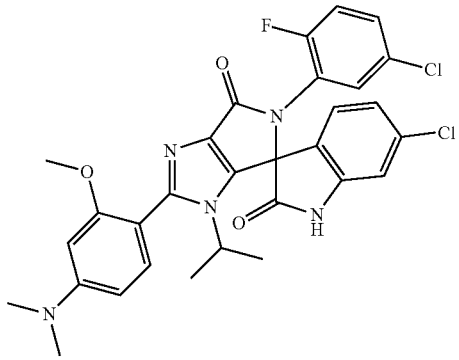 [SMILES: COc1cc(N(C)C)ccc1-c1nc2c(n1C(C)C)C1(C(=O)Nc3cc(Cl)ccc31)N(c1cc(Cl)ccc1F)C2=O]

Title compounds were obtained by steps similar to those in Example 1, and supercritical high-pressure preparative chromatography was performed to obtain 26.0 mg of (S)-6-chloro-5'-(5-chloro-2-fluorophenyl)-2'-(4-(dimethylamino)-2-methoxyphenyl)-3'-isopropyl-3'H-spiro[dihydroindole-3,4'-pyrrolo[3,4-d]imidazole]-2,6'(5'H)-dione (S-81), and 19.5 mg of (R)-6-chloro-5'-(5-chloro-2-fluorophenyl)-2'-(4-(dimethylamino)-2-methoxyphenyl)-3'-isopropyl-3'H-spiro[dihydroindole-3,4'-pyrrolo[3,4-d]imidazole]-2,6'(5'H)-dione (R-81). MS (ESI): mass calcd. for $C_{30}H_{26}Cl_2FN_5O_3$ 593.13, m/z found 594.2 [M+H]$^+$. $^1$H-NMR (400 MHz, DMSO-d$_6$) δ 11.52 (brs, 1H), 7.46-7.05 (m, 6H), 6.98 (s, 1H), 6.40 (d, 1H, J=8.4 Hz), 6.35 (s, 1H), 4.12-4.08 (m, 1H), 3.76 (s, 3H), 2.99 (s, 6H), 1.08 (d, 3H, J=5.6 Hz), 0.61 (d, 3H, J=5.6 Hz).

Example 82

6-chloro-5'-(5-chloro-2-methylphenyl)-2'-(2-(dimethylamino)-4-methoxypyrimidin-5-yl)-3'-isopropyl-3'H-spiro[dihydroindole-3,4'-pyrrolo[3,4-d]imidazole]-2,6'(5'H)-dione

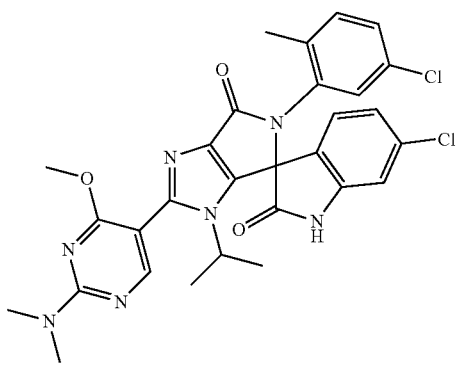 [SMILES: COc1nc(N(C)C)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 13.7 mg of (S)-6-chloro-5'-(5-chloro-2-methylphenyl)-2'-(2-(dimethylamino)-4-methoxypyrimidin-5-yl)-3'-isopropyl-3'H-spiro[dihydroindole-3,4'-pyrrolo[3,4-d]imidazole]-2,6'(5'H)-dione (S-82), and 13.6 mg of (R)-6-chloro-5'-(5-chloro-2-methylphenyl)-2'-(2-(dimethylamino)-4-methoxypyrimidin-5-yl)-3'-isopropyl-3'H-spiro[dihydroindole-3,4'-pyrrolo[3,4-d]imidazole]-2,6'(5'H)-dione (R-82). MS (ESI): mass calcd. for $C_{29}H_{27}Cl_2N_7O_3$ 591.15, m/z found 592.2 [M+H]$^+$. $^1$H-NMR (400 MHz, DMSO-d$_6$) δ 8.25 (d, 1H, J=4.4 Hz), 7.55-6.97 (m, 6H), 4.15-4.12 (m, 1H), 3.90 (s, 3H), 3.19 (s, 6H), 2.20 (s, 3H), 1.08 (d, 3H, J=6.4 Hz), 0.66 (d, 3H, J=6.4 Hz).

Example 83

6-chloro-5'-(5-chloro-2-methylphenyl)-2'-(2,4-dimethoxy-5-methylphenyl)-3'-isopropyl-3'H-spiro[dihydroindole-3,4'-pyrrolo[3,4-d]imidazole]-2,6'(5'H)-dione

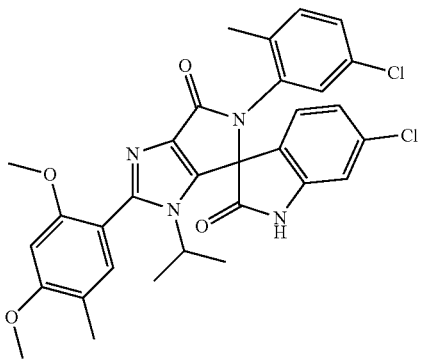 [SMILES: COc1cc(OC)c(-c2nc3c(n2C(C)C)C2(C(=O)Nc4cc(Cl)ccc42)N(c2cc(Cl)ccc2C)C3=O)cc1C]

Title compounds were obtained by steps similar to those in Example 1, and supercritical high-pressure preparative chromatography was performed to obtain 48.6 mg of (S)-6-chloro-5'-(5-chloro-2-methylphenyl)-2'-(2,4-dimethoxy-5-methylphenyl)-3'-isopropyl-3'H-spiro[dihydroindole-3,4'-pyrrolo[3,4-d]imidazole]-2,6'(5'H)-dione (S-83), and 30.5 mg of (R)-6-chloro-5'-(5-chloro-2-methylphenyl)-2'-(2,4-dimethoxy-5-methylphenyl)-3'-isopropyl-3'H-spiro[dihydroindole-3,4'-pyrrolo[3,4-d]imidazole]-2,6'(5'H)-dione (R-83). MS (ESI): mass calcd. for $C_{31}H_{28}Cl_2N_4O_4$ 590.19, m/z found 591.2 [M+H]$^+$. $^1$H-NMR (400 MHz, DMSO-d$_6$) δ 11.52 (brs, 1H), 7.47-7.04 (m, 6H), 6.98 (d, 1H, J=1.6 Hz), 6.40 (d, 1H, J=8.4 Hz), 6.35 (s, 1H), 4.12-4.08 (m, 1H), 3.76 (s, 3H), 2.99 (s, 6H), 2.22 (s, 3H), 1.08 (d, 3H, J=6.4 Hz), 0.61 (d, 3H, J=6.4 Hz).

Example 84

3-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxybenzoic acid

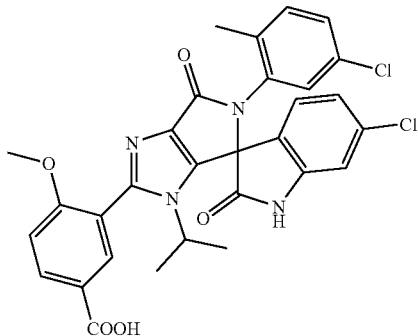 [SMILES: COc1ccc(C(=O)O)cc1-c1nc2c(n1C(C)C)C1(C(=O)Nc3cc(Cl)ccc31)N(c1cc(Cl)ccc1C)C2=O]

80 mg of the title compound was obtained by steps similar to those in Example 1. MS (ESI): mass calcd. for $C_{30}H_{24}Cl_2N_4O_5$, 590.11 m/z found 591.1 [M+H]$^+$. H-NMR (400 MHz, DMSO-d$_6$) δ 11.35 (brs, 1H), 8.12 (d, 1H, J=8.0 Hz), 7.96 (s, 1H), 7.60-6.97 (m, 7H), 4.07-4.06 (m, 1H), 3.87 (s, 3H), 2.23 (s, 3H), 1.17 (d, 3H, J=7.2 Hz), 0.62 (d, 3H, J=7.2 Hz).

Example 85

6-chloro-5'-(5-chloro-2-methylphenyl)-3'-isopropyl-2'-(2-methoxy-4-(trifluoromethyl)phenyl)-3'H-spiro[dihydroindole-3,4'-pyrrolo[3,4-d]imidazole]-2,6'(5'H)-dione

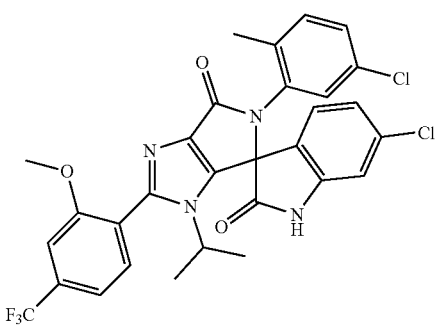 [SMILES: COc1cc(C(F)(F)F)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 10.1 mg of (S)-6-chloro-5'-(5-chloro-2-methylphenyl)-3'-isopropyl-2'-(2-methoxy-4-(trifluoromethyl)phenyl)-3'H-spiro[dihydroindole-3,4'-pyrrolo[3,4-d]imidazole]-2,6'(5'H)-dione (S-85), and 9.7 mg of (R)-6-chloro-5'-(5-chloro-2-methylphenyl)-3'-isopropyl-2'-(2-methoxy-4-(trifluoromethyl)phenyl)-3'H-spiro[dihydroindole-3,4'-pyrrolo[3,4-d]imidazole]-2,6'(5'H)-dione (R-85). MS (ESI): mass calcd. for $C_{30}H_{23}Cl_2F_3N_4O_3$ 614.11, m/z found 615.1 [M+H]$^+$. $^1$H-NMR (400 MHz, DMSO-d$_6$) δ 7.71-6.98 (m, 9H), 4.08-4.06 (m, 1H), 3.89 (s, 3H), 2.22 (s, 3H), 1.18 (d, 3H, J=4.0 Hz), 0.64 (d, 3H, J=4.0 Hz).

Example 86

6-chloro-5'-(5-chloro-2-methylphenyl)-2'-(4-cyclopropyl-2-methoxyphenyl)-3'-isopropyl-3'H-spiro[dihydroindole-3,4'-pyrrolo[3,4-d]imidazole]-2,6'(5'H)-dione

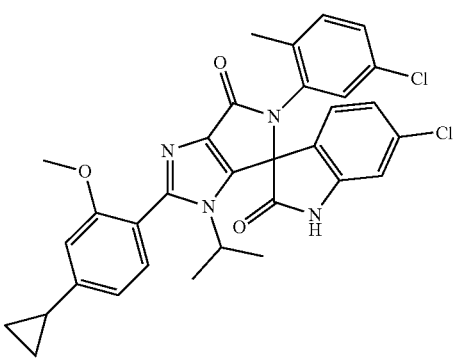 [SMILES: COc1cc(C2CC2)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 18.7 mg of (S)-6-chloro-5'-(5-chloro-2-methylphenyl)-2'-(4-cyclopropyl-2-methoxyphenyl)-3'-isopropyl-3'H-spiro[dihydroindole-3,4'-pyrrolo[3,4-d]imidazole]-2,6'(5'H)-dione (S-86), and 21.2 mg of (R)-6-chloro-5'-(5-chloro-2-methylphenyl)-2'-(4-cyclopropyl-2-methoxyphenyl)-3'-isopropyl-3'H-spiro[dihydroindole-3,4'-pyrrolo[3,4-d]imidazole]-2,6'(5'H)-dione (R-86). MS (ESI): mass calcd. for $C_{32}H_{28}Cl_2N_4O_3$ 586.15 m/z found 587.1 [M+H]$^+$. $^1$H-NMR (400 MHz, DMSO-d$_6$) δ 11.57 (brs, 1H), 7.53-6.47 (m, 9H), 4.07-4.03 (m, 1H), 3.78 (s, 3H), 2.21 (s, 3H), 2.01-2.00 (m, 1H), 1.16 (d, 3H, J=6.4 Hz), 1.05-1.00 (m, 4H), 0.64 (d, 3H, J=6.4 Hz).

Example 87

6-chloro-5'-(5-chloro-2-methylphenyl)-3'-isopropyl-2'-(2-methoxy-4-(trifluoromethoxy)phenyl)-3'H-spiro[dihydroindole-3,4'-pyrrolo[3,4-d]imidazole]-2,6'(5'H)-dione

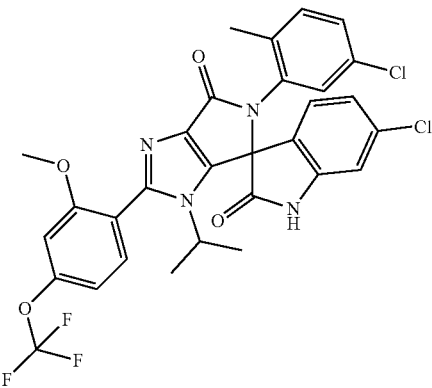 [SMILES: COc1cc(OC(F)(F)F)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 45.1 mg of (S)-

6-chloro-5'-(5-chloro-2-methylphenyl)-3'-isopropyl-2'-(2-methoxy-4-(trifluoromethoxy)phenyl)-3'H-spiro[dihydroindole-3,4'-pyrrolo[3,4-d]imidazole]-2,6'(5'H)-dione (S-87), and 44.6 mg of (R)-6-chloro-5'-(5-chloro-2-methylphenyl)-3'-isopropyl-2'-(2-methoxy-4-(trifluoromethoxy)phenyl)-3'H-spiro[dihydroindole-3,4'-pyrrolo[3,4-d]imidazole]-2,6'(5'H)-dione (R-87). MS (ESI): mass calcd. for $C_{30}H_{23}Cl_2F_3N_4O_4$, 630.10 m/z found 631.1 [M+H]$^+$. $^1$H-NMR (400 MHz, DMSO-d$_6$) δ 11.74 (brs, 1H), 7.60-6.48 (m, 9H), 4.07-4.02 (m, 1H), 3.84 (s, 3H), 2.22 (s, 3H), 1.14 (d, 3H, J=4.8 Hz), 0.64 (d, 3H, J=4.8 Hz).

Example 88

6-chloro-5'-(5-chloro-2-methylphenyl)-2'-(4-ethoxy-2-methoxyphenyl)-3'-isopropyl-3'H-spiro[dihydroindole-3,4'-pyrrolo[3,4-d]imidazole]-2,6'(5'H)-dione

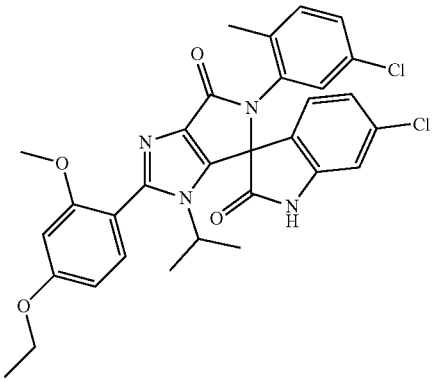 [SMILES: CCOc1ccc(-c2nc3c(n2C(C)C)C2(C(=O)Nc4cc(Cl)ccc42)N(c2cc(Cl)ccc2C)C3=O)c(OC)c1]

Title compounds were obtained by steps similar to those in Example 1, and supercritical high-pressure preparative chromatography was performed to obtain 36.2 mg of (S)-6-chloro-5'-(5-chloro-2-methylphenyl)-2'-(4-ethoxy-2-methoxyphenyl)-3'-isopropyl-3'H-spiro[dihydroindole-3,4'-pyrrolo[3,4-d]imidazole]-2,6'(5'H)-dione (S-88), and 42.5 mg of (R)-6-chloro-5'-(5-chloro-2-methylphenyl)-2'-(4-ethoxy-2-methoxyphenyl)-3'-isopropyl-3'H-spiro[dihydroindole-3,4'-pyrrolo[3,4-d]imidazole]-2,6'(5'H)-dione (R-88). MS (ESI): mass calcd. for $C_{31}H_{28}Cl_2N_4O_4$ 590.15 m/z found 591.1 [M+H]$^+$. $^1$H-NMR (400 MHz, DMSO-d$_6$) δ 11.54 (brs, 1H), 7.54-6.95 (m, 9H), 4.14-4.04 (m, 3H), 3.77 (s, 3H), 2.22 (s, 3H), 1.36 (t, 3H, J=6.8 Hz), 1.05 (d, 3H, J=5.2 Hz), 0.62 (d, 3H, J=5.2 Hz).

Example 89

6-chloro-5'-(5-chloro-2-methylpyridin-3-yl)-3'-isopropyl-2'-(4-isopropyl-2-methoxyphenyl)-3'H-spiro[dihydroindole-3,4'-pyrrolo[3,4-d]imidazole]-2,6'(5'H)-dione

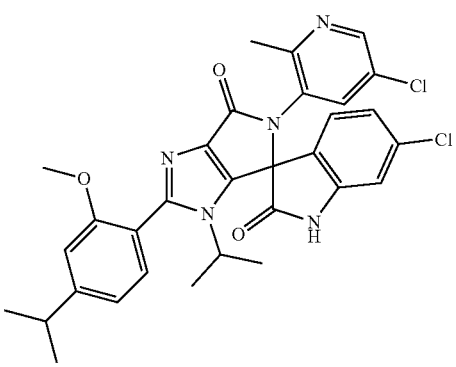 [SMILES: COc1cc(C(C)C)ccc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 43.2 mg of (S)-6-chloro-5'-(5-chloro-2-methylpyridin-3-yl)-3'-isopropyl-2'-(4-isopropyl-2-methoxyphenyl)-3'H-spiro[dihydroindole-3,4'-pyrrolo[3,4-d]imidazole]-2,6'(5'H)-dione (S-89), and 32.4 mg of (R)-6-chloro-5'-(5-chloro-2-methylpyridin-3-yl)-3'-isopropyl-2'-(4-isopropyl-2-methoxyphenyl)-3'H-spiro[dihydroindole-3,4'-pyrrolo[3,4-d]imidazole]-2,6'(5'H)-dione (R-89). MS (ESI): mass calcd. for $C_{31}H_{29}Cl_2N_5O_3$ 589.16, m/z found 590.2 [M+H]$^+$. $^1$H-NMR (400 MHz, DMSO-d$_6$) δ 11.69 (brs, 1H), 8.50 (d, 1H, J=8.0 Hz), 7.64-7.00 (m, 7H), 4.09-4.06 (m, 1H), 3.79 (s, 3H), 3.01-2.94 (m, 1H), 2.42 (s, 3H), 1.35 (d, 3H, J=7.6 Hz), 1.27 (d, 3H, J=7.6 Hz), 1.07 (d, 3H, J=4.0 Hz), 0.64 (d, 3H, J=4.0 Hz).

Example 90

2'-(2-amino-4-methoxypyrimidin-5-yl)-6-chloro-5'-(5-chloro-2-methylphenyl)-3'-isopropyl-3'H-spiro[dihydroindole-3,4'-pyrrolo[3,4-d]imidazole]-2,6'(5'H)-dione

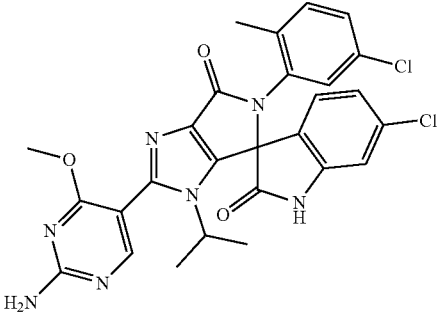 [SMILES: COc1nc(N)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 19.0 mg of (S)-2'-(2-amino-4-methoxypyrimidin-5-yl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (S-90), and 17.4 mg of (R)-2'-(2-amino-4-methoxypyrimidin-5-yl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (R-90). MS (ESI): mass calcd. for $C_{27}H_{23}Cl_2N_7O_3$ 563.12, m/z found 564.1 [M+H]$^+$. $^1$H-NMR (400 MHz, DMSO-d$_6$) δ 11.57 (brs, 1H), 8.14 (d, 1H, J=4.8 Hz), 7.54-6.96 (m, 8H), 4.18-4.13 (m, 1H), 3.84 (s, 3H), 2.20 (s, 3H), 1.08 (d, 3H, J=4.4 Hz), 0.67 (d, 3H, J=4.4 Hz).

Example 91

6-chloro-5'-(5-chloro-2-methylphenyl)-2'-(4-(dimethylamino)-2-methoxy-5-methylphenyl)-3'-isopropyl-3'H-spiro[dihydroindole-3,4'-pyrrolo[3,4-d]imidazole]-2,6'(5'H)-dione

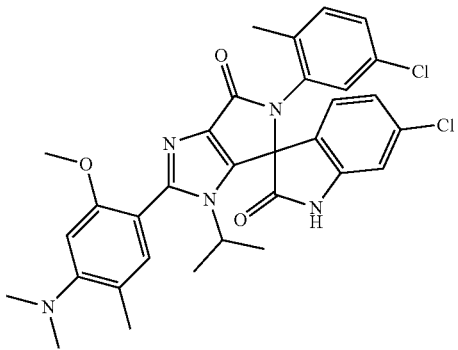 [SMILES: COc1cc(N(C)C)c(C)cc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 29.2 mg of (S)-6-chloro-5'-(5-chloro-2-methylphenyl)-2'-(4-(dimethylamino)-2-methoxy-5-methylphenyl)-3'-isopropyl-3'H-spiro[dihydroindole-3,4'-pyrrolo[3,4-d]imidazole]-2,6'(5'H)-dione (S-91), and 17.8 mg of (R)-6-chloro-5'-(5-chloro-2-methylphenyl)-2'-(4-(dimethylamino)-2-methoxy-5-methylphenyl)-3'-isopropyl-3'H-spiro[dihydroindole-3,4'-pyrrolo[3,4-d]imidazole]-2,6'(5'H)-dione (R-91). MS (ESI): mass calcd. for $C_{32}H_{31}Cl_2N_5O_3$ 603.18, m/z found 604.2 [M+H]$^+$. $^1$H-NMR (400 MHz, DMSO-d$_6$) δ 11.51 (brs, 1H), 7.53-6.47 (m, 8H), 4.11-4.08 (m, 1H), 3.77 (s, 3H), 2.73 (s, 6H), 2.22 (s, 3H), 2.07 (s, 3H), 1.06 (d, 3H, J=4.4 Hz), 0.62 (d, 3H, J=4.4 Hz).

Example 92

6-chloro-5'-(5-chloro-2-methylphenyl)-2'-(5-fluoro-2,4-dimethoxyphenyl)-3'-isopropyl-3'H-spiro[dihydroindole-3,4'-pyrrolo[3,4-d]imidazole]-2,6'(5'H)-dione

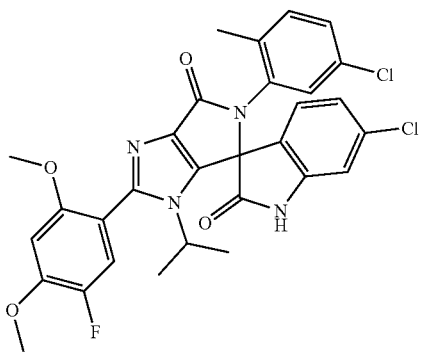 [SMILES: COc1cc(OC)c(-c2nc3c(n2C(C)C)C2(C(=O)Nc4cc(Cl)ccc42)N(c2cc(Cl)ccc2C)C3=O)cc1F]

Title compounds were obtained by steps similar to those in Example 1, and supercritical high-pressure preparative chromatography was performed to obtain 29.1 mg of (S)-6-chloro-5'-(5-chloro-2-methylphenyl)-2'-(5-fluoro-2,4-dimethoxyphenyl)-3'-isopropyl-3'H-spiro[dihydroindole-3,4'-pyrrolo[3,4-d]imidazole]-2,6'(5'H)-dione (S-92), and 33.8 mg of (R)-6-chloro-5'-(5-chloro-2-methylphenyl)-2'-(5-fluoro-2,4-dimethoxyphenyl)-3'-isopropyl-3'H-spiro[dihydroindole-3,4'-pyrrolo[3,4-d]imidazole]-2,6'(5'H)-dione (R-92). MS (ESI): mass calcd. for $C_{30}H_{25}Cl_2FN_4O_4$ 594.13, m/z found 595.2 [M+H]$^+$. $^1$H-NMR (400 MHz, DMSO-d$_6$) δ 11.75 (brs, 1H), 7.53-6.47 (m, 8H), 4.10-4.07 (m, 1H), 3.96 (s, 3H), 3.82 (s, 3H), 2.21 (s, 3H), 1.07 (d, 3H, J=4.4 Hz), 0.63 (d, 3H, J=4.4 Hz).

Example 93

6-chloro-5'-(3-chlorophenyl)-3'-isopropyl-2'-(4-isopropyl-2-methoxyphenyl)-3'H-spiro[dihydroindole-3,4'-pyrrolo[3,4-d]imidazole]-2,6'(5'H)-dione

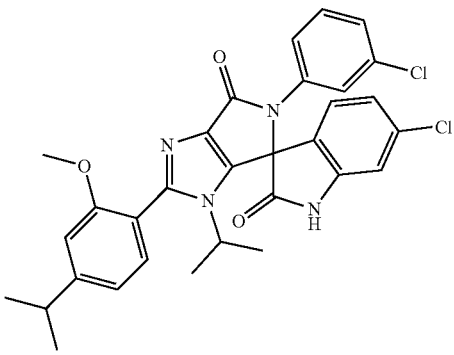 [SMILES: COc1cc(C(C)C)ccc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 125.0 mg of (S)-6-chloro-5'-(3-chlorophenyl)-3'-isopropyl-2'-(4-isopropyl-2-methoxyphenyl)-3'H-spiro[dihydroindole-3,4'-pyrrolo[3,4-d]imidazole]-2,6'(5'H)-dione (S-93), and 132.7 mg of (R)-6-chloro-5'-(3-chlorophenyl)-3'-isopropyl-2'-(4-isopropyl-2-methoxyphenyl)-3'H-spiro[dihydroindole-3,4'-pyrrolo[3,4-d]imidazole]-2,6'(5'H)-dione (R-93). MS (ESI): mass calcd. for $C_{31}H_{28}Cl_2N_4O_3$ 574.15, m/z found 575.2 [M+H]$^+$. $^1$H-NMR (400 MHz, DMSO-d$_6$) δ 11.58 (brs, 1H), 7.49 (d, 1H, J=8.0 Hz), 7.38-6.95 (m, 9H), 4.09-4.02 (m, 1H), 3.78 (s, 3H), 3.01-2.94 (m, 1H), 1.27 (d, 6H, J=7.2 Hz), 1.09 (d, 3H, J=6.4 Hz), 0.59 (d, 3H, J=6.4 Hz).

Example 94

6-chloro-5'-(5-chloro-2-fluorophenyl)-2'-(4-ethoxy-2-methoxyphenyl)-3'-isopropyl-3'H-spiro[dihydroindole-3,4'-pyrrolo[3,4-d]imidazole]-2,6'(5'H)-dione

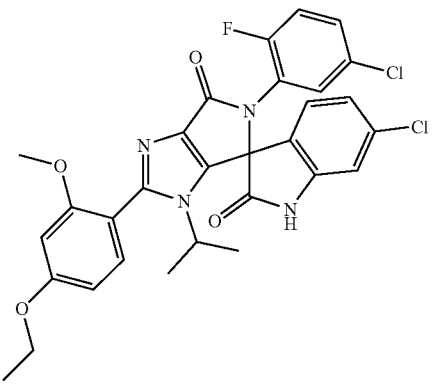

Title compounds were obtained by steps similar to those in Example 1, and supercritical high-pressure preparative chromatography was performed to obtain 7.8 mg of (S)-6-chloro-5'-(5-chloro-2-fluorophenyl)-2'-(4-ethoxy-2-methoxyphenyl)-3'-isopropyl-3'H-spiro[dihydroindole-3,4'-pyrrolo[3,4-d]imidazole]-2,6'(5'H)-dione (S-94), and 15.2 mg of (R)-6-chloro-5'-(5-chloro-2-fluorophenyl)-2'-(4-ethoxy-2-methoxyphenyl)-3'-isopropyl-3'H-spiro[dihydroindole-3,4'-pyrrolo[3,4-d]imidazole]-2,6'(5'H)-dione (R-94). MS (ESI): mass calcd. for $C_{30}H_{25}Cl_2FN_4O_4$ 594.12, m/z found 595.1 [M+H]$^+$. $^1$H-NMR (400 MHz, DMSO-d$_6$) δ 11.01 (brs, 1H), 7.48-6.64 (m, 9H), 4.14-4.04 (m, 3H), 3.76 (s, 3H), 1.37-1.18 (m, 3H), 1.04 (d, 3H, J=6.4 Hz), 0.62 (d, 3H, J=6.4 Hz).

Example 95

6-chloro-5'-(3-chlorophenyl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione

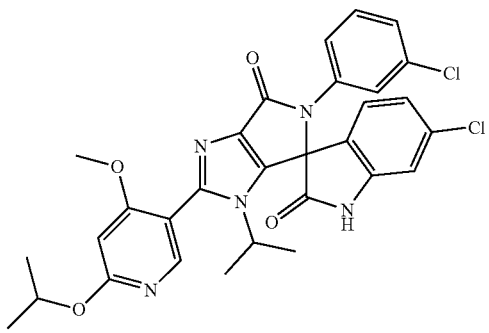 [SMILES: COc1cc(OC(C)C)ncc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 100.8 mg of (S)-6-chloro-5'-(3-chlorophenyl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione (S-95), and 108.8 mg of (R)-6-chloro-5'-(3-chlorophenyl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione (R-95). MS (ESI): mass calcd. for $C_{30}H_{27}Cl_2N_5O_4$ 591.14, m/z found 592.1[M+H]$^+$. $^1$H-NMR (400 MHz, DMSO-d$_6$) δ 11.53 (brs, 1H), 8.08 (s, 1H), 7.48 (d, 1H, J=8.4 Hz), 7.38 (d, 1H, J=8.0 Hz), 7.34 (d, 1H, J=8.4 Hz), 7.14 (d, 2H, J=9.2 Hz), 7.00 (d, 1H, J=1.6 Hz), 6.97 (d, 1H, J=7.2 Hz), 6.51 (s, 1H), 5.36-5.29 (m, 1H), 4.11-4.04 (m, 1H), 3.82 (s, 1H), 1.33 (d, 6H, J=6.0 Hz), 1.11 (d, 3H, J=6.4 Hz), 0.61 (d, 3H, J=6.4 Hz).

Example 96

6-chloro-5'-(5-chloro-2-methylpyridin-3-yl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione

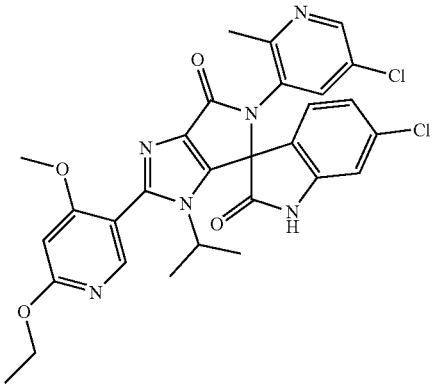 [SMILES: CCOc1cc(OC)c(-c2nc3c(n2C(C)C)C2(C(=O)Nc4cc(Cl)ccc42)N(c2cc(Cl)cnc2C)C3=O)cn1]

Title compounds were obtained by steps similar to those in Example 1, and supercritical high-pressure preparative chromatography was performed to obtain 27.1 mg of (S)-6-chloro-5'-(5-chloro-2-methylpyridin-3-yl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione (S-96), and 29.6 mg of (R)-6-chloro-5'-(5-chloro-2-methylpyridin-3-yl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione (R-96). MS (ESI): mass calcd. for $C_{29}H_{26}Cl_2N_6O_4$ 592, m/z found 593.1[M+H]$^+$. $^1$H-NMR (400 MHz, DMSO-d$_6$) δ 11.80 (brs, 1H), 8.50 (d, 1H, J=8.0 Hz), 8.12 (d, 1H, J=4.8 Hz), 7.64-7.00 (m, 4H), 6.58 (s, 1H), 4.40 (q, 2H, J=7.2 Hz), 4.09-4.04 (m, 1H), 3.84 (s, 3H), 2.27 (s, 3H), 1.36 (t, 3H, J=7.2 Hz), 1.08 (d, 3H, J=6.8 Hz), 0.65 (d, 3H, J=4.0 Hz).

Example 97

6-chloro-5'-(5-chloro-2-fluorophenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione

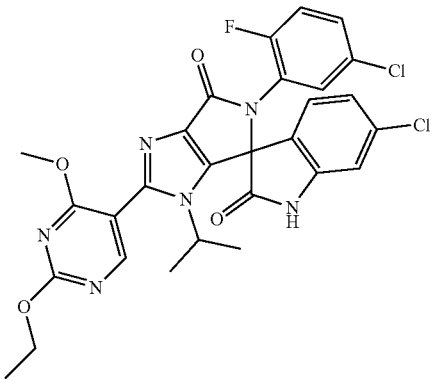 [SMILES: CCOc1ncc(-c2nc3c(n2C(C)C)C2(C(=O)Nc4cc(Cl)ccc42)N(c2cc(Cl)ccc2F)C3=O)c(OC)n1]

Title compounds were obtained by steps similar to those in Example 1, and supercritical high-pressure preparative chromatography was performed to obtain 0.8 mg of (S)-6-chloro-5'-(5-chloro-2-fluorophenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione (S-97), and 3.3 mg of (R)-6-chloro-5'-(5-chloro-2-fluorophenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione (R-97). MS (ESI): mass calcd. for $C_{28}H_{23}Cl_2FN_6O_4$ 596.11, m/z found 597.1 [M+H]$^+$. $^1$H-NMR (400 MHz, DMSO-d$_6$) δ 11.59 (brs, 1H), 8.51 (s, 1H), 7.48-7.00 (m, 6H), 4.46 (q, 2H, J=6.8 Hz), 4.10-4.07 (m, 1H), 3.94 (s, 3H), 1.39 (t, 3H, J=6.8 Hz), 1.11 (d, 3H, J=6.4 Hz), 0.66 (d, 3H, J=6.4 Hz).

Example 98

6-chloro-5'-(5-chloro-2-fluorophenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione

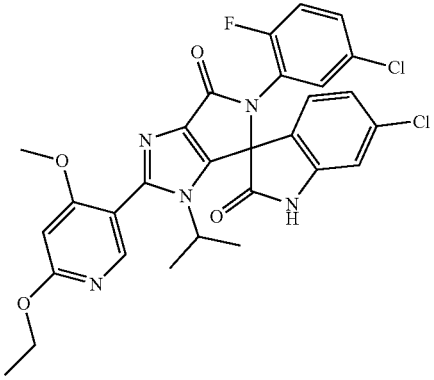 [SMILES: CCOc1cc(OC)c(-c2nc3c(n2C(C)C)C2(C(=O)Nc4cc(Cl)ccc42)N(c2cc(Cl)ccc2F)C3=O)cn1]

Title compounds were obtained by steps similar to those in Example 1, and supercritical high-pressure preparative chromatography was performed to obtain 17.5 mg of (S)-6-chloro-5'-(5-chloro-2-fluorophenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione (S-98), and 20.7 mg of (R)-6-chloro-5'-(5-chloro-2-fluorophenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione (R-98). MS (ESI): mass calcd. for $C_{29}H_{24}Cl_2FN_5O_4$ 595.11, m/z found 596.1 [M+H]$^+$. $^1$H-NMR (400 MHz, DMSO-d$_6$) δ 11.60 (brs, 1H), 8.11 (s, 1H), 7.48-7.00 (m, 6H), 6.57 (s, 1H), 4.40 (q, 2H, J=6.8 Hz), 4.08-4.04 (m, 1H), 3.83 (s, 3H), 1.35 (t, 3H, J=6.8 Hz), 1.08 (d, 3H, J=6.4 Hz), 0.64 (d, 3H, J=6.4 Hz).

Example 99

6-chloro-5'-(5-chloro-2-methylphenyl)-2'-(4-(ethyl(methyl)amino)-2-methoxyphenyl)-3'-isopropyl-3'H-spiro[dihydroindole-3,4'-pyrrolo[3,4-d]imidazole]-2,6'(5'H)-dione

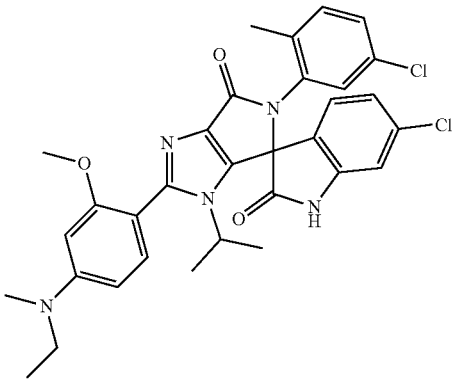 [SMILES: CCN(C)c1ccc(-c2nc3c(n2C(C)C)C2(C(=O)Nc4cc(Cl)ccc42)N(c2cc(Cl)ccc2C)C3=O)c(OC)c1]

Title compounds were obtained by steps similar to those in Example 1, and supercritical high-pressure preparative chromatography was performed to obtain 42.0 mg of (S)-6-chloro-5'-(5-chloro-2-methylphenyl)-2'-(4-(ethyl(methyl)amino)-2-methoxyphenyl)-3'-isopropyl-3'H-spiro[dihydroindole-3,4'-pyrrolo[3,4-d]imidazole]-2,6'(5'H)-dione (S-99), and 41.2 mg of (R)-6-chloro-5'-(5-chloro-2-methylphenyl)-2'-(4-(ethyl(methyl)amino)-2-methoxyphenyl)-3'-isopropyl-3'H-spiro[dihydroindole-3,4'-pyrrolo[3,4-d]imidazole]-2,6'(5'H)-dione (R-99). MS (ESI): mass calcd. for $C_{32}H_{31}Cl_2N_5O_3$ 603, m/z found 604.2[M+H]$^+$. $^1$H-NMR (400 MHz, DMSO-d$_6$) δ 11.69 (brs, 1H), 7.54-6.96 (m, 7H), 6.46-6.32 (m, 2H), 4.11-4.10 (m, 1H), 3.76 (s, 3H), 3.47-3.45 (m, 2H), 2.95 (s, 3H), 2.21 (s, 3H), 1.11-1.07 (m, 6H), 0.62 (d, 3H, J=6.4 Hz).

Example 100

6-chloro-5'-(3-chlorophenyl)-2'-(4-ethoxy-2-methoxyphenyl)-3'-isopropyl-3'H-spiro[dihydroindole-3,4'-pyrrolo[3,4-d]imidazole]-2,6'(5'H)-dione

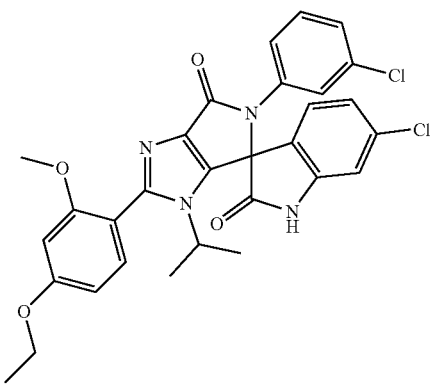 [SMILES: CCOc1ccc(-c2nc3c(n2C(C)C)C2(C(=O)Nc4cc(Cl)ccc42)N(c2cccc(Cl)c2)C3=O)c(OC)c1]

Title compounds were obtained by steps similar to those in Example 1, and supercritical high-pressure preparative chromatography was performed to obtain 19.1 mg of (S)-6-chloro-5'-(3-chlorophenyl)-2'-(4-ethoxy-2-methoxyphenyl)-3'-isopropyl-3'H-spiro[dihydroindole-3,4'-pyrrolo[3,4-d]imidazole]-2,6'(5'H)-dione (S-100), and 21.3 mg of (R)-6-chloro-5'-(3-chlorophenyl)-2'-(4-ethoxy-2-methoxyphenyl)-3'-isopropyl-3'H-spiro[dihydroindole-3,4'-pyrrolo[3,4-d]imidazole]-2,6'(5'H)-dione (R-100). MS (ESI): mass calcd. for $C_{30}H_{26}Cl_2N_4O_4$ 576.13, m/z found 577.2 [M+H]$^+$. $^1$H-NMR (400 MHz, DMSO-d$_6$) δ 11.56 (brs, 1H), 7.45 (d, 1H, J=8.0 Hz), 7.37-6.94 (m, 7H), 6.69 (s, 1H), 6.66 (d, 1H, J=8.4 Hz), 7.00-6.94 (m, 2H), 4.14-4.03 (m, 3H), 3.76 (s, 3H), 1.37 (t, 3H, J=6.8 Hz), 1.04 (d, 3H, J=6.4 Hz), 0.60 (d, 3H, J=6.4 Hz).

Example 101

2'-(4-(tert-butyl)-2-methoxyphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione

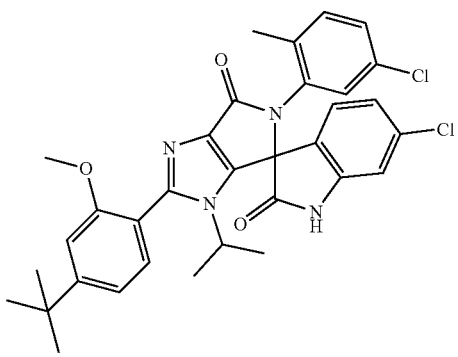 [SMILES: COc1cc(C(C)(C)C)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 17.1 mg of (S)-2'-(4-(tert-butyl)-2-methoxyphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (S-101), and 17.2 mg of (R)-2'-(4-(tert-butyl)-2-methoxyphenyl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (R-101). MS (ESI): mass calcd. for $C_{33}H_{32}Cl_2N_4O_3$ 602.2, m/z found 603.4 [M+H]$^+$. H-NMR (400 MHz, DMSO-d$_6$) δ 7.56-6.48 (m, 9H), 4.08-4.07 (m, 1H), 3.81 (s, 3H), 2.22 (s, 3H), 1.35 (s, 9H), 1.07 (d, 3H, J=5.2 Hz), 0.62 (d, 3H, J=5.2 Hz).

Example 102

6-chloro-5'-(3-chlorophenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione

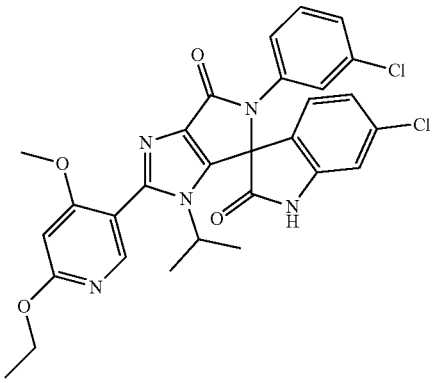 [SMILES: CCOc1cc(OC)c(-c2nc3c(n2C(C)C)C2(C(=O)Nc4cc(Cl)ccc42)N(c2cccc(Cl)c2)C3=O)cn1]

Title compounds were obtained by steps similar to those in Example 1, and supercritical high-pressure preparative chromatography was performed to obtain 53.4 mg of (S)-6-chloro-5'-(3-chlorophenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione (S-102), and 55.0 mg of (R)-6-chloro-5'-(3-chlorophenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione (R-102). MS (ESI): mass calcd. for $C_{29}H_{25}Cl_2N_5O_4$ 577.13, m/z found 578.4 [M+H]$^+$. $^1$H-NMR (400 MHz, DMSO-d$_6$) δ 11.54 (brs, 1H), 8.09 (s, 1H), 7.48 (d, 1H, J=8.0 Hz), 7.38 (d, 1H, J=8.4 Hz), 7.34 (s, 1H), 7.14-7.12 (m, 2H), 7.00 (s, 1H), 6.97 (d, 1H, J=7.2 Hz), 6.57 (s, 1H), 4.40 (q, 2H, J=6.8 Hz), 4.07-4.02 (m, 1H), 3.83 (s, 3H), 1.35 (t, 3H, J=6.8 Hz), 1.10 (d, 3H, J=6.4 Hz), 0.62 (d, 3H, J=6.4 Hz).

Example 103

6-chloro-5'-(5-chloro-2-methylphenyl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione

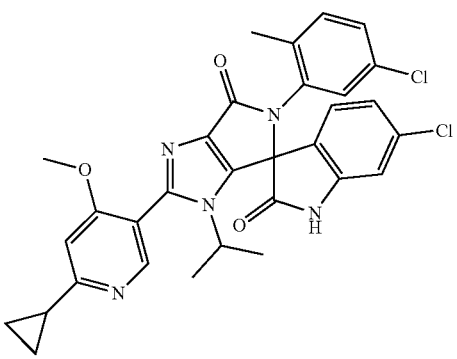 [SMILES: COc1cc(C2CC2)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 39.5 mg of (S)-6-chloro-5'-(5-chloro-2-methylphenyl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione (S-103), and 32.7 mg of (R)-6-chloro-5'-(5-chloro-2-methylphenyl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione (R-103). MS (ESI): mass calcd. for $C_{31}H_{27}Cl_2N_5O_3$ 587, m/z found 588.4 [M+H]$^+$. $^1$H-NMR (400 MHz, DMSO-d$_6$) δ 11.72 (brs, 1H), 8.30 (d, 1H, J=4.0 Hz), 7.57-6.97 (m, 7H), 4.08-4.06 (m, 2H), 3.88 (s, 3H), 2.21 (s, 3H), 2.07-1.98 (m, 4H), 1.08 (d, 3H, J=6.0 Hz), 0.66 (d, 3H, J=6.0 Hz).

Example 104

6-chloro-5'-(3-chlorophenyl)-2'-(4-(dimethylamino)-2-methoxyphenyl)-3'-isopropyl-3'H-spiro[dihydroindole-3,4'-pyrrolo[3,4-d]imidazole]-2,6'(5'H)-dione

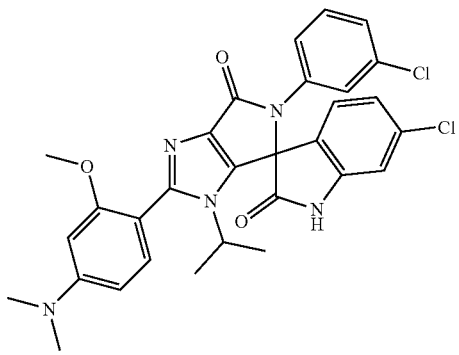 [SMILES: COc1cc(N(C)C)ccc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 80.2 mg of (S)-6-chloro-5'-(3-chlorophenyl)-2'-(4-(dimethylamino)-2-methoxyphenyl)-3'-isopropyl-3'H-spiro[dihydroindole-3,4'-pyrrolo[3,4-d]imidazole]-2,6'(5'H)-dione (S-104), and 70.0 mg of (R)-6-chloro-5'-(3-chlorophenyl)-2'-(4-(dimethylamino)-2-methoxyphenyl)-3'-isopropyl-3'H-spiro[dihydroindole-3,4'-pyrrolo[3,4-d]imidazole]-2,6'(5'H)-dione (R-104). MS (ESI): mass calcd. for $C_{30}H_{27}C_{12}N_5O_3$ 575.15, m/z found 576.6[M+H]$^+$. $^1$H-NMR (400 MHz, DMSO-d$_6$) δ 11.50 (brs, 1H), 7.45 (d, 1H, J=8.0 Hz), 7.37-7.30 (m, 2H), 7.17-7.11 (m, 3H), 7.00-6.94 (m, 2H), 6.40-6.35 (m, 2H), 4.13-4.06 (m, 1H), 4.06 (s, 3H), 3.76 (s, 3H), 2.99 (s, 6H), 1.09 (d, 3H, J=6.0 Hz), 0.60 (d, 3H, J=6.0 Hz).

Example 105

6-chloro-5'-(5-chloro-2-methylphenyl)-2'-(4-(diethylamino)-2-methoxyphenyl)-3'-isopropyl-3'H-spiro[dihydroindole-3,4'-pyrrolo[3,4-d]imidazole]-2,6'(5'H)-dione

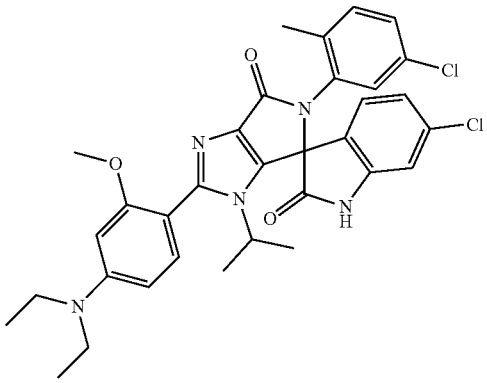 [SMILES: CCN(CC)c1ccc(-c2nc3c(n2C(C)C)C2(C(=O)Nc4cc(Cl)ccc42)N(c2cc(Cl)ccc2C)C3=O)c(OC)c1]

Title compounds were obtained by steps similar to those in Example 1, and supercritical high-pressure preparative chromatography was performed to obtain 11.6 mg of (S)-6-chloro-5'-(5-chloro-2-methylphenyl)-2'-(4-(diethylamino)-2-methoxyphenyl)-3'-isopropyl-3'H-spiro[dihydroindole-3,4'-pyrrolo[3,4-d]imidazole]-2,6'(5'H)-dione (S-105), and 16.3 mg of (R)-6-chloro-5'-(5-chloro-2-methylphenyl)-2'-(4-(diethylamino)-2-methoxyphenyl)-3'-isopropyl-3'H-spiro[dihydroindole-3,4'-pyrrolo[3,4-d]imidazole]-2,6'(5'H)-dione (R-105). MS (ESI): mass calcd. for $C_{33}H_{33}Cl_2N_5O_3$ 617.19, m/z found 618.5 [M+H]$^+$. $^1$H-NMR (400 MHz, DMSO-d$_6$) δ 11.68 (brs, 1H), 7.54-6.94 (m, 7H), 6.46-6.27 (m, 2H), 4.14-4.11 (m, 1H), 3.75 (s, 3H), 3.42-3.40 (m, 4H), 2.21 (s, 3H), 1.16-1.12 (m, 6H), 1.06 (d, 3H, J=5.2 Hz), 0.62 (d, 3H, J=5.2 Hz).

Example 106

6-chloro-5'-(3-chlorophenyl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione

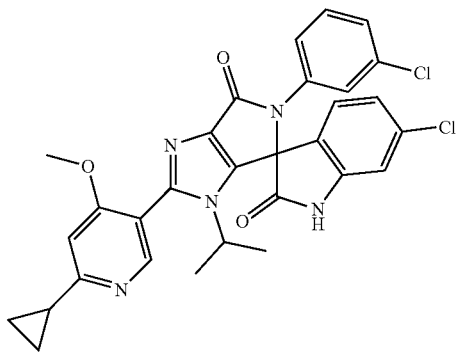 [SMILES: COc1cc(C2CC2)ncc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 47.4 mg of (S)-

6-chloro-5'-(3-chlorophenyl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione (S-106), and 57.5 mg of (R)-6-chloro-5'-(3-chlorophenyl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione (R-106). MS (ESI): mass calcd. for $C_{30}H_{25}Cl_2N_5O_3$ 573, m/z found 574.3[M+H]$^+$. $^1$H-NMR (400 MHz, DMSO-d$_6$) δ 11.56 (brs, 1H), 8.33 (s, 1H), 7.49 (d, 1H, J=8.0 Hz), 7.36-6.95 (m, 8H), 4.08-4.06 (m, 1H), 3.89 (s, 3H), 2.15-2.00 (m, 1H), 1.05 (d, 3H, J=6.0 Hz), 1.03-0.98 (m, 4H), 0.62 (d, 3H, J=6.0 Hz).

Example 107

6-chloro-5'-(3-chlorophenyl)-2'-(4-ethyl-2-methoxyphenyl)-3'-isopropyl-3'H-spiro[dihydroindole-3,4'-pyrrolo[3,4-d]imidazole]-2,6'(5'H)-dione

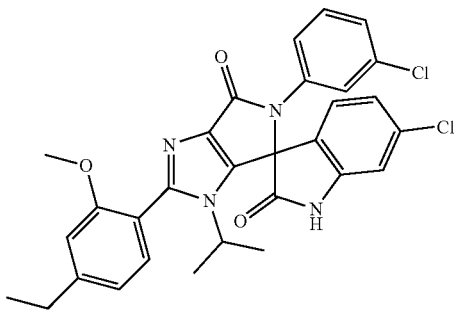 [SMILES: CCc1ccc(-c2nc3c(n2C(C)C)C2(C(=O)Nc4cc(Cl)ccc42)N(c2cccc(Cl)c2)C3=O)c(OC)c1]

Title compounds were obtained by steps similar to those in Example 1, and supercritical high-pressure preparative chromatography was performed to obtain 49.1 mg of (S)-6-chloro-5'-(3-chlorophenyl)-2'-(4-ethyl-2-methoxyphenyl)-3'-isopropyl-3'H-spiro[dihydroindole-3,4'-pyrrolo[3,4-d]imidazole]-2,6'(5'H)-dione (S-107), and 39.8 mg of (R)-6-chloro-5'-(3-chlorophenyl)-2'-(4-ethyl-2-methoxyphenyl)-3'-isopropyl-3'H-spiro[dihydroindole-3,4'-pyrrolo[3,4-d]imidazole]-2,6'(5'H)-dione (R-107). MS (ESI): mass calcd. for $C_{30}H_{26}Cl_2N_4O_3$ 560.13, m/z found 561.3 [M+H]$^+$. $^1$H-NMR (400 MHz, DMSO-d$_6$) δ 11.48 (brs, 1H), 7.48 (d, 1H, J=8.0 Hz), 7.37-6.94 (m, 9H), 4.09-4.02 (m, 1H), 3.77 (s, 3H), 2.72 (q, 2H, J=7.6 Hz), 1.26 (t, 3H, J=7.6 Hz), 1.04 (d, 3H, J=6.0 Hz), 0.61 (d, 3H, J=6.0 Hz).

Example 108

6-chloro-5'-(5-chloro-2-methylphenyl)-2'-(4-cyclopropyl-2,6-dimethoxyphenyl)-3'-isopropyl-3'H-spiro[dihydroindole-3,4'-pyrrolo[3,4-d]imidazole]-2,6'(5'H)-dione

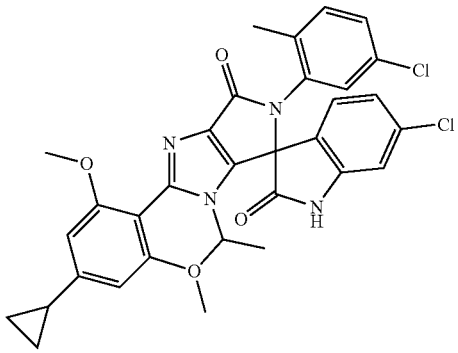

Title compounds were obtained by steps similar to those in Example 1, and supercritical high-pressure preparative chromatography was performed to obtain 28.4 mg of (S)-6-chloro-5'-(5-chloro-2-methylphenyl)-2'-(4-cyclopropyl-2,6-dimethoxyphenyl)-3'-isopropyl-3'H-spiro[dihydroindole-3,4'-pyrrolo[3,4-d]imidazole]-2,6'(5'H)-dione (S-108), and 29.9 mg of (R)-6-chloro-5'-(5-chloro-2-methylphenyl)-2'-(4-cyclopropyl-2,6-dimethoxyphenyl)-3'-isopropyl-3'H-spiro[dihydroindole-3,4'-pyrrolo[3,4-d]imidazole]-2,6'(5'H)-dione (R-108). MS (ESI): mass calcd. for $C_{33}H_{30}Cl_2N_4O_4$ 616.16, m/z found 617.4 [M+H]$^+$. $^1$H-NMR (400 MHz, DMSO-d$_6$) δ 11.66 (brs, 1H), 7.45-6.48 (m, 8H), 3.89-3.88 (m, 1H), 3.73 (s, 3H), 3.70 (s, 3H), 2.23 (s, 3H), 2.07-2.00 (m, 1H), 1.01-0.99 (m, 5H), 0.84-0.83 (m, 2H), 0.60 (d, 3H, J=6.8 Hz).

Example 109

6-chloro-5'-(3-chlorophenyl)-3'-isopropyl-2'-(2-methoxy-4-methylphenyl)-3'H-spiro[dihydroindole-3,4'-pyrrolo[3,4-d]imidazole]-2,6'(5'H)-dione

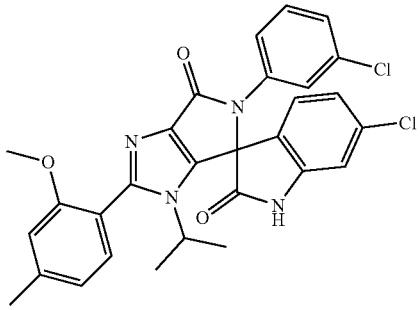 [SMILES: COc1cc(C)ccc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 34.0 mg of (S)-6-chloro-5'-(3-chlorophenyl)-3'-isopropyl-2'-(2-methoxy-4-methylphenyl)-3'H-spiro[dihydroindole-3,4'-pyrrolo[3,4-d]imidazole]-2,6'(5'H)-dione (S-[108]109), and 43.5 mg of (R)-6-chloro-5'-(3-chlorophenyl)-3'-isopropyl-2'-(2-methoxy-4-methylphenyl)-3'H-spiro[dihydroindole-3,4'-pyrrolo[3,4-d]imidazole]-2,6'(5'H)-dione (R-[108]109). MS (ESI): mass calcd. For $C_{29}H_{24}Cl_2N_4O_3$ 546.12, m/z found 547.4[M+H]$^+$. $^1$H-NMR (400 MHz, DMSO-d$_6$) δ 11.53 (brs, 1H), 7.47-6.90 (m, 10H), 4.07-4.02 (m, 1H), 3.76 (s, 3H), 2.39 (s, 3H), 1.04 (d, 3H, J=6.0 Hz), 0.59 (d, 3H, J=6.0 Hz).

Example 110

6-chloro-5'-(5-chloro-2-methylphenyl)-2'-(6-cyclopropoxy-4-methoxypyridin-3-yl)-3'-isopropyl-3'H-spiro[dihydroindole-3,4'-pyrrolo[3,4-d]imidazole]-2,6'(5'H)-dione

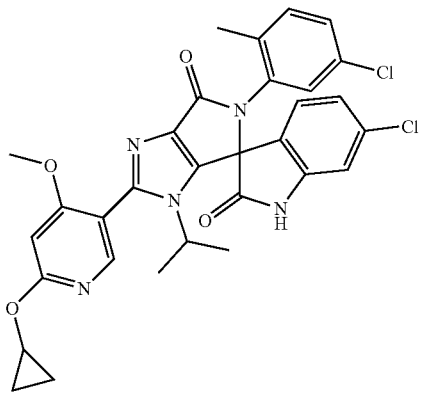 [SMILES: COc1cc(OC2CC2)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 13.6 mg of (S)-6-chloro-5'-(5-chloro-2-methylphenyl)-2'-(6-cyclopropoxy-4-methoxypyridin-3-yl)-3'-isopropyl-3'H-spiro[dihydroindole-3,4'-pyrrolo[3,4-d]imidazole]-2,6'(5'H)-dione (S-[109]110), and 13.1 mg of (R)-6-chloro-5'-(5-chloro-2-methylphenyl)-2'-(6-cyclopropoxy-4-methoxypyridin-3-yl)-3'-isopropyl-3'H-spiro[dihydroindole-3,4'-pyrrolo[3,4-d]imidazole]-2,6'(5'H)-dione (R-[109]110). MS (ESI): mass calcd. For $C_{31}H_{27}Cl_2N_5O_4$ 603.14, m/z found 604.3 [M+H]$^+$. $^1$H-NMR (400 MHz, DMSO-d$_6$) δ 11.73 (brs, 1H), 8.16-6.48 (m, 8H), 4.31-4.30 (m, 1H), 4.07-4.06 (m, 1H), 3.84 (s, 3H), 2.22 (s, 3H), 1.08 (d, 3H, J=5.6 Hz), 0.82-0.80 (m, 2H), 0.79-0.71 (m, 2H), 0.65 (d, 3H, J=5.6 Hz).

Example 111

6-chloro-5'-(5-chloro-2-methylphenyl)-2'-(6-(dimethylamino)-4-methoxypyridin-3-yl)-3'-isopropyl-3'H-spiro[dihydroindole-3,4'-pyrrolo[3,4-d]imidazole]-2,6'(5'H)-dione

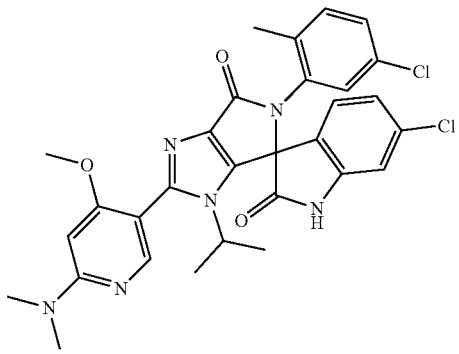 [SMILES: COc1cc(N(C)C)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 44.9 mg of (S)-6-chloro-5'-(5-chloro-2-methylphenyl)-2'-(6-(dimethylamino)-4-methoxypyridin-3-yl)-3'-isopropyl-3'H-spiro[dihydroindole-3,4'-pyrrolo[3,4-d]imidazole]-2,6'(5'H)-dione (S-[110]111), and 47.3 mg of (R)-6-chloro-5'-(5-chloro-2-methylphenyl)-2'-(6-(dimethylamino)-4-methoxypyridin-3-yl)-3'-isopropyl-3'H-spiro[dihydroindole-3,4'-pyrrolo[3,4-d]imidazole]-2,6'(5'H)-dione (R-[110]111). MS (ESI): mass calcd. For $C_{29}H_{27}Cl_2N_7O_3$ 591, m/z found 592.4 [M+H]$^+$. $^1$H-NMR (400 MHz, DMSO-d$_6$) δ 11.52 (brs, 1H), 7.98-6.21 (m, 8H), 4.11-4.07 (m, 1H), 3.84 (s, 3H), 3.10 (s, 6H), 2.22 (s, 3H), 1.07 (d, 3H, J=6.0 Hz), 0.63 (d, 3H, J=6.0 Hz)

Example 112

6-chloro-5'-(3-chlorophenyl)-2'-(2-(dimethylamino)-4-methoxypyrimidin-5-yl)-3'-isopropyl-3'H-spiro[dihydroindole-3,4'-pyrrolo[3,4-d]imidazole]-2,6'(5'H)-dione

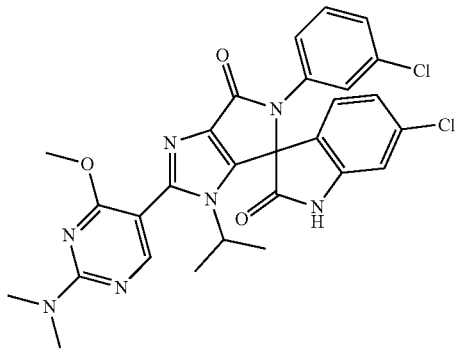 [SMILES: COc1nc(N(C)C)ncc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 50.9 mg of (S)-6-chloro-5'-(3-chlorophenyl)-2'-(2-(dimethylamino)-4-methoxypyrimidin-5-yl)-3'-isopropyl-3'H-spiro[dihydroindole-3,4'-pyrrolo[3,4-d]imidazole]-2,6'(5'H)-dione (S-[111]112), and 46.6 mg of (R)-6-chloro-5'-(3-chlorophenyl)-2'-(2-(dimethylamino)-4-methoxypyrimidin-5-yl)-3'-isopropyl-3'H-spiro[dihydroindole-3,4'-pyrrolo[3,4-d]imidazole]-2,6'(5'H)-dione (R-[111]112). MS (ESI): mass calcd. For $C_{28}H_{25}Cl_2N_7O_3$ 577.13, m/z found 578.3 [M+H]$^+$. $^1$H-NMR (400 MHz, DMSO-d$_6$) δ 11.52 (brs, 1H), 8.23 (s, 1H), 7.65-6.94 (m, 7H), 4.16-4.09 (m, 1H), 3.89 (s, 3H), 3.19 (s, 6H), 1.11 (d, 3H, J=6.8 Hz), 0.64 (d, 3H, J=6.4 Hz).

Example 113

6-chloro-5'-(3-chlorophenyl)-2'-(6-(dimethylamino)-4-methoxypyridin-3-yl)-3'-isopropyl-3'H-spiro[dihydroindole-3,4'-pyrrolo[3,4-d]imidazole]-2,6'(5'H)-dione

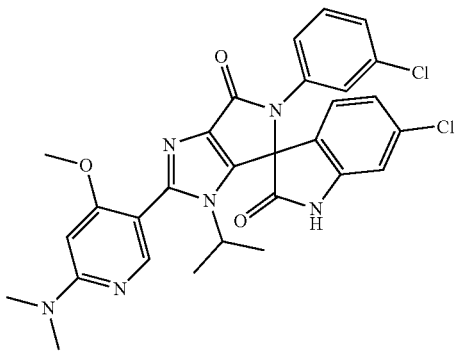 [SMILES: COc1cc(N(C)C)ncc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 45.0 mg of (S)-6-chloro-5'-(3-chlorophenyl)-2'-(6-(dimethylamino)-4-methoxypyridin-3-yl)-3'-isopropyl-3'H-spiro[dihydroindole-3,4'-pyrrolo[3,4-d]imidazole]-2,6'(5'H)-dione (S-[112]113), and 34.4 mg of (R)-6-chloro-5'-(3-chlorophenyl)-2'-(6-(dimethylamino)-4-methoxypyridin-3-yl)-3'-isopropyl-3'H-spiro[dihydroindole-3,4'-pyrrolo[3,4-d]imidazole]-2,6'(5'H)-dione (R-[112]113). MS (ESI): mass calcd. For $C_{29}H_{26}Cl_2N_6O_3$ 576, m/z found 577.4 [M+H]$^+$. $^1$H-NMR (400 MHz, DMSO-d$_6$) δ 11.60 (brs, 1H), 8.06 (s, 1H), 7.44-6.96 (m, 7H), 6.39 (s, 1H), 4.12-4.05 (m, 1H), 3.92 (s, 3H), 3.20 (s, 6H), 1.12 (d, 3H, J=6.8 Hz), 0.63 (d, 3H, J=6.4 Hz).

Example 114

6-chloro-5'-(5-chloro-2-methylphenyl)-3'-isopropyl-2'-(4-methoxy-2-(10zetidine10e-1-yl)pyrimidin-5-yl)-3'H-spiro[dihydroindole-3,4'-pyrrolo[3,4-d]imidazole]-2,6' (5' H)-dione

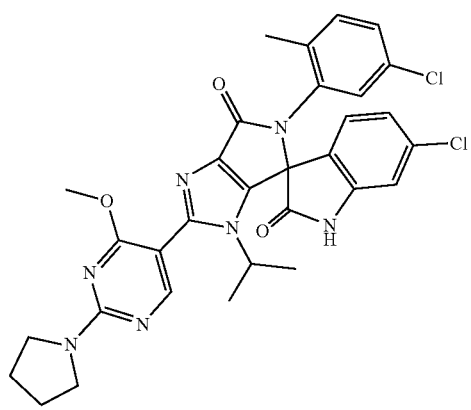 [SMILES: COc1nc(N2CCCC2)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 10.1 mg of (S)-6-chloro-5'-(5-chloro-2-methylphenyl)-3'-isopropyl-2'-(4-methoxy-2-(pyrrolidine-1-yl)pyrimidin-5-yl)-3'H-spiro[dihydroindole-3,4'-pyrrolo[3,4-d]imidazole]-2,6'(5'H)-dione (S-[113]114), and 13.5 mg of (R)-6-chloro-5'-(5-chloro-2-methylphenyl)-3'-isopropyl-2'-(4-methoxy-2-(10zetidine10e-1-yl)pyrimidin-5-yl)-3'H-spiro[dihydroindole-3,4'-pyrrolo[3,4-d]imidazole]-2,6'(5'H)-dione (R-[113]114). MS (ESI): mass calcd. For $C_{31}H_{29}Cl_2N_7O_3$ 617.17, m/z found 618.2[M+H]$^+$. $^1$H-NMR (400 MHz, DMSO-d$_6$) δ 11.63 (brs, 1H), 8.24 (d, 1H, J=4.4 Hz), 7.54-6.47 (m, 6H), 4.13-4.12 (m, 1H), 3.90 (s, 3H), 3.69-3.56 (m, 4H), 2.21 (s, 3H), 2.06-1.95 (m, 4H), 1.09 (d, 3H, J=5.2 Hz), 0.66 (d, 3H, J=6.0 Hz).

Example 115

6-chloro-5'-(3-chlorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione

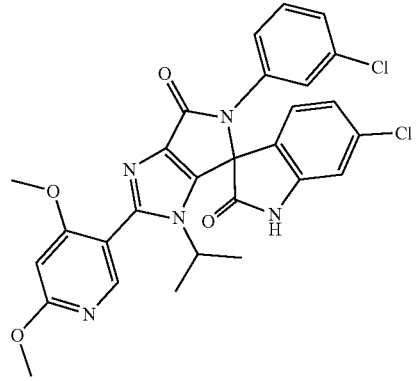 [SMILES: COc1cc(OC)c(-c2nc3c(n2C(C)C)C2(C(=O)Nc4cc(Cl)ccc42)N(c2cccc(Cl)c2)C3=O)cn1]

Title compounds were obtained by steps similar to those in Example 1, and supercritical high-pressure preparative chromatography was performed to obtain 171.8 mg of (S)-6-chloro-5'-(3-chlorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione (S-[114]115), and 137.4 mg of (R)-6-chloro-5'-(3-chlorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione (R-[114]115). MS (ESI): mass calcd. For $C_{28}H_{23}Cl_2N_5O_4$ 563.11, m/z found 564.1 [M+H]$^+$. $^1$H-NMR (400 MHz, DMSO-d$_6$) δ 11.57 (brs, 1H), 8.11 (s, 1H), 7.48-6.95 (m, 7H), 6.58 (s, 1H), 4.09-4.02 (m, 1H), 3.92 (s, 3H), 3.83 (s, 3H), 1.04 (d, 3H, J=3.6 Hz), 0.63 (d, 3H, J=6.4 Hz).

Example 116

6-chloro-5'-(3-chlorophenyl)-2'-(4-cyclopropyl-2-methoxyphenyl)-3'-isopropyl-3'H-spiro[dihydroindole-3,4'-pyrrolo[3,4-d]imidazole]-2,6'(5'H)-dione

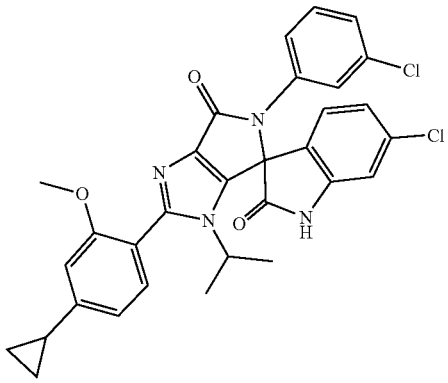 [SMILES: COc1cc(C2CC2)ccc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 9.2 mg of (S)-6-chloro-5'-(3-chlorophenyl)-2'-(4-cyclopropyl-2-methoxyphenyl)-3'-isopropyl-3'H-spiro[dihydroindole-3,4'-pyrrolo[3,4-d]imidazole]-2,6'(5'H)-dione (S-[115]116), and 9.2 mg of (R)-6-chloro-5'-(3-chlorophenyl)-2'-(4-cyclopropyl-2-methoxyphenyl)-3'-isopropyl-3'H-spiro[dihydroindole-3,4'-pyrrolo[3,4-d]imidazole]-2,6'(5'H)-dione (R-[115]116). MS (ESI): mass calcd. For $C_{31}H_{26}Cl_2N_4O_3$ 572.14, m/z found 573.2 [M+H]$^+$. $^1$H-NMR (400 MHz, DMSO-d$_6$) δ 11.06 (brs, 1H), 7.46-6.77 (m, 10H), 4.07-4.01 (m, 1H), 3.77 (s, 3H), 2.01-1.99 (m, 1H), 1.24-0.79 (m, 7H), 0.60 (d, 3H, J=4.4 Hz).

Example 117

2'-(2-(12zetidine-1-yl)-4-methoxypyrimidin-5-yl)-6-chloro-5'-(5-chloro-2-methylphenyl)-3'-isopropyl-3'H-spiro[dihydroindole-3,4'-pyrrolo[3,4-d]imidazole]-2,6'(5'H)-dione

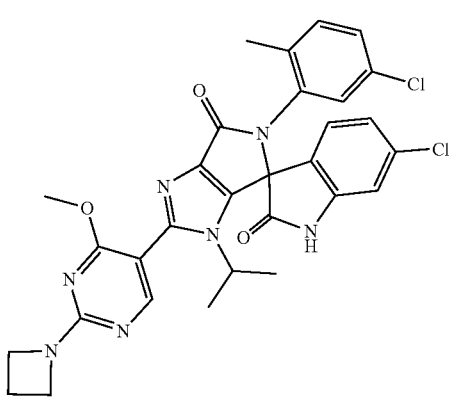 [SMILES: COc1nc(N2CCC2)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 42.3 mg of (S)-2'-(2-(12zetidine-1-yl)-4-methoxypyrimidin-5-yl)-6-chloro-5'-(5-chloro-2-methylphenyl)-3'-isopropyl-3'H-spiro[dihydroindole-3,4'-pyrrolo[3,4-d]imidazole]-2,6'(5'H)-dione (S-[116]117), and 41.8 mg of (R)-2'-(2-(12zetidine-1-yl)-4-methoxypyrimidin-5-yl)-6-chloro-5'-(5-chloro-2-methylphenyl)-3'-isopropyl-3'H-spiro[dihydroindole-3,4'-pyrrolo[3,4-d]imidazole]-2,6'(5' H)-dione (R-[116]117). MS (ESI): mass calcd. For $C_{30}H_{27}Cl_2N_7O_3$ 603.15, m/z found 604.4 [M+H]$^+$. $^1$H-NMR (400 MHz, DMSO-d$_6$) δ 11.27 (brs, 1H), 8.22 (d, 1H, J=4.8 Hz) 7.54-6.47 (m, 6H), 4.14 (t, 4H, J=7.2 Hz), 3.87 (s, 3H), 2.36-2.32 (m, 2H), 2.22 (s, 3H), 1.08 (d, 3H, J=5.2 Hz), 0.66 (d, 3H, J=5.6 Hz).

Example 118

6-chloro-5'-(5-chloro-2-methylphenyl)-3'-isopropyl-2'-(4-methoxy-2-methylpyrimidin-5-yl)-3'H-spiro[dihydroindole-3,4'-pyrrolo[3,4-d]imidazole]-2,6' (5'H)-dione

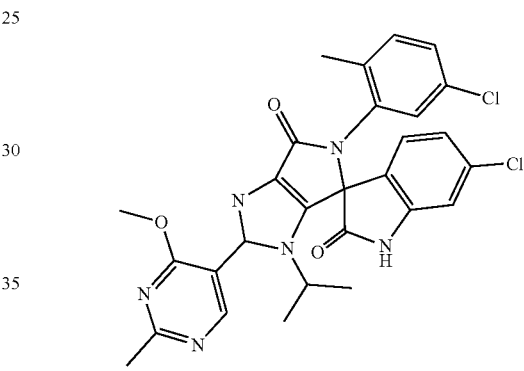

Title compounds were obtained by steps similar to those in Example 1, and supercritical high-pressure preparative chromatography was performed to obtain 61.9 mg of (S)-6-chloro-5'-(5-chloro-2-methylphenyl)-3'-isopropyl-2'-(4-methoxy-2-methylpyrimidin-5-yl)-3'H-spiro[dihydroindole-3,4'-pyrrolo[3,4-d]imidazole]-2,6'(5'H)-dione (S-[117]118), and 62.0 mg of (R)-6-chloro-5'-(5-chloro-2-methylphenyl)-3'-isopropyl-2'-(4-methoxy-2-methylpyrimidin-5-yl)-3'H-spiro[dihydroindole-3,4'-pyrrolo[3,4-d]imidazole]-2,6'(5'H)-dione (R-[117]118). MS (ESI): mass calcd. For $C_{28}H_{24}Cl_2N_6O_3$ 562, m/z found 563.4[M+H]$^+$. $^1$H-NMR (400 MHz, DMSO-d$_6$) δ 11.73 (brs, 1H), 8.62 (d, 1H, J=6.4 Hz), 7.57-6.48 (m, 6H), 4.15-4.12 (m, 1H), 3.96 (s, 3H), 2.63 (s, 3H), 2.22 (s, 3H), 1.09 (d, 3H, J=6.4 Hz), 0.66 (d, 3H, J=6.4 Hz).

Example 119

6-chloro-5'-(5-chloro-2-methylphenyl)-2'-(2-(ethyl(methyl)amino)-4-methoxypyrimidin-5-yl)-3'-isopropyl-3'H-spiro[dihydroindole-3,4'-pyrrolo[3,4-d]imidazole]-2,6'(5'H)-dione

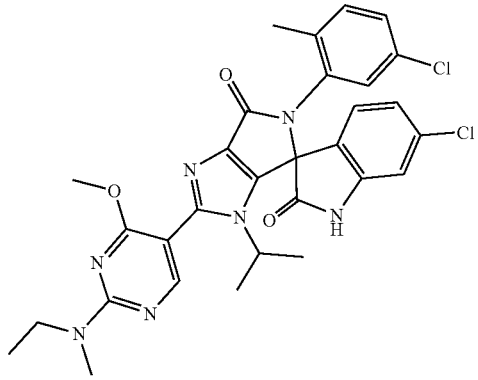 [SMILES: CCN(C)c1ncc(-c2nc3c(n2C(C)C)C2(C(=O)Nc4cc(Cl)ccc42)N(c2cc(Cl)ccc2C)C3=O)c(OC)n1]

Title compounds were obtained by steps similar to those in Example 1, and supercritical high-pressure preparative chromatography was performed to obtain 40.7 mg of (S)-6-chloro-5'-(5-chloro-2-methylphenyl)-2'-(2-(ethyl(methyl)amino)-4-methoxypyrimidin-5-yl)-3'-isopropyl-3'H-spiro[dihydroindole-3,4'-pyrrolo[3,4-d]imidazole]-2,6'(5'H)-dione (S-[118]119), and 24.5 mg of (R)-6-chloro-5'-(5-chloro-2-methylphenyl)-2'-(2-(ethyl(methyl)amino)-4-methoxypyrimidin-5-yl)-3'-isopropyl-3'H-spiro[dihydroindole-3,4'-pyrrolo[3,4-d]imidazole]-2,6'(5'H)-dione (R-[118]119). MS (ESI): mass calcd. For $C_{30}H_{29}Cl_2N_7O_3$ 605.17, m/z found 606.4[M+H]$^+$. $^1$H-NMR (400 MHz, DMSO-d$_6$) δ 11.61 (brs, 1H), 8.24 (d, 1H, J=4.0 Hz), 7.55-6.47 (m, 6H), 4.16-4.15 (m, 1H), 3.89 (s, 3H), 3.69-3.68 (m, 2H), 3.15 (s, 3H), 2.21 (s, 3H), 1.23-1.16 (m, 3H), 1.09 (d, 3H, J=5.2 Hz), 0.66 (d, 3H, J=5.2 Hz).

Example 120

6-chloro-5'-(3-chlorophenyl)-3'-isopropyl-2'-(2-methoxy-4-(trifluoromethoxy)phenyl)-3'H-spiro[dihydroindole-3,4'-pyrrolo[3,4-d]imidazole]-2,6'(5'H)-dione

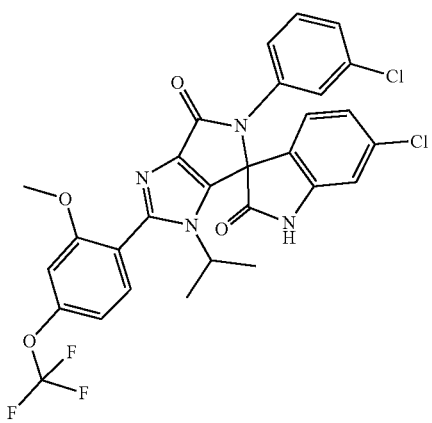 [SMILES: COc1cc(OC(F)(F)F)ccc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 115.1 mg of (S)-6-chloro-5'-(3-chlorophenyl)-3'-isopropyl-2'-(2-methoxy-4-(trifluoromethoxy)phenyl)-3'H-spiro[dihydroindole-3,4'-pyrrolo[3,4-d]imidazole]-2,6'(5'H)-dione (S-[119]120), and 44.0 mg of (R)-6-chloro-5'-(3-chlorophenyl)-3'-isopropyl-2'-(2-methoxy-4-(trifluoromethoxy)phenyl)-3'H-spiro[dihydroindole-3,4'-pyrrolo[3,4-d]imidazole]-2,6'(5'H)-dione (R-[119]120). MS (ESI): mass calcd. For Chemical Formula: $C_{29}H_{21}Cl_2F_3N_4O_4$, Exact Mass: 616.09, m/z found 617.1 [M+H]$^+$. $^1$H-NMR (400 MHz, DMSO-d$_6$) δ 11.51 (brs, 1H), 7.57-7.47 (m, 2H), 7.38-7.34 (m, 2H), 7.21 (s, 1H), 7.14-7.09 (m, 3H), 7.00-6.96 (m, 2H), 4.06-4.03 (m, 1H), 3.88 (s, 3H), 1.10 (d, 3H, J=4.4 Hz), 0.62 (d, 3H, J=4.4 Hz).

Example 121

6-chloro-5'-(5-chloro-2-methylphenyl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione

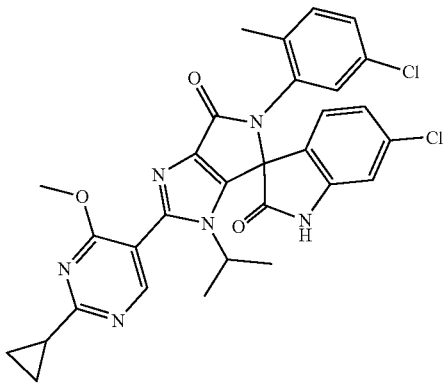 [SMILES: COc1nc(C2CC2)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 9.9 mg of (S)-6-chloro-5'-(5-chloro-2-methylphenyl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione (S-[120]121), and 9.4 mg of (R)-6-chloro-5'-(5-chloro-2-methylphenyl)-2'-(2-cyclopropyl-4-methoxypyrimidin-5-yl)-3'-isopropyl-3'H-spiro[dihydroindole-3,4'-pyrrolo[3,4-d]imidazole]-2,6' (5'H)-dione (R-[120]121). MS (ESI): mass calcd. For $C_{30}H_{26}Cl_2N_6O_3$ 588.14, m/z found 589.4[M+H]$^+$. $^1$H-NMR (400 MHz, DMSO-d$_6$) δ 11.76 (brs, 1H), 8.54 (d, 1H, J=6.4 Hz), 7.56-6.98 (m, 7H), 4.15-4.14 (m, 1H), 3.94 (s, 3H), 2.21 (s, 3H), 2.07-1.99 (m, 1H), 1.35-1.08 (m, 7H), 0.66 (d, 3H, J=6.0 Hz).

Example 122

6-chloro-5'-(3-chlorophenyl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione

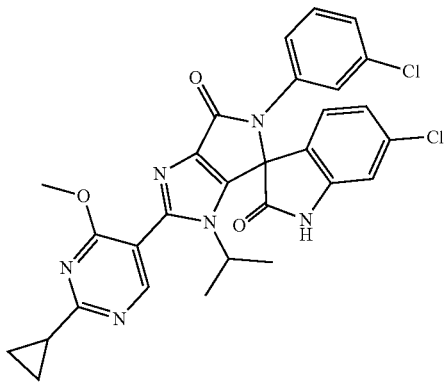 [SMILES: COc1nc(C2CC2)ncc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 13.1 mg of (S)-6-chloro-5'-(3-chlorophenyl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione (S-[121]122), and 13.3 mg of (R)-6-chloro-5'-(3-chlorophenyl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione (R-[121]122). MS (ESI): mass calcd. For $C_{29}H_{24}Cl_2N_6O_3$ 574.13, m/z found 575.4[M+H]$^+$. $^1$H-NMR (400 MHz, DMSO-$d_6$) δ 11.55 (brs, 1H), 8.52 (s, 1H), 7.48 (d, 1H, J=8.0 Hz), 7.38-7.34 (m, 2H), 7.15-7.12 (m, 2H), 7.01-0.95 (m, 2H), 4.14-4.11 (m, 1H), 3.93 (s, 3H), 2.22-1.19 (m, 1H), 1.12-1.10 (m, 6H), 0.64 (d, 3H, J=6.4 Hz).

Example 123

6-chloro-5'-(3-chlorophenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione Title compounds were obtained by steps similar to those in Example 1, and supercritical high-pressure preparative chromatography was performed to obtain 38.8 mg of (S)-6-chloro-5'-(3-chlorophenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione (S-[122]123), and 38.7 mg of (R)-6-chloro-5'-(3-chlorophenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione (R-[122]123). MS (ESI): mass calcd. For $C_{28}H_{24}Cl_2N_6O_4$ 578.12, m/z found 579.3 [M+H]$^+$. $^1$H-NMR (400 MHz, DMSO-$d_6$) δ 11.33 (brs, 1H), 8.49 (s, 1H), 7.48 (d, 1H, J=8.4 Hz), 7.38-7.34 (m, 2H), 7.15-7.11 (m, 2H), 7.01 (s, 1H), 6.97-6.95 (m, 1H), 4.46 (q, 2H, J=7.2 Hz), 4.19-4.14 (m, 1H), 3.93 (s, 3H), 1.39 (t, 3H, J=7.2 Hz), 1.12 (d, 3H, J=6.8 Hz), 0.65 (d, 3H, J=6.4 Hz).

Example 124

6-chloro-5'-(3-chlorophenyl)-2'-(2-isopropoxy-4-methoxypyrimidin-5-yl)-3'-isopropyl-3'H-spiro[dihydroindole-3,4'-pyrrolo[3,4-d]imidazole]-2,6'(5'H)-dione Title compounds were obtained by steps similar to those in Example 1, and supercritical high-pressure preparative chromatography was performed to obtain 43.9 mg of (S)-6-chloro-5'-(3-chlorophenyl)-2'-(2-isopropoxy-4-methoxypyrimidin-5-yl)-3'-isopropyl-3'H-spiro[dihydroindole-3,4'-pyrrolo[3,4-d]imidazole]-2,6'(5'H)-dione (S-[123]124), and 45.7 mg of (R)-6-chloro-5'-(3-chlorophenyl)-2'-(2-isopropoxy-4-methoxypyrimidin-5-yl)-3'-isopropyl-3'H-spiro[dihydroindole-3,4'-pyrrolo[3,4-d]imidazole]-2,6'(5'H)-dione (R-[123]124). MS (ESI): mass calcd. For $C_{29}H_{26}Cl_2N_6O_4$ 592.14, m/z found 593.4 [M+H]$^+$. $^1$H-NMR (400 MHz, DMSO-$d_6$) δ 11.58 (brs, 1H), 8.48 (s, 1H), 7.48-6.96 (m, 7H), 5.32-5.26 (m, 1H), 4.20-4.14 (m, 1H), 2.31 (s, 3H), 1.38 (d, 6H, J=6.0 Hz), 1.13 (d, 3H, J=6.8 Hz), 0.65 (d, 3H, J=6.8 Hz).

Example 125

6-chloro-5'-(5-chloro-2-methylphenyl)-2'-(4-(dimethylamino)-5-ethyl-2-methoxyphenyl)-3'-isopropyl-3'H-spiro[dihydroindole-3,4'-pyrrolo[3,4-d]imidazole]-2,6'(5'H)-dione

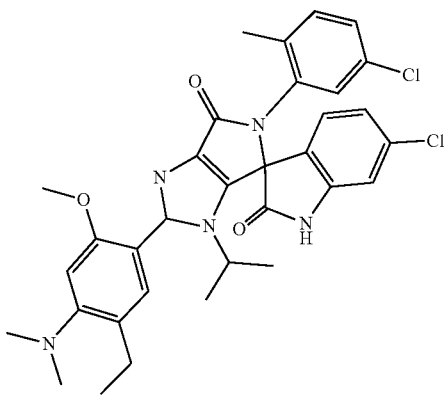

Title compounds were obtained by steps similar to those in Example 1, and supercritical high-pressure preparative chromatography was performed to obtain 53.23 mg of 6-chloro-5'-(5-chloro-2-methylphenyl)-2'-(4-(dimethylamino)-5-ethyl-2-methoxyphenyl)-3'-isopropyl-3'H-spiro[dihydroindole-3,4'-pyrrolo[3,4-d]imidazole]-2,6'(5'H)-dione. MS (ESI): mass calcd. for $C_{33}H_{33}Cl_2N_5O_3$ 617.20, m/z found 618.4 [M+H]$^+$. $^1$H-NMR (400 MHz, DMSO-d$_6$) δ 11.47 (brs, 1H), 7.95-6.47 (m, 8H), 4.11-4.08 (m, 1H), 3.78 (s, 3H), 2.74 (s, 6H), 2.66-2.61 (m, 2H), 2.22 (s, 3H), 1.238-1.071 (m, 6H), 0.68 (d, 3H, J=6.4 Hz).

Example 126

6-chloro-5'-(5-chloro-2-methylphenyl)-2'-(2-isopropoxy-4-methoxypyrimidin-5-yl)-3'-isopropyl-3'H-spiro[dihydroindole-3,4'-pyrrolo[3,4-d]imidazole]-2,6'(5'H)-dione

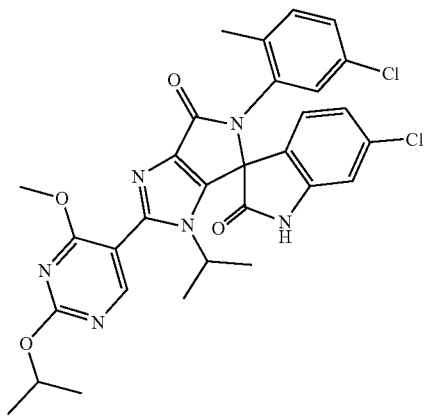 [SMILES: COc1nc(OC(C)C)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 28.9 mg of (S)-6-chloro-5'-(5-chloro-2-methylphenyl)-2'-(2-isopropoxy-4-methoxypyrimidin-5-yl)-3'-isopropyl-3'H-spiro[dihydroindole-3,4'-pyrrolo[3,4-d]imidazole]-2,6'(5'H)-dione (S-126), and 35.5 mg of (R)-6-chloro-5'-(5-chloro-2-methylphenyl)-2'-(2-isopropoxy-4-methoxypyrimidin-5-yl)-3'-isopropyl-3'H-spiro[dihydroindole-3,4'-pyrrolo[3,4-d]imidazole]-2,6'(5'H)-dione (R-126). MS (ESI): mass calcd. for $C_{30}H_{28}Cl_2N_6O_4$ 606.15, m/z found 607.4 [M+H]$^+$. $^1$H-NMR (400 MHz, DMSO-d$_6$) δ 11.76 (brs, 1H), 8.50 (d, 1H, J=6.4 Hz), 7.57-6.49 (m, 6H), 5.32-5.26 (m, 1H), 4.20-4.16 (m, 1H), 3.94 (s, 3H), 2.22 (s, 3H), 1.38 (d, 6H, J=6.0 Hz), 1.09 (d, 3H, J=4.4 Hz), 0.67 (d, 3H, J=6.0 Hz).

Example 127

6-chloro-5'-(5-chloro-2-methylphenyl)-2'-(2-ethoxy-4-methoxypyrimidin-5-yl)-3'-isopropyl-3'H-spiro[dihydroindole-3,4'-prrolo[3,4-d]imidazole]-2,6'(5'H)-dione

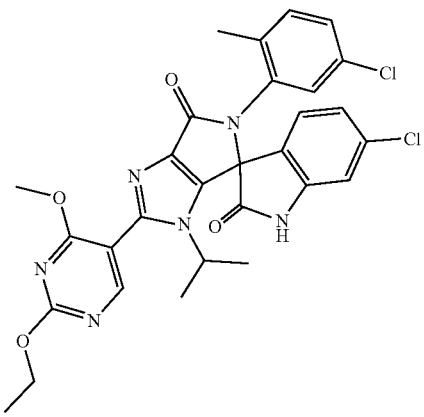 [SMILES: CCOc1ncc(-c2nc3c(n2C(C)C)C2(C(=O)Nc4cc(Cl)ccc42)N(c2cc(Cl)ccc2C)C3=O)c(OC)n1]

Title compounds were obtained by steps similar to those in Example 1, and supercritical high-pressure preparative chromatography was performed to obtain 27.9 mg of (S)-6-chloro-5'-(5-chloro-2-methylphenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione (S-127), and 32.0 mg of (R)-6-chloro-5'-(5-chloro-2-methylphenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione (R-127). MS (ESI): mass calcd. for $C_{29}H_{26}Cl_2N_6O_4$ 592.14, m/z found 593.4 [M+H]$^+$. $^1$H-NMR (400 MHz, DMSO-d$_6$) δ 11.75 (brs, 1H), 8.52 (d, 1H, J=6.8 Hz), 7.567-6.486 (m, 6H), 4.46 (q, 2H, J=7.2 Hz), 4.18-4.09 (m, 1H), 3.94 (s, 3H), 2.21 (s, 3H), 1.39 (t, 3H, J=7.2 Hz), 1.09 (d, 3H, J=4.8 Hz), 0.67 (d, 3H, J=6.0 Hz).

Example 128

4-(6-chloro-5'-(3-chlorophenyl)-3'-isopropyl-2,6'-dioxo-5',6'-dihydro-3'H-spiro[dihydroindole-3,4'-pyrrolo[3,4-d]imidazole]-2'-yl)-3-methoxybenzonitrile

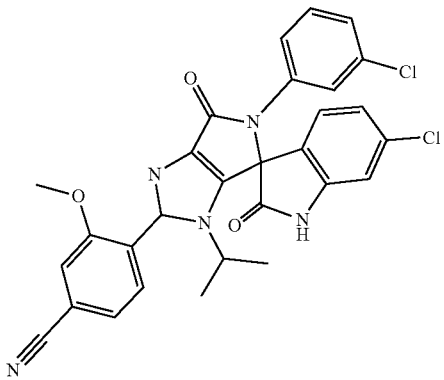

Title compounds were obtained by steps similar to those in Example 1, and supercritical high-pressure preparative chromatography was performed to obtain 35.3 mg of (S)-4-(6-chloro-5'-(3-chlorophenyl)-3'-isopropyl-2,6'-dioxo-5',6'-dihydro-3'H-spiro[dihydroindole-3,4'-pyrrolo[3,4-d]imidazole]-2'-yl)-3-methoxybenzonitrile (S-128), and 34.5 mg of (R)-4-(6-chloro-5'-(3-chlorophenyl)-3'-isopropyl-2,6'-dioxo-5',6'-dihydro-3'H-spiro[dihydroindole-3,4'-pyrrolo[3,4-d]imidazole]-2'-yl)-3-methoxybenzonitrile (R-128). MS (ESI): mass calcd. for $C_{29}H_{21}Cl_2N_5O_3$ 557.10, m/z found 558.3 $[M+H]^+$. $^1$H-NMR (400 MHz, DMSO-$d_6$) δ 11.43 (brs, 1H), 7.73-6.96 (m, 10H), 4.06-4.04 (m, 1H), 3.86 (s, 3H), 1.04 (d, 3H, J=5.6 Hz), 0.61 (d, 3H, J=5.6 Hz).

Example 129

6-chloro-5'-(3-chlorophenyl)-3'-isopropyl-2'-(2-methoxy-4-(trifluoromethyl)phenyl)-3'H-spiro[dihydroindole-3,4'-pyrrolo[3,4-d]imidazole]-2,6'(5'H)-dione

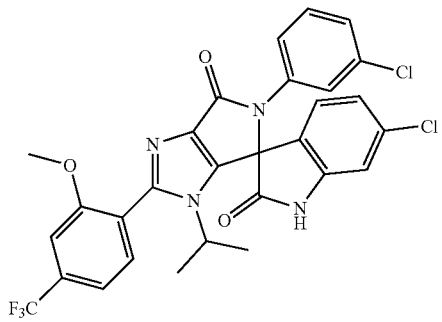 [SMILES: COc1cc(C(F)(F)F)ccc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 40.2 mg of (S)-6-chloro-5'-(3-chlorophenyl)-3'-isopropyl-2'-(2-methoxy-4-(trifluoromethyl)phenyl)-3'H-spiro[dihydroindole-3,4'-pyrrolo[3,4-d]imidazole]-2,6'(5'H)-dione (S-129), and 44.7 mg of (R)-6-chloro-5'-(3-chlorophenyl)-3'-isopropyl-2'-(2-methoxy-4-(trifluoromethyl)phenyl)-3'H-spiro[dihydroindole-3,4'-pyrrolo[3,4-d]imidazole]-2,6'(5'H)-dione (R-129). MS (ESI): mass calcd. for $C_{29}H_{21}Cl_2F_3N_4O_3$ 600.1, m/z found 601.3 $[M+H]^+$. $^1$H-NMR (400 MHz, DMSO-$d_6$) δ 11.56 (brs, 1H), 7.68-6.95 (m, 10H), 4.07-4.04 (m, 1H), 3.88 (s, 3H), 1.10 (d, 3H, J=6.0 Hz), 0.62 (d, 3H, J=6.0 Hz).

Example 130

6-chloro-5'-(5-chloro-2-methylphenyl)-2'-(2-fluoro-4,6-dimethoxyphenyl)-3'-isopropyl-3'H-spiro[dihydroindole-3,4'-pyrrolo[3,4-d]imidazole]-2,6'(5'H)-dione

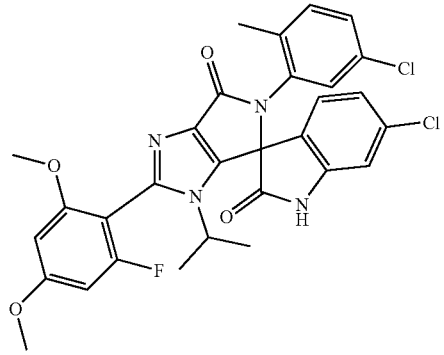 [SMILES: COc1cc(F)c(-c2nc3c(n2C(C)C)C2(C(=O)Nc4cc(Cl)ccc42)N(c2cc(Cl)ccc2C)C3=O)c(OC)c1]

Title compounds were obtained by steps similar to those in Example 1, and supercritical high-pressure preparative chromatography was performed to obtain 42.7 mg of (S)-6-chloro-5'-(5-chloro-2-methylphenyl)-2'-(2-fluoro-4,6-dimethoxyphenyl)-3'-isopropyl-3'H-spiro[dihydroindole-3,4'-pyrrolo[3,4-d]imidazole]-2,6'(5'H)-dione (S-130), and 30.0 mg of (R)-6-chloro-5'-(5-chloro-2-methylphenyl)-2'-(2-fluoro-4,6-dimethoxyphenyl)-3'-isopropyl-3'H-spiro[dihydroindole-3,4'-pyrrolo[3,4-d]imidazole]-2,6'(5'H)-dione (R-130). MS (ESI): mass calcd. for $C_{30}H_{25}Cl_2FN_4O_4$ 594.12, m/z found 595.3 $[M+H]^+$. $^1$H-NMR (400 MHz, DMSO-$d_6$) δ 11.75 (brs, 1H), 7.44-6.60 (m, 8H), 4.00 (s, 1H), 3.86-3.77 (m, 6H), 3.86 (s, 3H), 3.81 (d, 3H, J=2.8 Hz), 2.22 (s, 3H), 1.23-1.01 (m, 3H), 0.69-0.61 (m, 3H).

Example 131

6-chloro-5'-(5-chloro-2-methylpyridin-3-yl)-2'-(4,6-dimethoxypyridin-3-yl)-3'-isopropyl-3'H-spiro[dihydroindole-3,4'-pyrrolo[3,4-d]imidazole]-2,6'(5'H)-dione

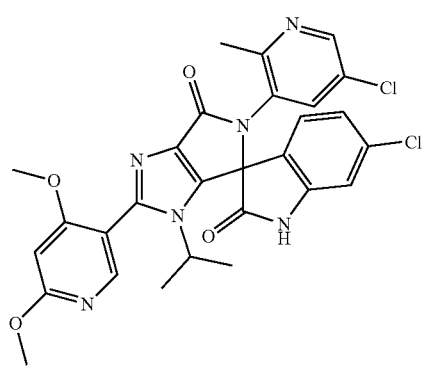 [SMILES: COc1cc(OC)c(-c2nc3c(n2C(C)C)C2(C(=O)Nc4cc(Cl)ccc42)N(c2cc(Cl)cnc2C)C3=O)cn1]

Title compounds were obtained by steps similar to those in Example 1, and supercritical high-pressure preparative chromatography was performed to obtain 45.5 mg of (S)-6-chloro-5'-(5-chloro-2-methylpyridin-3-yl)-2'-(4,6-dimethoxypyridin-3-yl)-3'-isopropyl-3'H-spiro[dihydroindole-3,4'-pyrrolo[3,4-d]imidazole]-2,6'(5'H)-dione (S-131), and 50.5 mg of (R)-6-chloro-5'-(5-chloro-2-methylpyridin-3-yl)-2'-(4,6-dimethoxypyridin-3-yl)-3'-isopropyl-3'H-spiro[dihydroindole-3,4'-pyrrolo[3,4-d]imidazole]-2,6'(5'H)-dione (R-131). MS (ESI): mass calcd. for $C_{28}H_{24}Cl_2N_6O_4$ 578, m/z found 579.3[M+H]$^+$. $^1$H-NMR (400 MHz, DMSO-d$_6$) δ 11.80 (brs, 1H), 8.50 (d, 1H, J=1.6 Hz), 8.48 (d, 1H, J=2.0 Hz), 8.14-7.00 (m, 4H), 6.60 (s, 1H), 4.09-4.06 (m, 1H), 3.92 (s, 3H), 3.84 (s, 3H), 2.27 (s, 3H), 1.08 (d, 3H, J=4.0 Hz), 0.65 (d, 3H, J=4.0 Hz).

Example 132

5-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxypyridylmethylcyanide

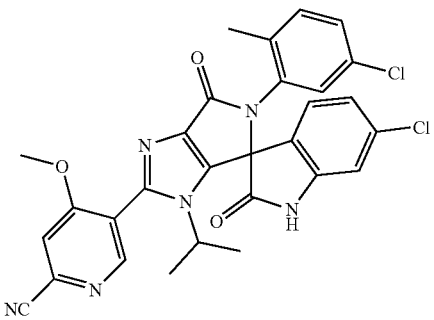 [SMILES: COc1cc(C#N)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 4.9 mg of (S)-5-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxypyridylmethylcyanide (S-132), and 5.4 mg of (R)-5-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxypyridylmethylcyanide (R-132). MS (ESI): mass calcd. for $C_{29}H_{22}Cl_2N_6O_3$ 572.11, m/z found 573.4 [M+H]$^+$. $^1$H-NMR (400 MHz, DMSO-d$_6$) δ 11.36 (brs, 1H), 8.69 (d, 1H, J=6.8 Hz), 8.06 (s, 1H), 7.57-6.99 (m, 6H), 4.12-4.10 (m, 1H), 3.97 (s, 3H), 2.21 (s, 3H), 1.08 (d, 3H, J=7.6 Hz), 0.65 (d, 3H, J=7.6 Hz).

Example 133

6-chloro-5'-(5-chloro-2-fluorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione

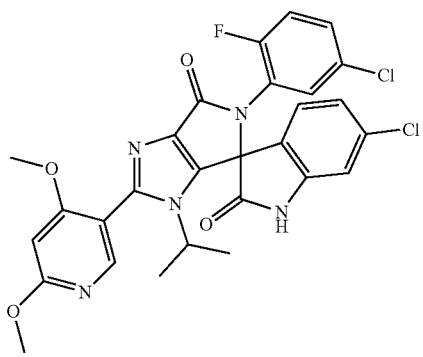 [SMILES: COc1cc(OC)c(-c2nc3c(n2C(C)C)C2(C(=O)Nc4cc(Cl)ccc42)N(c2cc(Cl)ccc2F)C3=O)cn1]

Title compounds were obtained by steps similar to those in Example 1, and supercritical high-pressure preparative chromatography was performed to obtain 63.3 mg of (S)-6-chloro-5'-(5-chloro-2-fluorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione (S-133), and 66.9 mg of (R)-6-chloro-5'-(5-chloro-2-fluorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione (R-133). MS (ESI): mass calcd. for Chemical Formula: $C_{28}H_{22}Cl_2FN_5O_4$ 581.10, m/z found 582.4 [M+H]$^+$. $^1$H-NMR (400 MHz, DMSO-d$_6$) δ 11.57 (brs, 1H), 8.13 (s, 1H), 7.48 (d, 1H, J=7.2 Hz), 7.36-7.32 (m, 2H), 7.15 (d, 1H, J=8.0 Hz), 7.06 (d, 1H, J=3.6 Hz), 7.05 (s, 1H), 6.59 (s, 1H), 4.09-4.05 (m, 1H), 3.92 (s, 3H), 3.84 (s, 3H), 1.10 (d, 3H, J=6.4 Hz), 0.64 (d, 3H, J=6.4 Hz).

Example 134

6-chloro-5'-(5-chloro-2-methylpyridin-3-yl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione

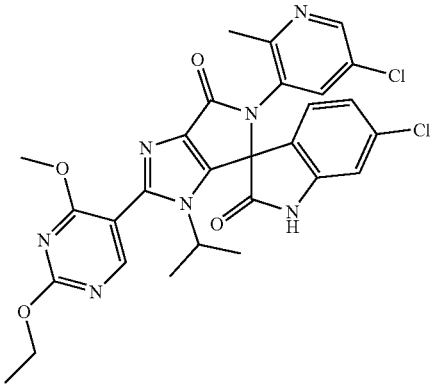

Title compounds were obtained by steps similar to those in Example 1, and supercritical high-pressure preparative chromatography was performed to obtain 38.8 mg of (S)-6-chloro-5'-(5-chloro-2-methylpyridin-3-yl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione (S-134), and 40.0 mg of (R)-6-chloro-5'-(5-chloro-2-methylpyridin-3-yl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione (R-134). MS (ESI): mass calcd. for $C_{28}H_{25}Cl_2N_7O_4$ 593, m/z found 594.4[M+H]$^+$. $^1$H-NMR (400 MHz, DMSO-d$_6$) δ 11.79 (brs, 1H), 8.52-8.48 (m, 2H), 7.64-7.00 (m, 4H), 4.47 (q, 2H, J=6.8 Hz), 4.21-4.18 (m, 1H), 3.99 (s, 3H), 2.27 (s, 3H), 1.39 (t, 3H, J=6.8 Hz), 1.09 (d, 3H, J=6.4 Hz), 0.68 (d, 3H, J=6.4 Hz).

Example 135

6-chloro-5'-(5-chloro-2-methylpyridin-3-yl)-2'-(2-(dimethylamino)-4-methoxypyrimidin-5-yl)-3'-isopropyl-3'H-spiro[dihydroindole-3,4'-pyrrolo[3,4-d]imidazole]-2,6'(5'H)-dione

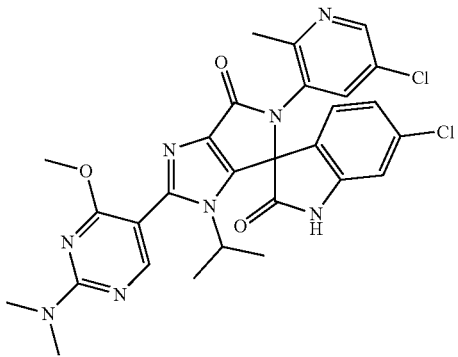 [SMILES: COc1nc(N(C)C)ncc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 50.6 mg of (S)-6-chloro-5'-(5-chloro-2-methylpyridin-3-yl)-2'-(2-(dimethylamino)-4-methoxypyrimidin-5-yl)-3'-isopropyl-3'H-spiro[dihydroindole-3,4'-pyrrolo[3,4-d]imidazole]-2,6'(5'H)-dione (S-135), and 50.9 mg of (R)-6-chloro-5'-(5-chloro-2-methylpyridin-3-yl)-2'-(2-(dimethylamino)-4-methoxypyrimidin-5-yl)-3'-isopropyl-3'H-spiro[dihydroindole-3,4'-pyrrolo[3,4-d]imidazole]-2,6'(5'H)-dione (R-135). MS (ESI): mass calcd. for $C_{28}H_{26}Cl_2N_8O_3$ 592, m/z found 593.4 [M+H]$^+$. $^1$H-NMR (400 MHz, DMSO-d$_6$) δ 11.77 (brs, 1H), 8.50 (d, 1H, J=7.2 Hz), 8.26 (d, 1H, J=5.2 Hz), 7.62-6.99 (m, 4H), 4.17-4.14 (m, 1H), 3.90 (s, 3H), 3.19 (s, 6H), 2.26 (s, 3H), 1.09 (d, 3H, J=6.4 Hz), 0.68 (d, 3H, J=6.4 Hz).

Example 136

6-chloro-5'-(5-chloro-2-methylpyridin-3-yl)-2'-(2-isopropoxy-4-methoxypyrimidin-5-yl)-3'-isopropyl-3'H-spiro[dihydroindole-3,4'-pyrrolo[3,4-d]imidazole]-2,6'(5'H)-dione

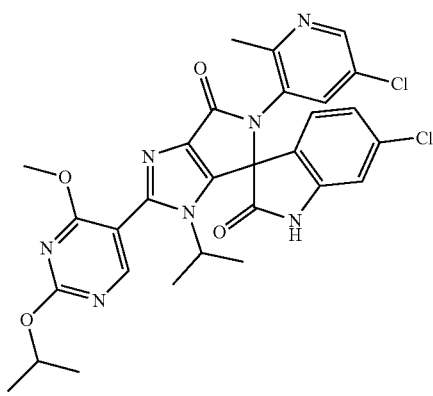 [SMILES: COc1nc(OC(C)C)ncc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 33.0 mg of (S)-6-chloro-5'-(5-chloro-2-methylpyridin-3-yl)-2'-(2-isopropoxy-4-methoxypyrimidin-5-yl)-3'-isopropyl-3'H-spiro[dihydroindole-3,4'-pyrrolo[3,4-d]imidazole]-2,6'(5'H)-dione (S-136), and 30.5 mg of (R)-6-chloro-5'-(5-chloro-2-methylpyridin-3-yl)-2'-(2-isopropoxy-4-methoxypyrimidin-5-yl)-3'-isopropyl-3'H-spiro[dihydroindole-3,4'-pyrrolo[3,4-d]imidazole]-2,6'(5'H)-dione (R-136). MS (ESI): mass calcd. for $C_{30}H_{28}Cl_2N_6O_4$ 606 m/z found 607.4[M+H]$^+$. $^1$H-NMR (400 MHz, DMSO-d$_6$) δ 11.79 (brs, 1H), 8.51 (m, 2H), 7.63-7.00 (m, 4H), 5.32-5.28 (m, 1H), 4.22-4.16 (m, 1H), 3.94 (s, 3H), 2.27 (s, 3H), 1.37 (d, 6H, J=6.4 Hz), 1.09 (d, 3H, J=6.4 Hz), 0.68 (d, 3H, J=6.4 Hz).

Example 137

6-chloro-5'-(5-chloro-2-methylpyridin-3-yl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione

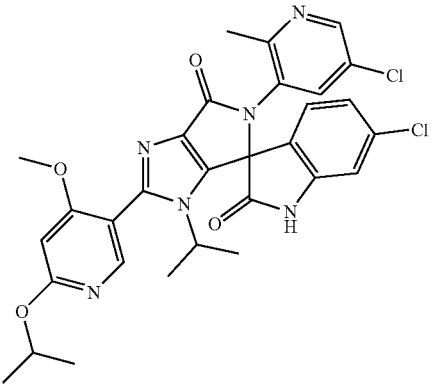 [SMILES: COc1cc(OC(C)C)ncc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 30.9 mg of (S)-6-chloro-5'-(5-chloro-2-methylpyridin-3-yl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione (S-137), and 32.3 mg of (R)-6-chloro-5'-(5-chloro-2-methylpyridin-3-yl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione (R-137). MS (ESI): mass calcd. for $C_{30}H_{28}Cl_2N_6O_4$ 606, m/z found 607.4 [M+H]$^+$. $^1$H-NMR (400 MHz, DMSO-d$_6$) δ 11.77 (brs, 1H), 8.50 (d, 1H, J=6.8 Hz), 8.11 (d, 3H, J=6.4 Hz), 7.64-7.00 (m, 4H), 6.52 (s, 1H), 5.35-5.32 (m, 1H), 4.10-4.07 (m, 1H), 3.83 (s, 3H), 2.27 (s, 3H), 1.33 (d, 6H, J=6.0 Hz), 1.08 (d, 3H, J=6.4 Hz), 0.66 (d, 3H, J=6.4 Hz).

Example 138

6-chloro-5'-(5-chloro-2-methylphenyl)-3'-isopropyl-2'-(4-methoxy-6-(trifluoromethyl)pyridin-3-yl)-3'H-spiro[dihydroindole-3,4'-pyrrolo[3,4-d]imidazole]-2,6'(5'H)-dione

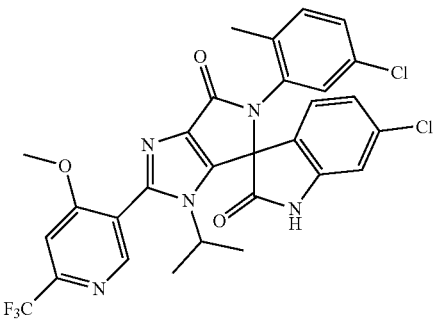 [SMILES: COc1cc(C(F)(F)F)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 42.6 mg of (S)-6-chloro-5'-(5-chloro-2-methylphenyl)-3'-isopropyl-2'-(4-methoxy-6-(trifluoromethyl)pyridin-3-yl)-3'H-spiro[dihydroindole-3,4'-pyrrolo[3,4-d]imidazole]-2,6'(5'H)-dione (S-138), and 40.9 mg of (R)-6-chloro-5'-(5-chloro-2-methylphenyl)-3'-isopropyl-2'-(4-methoxy-6-(trifluoromethyl)pyridin-3-yl)-3'H-spiro[dihydroindole-3,4'-pyrrolo[3,4-d]imidazole]-2,6'(5'H)-dione (R-138). MS (ESI): mass calcd. for $C_{29}H_{22}Cl_2F_3N_5O_3$ 615.10, m/z found 616.3 $[M+H]^+$. H-NMR (400 MHz, DMSO-$d_6$) δ 11.75 (brs, 1H), 8.72 (d, 1H, J=6.8 Hz), 7.74 (s, 1H), 7.59-6.49 (m, 6H), 4.20-4.11 (m, 1H), 4.02 (s, 3H), 2.22 (s, 3H), 1.18 (d, 3H, J=6.4 Hz), 0.66 (d, 3H, J=6.4 Hz).

Example 139

6-chloro-5'-(3-chloro-5-fluorophenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione

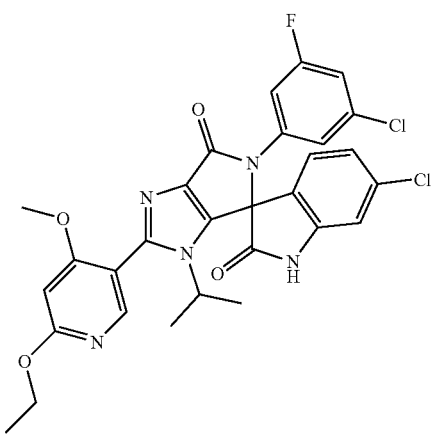 [SMILES: CCOc1cc(OC)c(-c2nc3c(n2C(C)C)C2(C(=O)Nc4cc(Cl)ccc42)N(c2cc(F)cc(Cl)c2)C3=O)cn1]

Title compounds were obtained by steps similar to those in Example 1, and supercritical high-pressure preparative chromatography was performed to obtain 45.7 mg of (S)-6-chloro-5'-(3-chloro-5-fluorophenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione (S-139), and 42.1 mg of (R)-6-chloro-5'-(3-chloro-5-fluorophenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione (R-139). MS (ESI): mass calcd. for Chemical Formula: $C_{29}H_{24}Cl_2FN_5O_4$ Exact Mass: 595.12, m/z found 596.5 $[M+H]^+$. H-NMR (400 MHz, DMSO-$d_6$) δ 11.58 (brs, 1H), 8.08 (s, 1H), 7.49 (d, 1H, J=8.0 Hz), 7.38 (d, 1H, J=8.4 Hz), 7.16 (d, 1H, J=7.6 Hz), 7.06 (s, 1H), 6.96 (s, 1H), 6.92 (d, 1H, J=9.6 Hz), 6.56 (s, 1H), 4.40 (q, 2H, J=6.8 Hz), 4.07-4.02 (m, 1H), 3.83 (s, 3H), 1.35 (t, 3H, J=6.8 Hz), 1.11 (d, 3H, J=5.6 Hz), 0.62 (d, 3H, J=6.0 Hz).

Example 140

6-chloro-5'-(5-chloro-2-methylphenyl)-2'-(2-(2-fluoroethoxy)-4-methoxypyrimidin-5-yl)-3'-isopropyl-3'H-spiro[dihydroindole-3,4'-pyrrolo[3,4-d]imidazole]-2,6'(5'H)-dione

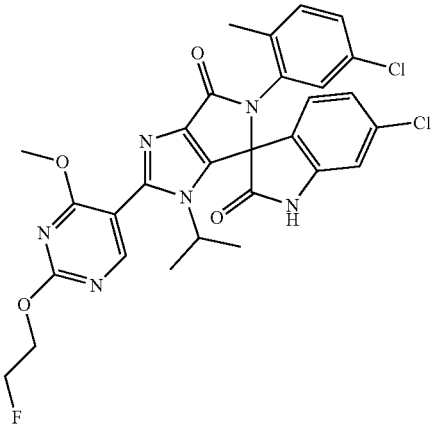 [SMILES: COc1nc(OCCF)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 36.1 mg of (S)-6-chloro-5'-(5-chloro-2-methylphenyl)-2'-(2-(2-fluoroethoxy)-4-methoxypyrimidin-5-yl)-3'-isopropyl-3'H-spiro[dihydroindole-3,4'-pyrrolo[3,4-d]imidazole]-2,6'(5'H)-dione (S-140), and 31.5 mg of (R)-6-chloro-5'-(5-chloro-2-methylphenyl)-2'-(2-(2-fluoroethoxy)-4-methoxypyrimidin-5-yl)-3'-isopropyl-3'H-spiro[dihydroindole-3,4'-pyrrolo[3,4-d]imidazole]-2,6'(5'H)-dione (R-140). MS (ESI): mass calcd. for $C_{29}H_{25}Cl_2FN_6O_4$ 610.13, m/z found 611.4 $[M+H]^+$. H-NMR (400 MHz, DMSO-$d_6$): δ 11.50 (brs, 1H), 8.539 (d, J=7.2 Hz, 1H), 7.57-6.48 (m, 6H), 4.86-4.61 (m, 4H), 4.19-4.16 (m, 1H), 3.96 (s, 3H), 2.145 (s, 3H), 1.09 (d, J=4.8 Hz, 3H), 0.66 (d, J=6.0 Hz, 3H).

Example 141

6-chloro-5'-(5-chloro-2-methylphenyl)-3'-isopropyl-2'-(4-methoxy-2-(2,2,2-trifluoroethoxy)pyrimidin-5-yl)-3'H-spiro[dihydroindole-3,4'-pyrrolo[3,4-d]imidazole]-2,6'(5'H)-dione

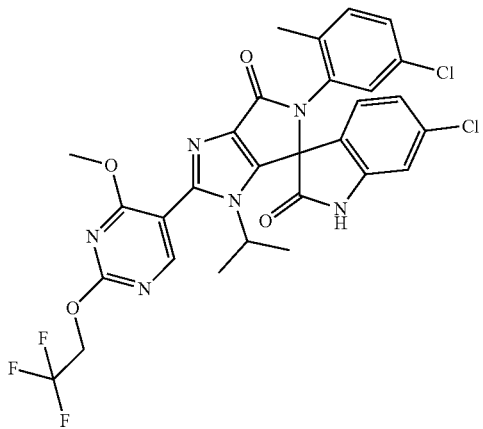 [SMILES: COc1nc(OCC(F)(F)F)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 36.4 mg of (S)-6-chloro-5'-(5-chloro-2-methylphenyl)-3'-isopropyl-2'-(4-methoxy-2-(2,2,2-trifluoroethoxy)pyrimidin-5-yl)-3'H-spiro[dihydroindole-3,4'-pyrrolo[3,4-d]imidazole]-2,6'(5'H)-dione (S-141), and 43.1 mg of (R)-6-chloro-5'-(5-chloro-2-methylphenyl)-3'-isopropyl-2'-(4-methoxy-2-(2,2,2-trifluoroethoxy)pyrimidin-5-yl)-3'H-spiro[dihydroindole-3,4'-pyrrolo[3,4-d]imidazole]-2,6'(5'H)-dione (R-141). MS (ESI): mass calcd. for $C_{28}H_{21}Cl_2F_3N_6O_4$ 646.11, m/z found 649.1 [M+H]$^+$. $^1$H-NMR (400 MHz, DMSO-d$_6$) δ 11.45 (brs, 1H), 8.60 (d, J=7.6 Hz, 1H), 7.56-6.49 (m, 6H), 5.15-5.01 (m, 2H), 4.21-4.15 (m, 1H), 3.99 (s, 3H), 2.07 (s, 3H), 1.08 (d, J=6.4 Hz, 3H), 0.66 (d, J=6.4 Hz, 3H).

Example 142

6-chloro-5'-(3-chlorophenyl)-3'-isopropyl-2'-(4-methoxy-6-(trifluoromethyl)pyridin-3-yl)-3'H-spiro[dihydroindole-3,4'-pyrrolo[3,4-d]imidazole]-2,6'(5'H)-dione

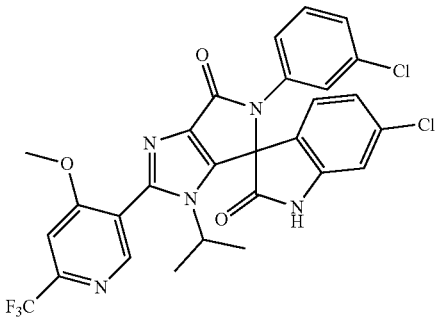

Title compounds were obtained by steps similar to those in Example 1, and supercritical high-pressure preparative chromatography was performed to obtain 20.9 mg of (S)-6-chloro-5'-(3-chlorophenyl)-3'-isopropyl-2'-(4-methoxy-6-(trifluoromethyl)pyridin-3-yl)-3'H-spiro[dihydroindole-3,4'-pyrrolo[3,4-d]imidazole]-2,6'(5'H)-dione (S-142), and 21.6 mg of (R)-6-chloro-5'-(3-chlorophenyl)-3'-isopropyl-2'-(4-methoxy-6-(trifluoromethyl)pyridin-3-yl)-3'H-spiro[dihydroindole-3,4'-pyrrolo[3,4-d]imidazole]-2,6'(5'H)-dione (R-142). MS (ESI): mass calcd. for $C_{28}H_{20}Cl_2F_3N_5O_3$ 601.08, m/z found 602.1 [M+H]$^+$. $^1$H-NMR (400 MHz, DMSO-d$_6$) δ 11.56 (brs, 1H), 8.69 (s, 1H), 7.73 (s, 1H), 7.51 (d, 1H, J=8.8 Hz), 7.39-7.35 (m, 2H), 7.16-7.01 (m, 2H), 6.98-6.97 (m, 2H), 4.13-4.08 (m, 1H), 4.01 (s, 3H), 1.12 (d, 3H, J=6.4 Hz), 0.64 (d, 3H, J=6.4 Hz).

Example 143

6-chloro-5'-(5-chloro-2-methylpyridin-3-yl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione

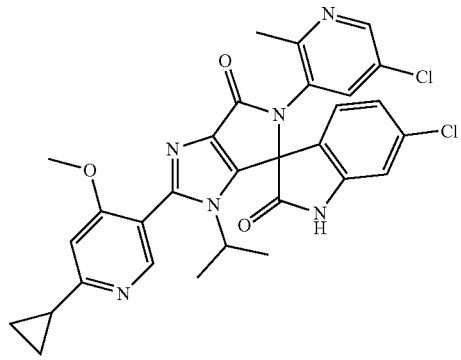 [SMILES: COc1cc(C2CC2)ncc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 23.6 mg of (S)-6-chloro-5'-(5-chloro-2-methylpyridin-3-yl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione (S-143), and 23.8 mg of (R)-6-chloro-5'-(5-chloro-2-methylpyridin-3-yl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione (R-143). MS (ESI): mass calcd. for $C_{30}H_{26}Cl_2N_6O_3$ 588, m/z found 589.2 [M+H]$^+$. $^1$H-NMR (400 MHz, DMSO-d$_6$) δ 11.76 (brs, 1H), 8.50 (d, 1H, J=8.0 Hz), 8.30 (d, 1H, J=3.6 Hz), 7.64-6.99 (m, 5H), 4.09-4.05 (m, 1H), 3.88 (s, 3H), 2.27 (s, 3H), 2.19-2.17 (m, 1H), 1.08 (d, 3H, J=6.4 Hz), 1.02-1.00 (m, 4H), 0.65 (d, 3H, J=4.0 Hz).

Example 144

6-chloro-5'-(5-chloro-2-methylpyridin-3-yl)-3'-isopropyl-2'-(2-methoxy-4-(trifluoromethyl)phenyl)-3'H-spiro[dihydroindole-3,4'-pyrrolo[3,4-d]imidazole]-2,6'(5'H)-dione

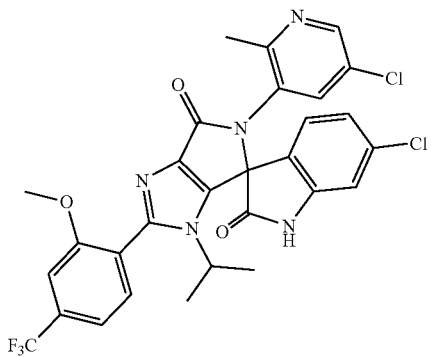 [SMILES: COc1cc(C(F)(F)F)ccc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 40.9 mg of (S)-6-chloro-5'-(5-chloro-2-methylpyridin-3-yl)-3'-isopropyl-2'-(2-methoxy-4-(trifluoromethyl)phenyl)-3'H-spiro[dihydroindole-3,4'-pyrrolo[3,4-d]imidazole]-2,6'(5'H)-dione (S-144), and 47.4 mg of (R)-6-chloro-5'-(5-chloro-2-methylpyridin-3-yl)-3'-isopropyl-2'-(2-methoxy-4-(trifluoromethyl)phenyl)-3'H-spiro[dihydroindole-3,4'-pyrrolo[3,4-d]imidazole]-2,6'(5'H)-dione (R-144). MS (ESI): mass calcd. for $C_{29}H_{22}Cl_2F_3N_5O_3$ 615, m/z found 616.4[M+H]$^+$. $^1$H-NMR (400 MHz, DMSO-d$_6$) δ 11.79 (brs, 1H), 8.51 (d, 1H, J=7.6 Hz), 7.71-7.00 (m, 7H), 4.10-4.07 (m, 1H), 3.90 (s, 3H), 2.28 (s, 3H), 1.07 (d, 3H, J=5.2 Hz), 0.66 (d, 3H, J=5.6 Hz).

Example 145

6-chloro-5'-(5-chloro-2-methylpyridin-3-yl)-2'-(4-cyclopropyl-2-methoxyphenyl)-3'-isopropyl-3'H-spiro[dihydroindole-3,4'-pyrrolo[3,4-d]imidazole]-2,6'(5'H)-dione

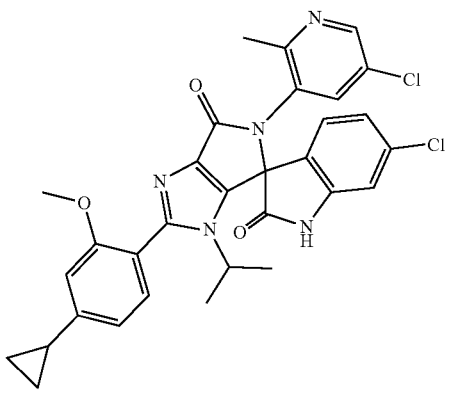 [SMILES: COc1cc(C2CC2)ccc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 23.3 mg of (S)-6-chloro-5'-(5-chloro-2-methylpyridin-3-yl)-2'-(4-cyclopropyl-2-methoxyphenyl)-3'-isopropyl-3'H-spiro[dihydroindole-3,4'-pyrrolo[3,4-d]imidazole]-2,6'(5'H)-dione (S-145), and 21.9 mg of (R)-6-chloro-5'-(5-chloro-2-methylpyridin-3-yl)-2'-(4-cyclopropyl-2-methoxyphenyl)-3'-isopropyl-3'H-spiro[dihydroindole-3,4'-pyrrolo[3,4-d]imidazole]-2,6'(5'H)-dione (R-145). MS (ESI): mass calcd. for $C_{31}H_{27}Cl_2N_5O_3$ 587, m/z found 588.2 [M+H]$^+$. $^1$H-NMR (400 MHz, DMSO-d$_6$) δ 11.71 (brs, 1H), 8.50 (d, 1H, J=7.6 Hz), 7.62-6.78 (m, 7H), 4.09-4.06 (m, 1H), 3.78 (s, 3H), 2.27 (s, 3H), 2.01-1.99 (m, 1H), 1.06-1.01 (m, 5H), 0.85-0.80 (m, 2H), 0.62 (d, 3H, J=5.6 Hz).

Example 146

6-chloro-5'-(5-chloro-2-methylphenyl)-2'-(6-ethoxy-2-methoxypyridin-3-yl)-3'-isopropyl-3'H-spiro[dihydroindole-3,4'-pyrrolo[3,4-d]imidazole]-2,6'(5'H)-dione

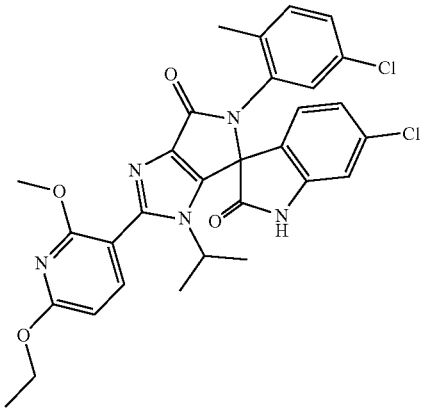 [SMILES: CCOc1ccc(-c2nc3c(n2C(C)C)C2(C(=O)Nc4cc(Cl)ccc42)N(c2cc(Cl)ccc2C)C3=O)c(OC)n1]

Title compounds were obtained by steps similar to those in Example 1, and supercritical high-pressure preparative chromatography was performed to obtain 17.2 mg of (S)-6-chloro-5'-(5-chloro-2-methylphenyl)-2'-(6-ethoxy-2-methoxypyridin-3-yl)-3'-isopropyl-3'H-spiro[dihydroindole-3,4'-pyrrolo[3,4-d]imidazole]-2,6'(5'H)-dione (S-146), and 21.7 mg of (R)-6-chloro-5'-(5-chloro-2-methylphenyl)-2'-(6-ethoxy-2-methoxypyridin-3-yl)-3'-isopropyl-3'H-spiro[dihydroindole-3,4'-pyrrolo[3,4-d]imidazole]-2,6'(5'H)-dione (R-146). MS (ESI): mass calcd. for $C_{30}H_{27}Cl_2N_5O_4$ 591.14, m/z found 592.2 [M+H]$^+$. $^1$H-NMR (400 MHz, DMSO-d$_6$) δ 11.55 (brs, 1H), 7.81-6.48 (m, 8H), 4.42 (q, 2H, J=7.2 Hz), 4.13-4.11 (m, 1H), 3.88 (s, 3H), 2.22 (s, 3H), 1.38 (t, 3H, J=7.2 Hz), 1.08 (d, 3H, J=6.4 Hz), 0.66 (d, 3H, J=6.8 Hz).

Example 147

6-chloro-5'-(5-chloro-2-methylphenyl)-2'-(2-(2,2-difluoroethoxy)-4-methoxypyrimidin-5-yl)-3'-isopropyl-3'H-spiro[dihydroindole-3,4'-pyrrolo[3,4-d]imidazole]-2,6'(5'H)-dione

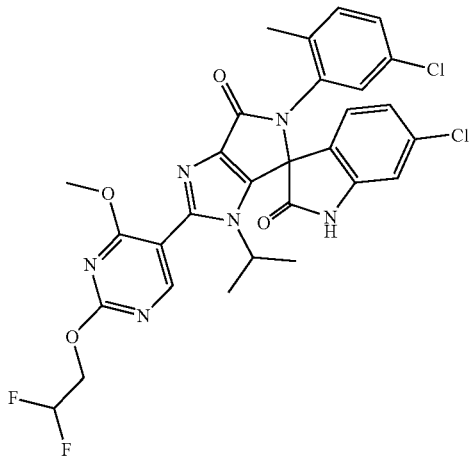 [SMILES: COc1nc(OCC(F)F)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 52.3 mg of (S)-6-chloro-5'-(5-chloro-2-methylphenyl)-2'-(2-(2,2-difluoroethoxy)-4-methoxypyrimidin-5-yl)-3'-isopropyl-3'H-spiro[dihydroindole-3,4'-pyrrolo[3,4-d]imidazole]-2,6'(5'H)-dione (S-147), and 48.2 mg of (R)-6-chloro-5'-(5-chloro-2-methylphenyl)-2'-(2-(2,2-difluoroethoxy)-4-methoxypyrimidin-5-yl)-3'-isopropyl-3'H-spiro[dihydroindole-3,4'-pyrrolo[3,4-d]imidazole]-2,6'(5'H)-dione (R-147). MS (ESI): mass calcd. for $C_{29}H_{24}Cl_2F_2N_6O_4$ 628.12, m/z found 629.1 [M+H]$^+$. H-NMR (400 MHz, DMSO-d$_6$) δ 8.58 (d, 1H, J=7.2 Hz), 7.56-6.46 (m, 7H), 4.74-4.66 (m, 2H), 4.17-4.10 (m, 1H), 3.98 (s, 3H), 2.21 (s, 3H), 2.01-1.98 (m, 1H), 1.09 (d, 3H, J=6.8 Hz), 0.68 (d, 3H, J=7.2 Hz).

Example 148

6-chloro-5'-(5-chloro-2-methylphenyl)-2'-(4-(2-hydroxyethoxy)-2-methoxyphenyl)-3'-isopropyl-3'H-spiro[dihydroindole-3,4'-pyrrolo[3,4-d]imidazole]-2,6'(5'H)-dione

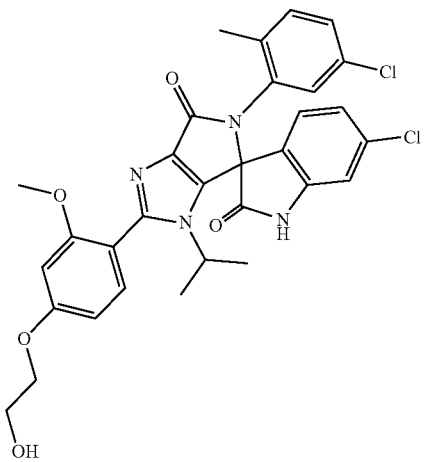 [SMILES: COc1cc(OCCO)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 43.3 mg of (S)-6-chloro-5'-(5-chloro-2-methylphenyl)-2'-(4-(2-hydroxyethoxy)-2-methoxyphenyl)-3'-isopropyl-3'H-spiro[dihydroindole-3,4'-pyrrolo[3,4-d]imidazole]-2,6'(5'H)-dione (S-148), and 43.7 mg of (R)-6-chloro-5'-(5-chloro-2-methylphenyl)-2'-(4-(2-hydroxyethoxy)-2-methoxyphenyl)-3'-isopropyl-3'H-spiro[dihydroindole-3,4'-pyrrolo[3,4-d]imidazole]-2,6'(5'H)-dione (R-148). MS (ESI): mass calcd. for $C_{31}H_{28}Cl_2N_4O_5$ 606.14, m/z found 607.2 [M+H]$^+$. $^1$H-NMR (400 MHz, DMSO-d$_6$) δ 7.55-6.48 (m, 10H), 4.89 (t, J=5.2 Hz, 1H), 4.10-4.05 (m, 3H), 3.78-3.74 (m, 5H), 2.07 (s, 3H), 1.06 (d, J=5.6 Hz, 3H), 0.63 (d, J=5.6 Hz, 3H).

Example 149

6-chloro-5'-(5-chloro-2-methylphenyl)-3'-isopropyl-2'-(6-isopropyl-2-methoxypyridin-3-yl)-3'H-spiro[dihydroindole-3,4'-pyrrolo[3,4-d]imidazole]-2,6'(5'H)-dione

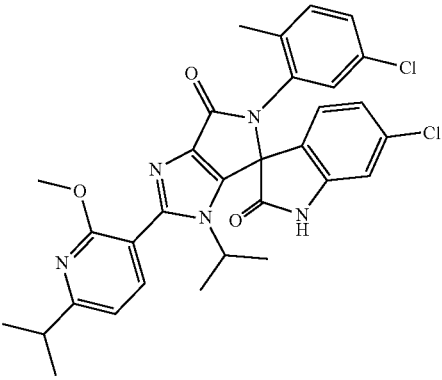 [SMILES: COc1nc(C(C)C)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 16.3 mg of (S)-6-chloro-5'-(5-chloro-2-methylphenyl)-3'-isopropyl-2'-(6-isopropyl-2-methoxypyridin-3-yl)-3'H-spiro[dihydroindole-3,4'-pyrrolo[3,4-d]imidazole]-2,6'(5'H)-dione (S-149), and 17.0 mg of (R)-6-chloro-5'-(5-chloro-2-methylphenyl)-3'-isopropyl-2'-(6-isopropyl-2-methoxypyridin-3-yl)-3'H-spiro[dihydroindole-3,4'-pyrrolo[3,4-d]imidazole]-2,6'(5'H)-dione (R-149). MS (ESI): mass calcd. for $C_{29}H_{31}Cl_2N_5O_3$ 589.16, m/z found 589.5[M+H]$^+$. $^1$H-NMR (400 MHz, DMSO-d$_6$) δ 11.72 (brs, 1H), 7.84-7.81 (m, 1H), 7.57 (d, 1H, J=8.0 Hz), 7.47 (d, 1H, J=8.0 Hz), 7.33-6.97 (m, 4H), 6.49 (s, 1H), 4.10-4.07 (m, 1H), 3.89 (s, 3H), 3.04-3.01 (m, 1H), 2.22 (s, 3H), 1.29 (d, 6H, J=6.8 Hz), 1.10 (d, 1H, J=6.8 Hz), 0.66 (d, 1H, J=6.8 Hz).

Example 150

6-chloro-5'-(5-chloro-2-methylphenyl)-2'-(6-(difluoromethoxy)-4-methoxypyridin-3-yl)-3'-isopropyl-3'H-spiro[dihydroindole-3,4'-pyrrolo[3,4-d]imidazole]-2,6'(5'H)-dione

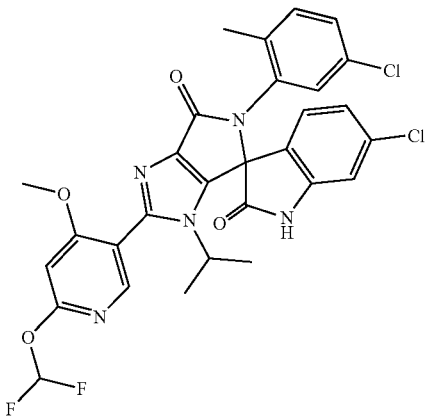 [SMILES: COc1cc(OC(F)F)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 42.1 mg of (S)-6-chloro-5'-(5-chloro-2-methylphenyl)-2'-(6-(difluoromethoxy)-4-methoxypyridin-3-yl)-3'-isopropyl-3'H-spiro[dihydroindole-3,4'-pyrrolo[3,4-d]imidazole]-2,6'(5'H)-dione (S-150), and 46.0 mg of (R)-6-chloro-5'-(5-chloro-2-methylphenyl)-2'-(6-(difluoromethoxy)-4-methoxypyridin-3-yl)-3'-isopropyl-3'H-spiro[dihydroindole-3,4'-pyrrolo[3,4-d]imidazole]-2,6'(5'H)-dione (R-150). MS (ESI): mass calcd. for $C_{29}H_{23}Cl_2F_2N_5O_4$ 613.11, m/z found 614.5 [M+H]$^+$. H-NMR (400 MHz, DMSO-d$_6$) δ 11.65 (brs, 1H), 8.25-6.48 (m, 8H), 4.09-4.07 (m, 1H), 3.91 (s, 3H), 2.22 (s, 3H), 1.08 (d, 3H, J=6.4 Hz), 0.66 (d, 3H, J=6.4 Hz).

Example 151

4-chloro-2-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzonitrile

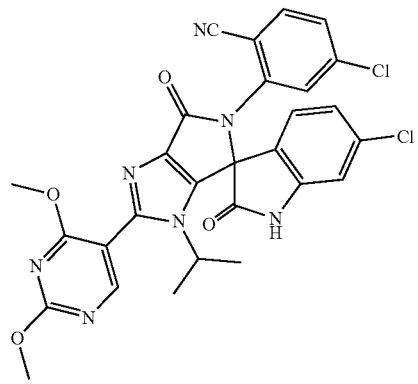 [SMILES: COc1ncc(-c2nc3c(n2C(C)C)C2(C(=O)Nc4cc(Cl)ccc42)N(c2cc(Cl)ccc2C#N)C3=O)c(OC)n1]

Title compounds were obtained by steps similar to those in Example 1, and supercritical high-pressure preparative chromatography was performed to obtain 119.4 mg of (S)-4-chloro-2-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzonitrile (S-151), and 105.8 mg of (R)-4-chloro-2-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzonitrile (R-151). MS (ESI): mass calcd. for $C_{28}H_{21}Cl_2N_7O_4$ 589.10, m/z found 590.1 [M+H]$^+$. $^1$H-NMR (400 MHz, DMSO-d$_6$) δ 11.81 (brs, 1H), 8.56 (s, 1H), 8.01 (d, J=8.8 Hz, 1H), 7.86 (d, J=1.6 Hz, 1H), 7.56-7.53 (m, 1H), 7.25 (d, J=8.4 Hz, 1H), 7.16 (d, J=1.6 Hz, 1H), 7.09-7.07 (m, 1H), 4.24-4.17 (m, 1H), 4.00 (s, 3H), 3.95 (s, 3H), 1.21 (d, J=6.4 Hz, 3H), 0.63 (d, J=6.4 Hz, 3H).

Example 152

6-chloro-5'-(5-chloro-2-methylpyridin-3-yl)-3'-isopropyl-2'-(4-methoxy-6-(trifluoromethyl)pyridine-3-yl)-3'H-spiro[dihydroindole-3,4'-pyrrolo[3,4-d]imidazole]-2,6'(5'H)-dione

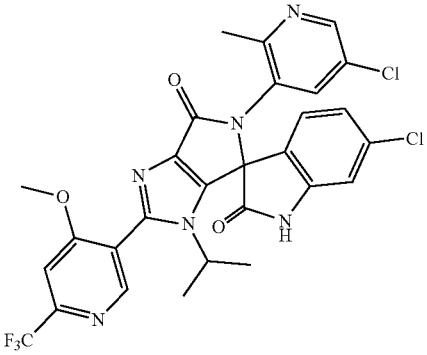 [SMILES: COc1cc(C(F)(F)F)ncc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 41.8 mg of (S)-6-chloro-5'-(5-chloro-2-methylpyridin-3-yl)-3'-isopropyl-2'-(4-methoxy-6-(trifluoromethyl)pyridine-3-yl)-3'H-spiro[dihydroindole-3,4'-pyrrolo[3,4-d]imidazole]-2,6'(5'H)-dione (S-152), and 45.3 mg of (R)-6-chloro-5'-(5-chloro-2-methylpyridin-3-yl)-3'-isopropyl-2'-(4-methoxy-6-(trifluoromethyl)pyridine-3-yl)-3'H-spiro[dihydroindole-3,4'-pyrrolo[3,4-d]imidazole]-2,6'(5'H)-dione (R-152). MS (ESI): mass calcd. for $C_{28}H_{21}Cl_2F_3N_6O_3$ 616 m/z found 617.1[M+H]$^+$. $^1$H-NMR (400 MHz, DMSO-d$_6$) δ 11.57 (brs, 1H), 8.72 (d, 1H, J=7.2 Hz), 8.51 (d, 1H, J=6.4 Hz), 7.74 (s, 1H), 7.66-7.01 (m, 5H), 4.16-4.11 (m, 1H), 4.02 (s, 3H), 2.27 (s, 3H), 1.10 (d, 3H, J=6.8 Hz), 0.67 (d, 3H, J=6.4 Hz).

Example 153

6-chloro-5'-(5-chloro-2-methylphenyl)-2'-(6-(2,2-difluoroethoxy)-4-methoxypyridin-3-yl)-3'-isopropyl-3'H-spiro[dihydroindole-3,4'-pyrrolo[3,4-d]imidazole]-2,6'(5'H)-dione

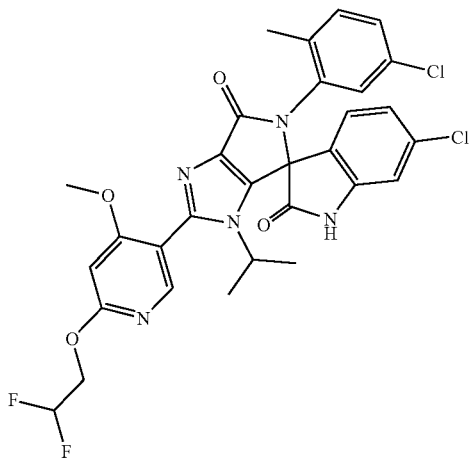 [SMILES: COc1cc(OCC(F)F)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 45.1 mg of (S)-6-chloro-5'-(5-chloro-2-methylphenyl)-2'-(6-(2,2-difluoroethoxy)-4-methoxypyridin-3-yl)-3'-isopropyl-3'H-spiro[dihydroindole-3,4'-pyrrolo[3,4-d]imidazole]-2,6'(5'H)-dione (S-153), and 46.6 mg of (R)-6-chloro-5'-(5-chloro-2-methylphenyl)-2'-(6-(2,2-difluoroethoxy)-4-methoxypyridin-3-yl)-3'-isopropyl-3'H-spiro[dihydroindole-3,4'-pyrrolo[3,4-d]imidazole]-2,6'(5'H)-dione (R-153). MS (ESI): mass calcd. for $C_{30}H_{25}Cl_2F_2N_5O_4$ 627.12, m/z found 628.2[M+H]$^+$. $^1$H-NMR (400 MHz, DMSO-$d_6$) δ 11.73 (brs, 1H), 8.16 (d, 1H, J=5.2 Hz), 7.57-6.42 (m, 7H), 4.68-4.61 (m, 2H), 4.08-4.04 (m, 1H), 3.87 (s, 3H), 2.22 (s, 3H), 1.08 (d, 3H, J=6.4 Hz), 0.65 (d, 3H, J=6.4 Hz).

Example 154

6-chloro-5'-(5-chloro-2-methylphenyl)-3'-isopropyl-2'-(4-methoxy-6-methylpyridin-3-yl)-3'H-spiro[dihydroindole-3,4'-pyrrolo[3,4-d]imidazole]-2,6'(5'H)-dione

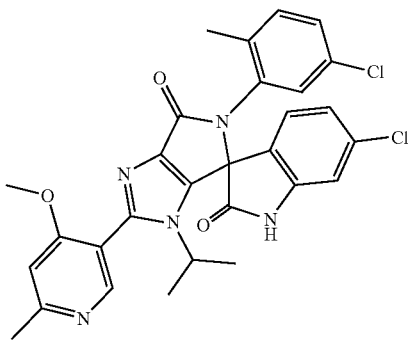 [SMILES: COc1cc(C)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 39.3 mg of (S)-6-chloro-5'-(5-chloro-2-methylphenyl)-3'-isopropyl-2'-(4-methoxy-6-methylpyridin-3-yl)-3'H-spiro[dihydroindole-3,4'-pyrrolo[3,4-d]imidazole]-2,6'(5'H)-dione (S-154), and 39.5 mg of (R)-6-chloro-5'-(5-chloro-2-methylphenyl)-3'-isopropyl-2'-(4-methoxy-6-methylpyridin-3-yl)-3'H-spiro[dihydroindole-3,4'-pyrrolo[3,4-d]imidazole]-2,6'(5'H)-dione (R-154). MS (ESI): mass calcd. for $C_{29}H_{25}Cl_2N_5O_3$ 561.13, m/z found 562.2 [M+H]$^+$. $^1$H-NMR (400 MHz, DMSO-$d_6$) δ 11.73 (brs, 1H), 8.35 (d, 1H, J=4.4 Hz), 7.57-6.48 (m, 7H), 4.07-4.03 (m, 1H), 3.87 (s, 3H), 2.22 (s, 3H), 1.08 (d, 3H, J=6.8 Hz), 0.64 (d, 3H, J=6.4 Hz).

Example 155

6-chloro-5'-(5-chloro-2-methylpyridin-3-yl)-2'-(6-(dimethylamino)-4-methoxypyridin-3-yl)-3'-isopropyl-3'H-spiro[dihydroindole-3,4'-pyrrolo[3,4-d]imidazole]-2,6'(5'H)-dione

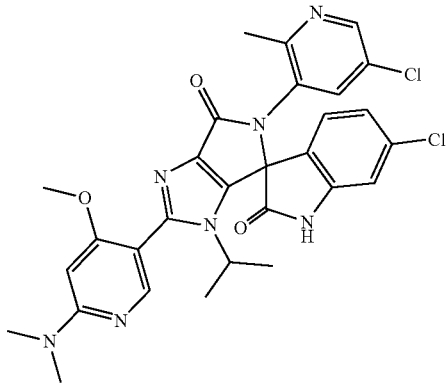 [SMILES: COc1cc(N(C)C)ncc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 9.1 mg of (S)-6-chloro-5'-(5-chloro-2-methylpyridin-3-yl)-2'-(6-(dimethylamino)-4-methoxypyridin-3-yl)-3'-isopropyl-3'H-spiro[dihydroindole-3,4'-pyrrolo[3,4-d]imidazole]-2,6'(5'H)-dione (S-155), and 9.9 mg of (R)-6-chloro-5'-(5-chloro-2-methylpyridin-3-yl)-2'-(6-(dimethylamino)-4-methoxypyridin-3-yl)-3'-isopropyl-3'H-spiro[dihydroindole-3,4'-pyrrolo[3,4-d]imidazole]-2,6'(5'H)-dione (R-155). MS (ESI): mass calcd. for $C_{29}H_{27}Cl_2N_7O_3$ 591.16, m/z found 594.2 [M+H]$^+$. $^1$H-NMR (400 MHz, DMSO-$d_6$) δ 11.79 (brs, 1H), 8.50 (s, 1H), 8.49 (d, 1H, J=5.6 Hz), 7.99-6.99 (m, 4H), 6.22 (s, 1H), 4.11-4.08 (m, 1H), 3.84 (s, 3H), 3.11 (s, 6H), 2.27 (s, 3H), 1.08 (d, 3H, J=6.4 Hz), 0.65 (d, 3H, J=4.0 Hz).

Example 156

6-chloro-5'-(5-chloro-2-isopropylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

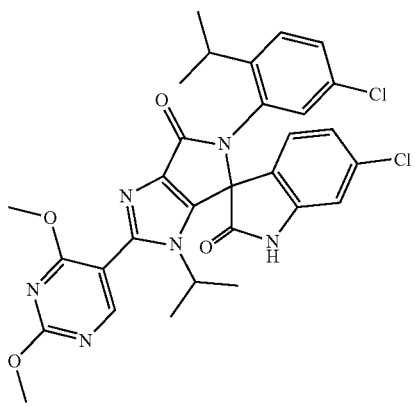 [SMILES: COc1ncc(-c2nc3c(n2C(C)C)C2(C(=O)Nc4cc(Cl)ccc42)N(c2cc(Cl)ccc2C(C)C)C3=O)c(OC)n1]

Title compounds were obtained by steps similar to those in Example 1, and supercritical high-pressure preparative chromatography was performed to obtain 50.95 mg of 6-chloro-5'-(5-chloro-2-isopropylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione. MS (ESI): mass calcd. for $C_{30}H_{28}Cl_2N_6O_4$ 606.15, m/z found 607.2 [M+H]$^+$. H-NMR (400 MHz, DMSO-d$_6$) δ 8.53 (d, 1H, J=6.0 Hz), 7.65-7.07 (m, 6H), 4.13-4.06 (m, 1H), 3.99 (d, 3H, J=13.6 Hz), 3.96 (d, 3H, J=13.6 Hz), 3.17-3.16 (m, 1H), 1.15-1.03 (m, 9H), 0.63 (d, 3H, J=5.6 Hz).

Example 157

6-chloro-5'-(5-chloro-2-methylphenyl)-2'-(6-(dimethylamino)-2-methoxypyridin-3-yl)-3'-isopropyl-3'H-spiro[dihydroindole-3,4'-pyrrolo[3,4-d]imidazole]-2,6'(5'H)-dione

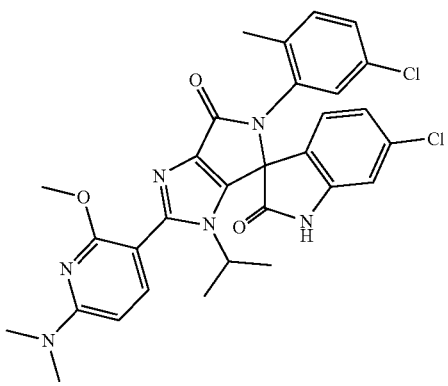 [SMILES: COc1nc(N(C)C)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 16.2 mg of (S)-6-chloro-5'-(5-chloro-2-methylphenyl)-2'-(6-(dimethylamino)-2-methoxypyridin-3-yl)-3'-isopropyl-3'H-spiro[dihydroindole-3,4'-pyrrolo[3,4-d]imidazole]-2,6'(5'H)-dione (S-157), and 17.6 mg of (R)-6-chloro-5'-(5-chloro-2-methylphenyl)-2'-(6-(dimethylamino)-2-methoxypyridin-3-yl)-3'-isopropyl-3'H-spiro[dihydroindole-3,4'-pyrrolo[3,4-d]imidazole]-2,6'(5'H)-dione (R-157). MS (ESI): mass calcd. for $C_{30}H_{28}Cl_2N_6O_3$ 590.16, m/z found 591.1 [M+H]$^+$. $^1$H-NMR (400 MHz, DMSO-d$_6$) δ 11.60 (brs, 1H), 7.58-6.29 (m, 8H), 4.21-4.14 (m, 1H), 3.83 (s, 3H), 3.09 (s, 6H), 2.14 (s, 3H), 1.07 (d, J=6.8 Hz, 3H), 0.64 (d, J=6.8 Hz, 3H).

Example 158

2-chloro-4-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzonitrile

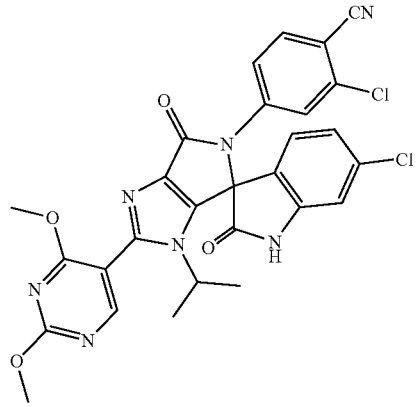 [SMILES: COc1ncc(-c2nc3c(n2C(C)C)C2(C(=O)Nc4cc(Cl)ccc42)N(c2ccc(C#N)c(Cl)c2)C3=O)c(OC)n1]

Title compounds were obtained by steps similar to those in Example 1, and supercritical high-pressure preparative chromatography was performed to obtain 119.4 mg of (S)-2-chloro-4-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzonitrile (S-158), and 105.8 mg of (R)-2-chloro-4-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzonitrile (R-158). MS (ESI): mass calcd. for $C_{28}H_{21}Cl_2N_7O_4$ 589.10, m/z found 590.1 [M+H]$^+$. $^1$H-NMR (400 MHz, DMSO-d$_6$) δ 11.81 (brs, 1H), 8.52 (s, 1H), 7.95 (d, J=8.4 Hz, 1H), 7.54 (d, J=2.4 Hz, 1H), 7.47 (d, J=8.0 Hz, 1H), 7.17-7.09 (m, 3H), 4.20-4.13 (m, 1H), 3.99 (s, 3H), 3.94 (s, 3H), 1.13 (d, J=6.8 Hz, 3H), 0.61 (d, J=6.8 Hz, 3H).

Example 159

6-chloro-5'-(5-chloro-2-methylpyridin-3-yl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione

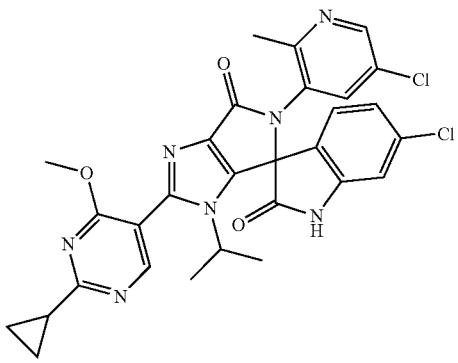 [SMILES: COc1nc(C2CC2)ncc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 55.9 mg of (S)-6-chloro-5'-(5-chloro-2-methylpyridin-3-yl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione (S-159), and 55.7 mg of (R)-6-chloro-5'-(5-chloro-2-methylpyridin-3-yl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione (R-159). MS (ESI): mass calcd. for $C_{30}H_{26}Cl_2N_6O_3$ 589.14, m/z found 590.2 [M+H]$^+$. $^1$H-NMR (400 MHz, DMSO-d$_6$) δ 11.65 (brs, 1H), 8.56-7.00 (m, 6H), 4.17-4.14 (m, 1H), 3.94 (s, 3H), 2.27 (s, 3H), 2.20-2.19 (m, 1H), 1.13-1.07 (m, 7H), 0.68 (d, 3H, J=6.8 Hz).

Example 160

3-chloro-5-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzonitrile

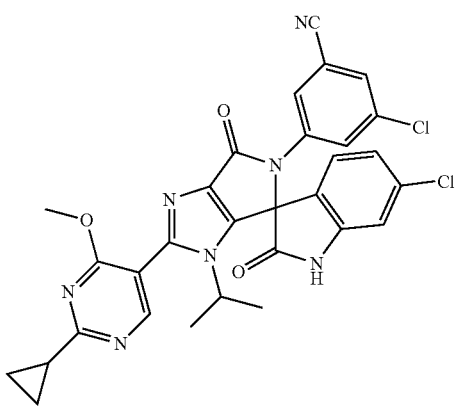 [SMILES: COc1nc(C2CC2)ncc1-c1nc2c(n1C(C)C)C1(C(=O)Nc3cc(Cl)ccc31)N(c1cc(Cl)cc(C#N)c1)C2=O]

Title compounds were obtained by steps similar to those in Example 1, and supercritical high-pressure preparative chromatography was performed to obtain 20.4 mg of (S)-3-chloro-5-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzonitrile (S-160), and 23.3 mg of (R)-3-chloro-5-(6-chloro-2'-(2,4-dimethoxypyrimidin-5-yl)-3'-isopropyl-2,6'-dioxo-3',6'-dihydro-5'H-spiro[dihydroindole-3,4'-pyrrolo[3,4-d]imidazole]-5'-yl)benzonitrile (R-160). MS (ESI): mass calcd. for $C_{28}H_{21}Cl_2N_7O_4$ 589.10, m/z found 590.1 [M+H]$^+$. $^1$H-NMR (400 MHz, DMSO-d$_6$) δ 11.71 (brs, 1H), 8.52 (s, 1H), 7.98 (s, 1H), 7.51-7.45 (m, 3H), 7.18-7.16 (m, 1H), 7.08 (s, 1H), 4.17-4.16 (m, 1H), 3.99 (s, 3H), 3.94 (s, 3H), 1.12 (d, 3H, J=5.2 Hz), 0.64 (d, 3H, J=4.8 Hz).

Example 161

6-chloro-5'-(3-chloro-4-(trifluoromethoxy)phenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione

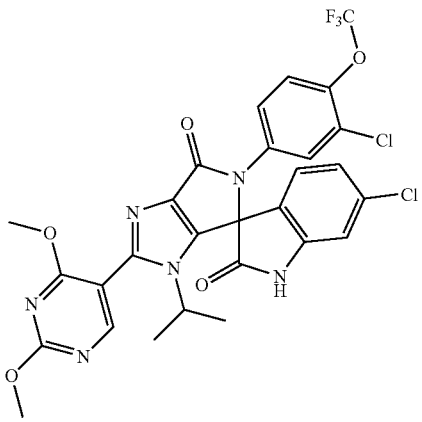 [SMILES: COc1ncc(-c2nc3c(n2C(C)C)C2(C(=O)Nc4cc(Cl)ccc42)N(c2ccc(OC(F)(F)F)c(Cl)c2)C3=O)c(OC)n1]

Title compounds were obtained by steps similar to those in Example 1, and supercritical high-pressure preparative chromatography was performed to obtain 20.4 mg of (S)-6-chloro-5'-(3-chloro-4-(trifluoromethoxy)phenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (S-161), and 23.3 mg of (R)-6-chloro-5'-(3-chloro-4-(trifluoromethoxy)phenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione (R-161). MS (ESI): mass calcd. for $C_{28}H_{21}Cl_2F_3N_6O_5$ 648.09, m/z found 649.1 [M+H]$^+$. H-NMR (400 MHz, DMSO-d$_6$) δ 11.63 (brs, 1H), 8.52 (s, 1H), 7.61-7.50 (m, 2H), 7.38 (d, J=2.4 Hz, 1H), 7.18-7.05 (m, 3H), 4.20-4.13 (m, 1H), 3.99 (s, 3H), 3.95 (s, 3H), 1.11 (d, J=6.8 Hz, 3H), 0.64 (d, J=6.8 Hz, 3H).

Example 162

6-chloro-5'-(5-chloro-2-methylphenyl)-2'-(4-((2-hydroxyethyl)(methyl)amino)-2-methoxyphenyl)-3'-isopropyl-3'H-spiro[dihydroindole-3,4'-pyrrolo[3,4-d]imidazole]-2,6'(5'H)-dione

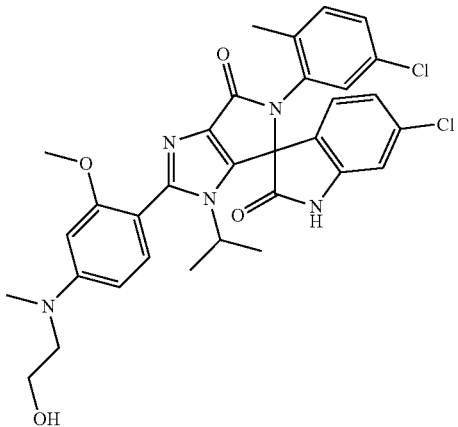 [SMILES: COc1cc(N(C)CCO)ccc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 16.7 mg of (S)-6-chloro-5'-(5-chloro-2-methylphenyl)-2'-(4-((2-hydroxyethyl)(methyl) amino)-2-methoxyphenyl)-3'-isopropyl-3'H-spiro[dihydroindole-3,4'-pyrrolo[3,4-d]imidazole]-2,6'(5'H)-dione (S-162), and 16.7 mg of (R)-6-chloro-5'-(5-chloro-2-methylphenyl)-2'-(4-((2-hydroxyethyl)(methyl) amino)-2-methoxyphenyl)-3'-isopropyl-3'H-spiro [dihydroindole-3,4'-pyrrolo[3,4-d]imidazole]-2,6'(5'H)-dione (R-162). MS (ESI): mass calcd. for $C_{32}H_{31}Cl_2N_5O_4$, 619.18 m/z found 620.2 [M+H]$^+$. $^1$H-NMR (400 MHz, DMSO-d$_6$) δ 11.80 (brs, 1H), 7.51-6.34 (m, 9H), 4.72 (t, 1H, J=5.0 Hz), 4.13-4.10 (m, 1H), 3.76 (s, 3H), 3.60-3.57 (m, 2H), 3.49-3.47 (m, 2H), 3.02 (s, 3H), 2.22 (s, 3H), 1.05 (d, 3H, J=6.0 Hz), 0.62 (d, 3H, J=5.6 Hz).

Example 163

6-chloro-5'-(5-chloro-2-methylphenyl)-2'-(6-(2-fluoroethoxy)-4-methoxypyridin-3-yl)-3'-isopropyl-3'H-spiro[dihydroindole-3,4'-pyrrolo[3,4-d]imidazole]-2,6'(5'H)-dione

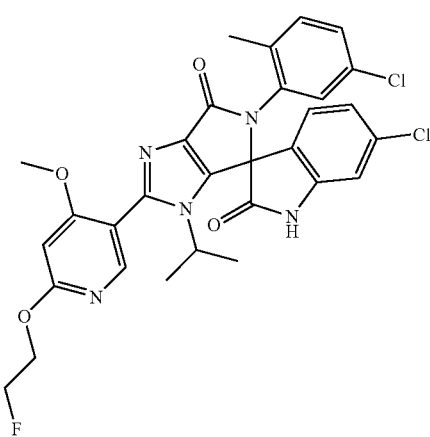 [SMILES: COc1cc(OCCF)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 12.4 mg of (S)-6-chloro-5'-(5-chloro-2-methylphenyl)-2'-(6-(2-fluoroethoxy)-4-methoxypyridin-3-yl)-3'-isopropyl-3'H-spiro[dihydroindole-3,4'-pyrrolo[3,4-d]imidazole]-2,6'(5'H)-dione (S-163), and 12.4 mg of (R)-6-chloro-5'-(5-chloro-2-methylphenyl)-2'-(6-(2-fluoroethoxy)-4-methoxypyridin-3-yl)-3'-isopropyl-3'H-spiro[dihydroindole-3,4'-pyrrolo[3,4-d]imidazole]-2,6'(5'H)-dione (R-163). MS (ESI): mass calcd. for $C_{30}H_{26}Cl_2FN_5O_4$ 609.13, m/z found 610.1[M+H]$^+$. $^1$H-NMR (400 MHz, DMSO-d$_6$) δ 11.73 (brs, 1H), 8.13 (d, 1H, J=4.8 Hz), 7.54-6.91 (m, 6H), 6.67 (s, 1H), 4.83-4.54 (m, 4H), 4.07-4.06 (m, 1H), 3.86 (s, 3H), 2.21 (s, 3H), 1.08 (d, 3H, J=6.0 Hz), 0.65 (d, 3H, J=6.0 Hz).

Example 164

6-chloro-5'-(5-chloro-2-methylphenyl)-3'-isopropyl-2'-(6-isopropyl-4-methoxypyridin-3-yl)-3'H-spiro[dihydroindole-3,4'-pyrrolo[3,4-d]imidazole]-2,6'(5'H)-dione

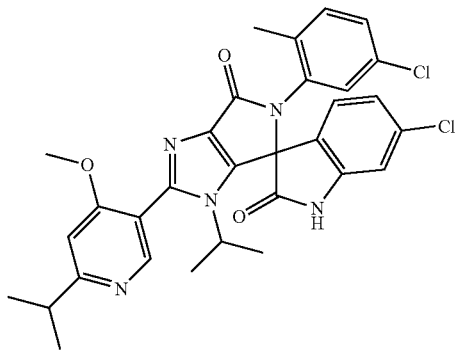

Title compounds were obtained by steps similar to those in Example 1, and supercritical high-pressure preparative chromatography was performed to obtain 14.4 mg of (S)-6-chloro-5'-(5-chloro-2-methylphenyl)-3'-isopropyl-2'-(6-isopropyl-4-methoxypyridin-3-yl)-3'H-spiro[dihydroindole-3,4'-pyrrolo[3,4-d]imidazole]-2,6'(5'H)-dione (S-164), and 14.5 mg of (R)-6-chloro-5'-(5-chloro-2-methylphenyl)-3'-isopropyl-2'-(6-isopropyl-4-methoxypyridin-3-yl)-3'H-spiro[dihydroindole-3,4'-pyrrolo[3,4-d]imidazole]-2,6'(5'H)-dione (R-164). MS (ESI): mass calcd. for $C_{31}H_{29}Cl_2N_5O_3$, 589.16 m/z found 590.2 [M+H]$^+$. $^1$H-NMR (400 MHz, DMSO-d$_6$) δ 11.5 (brs, 1H), 8.43 (d, 1H, J=4.8 Hz), 7.59-6.49 (m, 7H), 4.11-4.02 (m, 1H), 3.91 (s, 3H), 3.12-3.09 (m, 1H), 2.22 (s, 3H), 1.30-1.29 (m, 6H), 1.07 (d, 3H, J=6.8 Hz), 0.65 (d, 3H, J=6.8 Hz).

Example 165

6-chloro-5'-(5-chloro-2-methylphenyl)-2'-(2,4-dimethoxyphenyl)-3'-(1-hydroxypropan-2-yl)-3'H-spiro[dihydroindole-3,4'-pyrrolo[3,4-d]imidazole]-2,6'(5'H)-dione

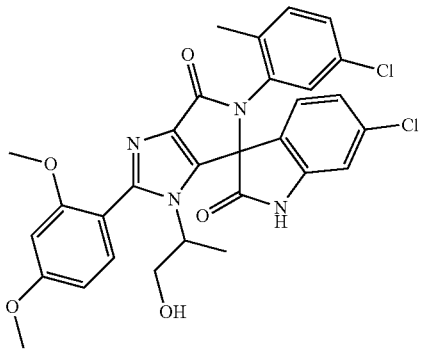 [SMILES: COc1ccc(-c2nc3c(n2C(C)CO)C2(C(=O)Nc4cc(Cl)ccc42)N(c2cc(Cl)ccc2C)C3=O)c(OC)c1]

Steps similar to those in Example 1 were performed to obtain 20.0 mg of the title compound 6-chloro-5'-(5-chloro-2-methylphenyl)-2'-(2,4-dimethoxyphenyl)-3'-(1-hydroxypropan-2-yl)-3'H-spiro[dihydroindole-3,4'-pyrrolo[3,4-d]imidazole]-2,6'(5'H)-dione. MS (ESI): mass calcd. for $C_{30}H_{26}Cl_2N_4O_5$ 592.13, m/z found 593.1 [M+H]$^+$. $^1$H-NMR (400 MHz, DMSO-d$_6$) δ 10.80 (brs, 1H), 9.35 (s, 1H), 7.59-6.71 (m, 9H), 4.33-4.29 (m, 2H), 3.93-3.85 (m, 7H), 2.07 (s, 3H), 1.18 (d, J=6.0 Hz, 3H).

Example 166

6-chloro-5'-(5-chloro-2-methylpyridin-3-yl)-3'-isopropyl-2'-(6-isopropyl-4-methoxypyridin-3-yl)-3'H-spiro[dihydroindole-3,4'-pyrrolo[3,4-d]imidazole]-2,6'(5'H)-dione

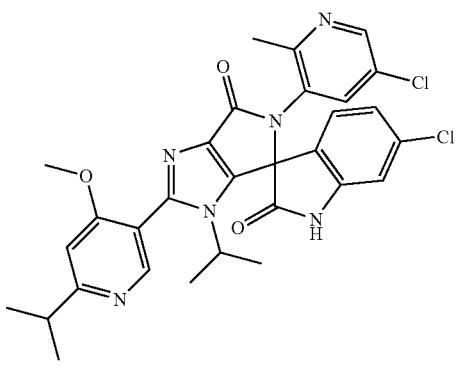 [SMILES: COc1cc(C(C)C)ncc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 31.8 mg of (S)-6-chloro-5'-(5-chloro-2-methylpyridin-3-yl)-3'-isopropyl-2'-(6-isopropyl-4-methoxypyridin-3-yl)-3'H-spiro[dihydroindole-3,4'-pyrrolo[3,4-d]imidazole]-2,6'(5'H)-dione (S-166), and 33.1 mg of (R)-6-chloro-5'-(5-chloro-2-methylpyridin-3-yl)-3'-isopropyl-2'-(6-isopropyl-4-methoxypyridin-3-yl)-3'H-spiro[dihydroindole-3,4'-pyrrolo[3,4-d]imidazole]-2,6'(5'H)-dione (R-166). MS (ESI): mass calcd. for $C_{30}H_{28}Cl_2N_6O_3$, 590.16 m/z found 591.2 [M+H]$^+$. $^1$H-NMR (400 MHz, DMSO-d$_6$) δ 11.59 (brs, 1H), 8.51-8.41 (m, 2H), 7.67-7.01 (m, 5H), 4.12-4.05 (m, 1H), 3.90 (s, 3H), 3.11-3.06 (m, 1H), 2.50 (s, 3H), 1.30 (d, 6H, J=6.8 Hz), 1.09 (d, 3H, J=6.4 Hz), 0.66 (d, 3H, J=4.0 Hz).

Example 167

6-chloro-5'-(5-chloro-2-methylphenyl)-2'-(2,4-dimethoxypyrimidin-5-yl)-3'-(1-hydroxymethylpropane-2-yl)-3'H-spiro[dihydroindole-3,4'-pyrrolo[3,4-d]imidazole]-2,6'(5'H)-dione

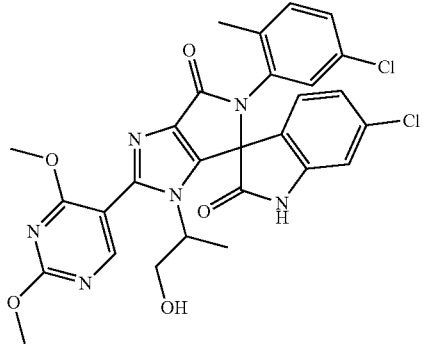 [SMILES: COc1ncc(-c2nc3c(n2C(C)CO)C2(C(=O)Nc4cc(Cl)ccc42)N(c2cc(Cl)ccc2C)C3=O)c(OC)n1]

Steps similar to those in Example 1 were performed to obtain 50.6 mg of the title compound 6-chloro-5'-(5-chloro-2-methylphenyl)-2'-(2,4-dimethoxypyrimidin-5-yl)-3'-(1-hydroxymethylpropan-2-yl)-3'H-spiro[dihydroindole-3,4'-pyrrolo[3,4-d]imidazole]-2,6'(5'H)-dione. MS (ESI): mass calcd. for $C_{28}H_{24}Cl_2N_6O_5$ 594.12, m/z found 595.1 [M+H]$^+$. $^1$H-NMR (400 MHz, DMSO-d$_6$) δ 10.80 (brs, 1H), 9.43 (s, 1H), 8.66 (s, 1H), 7.50 (s, 1H), 7.50-6.88 (m, 5H), 4.40-4.31 (m, 2H), 4.02 (s, 6H), 3.93 (d, J=12.0 Hz), 2.05 (s, 3H), 1.24 (s, 3H).

Example 168

6-chloro-5'-(5-chloro-2-methylphenyl)-2'-(4,6-dimethoxypyridin-3-yl)-3'-(1-hydroxypropan-2-yl)-3'H-spiro[dihydroindole-3,4'-pyrrolo[3,4-d]imidazole]-2,6'(5'H)-dione

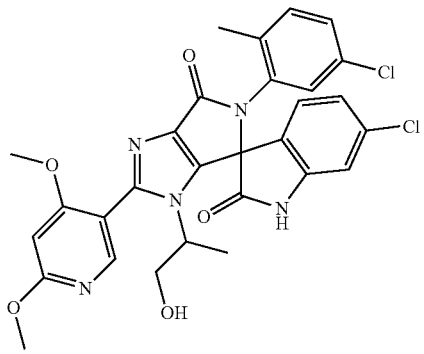 [SMILES: COc1cc(OC)c(-c2nc3c(n2C(C)CO)C2(C(=O)Nc4cc(Cl)ccc42)N(c2cc(Cl)ccc2C)C3=O)cn1]

Steps similar to those in Example 1 were performed to obtain 101.2 mg of the title compound 6-chloro-5'-(5- chloro-2-methylphenyl)-2'-(4,6-dimethoxypyridin-3-yl)-3'-(1-hydroxypropan-2-yl)-3'H-spiro[dihydroindole-3,4'-pyrrolo[3,4-d]imidazole]-2,6'(5'H)-dione. MS (ESI): mass calcd. for $C_{29}H_{25}Cl_2N_5O_5$ 593.12, m/z found 594.1 [M+H]$^+$. $^1$H-NMR (400 MHz, DMSO-d$_6$) δ 10.83 (brs, 1H), 9.42 (s, 1H), 8.25 (s, 1H), 7.53 (d, J=2.4 Hz, 1H), 7.28-6.88 (m, 6H), 6.64 (s, 1H), 4.34-4.30 (m, 2H), 3.94-3.91 (m, 7H), 2.06 (s, 3H), 1.21 (d, 6.8 Hz, 3H).

Example 169

6-chloro-5'-(5-chloro-2-methylphenyl)-2'-(6-ethoxy-4-methoxypyridin-3-yl)-3'-(1-hydroxypropan-2-yl)-3'H-spiro[dihydroindole-3,4'-pyrrolo[3,4-d]imidazole]-2,6'(5'H)-dione

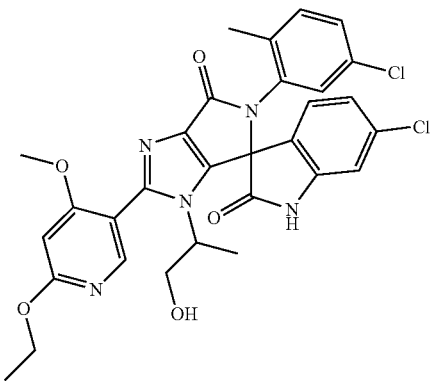 [SMILES: CCOc1cc(OC)c(-c2nc3c(n2C(C)CO)C2(C(=O)Nc4cc(Cl)ccc42)N(c2cc(Cl)ccc2C)C3=O)cn1]

Steps similar to those in Example 1 were performed to obtain 151.1 mg of the title compound 6-chloro-5'-(5-chloro-2-methylphenyl)-2'-(6-ethoxy-4-methoxypyridin-3-yl)-3'-(1-hydroxypropan-2-yl)-3'H-spiro[dihydroindole-3,4'-pyrrolo[3,4-d]imidazole]-2,6'(5'H)-dione. MS (ESI): mass calcd. for $C_{27}H_{22}Cl_2N_6O_3$ 607.14, m/z found 608.1 [M+H]$^+$. $^1$H-NMR (400 MHz, DMSO-d$_6$) δ 10.83 (brs, 1H), 9.41 (s, 1H), 8.23 (s, 1H), 7.53 (d, J=2.4 Hz, 1H), 7.28-6.89 (m, 5H), 6.62 (s, 1H), 4.42-4.30 (m, 4H), 3.93-3.90 (m, 4H), 2.06 (s, 3H), 1.36 (t, J=6.8 Hz, 3H), 1.21 (d, J=6.8 Hz, 3H).

Example 170

6-chloro-5'-(5-chloro-2-methylpyridin-3-yl)-2'-(2-(2-fluoroethoxy)-4-methoxypyrimidin-5-yl)-3'-isopropyl-3'H-spiro[dihydroindole-3,4'-pyrrolo[3,4-d]imidazole]-2,6'(5'H)-dione

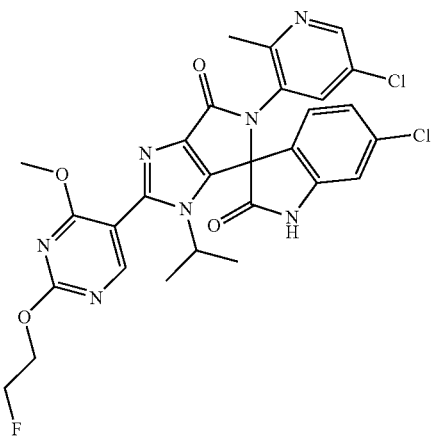 [SMILES: COc1nc(OCCF)ncc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 25.2 mg of (S)-6-chloro-5'-(5-chloro-2-methylpyridin-3-yl)-2'-(2-(2-fluoroethoxy)-4-methoxypyrimidin-5-yl)-3'-isopropyl-3'H-spiro[dihydroindole-3,4'-pyrrolo[3,4-d]imidazole]-2,6'(5'H)-dione (S-170), and 25.9 mg of (R)-6-chloro-5'-(5-chloro-2-methylpyridin-3-yl)-2'-(2-(2-fluoroethoxy)-4-methoxypyrimidin-5-yl)-3'-isopropyl-3'H-spiro[dihydroindole-3,4'-pyrrolo[3,4-d]imidazole]-2,6'(5'H)-dione (R-170). MS (ESI): mass calcd. for $C_{28}H_{24}Cl_2FN_7O_4$ 611.12, m/z found 612.1 [M+H]$^+$. $^1$H-NMR (400 MHz, DMSO-d$_6$) δ 11.65 (brs, 1H), 8.56-8.49 (m, 2H), 7.64-7.00 (m, 4H), 4.87-4.85 (m, 1H), 4.75-4.73 (m, 1H), 4.69-4.67 (m, 1H), 4.61-4.59 (m, 1H), 4.19-4.18 (m, 1H), 3.96 (s, 3H), 2.27 (s, 3H), 1.09 (d, 3H, J=6.8 Hz), 0.68 (d, 3H, J=5.6 Hz).

Example 171

6-chloro-5'-(3-chlorophenyl)-2'-(2-(2-fluoroethoxy)-4-methoxypyrimidin-5-yl)-3'-isopropyl-3'H-spiro[dihydroindole-3,4'-pyrrolo[3,4-d]imidazole]-2,6'(5'H)-dione

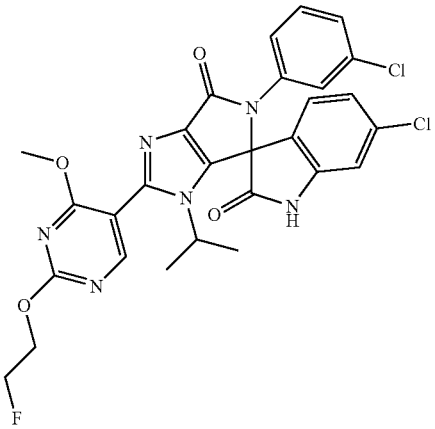 [SMILES: COc1nc(OCCF)ncc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 5.3 mg of (S)-6-chloro-5'-(3-chlorophenyl)-2'-(2-(2-fluoroethoxy)-4-methoxypyrimidin-5-yl)-3'-isopropyl-3'H-spiro[dihydroindole-3,4'-pyrrolo[3,4-d]imidazole]-2,6'(5'H)-dione (S-171), and 4.3 mg of (R)-6-chloro-5'-(3-chlorophenyl)-2'-(2-(2-fluoroethoxy)-4-methoxypyrimidin-5-yl)-3'-isopropyl-3'H-spiro[dihydroindole-3,4'-pyrrolo[3,4-d]imidazole]-2,6'(5'H)-dione (R-171). MS (ESI): mass calcd. for $C_{28}H_{23}Cl_2FN_6O_4$, 596.11 m/z found 597.1 [M+H]$^+$. $^1$H-NMR (400 MHz, DMSO-d$_6$) δ 11.59 (brs, 1H), 8.52 (s, 1H), 7.49 (d, 1H, J=8.0 Hz), 7.38-7.35 (m, 2H), 7.15-7.12 (m, 2H), 7.01 (d, 1H, J=2.0 Hz), 6.98-6.95 (m, 1H), 4.87-4.59 (m, 4H), 4.18-4.15 (m, 1H), 3.95 (s, 3H), 1.12 (d, 3H, J=6.8 Hz), 0.65 (d, 3H, J=6.8 Hz).

Example 172

6-chloro-5'-(5-chloro-2-methylphenyl)-3'-isopropyl-2'-(2-isopropyl-4-methoxypyrimidin-5-yl)-3'H-spiro[dihydroindole-3,4'-pyrrolo[3,4-d]imidazole]-2,6'(5'H)-dione

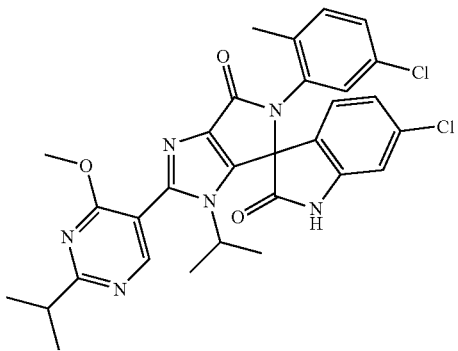 [SMILES: COc1nc(C(C)C)ncc1-c1nc2c(n1C(C)C)C1(C(=O)Nc3cc(Cl)ccc31)N(c1cc(Cl)ccc1C)C2=O]

Title compounds were obtained by steps similar to those in Example 1, and supercritical high-pressure preparative chromatography was performed to obtain 19.6 mg of (S)-6-chloro-5'-(5-chloro-2-methylphenyl)-3'-isopropyl-2'-(2-isopropyl-4-methoxypyrimidin-5-yl)-3'H-spiro[dihydroindole-3,4'-pyrrolo[3,4-d]imidazole]-2,6'(5'H)-dione (S-172), and 18.1 mg of (R)-6-chloro-5'-(5-chloro-2-methylphenyl)-3'-isopropyl-2'-(2-isopropyl-4-methoxypyrimidin-5-yl)-3'H-spiro[dihydroindole-3,4'-pyrrolo[3,4-d]imidazole]-2,6'(5'H)-dione (R-172). MS (ESI): mass calcd. for $C_{30}H_{28}Cl_2N_6O_3$ 590.19, m/z found 591.1[M+H]$^+$. $^1$H-NMR (400 MHz, DMSO-d$_6$) δ 11.78 (brs, 1H), 8.67 (d, 1H, J=6.4 Hz), 8.29-6.48 (m, 6H), 4.08-4.06 (m, 1H), 3.98 (s, 3H), 3.14-3.11 (m, 1H), 2.22 (s, 3H), 1.34 (d, 6H, J=6.8 Hz), 1.10 (d, 3H, J=6.4 Hz), 0.68 (d, 3H, J=6.8 Hz).

Example 173

6-chloro-5'-(5-chloro-2-methylpyridin-3-yl)-2'-(6-(2-fluoroethoxy)-4-methoxypyridin-3-yl)-3'-isopropyl-3'H-spiro[dihydroindole-3,4'-pyrrolo[3,4-d]imidazole]-2,6'(5'H)-dione

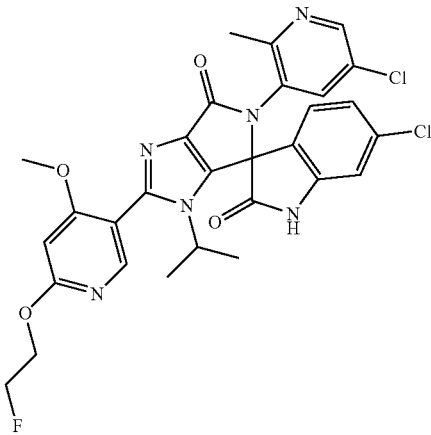 [SMILES: COc1cc(OCCF)ncc1-c1nc2c(n1C(C)C)C1(C(=O)Nc3cc(Cl)ccc31)N(c1cc(Cl)cnc1C)C2=O]

Title compounds were obtained by steps similar to those in Example 1, and supercritical high-pressure preparative chromatography was performed to obtain 20.1 mg of (S)-6-chloro-5'-(5-chloro-2-methylpyridin-3-yl)-2'-(6-(2-fluoroethoxy)-4-methoxypyridin-3-yl)-3'-isopropyl-3'H-spiro[dihydroindole-3,4'-pyrrolo[3,4-d]imidazole]-2,6'(5'H)-dione (S-173), and 19.6 mg of (R)-6-chloro-5'-(5-chloro-2-methylpyridin-3-yl)-2'-(6-(2-fluoroethoxy)-4-methoxypyridin-3-yl)-3'-isopropyl-3'H-spiro[dihydroindole-3,4'-pyrrolo[3,4-d]imidazole]-2,6'(5'H)-dione (R-173). MS (ESI): mass calcd. for $C_{29}H_{25}Cl_2FN_6O_4$ 610.12, m/z found 611.2 [M+H]$^+$. H-NMR (400 MHz, DMSO-d$_6$) δ 11.81 (brs, 1H), 8.51 (dd, 1H, J$^1$=8.4 Hz, J$^2$=2.4 Hz), 8.14 (d, 1H, J=5.6 Hz), 7.62-7.00 (m, 4H), 6.69 (s, 3H), 4.84-4.82 (m, 1H), 4.72-4.70 (m, 1H), 4.63-4.61 (m, 1H), 4.55-4.54 (m, 1H), 4.09-4.07 (m, 1H), 3.86 (s, 3H), 2.27 (s, 3H), 1.08 (d, 3H, J=6.4 Hz), 0.65 (d, 3H, J=6.4 Hz).

Example 174

6-chloro-5'-(3-chloro-5-fluorophenyl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione

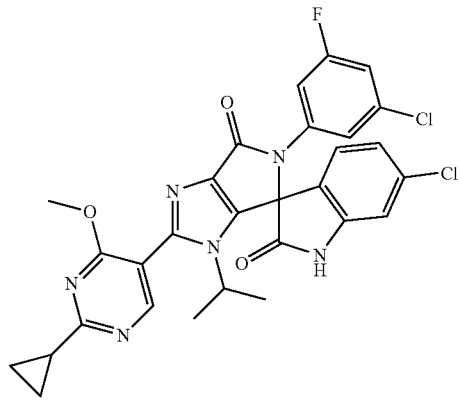 [SMILES: COc1nc(C2CC2)ncc1-c1nc2c(n1C(C)C)C1(C(=O)Nc3cc(Cl)ccc31)N(c1cc(F)cc(Cl)c1)C2=O]

Title compounds were obtained by steps similar to those in Example 1, and supercritical high-pressure preparative chromatography was performed to obtain 37.8 mg of (S)-6-chloro-5'-(3-chloro-5-fluorophenyl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione (S-174), and 39.0 mg of (R)-6-chloro-5'-(3-chloro-5-fluorophenyl)-2'-(2-cyclopropyl-4-methoxypyrimidin-5-yl)-3'-isopropyl-3'H-spiro[dihydroindole-3,4'-pyrrolo[3,4-d]imidazole]-2,6'(5'H)-dione (R-174). MS (ESI): mass calcd. for $C_{29}H_{23}Cl_2FN_6O_3$ 592.12, m/z found 593.1 [M+H]$^+$. H-NMR (400 MHz, DMSO-d$_6$) δ 11.75 (brs, 1H), 8.53 (s, 1H), 7.50 (d, 1H, J=8.0 Hz), 7.41-6.89 (m, 5H), 4.17-4.10 (m, 1H), 3.93 (s, 3H), 2.23-2.17 (m, 1H), 1.12-1.11 (m, 7H), 0.65 (d, 3H, J=6.8 Hz).

Example 175

6-chloro-5'-(3-chloro-5-fluorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione

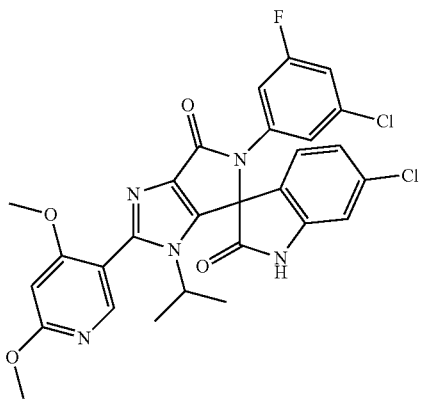 [SMILES: COc1cc(OC)c(-c2nc3c(n2C(C)C)C2(C(=O)Nc4cc(Cl)ccc42)N(c2cc(F)cc(Cl)c2)C3=O)cn1]

Title compounds were obtained by steps similar to those in Example 1, and supercritical high-pressure preparative chromatography was performed to obtain 45.2 mg of (S)-6-chloro-5'-(3-chloro-5-fluorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione (S-175), and 44.9 mg of (R)-6-chloro-5'-(3-chloro-5-fluorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione (R-175). MS (ESI): mass calcd. for $C_{28}H_{22}Cl_2FN_5O_4$ 581.10, m/z found 582.1 [M+H]$^+$. $^1$H-NMR (400 MHz, DMSO-d$_6$) δ 11.69 (brs, 1H), 8.11 (s, 1H), 7.50 (d, 1H, J=8.4 Hz), 7.48-6.90 (m, 5H), 6.60 (s, 1H), 4.09-4.02 (m, 1H), 3.91 (s, 3H), 3.83 (s, 3H), 1.11 (d, 3H, J=6.4 Hz), 0.61 (d, 3H, J=6.0 Hz).

Example 176

6-chloro-5'-(3-chloro-5-fluorophenyl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione

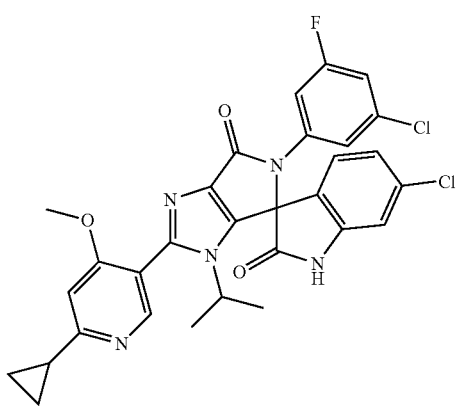 [SMILES: COc1cc(C2CC2)ncc1-c1nc2c(n1C(C)C)C1(C(=O)Nc3cc(Cl)ccc31)N(c1cc(F)cc(Cl)c1)C2=O]

Title compounds were obtained by steps similar to those in Example 1, and supercritical high-pressure preparative chromatography was performed to obtain 40.3 mg of (S)-6-chloro-5'-(3-chloro-5-fluorophenyl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione (S-176), and 40.6 mg of (R)-6-chloro-5'-(3-chloro-5-fluorophenyl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione (R-176). MS (ESI): mass calcd. for $C_{30}H_{24}Cl_2FN_5O_3$ 591.12, m/z found 592.1 [M+H]$^+$. $^1$H-NMR (400 MHz, DMSO-d$_6$) δ 11.69 (brs, 1H), 8.27 (s, 1H), 7.51 (d, 1H, J=8.4 Hz), 7.40-6.80 (m, 6H), 4.09-4.04 (m, 1H), 3.87 (s, 3H), 2.21-2.07 (m, 1H), 1.11 (d, 3H, J=6.4 Hz), 1.10-0.99 (m, 4H), 0.60 (d, 3H, J=6.4 Hz).

Example 177

6-chloro-5'-(3-chlorophenyl)-2'-(6-(2-fluoroethoxy)-4-methoxypyridin-3-yl)-3'-isopropyl-3'H-spiro[dihydroindole-3,4'-pyrrolo[3,4-d]imidazole]-2,6'(5'H)-dione

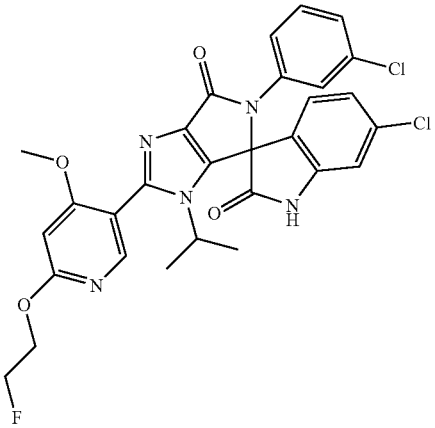 [SMILES: COc1cc(OCCF)ncc1-c1nc2c(n1C(C)C)C1(C(=O)Nc3cc(Cl)ccc31)N(c1cccc(Cl)c1)C2=O]

Title compounds were obtained by steps similar to those in Example 1, and supercritical high-pressure preparative chromatography was performed to obtain 5.3 mg of (S)-6-chloro-5'-(3-chlorophenyl)-2'-(6-(2-fluoroethoxy)-4-methoxypyridin-3-yl)-3'-isopropyl-3'H-spiro[dihydroindole-3,4'-pyrrolo[3,4-d]imidazole]-2,6'(5'H)-dione (S-177), and 4.3 mg of (R)-6-chloro-5'-(3-chlorophenyl)-2'-(6-(2-fluoroethoxy)-4-methoxypyridin-3-yl)-3'-isopropyl-3'H-spiro[dihydroindole-3,4'-pyrrolo[3,4-d]imidazole]-2,6'(5'H)-dione (R-177). MS (ESI): mass calcd. for $C_{29}H_{24}Cl_2FN_5O_4$ 595.12, m/z found 596.2 [M+H]$^+$. $^1$H-NMR (400 MHz, DMSO-d$_6$) δ 11.56 (brs, 1H), 8.11 (s, 1H), 7.49-6.95 (m, 7H), 6.68 (s, 1H), 4.83-4.53 (m, 4H), 4.09-4.02 (m, 1H), 1.11 (d, 3H, J=6.4 Hz), 0.62 (d, 3H, J=6.4 Hz).

Example 178

6-chloro-5'-(3-chlorophenyl)-2'-(4,6-dimethoxypyridin-3-yl)-3'-(1-hydroxypropan-2-yl)-3'H-spiro[dihydroindole-3,4'-pyrrolo[3,4-d]imidazole]-2,6'(5'H)-dione

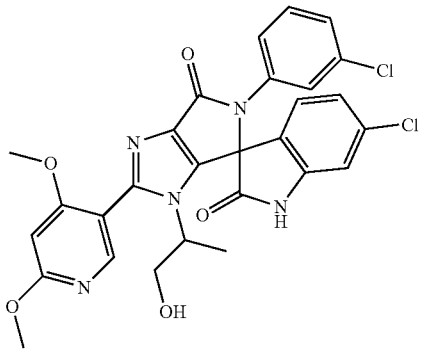 [SMILES: COc1cc(OC)c(-c2nc3c(n2C(C)CO)C2(C(=O)Nc4cc(Cl)ccc42)N(c2cccc(Cl)c2)C3=O)cn1]

Steps similar to those in Example 1 were performed to obtain 120.1 mg of the title compound 6-chloro-5'-(3-chlorophenyl)-2'-(4,6-dimethoxypyridin-3-yl)-3'-(1-hydroxypropan-2-yl)-3'H-spiro[dihydroindole-3,4'-pyrrolo[3,4-d]imidazole]-2,6'(5'H)-dione. MS (ESI): mass calcd. for $C_{28}H_{23}Cl_2N_5O_5$ 579.11, m/z found 580.1 [M+H]$^+$. $^1$H-NMR (400 MHz, DMSO-d$_6$) δ 10.88 (brs, 1H), 10.06 (s, 1H), 8.24 (s, 1H), 7.80 (s, 1H), 7.79-6.92 (m, 6H), 6.63 (s, 1H), 4.32-4.29 (m, 2H), 3.94 (s, 6H), 3.92-3.89 (m, 1H), 1.22 (d, 3H, J=6.8 Hz).

Example 179

5-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxypyrimidine-2-methylcyanide

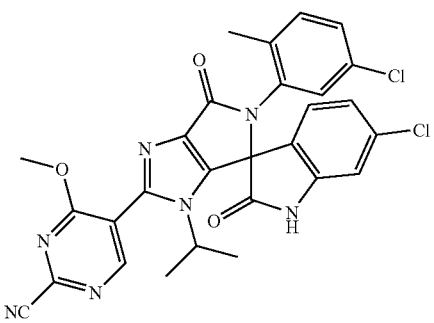 [SMILES: COc1nc(C#N)ncc1-c1nc2c(n1C(C)C)C1(C(=O)Nc3cc(Cl)ccc31)N(c1cc(Cl)ccc1C)C2=O]

Steps similar to those in Example 1 were performed to obtain 4.3 mg of the title compound 5-(6-chloro-5'-(5-chloro-2-methylphenyl)-3'-isopropyl-2,6'-dioxo-5',6'-dihydro-3'H-spiro[dihydroindole-3,4'-pyrrolo[3,4-d]imidazole]-2'-yl)-4-methoxypyrimidine-2-methylcyanide. MS (ESI): mass calcd. for $C_{28}H_{21}Cl_2N_7O_3$ Exact Mass: 573.11, m/z found 574.1 [M+H]$^+$. $^1$H-NMR (400 MHz, DMSO-d$_6$) δ 11.81 (brs, 1H), 8.96 (d, J=8.4 Hz, 1H), 7.59-6.50 (m, 6H), 4.27-4.22 (m, 1H), 4.05 (s, 3H), 2.21 (s, 3H), 1.10 (d, J=6.8 Hz, 3H), 0.67 (d, J=6.4 Hz, 3H).

Example 180

6-chloro-5'-(3-chloro-5-fluorophenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione

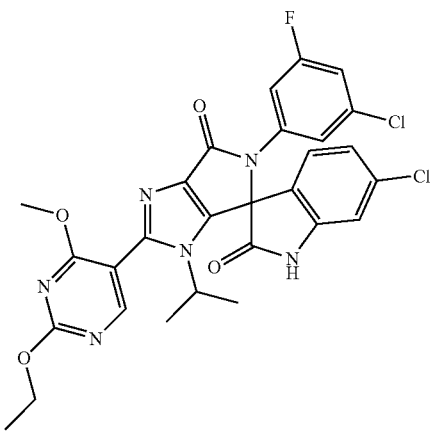 [SMILES: CCOc1ncc(-c2nc3c(n2C(C)C)C2(C(=O)Nc4cc(Cl)ccc42)N(c2cc(F)cc(Cl)c2)C3=O)c(OC)n1]

Title compounds were obtained by steps similar to those in Example 1, and supercritical high-pressure preparative chromatography was performed to obtain 44.3 mg of (S)-6-chloro-5'-(3-chloro-5-fluorophenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione (S-180), and 45.1 mg of (R)-6-chloro-5'-(3-chloro-5-fluorophenyl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione (R-180). MS (ESI): mass calcd. for $C_{28}H_{23}Cl_2FN_6O_4$ 596.11, m/z found 597.1 [M+H]$^+$. $^1$H-NMR (400 MHz, DMSO-d$_6$) δ 11.69 (brs, 1H), 8.50 (d, J=3.2 Hz, 1H), 7.50 (d, J=8.4 Hz, 1H), 7.41-6.90 (m, 5H), 4.47 (q, J=6.8 Hz, 2H), 4.21-4.14 (m, 1H), 3.97 (s, 3H), 1.27 (t, J=6.4 Hz, 2H), 1.13 (d, J=6.8 Hz, 3H), 0.64 (d, J=6.4 Hz, 3H).

In order to verify the activity of the MDM2 inhibitors according to the present invention, the present invention further provides several representative Experimental Examples.

Experimental Example 1 Determination of the Inhibitory Activities of the Compounds OF THE PRESENT INVENTION ON MDM2 BY A BIOLOGICAL ASSAY METHOD Experimental purpose: To determine the inhibitory activities of the compounds of the present invention on MDM2.

The present experiment uses the following assay methods/instruments/reagents:

| Name | Type (Product code) | Manufacturer |
|---|---|---|
| Plate shaker | MTS2/4 | IKA |
| Microplate reader | M1000pro | TECAN |
| Centrifuge | Avanti J-26XP | Beckman Coulter |
| GST-MDM2 (70 μM) | | In-house purification |
| Biotin-P53 (100 μM) | | GL Biochem |
| Anti-GST-Tb(100x) | 61GSTTLA | Cisbio |

| Name | Type (Product code) | Manufacturer |
|---|---|---|
| SA-XL665(16.67 μM) | 610SAXLA | Cisbio |
| BSA | B2064 | Sigma |
| AEBSF | 76307 | Sigma |
| DTT | 43816 | Sigma |
| PBS | 20012-027 | Cisbio |

Experiment Subjects:

Positive control group: Compound HDM201, disclosed in patent No. 201380016617.6; synthesized in laboratory.

Experimental groups S-1 to R-180, corresponding to the compounds prepared in Examples 1-180, respectively.

Experiment Procedure:

Solution Preparation:

Buffer: 1×PBS+0.1% BSA+5 mM DTT; MDM2 Buffer: Buffer+1 mM AEBSF

GST-MDM2: The final concentration is 4 nM, and it is required to formulate a 20 nM (5×) solution. A mother liquor is diluted by 3500 folds, wherein the mother liquor is 10-fold diluted first, and then 350-fold diluted.

Biotin-P53: The final concentration is 37 nM, and it is required to formulate a 185 nM (5×) solution. A mother liquor is diluted by 540.5 folds.

SA-XL665: The final concentration is 4.625 nM, and it is required to formulated a 1805 nM (4×) solution. A mother liquor is diluted by 901 folds.

Anti-GST-Tb: The final concentration is 2×, and a mother liquor is diluted by 50 folds.

MIX: GST-MDM2, Biotin-P53, SA-XL665 and Anti-GST-Tb were mixed according to a ratio of 4:4:5:5.

Sample: Preparation of a sample (10 mM in DMSO) solution: a. 3 μL sample+7 μL DMSO+20 μL DMSO were formulated to give an initial concentration of 1 mM and mixed well; b. in plate 1, twelve 5-fold serial dilutions (sequentially prepared by adding 10 μL of the last sample to 40 μL DMSO) were prepared and mixed well, individually; c. plate 2 was taken, 45 μL of Buffer was added to each well, and 5 μL of dilution at each concentration was taken from plate 1 and added to the corresponding well in plate 2 (the concentration in well 1 was 100 μM), and mixed well.

Experimental Steps:

1. 18 μL of MIX was added to a 384-well plate, and centrifugation was performed at 4500 rpm for 5 min.

2. 2 μL of sample was added correspondingly to each well, the resultant was centrifuged at 25° C. and 4500 rpm for 5 min, and shaked at 25° C. for 90 min on a shaker.

Readings were obtained from the Microplate reader, and data was processed by Graphpad Prism 6.0.

$$\text{Inhibition rate at each concentration point } (inh \%) = \frac{\text{fluorescence value at zero point concentration} - \text{fluorescence value at each concentration point}}{\text{fluorescence value at zero concentration}} \times 100\%$$

TABLE 1

Test results of inhibitory activities of the compounds of the present invention on MDM2 (IC$_{50}$: nM)

| Experimental 实验对象 | Inhibition test of MDM2-P53, IC$_{50}$ (nM) MDM2-PS3 的抑制测试 IC$_{50}$ (nM) |
|---|---|
| HDM201 | 2.50 |
| S-1 | 2.21 |
| R-1 | 617.89 |
| S-2 | 1.13 |
| R-2 | 117.50 |
| S-3 | 4.92 |
| R-3 | 1194.23 |
| S-4 | 3.37 |
| R-4 | 132.48 |
| S-5 | 3.22 |
| R-5 | 109.29 |
| S-6 | 2.21 |
| R-6 | 42.26 |
| S-7 | 73.24 |
| R-7 | 35972.70 |
| S-8 | 3.29 |
| R-8 | 329.21 |
| S-9 | 2.38 |
| R-9 | 332.39 |
| S-10 | 2.77 |
| R-10 | 116.59 |
| S-11 | 1.58 |
| R-11 | 257.20 |
| S-12 | 3.55 |
| R-12 | 367.64 |
| S-13 | 2.55 |
| R-13 | 120.80 |
| S-14 | 1.34 |
| R-14 | 460.77 |
| S-15 | 1.62 |
| R-15 | 107.21 |
| S-16 | 3.39 |
| R-16 | 570.33 |
| S-17 | 3.75 |
| R-17 | 49.37 |
| S-18 | 1.43 |
| R-18 | 158.09 |
| S-19 | 34.6 |
| R-19 | NA |
| S-20 | 4.39 |
| R-20 | 256.30 |
| S-21 | 1.34 |
| R-21 | 222.76 |
| S-22 | 1.10 |
| R-22 | 626.74 |
| S-23 | 2.80 |
| R-23 | 174.99 |
| S-24 | 4.40 |
| R-24 | 391.92 |
| S-25. | 2.52 |
| R-25 | 51.85 |
| S-26 | 2.37 |
| R-26 | 235.74 |
| S-27 | 3.45 |
| R-27 | 924.43 |
| S-28 | 54.32 |
| R-28 | 3109.44 |
| S-29 | 1.01 |
| R-29 | 93.57 |
| S-30 | 3.31 |
| S-31 | 60.11 |
| R-31 | 1403.96 |
| S-32 | 3.89 |
| R-32 | 1100.34 |
| S-33 | 2.47 |
| R-33 | 591.54 |
| S-34 | 139.47 |
| R-34 | NA |
| S-35 | 23.40 |
| R-35 | NA |
| S-36 | 4.67 |
| R-66 | 464.19 |
| S-37 | 22.01 |

TABLE 1-continued

Test results of inhibitory activities of the compounds of the present invention on MDM2 (IC$_{50}$: nM)

| Experimental | Inhibition test of MDM2-P53, IC$_{50}$ (nM) |
|---|---|
| R-37 | 3111.09 |
| S-38 | 12.01 |
| R-38 | 1115.99 |
| S-39 | 3.93 |
| R-39 | 1847.84 |
| S-40 | 3.85 |
| R-40 | 322.24 |
| S-41 | 149.29 |
| R-41 | 7317.32 |
| S-42 | 1.51 |
| R-42 | 364.49 |
| S-43 | 3.28 |
| R-43 | 129.78 |
| S-44 | 1.18 |
| R-44 | 51.11 |
| S-45 | 1.72 |
| R-45 | 170.63 |
| S-46 | 236.27 |
| R-46 | 2332.41 |
| S-47 | 4.16 |
| R-47 | 209.81 |
| S-48 | 1.46 |
| R-48 | 195.57 |
| S-49 | 1.72 |
| R-49 | 71.38 |
| S-50 | 85.52 |
| R-50 | 20410.23 |
| S-51 | 4.36 |
| R-51 | 547.30 |
| S-52 | 0.87 |
| R-52 | 540.41 |
| S-53 | 0.84 |
| R-53 | 3768.80 |
| S-54 | 2.25 |
| R-54 | 1961.81 |
| S-55 | 4.25 |
| R-55 | 437.30 |
| S-56 | 5.19 |
| R-56 | 154.99 |
| S-57 | 3.04 |
| R-57 | 426.50 |
| S-58 | 11.42 |
| R-58 | 1429.18 |
| S-50 | 2.29 |
| R-59 | 689.37 |
| S-60 | 4.81 |
| R..60 | 1072.13 |
| S-61 | 1.31 |
| R-61 | 135.68 |
| S-62 | 1.61 |
| R-62 | 252.45 |
| S-63 | 1.16 |
| R-63 | 537.10 |
| S-64 | 11.83 |
| R-64 | 1023.67 |
| S-65 | 4.04 |
| R-65 | 497.90 |
| S-66 | 1.50 |
| R-66 | 85.88 |
| S-67 | 1.22 |
| R-67 | 354.64 |
| S-68 | 2.32 |
| R-68 | 656.97 |
| S-69 | 1.78 |
| R-69 | 635.65 |
| S-70 | 0.94 |
| R-70 | 111.12 |
| S-71 | 2.96 |
| R-71 | 100.03 |
| S-72 | 0.90 |
| R-72 | 213.52 |
| S-73 | 1.10 |
| R-73 | 142.35 |
| S-74 | 0.98 |
| R-74 | 93.42 |
| S-75 | 0.97 |
| R-75 | 122.38 |
| S-76 | 4.23 |
| R-76 | 579.08 |
| S-77 | 1.86 |
| R-77 | 139.30 |
| S-78 | 1.42 |
| R-78 | 222.23 |
| S-79 | 1.89 |
| R-79 | 285.33 |
| S-80 | 2.56 |
| R-80 | 362.85 |
| S-81 | 1.23 |
| R-81 | 53.27 |
| S-82 | 1.16 |
| R-82 | 394.36 |
| S-83 | 2.23 |
| R-83 | 87.64 |
| 84 | 3.78 |
| S-85 | 3.30 |
| R-85 | 493.70 |
| S-86 | 2.59 |
| R-86 | 142.00 |
| S-87 | 3.31 |
| R-87 | 473.20 |
| S-88 | 2.34 |
| R-88 | 399.20 |
| S-89 | 4.32 |
| R-89 | 568.90 |
| S-90 | 1.38 |
| R-90 | 309.80 |
| S-91 | 3.56 |
| R-91 | 460.90 |
| S-92 | 1.72 |
| R-92 | 377.83 |
| S-93 | 3.89 |
| R-93 | 658.14 |
| S-94 | 4.72 |
| R-94 | 840.35 |
| S-95 | 1.92 |
| R-95 | 1668.15 |
| S-96 | 1.04 |
| R-96 | 150.65 |
| S-97 | 3.94 |
| R-97 | 5.73 |
| S-98 | 1.27 |
| R-98 | 1034.32 |
| S-99 | 2.56 |
| R-99 | 115.26 |
| S-100 | 3.14 |
| R-100 | 632.69 |
| S-101 | 9.86 |
| R-101 | 1999.88 |
| S-102 | 2.01 |
| R-102 | 412.91 |
| S-103 | 1.81 |
| R-103 | 180.98 |
| S-104 | 2.26 |
| R-104 | 146.16 |
| S-105 | 11.20 |
| R-105 | 342.96 |
| S-106 | 2.59 |
| R-106 | 481.33 |
| S-107 | 4.55 |
| R-107 | 535.69 |
| S-108 | 8.87 |
| R-108 | 690.54 |
| S-109 | 2.34 |
| R-109 | 380.99 |
| S-110 | 1.60 |
| R-110 | 704.44 |

TABLE 1-continued

Test results of inhibitory activities of the compounds of the present invention on MDM2 ($IC_{50}$: nM)

| Experimental 实验对象 | Inhibition test of MDM2-P53, $IC_{50}$ (nM) MDM2-PS3 的抑制测试$_{50}$ (nM) |
|---|---|
| S-111 | 1.52 |
| R-111 | 110.36 |
| S-112 | 1.15 |
| R-112 | 103.77 |
| S-113 | 1.25 |
| R-113 | 50.54 |
| S-114 | 3.20 |
| R-114 | 261.25 |
| S-115 | 1.30 |
| R-115 | 268.55 |
| S-116 | 4.18 |
| R-116 | 689.19 |
| S-117 | 2.15 |
| R-117 | 232.73 |
| S-118 | 3.51 |
| R-118 | 436.15 |
| S-119 | 2.39 |
| R-119 | 851.01 |
| S-120 | 9.01 |
| R-120 | 4778.08 |
| S-121 | 3.35 |
| R-121 | 300.14 |
| S-122 | 2.76 |
| R-122 | 794.09 |
| S-123 | 2.11 |
| R-123 | 115.65 |
| S-124 | 2.91 |
| R-124 | 1314.68 |
| 125 | 20.79 |
| S-126 | 1.52 |
| R-126 | 193.43 |
| S-127 | 2.76 |
| R-127 | 91.04 |
| S-128 | 1.09 |
| R-128 | 612.42 |
| S-129 | 3.84 |
| R-129 | 149.30 |
| S-130 | 5.59 |
| R-130 | 568.03 |
| S-131 | 1.17 |
| R-131 | 119.79 |
| S-132 | 3.60 |
| R-132 | 1320.63 |
| S-133 | 1.41 |
| R-133 | 1109.64 |
| S-134 | 2.60 |
| R-134 | 322.16 |
| S-135 | 1.36 |
| R-135 | 422.57 |
| S-136 | 2.35 |
| R-136 | 1800.00 |
| S-137 | 1.65 |
| R-137 | 421.88 |
| S-138 | 1.04 |
| R-138 | 132.36 |
| S-139 | 1.36 |
| R-139 | 341.78 |
| S-140 | 1.06 |
| R-140 | 147.08 |
| S-141 | 3.42 |
| R-141 | 762.36 |
| S-142 | 1.45 |
| R-142 | 137.08 |
| S-143 | 1.10 |
| R-143 | 214.30 |
| S-144 | 3.84 |
| R-144 | 119.22 |
| S-145 | 2.05 |
| R-145 | 749.40 |
| S-146 | 5.44 |
| R-146 | 6712.03 |
| S-147 | 5.89 |
| R-147 | 118.69 |
| S-148 | 1.58 |
| R-148 | 200.92 |
| S-149 | 18.49 |
| R-149 | 2282.00 |
| S-150 | 1.93 |
| R-150 | 377.20 |
| S-151 | 1410.00 |
| R-151 | 5373.00 |
| S-152 | 0.78 |
| R-152 | 134.00 |
| S-153 | 0.49 |
| R-153 | 31.11 |
| S-154 | 0.90 |
| R-154 | 31.11 |
| S-155 | 0.95 |
| R-155 | 96.44 |
| 156 | 11.23 |
| S-157 | 3.81 |
| R-157 | 369.60 |
| S-158 | 4.07 |
| R-158 | 2203.00 |
| S-159 | 2.80 |
| R-159 | 467.60 |
| S-160 | 5.91 |
| R-160 | 5713.00 |
| S-161 | 8.09 |
| R-161 | 126.30 |
| S-162 | 2.07 |
| R-162 | 119.90 |
| S-163 | 1.36 |
| R-163 | 166.34 |
| S-164 | 0.94 |
| R-164 | 591.56 |
| 165 | NA |
| S-166 | 1.88 |
| R-166 | 957.19 |
| 167 | NA |
| 168 | NA |
| 169 | NA |
| S-170 | 1.86 |
| R-170 | 234.96 |
| S-171 | 2.86 |
| R-171 | 8830.80 |
| S-172 | 4.15 |
| R-172 | 408.32 |
| S-173 | 1.39 |
| R-173 | 528.45 |
| S-174 | 4.12 |
| R-174 | 515.23 |
| S-175 | 1.96 |
| R-175 | 522.39 |
| S-176 | 1.76 |
| R-176 | 320.63 |
| S-177 | 2.37 |
| R-177 | 108.63 |
| 178 | NA |
| 179 | 4.27 |
| S-180 | 4.60 |
| R-180 | 679.20 |

NA: data not available

Experimental Results:

The experimental results in Table 1 above demonstrate that:

1) The compounds of the present invention, such as the compounds prepared in Examples 1-180, have an inhibitory effect on MDM2, especially compounds with S-configuration therein have a significant inhibitory effect on MDM2.

2) Some compounds of the present invention have a better inhibitory effect on MDM2 than the positive control compound HDM201, for example, the activities of the compounds with S-configuration in Examples 2, 11, 14, 15, 18, 21, 22, 29, 42, 44, 45, 48, 49, 52, 53, 61, 62, 63, 66, 67, 69, 70, 72, 73, 74, 75, 77, 78, 79, 81, 82, 90, 92, 95, 96, 98, 102, 103, 110, 111, 112, 113, 115, 126, 128, 131, 133, 135, 137, 138, 139, 140, 142, 143, 148, 150, 152, 153, 154, 155, 163, 164, 166, 170, 173, 175 and 176 are better than that of the positive control compound HDM201.

Experimental Example 2 Determination of the Inhibition of the Mdm2 Inhibitors According to the Present Invention on the Proliferation of Human Osteosarcoma Cell Line SJSA-1 (the Same Test Subjects as Experimental Example 1)

2.1 Experimental materials: human osteosarcoma cell line SJSA-1 (Nanjing Kebai Biotechnology Co., Ltd.), DAPI (5 mg/mL, Beyotime, c1002), 4% paraformaldehyde (Ding Guo Biotech., AR-0211), 96-well plate with black transparent bottom (PE, 6005182), In Cell Analyzer 2200 (GE Healthcare).

2.2 Experiment Preparation:

2.2.1 Preparation of a culture medium for human osteosarcoma cell line SJSA-1: RPMI1640+10% FBS+1% penicillin/streptomycin 2.2.2 Preparation of a test compound solution:

a. the test compound solution with a certain concentration was taken, and diluted with the culture medium to obtain a compound solution with a final concentration of 20 μM;

b. 200 μL of a culture medium containing 0.2% DMSO (dimethyl sulfoxide) was added into $H_2$-$H_{10}$ of a 96-well plate; 300 μl of the above solution was added into $H_1$; and c. 100 μL was taken out from well $H_1$, added into $H_2$, and mixed well; then 100 μl of the resultant solution was taken and added into $H_3$, and dilution was carried out in sequence until $H_9$ to obtain the 3-fold serial dilution of the test compound.

2.3 Experimental Process:

2.3.1 SJSA-1 cells were inoculated into a 96-well cell plate with black transparent bottom at 4000 cells/100 μl/well, and cultured overnight at 37° C.;

2.3.2 The above samples were added at 100 μl/well to a culture plate inoculated with cells, gently patted to mix well, and incubated at 37° C. for 72 h;

2.3.3 Fixation: the cell plate was taken out, the culture medium was removed, and 50 μL of 4% paraformaldehyde solution was added to each well to fix for 10 min;

2.3.4 50 μl of 0.1 M glycine was added to neutralize for 10 min;

2.3.5 Washing was performed with 1×PBS (phosphate buffer solution pH7.2) twice;

2.3.6 Permeabilization: 50 μL of 0.2% TritonX-100 (Triton) was added per well, and permeabilization was carried out at room temperature for 10 min;

2.3.7 Washing was performed with 1×PBS (phosphate buffer solution pH7.2) twice;

2.3.8 5 mg/mL DAPI stock solution was diluted at a ratio of 1:5000 (final concentration of 1 g/ml), and staining was performed at room temperature for 20 min;

2.3.9 Washing was performed with 1×PBS (phosphate buffer solution pH7.2) for three times; and 2.3.10 Scanning and analysis were performed by In cell analyzer.

2.4 Data Processing:

The inhibition rate of each compound at each concentration point was calculated according to the following formula, and curve fitting was performed by GraphPad Prism 6.0 software to obtain the $IC_{50}$ value.

$$\text{Cell relative inhibition rate } (\%) = \frac{\text{fluorescence value of control group} - \text{fluorescence value of expreimental group}}{\text{fluorescence value of control group}} \times 100\%$$

TABLE 2

Inhibitory activities of the compounds of the present invention on proliferation of human osteosarcoma cell line SJSA-1

| Compounds | $IC_{50}$ (nM) |
| --- | --- |
| HDM201 | 91.31 |
| S-1 | 39.62 |
| R-1 | 16660.88 |
| S-2 | 7.40 |
| R-2 | 2772.00 |
| S-3 | 173.71 |
| R-3 | 16271.55 |
| S-4 | 7.92 |
| R-4 | 2188.17 |
| S-5 | 25.44 |
| R-5 | 1595.07 |
| S-6 | 6.20 |
| R-6 | 1766.00 |
| S-7 | 1271.50 |
| R-7 | NA |
| S-8 | 10.33 |
| R-8 | 2293.00 |
| S-9 | 7.39 |
| R-9 | 2817.23 |
| S-10 | 124.27 |
| R-10 | 2169.08 |
| S-11 | 1.67 |
| R-11 | 1508.07 |
| S-12 | 5.27 |
| R-12 | 2441.56 |
| S-13 | 5.95 |
| R-13 | 1124.55 |
| S-14 | 63.47 |
| R-14 | 5378.16 |
| S-15 | 10.87 |
| R-15 | 840.33 |
| S-16 | 3557.71 |
| R-16 | 20057.44 |
| S-17 | 201.10 |
| R-17 | 1311.66 |
| S-18 | 13.91 |
| R-18 | 1615.66 |
| S-19 | 352.22 |
| R-19 | NA |
| S-20 | 48.08 |
| R-20 | 4005.08 |
| S-21 | 62.19 |
| R-21 | 5232.02 |
| S-22 | 7.46 |
| R-22 | 6954.13 |
| S-23 | 1.24 |
| R-23 | 353.78 |
| S-24 | 4.17 |
| R-24 | 872.23 |
| S-25 | 8.83 |
| R-25 | 265.16 |
| S-26 | 22.23 |
| R-26 | 3646.55 |
| S-27 | 119.33 |
| R-27 | NA |
| S-28 | 1289.92 |
| R-28 | NA |
| S-29 | 196.37 |
| R-29 | 10856.23 |
| S-30 | 58.10 |
| R-30 | NA |
| S-31 | 1584.88 |

TABLE 2-continued

Inhibitory activities of the compounds of the present invention on proliferation of human osteosarcoma cell line SJSA-1

| Compounds | IC$_{50}$ (nM) |
|---|---|
| R-31 | 3575.10 |
| S-32 | 10.09 |
| R-32 | 8197.15 |
| S-33 | 9.70 |
| R-33 | 4885.16 |
| S-34 | 618.96 |
| R-34 | NA |
| S-35 | 257.65 |
| R-35 | NA |
| S-36 | 72.27 |
| R-36 | 3176.49 |
| S-37 | 14.16 |
| R-17 | 2439.34 |
| S-38 | 14.74 |
| R-38 | NA |
| S-39 | 1183.40 |
| R-39 | NA |
| S-40 | 14.08 |
| R-40 | 3086.90 |
| S-41 | 1205.42 |
| R-41 | NA |
| S-42 | 5.60 |
| R-42 | 4555.29 |
| S-43 | 563.67 |
| R-43 | NA |
| S-44 | 11.95 |
| R-44 | 1332.43 |
| S-45 | 6.20 |
| R-45 | 4307.06 |
| S-46 | 5981.97 |
| R-46 | NA |
| S-47 | 14.02 |
| R-47 | 3851.55 |
| S-48 | 16.84 |
| R-48 | 3630.98 |
| S-49 | 5.92 |
| R-49 | 1486.41 |
| S-50 | 1315.42 |
| R-50 | 8427.52 |
| S-51 | 62.56 |
| R-51 | 9516.69 |
| S-52 | 466.77 |
| R-52 | 22436.03 |
| S-53 | 213.39 |
| R-53 | 77439.40 |
| S-54 | 468.31 |
| R-54 | NA |
| S-55 | 117.29 |
| R-55 | 9939.33 |
| S-36 | 83.85 |
| R-56 | 3481.69 |
| S-57 | 11.78 |
| R-57 | 3958.52 |
| S-58 | 50.75 |
| R-58 | 5892.75 |
| S-59 | 262.70 |
| R-59 | NA |
| S-60 | NA |
| R-60 | NA |
| S-61 | 5.50 |
| R-61 | 135.68 |
| S-62 | 10.54 |
| R-62 | 4357.85 |
| S-63 | 77.62 |
| R-63 | NA |
| S-64 | 725.96 |
| R-64 | NA |
| S-65 | NA |
| R-65 | NA |
| S-66 | 39.59 |
| R-66 | 3861.83 |
| S-67 | 20.76 |
| R-67 | 8492.33 |
| S-68 | 1702.99 |
| R-68 | NA |
| S-69 | 2.29 |
| R-69 | 6584.81 |
| S-70 | 73.64 |
| R-70 | 4205.60 |
| S-71 | 291.56 |
| R-71 | 7017.36 |
| S-72 | 5.90 |
| R-72 | 3480.88 |
| S-73 | 250.87 |
| R-73 | NA |
| S-74 | 7.85 |
| R-74 | 1839.65 |
| S-75 | 9.84 |
| R-75 | 3040.51 |
| S-76 | 308.66 |
| R-76 | NA |
| S-77 | 535.23 |
| R-77 | NA |
| S-78 | 7.88 |
| R-78 | 1363.64 |
| 8-79 | 72.44 |
| R-79 | NA |
| S-80 | 16.85 |
| R-80 | NA |
| S-81 | 82.79 |
| R-81 | 1603.25 |
| S-82 | 7.43 |
| R-82 | NA |
| S-83 | 6.21 |
| R-83 | 588.54 |
| 84 | 2606.15 |
| S-85 | 40.18 |
| R-85 | 2187.76 |
| S-86 | 21.18 |
| R-86 | NA |
| S-87 | 11.12 |
| R-87 | 7345.13 |
| S-88 | 77.27 |
| R-88 | NA |
| S-89 | 43.25 |
| R-89 | NA |
| S-90 | 254.68 |
| R-90 | NA |
| S-91 | 14.42 |
| R-91 | 993.12 |
| S-92 | 19.86 |
| R-92 | 4875.28 |
| R-91 | NA |
| S-94 | 309.03 |
| R-94 | NA |
| S-95 | 49.55 |
| R-95 | NA |
| S-96 | 25.29 |
| R-96 | NA |
| S-97 | 167.49 |
| R-97 | 395.80 |
| S-98 | 56.10 |
| R-98 | NA |
| S-99 | 34.20 |
| R-99 | 1472.31 |
| S-100 | 1210.60 |
| R-100 | NA |
| S-101 | 48.53 |
| R-101 | NA |
| S-102 | 57.41 |
| R-102 | NA |
| S-103 | 40.46 |
| R-103 | 2426.61 |
| S-104 | 266.07 |
| R-104 | 6886.52 |
| S-105 | 243.22 |
| R-105 | NA |
| S-106 | 33.50 |

TABLE 2-continued

Inhibitory activities of the compounds of the present invention on proliferation of human osteosarcoma cell line SJSA-1

| Compounds | IC$_{50}$ (nM) |
|---|---|
| R-106 | NA |
| S-107 | 114.82 |
| R-107 | 3235.93 |
| S-108 | 28.77 |
| R-108 | NA |
| S-109 | 54.58 |
| R-109 | 8203.52 |
| S-110 | 77.98 |
| R-110 | NA |
| S-111 | 13.03 |
| R-111 | 561.05 |
| S-112 | 90.57 |
| R-112 | NA |
| S-113 | 26.73 |
| R-113 | 2172.70 |
| S-114 | 10.12 |
| R-114 | 1870.68 |
| S-115 | 3357.38 |
| R-115 | 26.92 |
| S-116 | 212.81 |
| R-117 | NA |
| S-117 | 14.42 |
| R-117 | NA |
| S-118 | 107.15 |
| R-118 | NA |
| S-119 | 20.00 |
| R-119 | NA |
| S-120 | 363.92 |
| R-120 | NA |
| S-121 | 66.99 |
| R-121 | NA |
| S-122 | 117.21 |
| R-122 | NA |
| S-123 | 321.37 |
| R-123 | NA |
| S-124 | 129.41 |
| R-124 | NA |
| 125 | 60.26 |
| S-126 | 79.62 |
| R-126 | 1592.21 |
| S-127 | 83.18 |
| R-127 | 1570.36 |
| S-128 | 144.88 |
| R-128 | NA |
| S-129 | 146.22 |
| R-129 | NA |
| S-130 | NA |
| R-130 | NA |
| S-131 | 46.34 |
| R-131 | NA |
| S-132 | 163.68 |
| R-132 | NA |
| S-133 | 99.77 |
| R-133 | NA |
| S-134 | 82.22 |
| R-134 | NA |
| S-135 | 96.16 |
| R-135 | NA |
| S-136 | 108.39 |
| R-136 | NA |
| S-137 | 65.92 |
| R-137 | NA |
| S-138 | 75.68 |
| R-138 | NA |
| S-139 | 50.70 |
| R-139 | NA |
| S-140 | 81.47 |
| R-140 | 862.98 |
| S-141 | 73.62 |
| R-141 | NA |
| S-142 | 137.72 |
| R-142 | NA |
| S-143 | 24.89 |
| R-143 | 6223.00 |
| S-144 | 100.92 |
| R-144 | 2449.06 |
| S-145 | 28.25 |
| R-145 | NA |
| S-146 | 67.76 |
| R-146 | NA |
| S-147 | 271.02 |
| R-147 | 5741.16 |
| S-148 | 71.78 |
| R-148 | NA |
| S-149 | 153.46 |
| R-149 | NA |
| S-150 | 80.53 |
| R-150 | 5701.63 |
| S-151 | NA |
| R-151 | NA |
| S-152 | 79.80 |
| R-152 | NA |
| S-153 | 21.99 |
| R-153 | NA |
| S-154 | 22.03 |
| R-154 | NA |
| S-155 | 14.59 |
| R-155 | 1524.05 |
| 156 | NA |
| S-157 | 16.67 |
| R-157 | 1798.87 |
| S-158 | 549.54 |
| R.158 | NA |
| S-159 | 34.20 |
| R-159 | 5333.35 |
| S-160 | 350.75 |
| R-160 | NA |
| S-161 | 557.18 |
| R-161 | NA |
| S-162 | 14.93 |
| R-162 | 781.63 |
| S-163 | 125.60 |
| R-163 | NA |
| S-164 | 16.79 |
| R-164 | NA |
| 165 | NA |
| S-166 | 38.11 |
| R-166 | NA |
| 167 | NA |
| 168 | NA |
| 169 | NA |
| S-170 | 130.62 |
| R-170 | NA |
| S-171 | 379.31 |
| R-171 | NA |
| S-172 | 53.33 |
| R-172 | NA |
| S-173 | 216.77 |
| R-173 | NA |
| S-174 | 93.50 |
| R-174 | NA |
| S-175 | 49.20 |
| R-175 | NA |
| S-176 | 28.84 |
| R-176 | NA |
| S-177 | 420.72 |
| R-177 | 4246.20 |
| 178 | NA |
| 179 | 52.72 |
| S-180 | 56.75 |
| R-180 | 2172.70 |

NA: data not available

Experimental Results:

The experimental results of Table 2 above demonstrate that:

1) The compounds of the present invention, such as the compounds prepared in Examples 1-180, have an inhibitory effect on the human osteosarcoma cell line SJSA-1, and especially the compounds with S-configuration therein have a significant inhibitory effect on the human osteosarcoma cell line SJSA-1.

2) Some compounds of the present invention have a better inhibitory effect on the human osteosarcoma cell line SJSA-1 than the positive control compound HDM201, for example, the inhibitory effects on the human osteosarcoma cell line SJSA-1 of the compounds with S-configuration in Examples 2, 4, 6, 9, 11, 12, 13, 15, 22, 23, 24, 25, 32, 33, 42, 45, 49, 61, 69, 72, 74, 75, 78, 82, 83, 86, 89, 91, 92, 96, 98, 99, 101, 102, 103, 106, 108, 110, 113, 114, 115, 119, 121, 126, 127, 131, 137, 138, 139, 141, 143, 145, 146, 153, 154, 155, 157, 159, 162, 164, 166, 172, and 176 are better than that of the positive control compound HDM201.

Experimental Example 3 Determination of the Pharmacokinetics of the Mdm2 Inhibitors of the Present Invention in Mice 3.1 Experimental Summary ICR mice were used as the test animals, and the concentrations of the drugs in plasma of mice at different time points after intravenous administration and intragastric administration of the representative compounds were measured by a LC/MS/MS method, so as to study the pharmacokinetic behavior of the compounds of the present invention in mice and evaluate the pharmacokinetic characteristics thereof.

3.2 Experimental Scheme 3.2.1 Test Drugs:

Some compounds prepared in Examples 1-180 of the present invention.

The control drug HDM201 was prepared by the method disclosed in patent No. CN104203952A.

3.2.2 Test Animals:

Healthy adult ICR mice, male, 6-9 weeks old, weighing 20-30 g, purchased from Shanghai Xipuer-Bikai Laboratory Animal Co., Ltd., Animal Production License No.: SCXK (HU) 2013-0016

3.2.3 Preparation of Test Drugs

Intragastric or intravenous administration: an appropriate amount of sample was weighed, dissolved in 5% DMSO+ 40% PEG400+55% (10% HP-β-CD in Saline) to prepare a 0.5 mg/ml solution for intragastric or intravenous administration.

3.2.4 Administration of Test Drugs

Intravenous administration: for each test compound, 3 male ICR mice were administered intravenously at a dose of 2 mg/kg and an administration volume of 1 ml/kg after fasting overnight.

Intragastric administration: for each test compound, 3 male ICR mice were administered intragastrically at a dose of 5 mg/kg and an administration volume of 5 ml/kg after fasting overnight.

3.3 Experimental Operation

Before administration and 0.083 h, 0.167 h, 0.25 h, 0.33 h, 0.5 h, 1 h, 2 h, 4 h, 8 h and 24 h after administration, approximately 0.2 mL blood was collected via jugular vein puncture, the obtained blood was anticoagulated with heparin sodium, and placed on ice after collection, and the blood was centrifuged to separate plasma (centrifugation conditions: 8000 rpm, 6 min, and 4° C.). The collected plasma was stored at −80° C. before analysis. The plasma sample was analyzed by LC-MS/MS, and the sample was pretreated by protein precipitation method. The linear range of sample analysis was 1 to 2000 ng/ml. The lowest quantification limit was 1 ng/mL. WinNonlin (Pharsight, USA) was used to calculate the following pharmacokinetic parameters: area under the curve $AUC_{(0-t)}$, area under the curve $AUC_{(0-\infty)}$, half-life $t_{1/2}$, retention time $MRT_{(0-\infty)}$, blood drug concentration $C_{max}$, time taken to reach the peak blood drug concentration $T_{max}$, bioavailability F, apparent volume of distribution $V_z$, and clearance rate CL.

3.4 Results of Pharmacokinetic Data

TABLE 3

Pharmacokinetic parameters of ICR mice after intravenous and oral administration of HDM201

| | | | | IV- 2 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz mL/kg | CL mL/h/kg |
| 101 | 0.67 | 0.08 | 585.03 | 622.13 | 713.62 | 0.66 | 0.96 | 2717.30 | 2802.63 |
| 102 | 0.53 | 0.08 | 605.51 | 573.66 | 619.30 | 0.59 | 0.75 | 2456.27 | 3229.47 |
| 103 | 0.67 | 0.08 | 459.85 | 520.23 | 600.29 | 0.68 | 0.98 | 3231.81 | 3331.71 |
| Mean | 0.62 | 0.083 | 550.13 | 572.01 | 644.40 | 0.64 | 0.90 | 2801.79 | 3121.27 |
| SD | 0.08 | 0.000 | 78.85 | 50.97 | 60.69 | 0.04 | 0.13 | 394.61 | 280.65 |

| | | | | PO- 5 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % | |
| 201 | 1.34 | 0.50 | 408.75 | 1058.75 | 1078.76 | 1.94 | 2.09 | | |
| 202 | 0.74 | 0.50 | 584.08 | 797.19 | 818.45 | 1.04 | 1.15 | | |
| 203 | 1.24 | 0.50 | 715.01 | 1522.78 | 1539.76 | 1.82 | 1.91 | | |
| Mean | 1.11 | 0.50 | 569.28 | 1126.24 | 1145.66 | 1.60 | 1.72 | 78.76 | |
| SD | 0.32 | 0.00 | 153.66 | 367.47 | 365.28 | 0.49 | 0.50 | | |

$$*F = \frac{AUC_{(0-t)(PO)} \times Dose_{(IV)}}{AUC_{(0-t)(IV)} \times Dose_{(PO)}} \times 100\%$$

TABLE 4

Pharmacokinetic parameters of ICR mice after intravenous and oral administration of compound S-1

IV- 2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz mL/kg | CL mL/h/kg |
|---|---|---|---|---|---|---|---|---|---|
| 301 | 1.21 | 0.08 | 307.80 | 532.69 | 548.82 | 1.33 | 1.52 | 6380.69 | 3644.18 |
| 302 | 1.00 | 0.08 | 329.89 | 725.28 | 736.92 | 1.31 | 1.41 | 3917.79 | 2713.99 |
| 303 | 0.98 | 0.08 | 336.17 | 843.53 | 855.63 | 1.34 | 1.43 | 3308.82 | 2337.47 |
| Mean | 1.07 | 0.083 | 324.62 | 700.50 | 713.79 | 1.33 | 1.45 | 4535.77 | 2898.55 |
| SD | 0.13 | 0.000 | 14.90 | 156.90 | 154.71 | 0.01 | 0.06 | 1626.50 | 672.62 |

PO- 5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 1.03 | 1.00 | 629.23 | 1822.90 | 1834.25 | 1.94 | 1.99 | |
| 402 | 1.98 | 1.00 | 471.21 | 1944.41 | 2088.41 | 2.60 | 3.17 | |
| 403 | 1.92 | 1.00 | 92.81 | 241.17 | 330.15 | 1.79 | 3.13 | |
| Mean | 1.64 | 1.00 | 397.75 | 1336.16 | 1417.60 | 2.11 | 2.76 | 76.30 |
| SD | 0.54 | 0.00 | 275.65 | 950.23 | 950.30 | 0.43 | 0.67 | |

$$^*F = \frac{AUC_{(0-t)(PO)} \times Dose_{(IV)}}{AUC_{(0-t)(IV)} \times Dose_{(PO)}} \times 100\%$$

TABLE 5

Pharmacokinetic parameters of ICR mice after intravenous and oral administration of compound S-2

IV- 2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz mL/kg | CL mL/h/kg |
|---|---|---|---|---|---|---|---|---|---|
| 501 | 1.11 | 0.08 | 492.38 | 1362.57 | 1392.31 | 1.51 | 1.64 | 2291.83 | 1436.46 |
| 502 | 0.84 | 0.50 | 477.30 | 1554.01 | 1564.61 | 1.47 | 1.51 | 1552.17 | 1278.27 |
| 503 | 0.93 | 1.00 | 456.11 | 1477.86 | 1494.93 | 1.47 | 1.54 | 1804.36 | 1337.86 |
| Mean | 0.96 | 0.528 | 475.26 | 1464.81 | 1483.95 | 1.48 | 1.56 | 1882.79 | 1350.86 |
| SD | 0.13 | 0.459 | 18.22 | 96.38 | 86.68 | 0.02 | 0.07 | 376.01 | 79.90 |

PO- 5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 601 | 1.45 | 2.00 | 655.97 | 3165.38 | 3254.89 | 2.89 | 3.09 | |
| 602 | 1.83 | 1.00 | 729.77 | 3883.23 | 4100.77 | 2.87 | 3.28 | |
| 603 | 1.50 | 2.00 | 804.59 | 4136.52 | 4259.08 | 2.76 | 2.97 | |
| Mean | 1.59 | 1.67 | 730.11 | 3728.38 | 3871.58 | 2.84 | 3.12 | 101.81 |
| SD | 0.21 | 0.58 | 74.31 | 503.75 | 539.90 | 0.07 | 0.16 | |

$$^*F = \frac{AUC_{(0-t)(PO)} \times Dose_{(IV)}}{AUC_{(0-t)(IV)} \times Dose_{(PO)}} \times 100\%$$

TABLE 6

Pharmacokinetic parameters of ICR mice after intravenous and oral administration of compound S-9

IV- 2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz mL/kg | CL mL/h/kg |
|---|---|---|---|---|---|---|---|---|---|
| 701 | 1.26 | 0.08 | 1403.26 | 3334.44 | 3452.37 | 1.47 | 1.68 | 1055.16 | 579.31 |
| 702 | 1.40 | 0.08 | 1274.58 | 3650.23 | 3830.08 | 1.58 | 1.88 | 1054.38 | 522.18 |
| 703 | 1.16 | 0.08 | 1643.99 | 4107.04 | 4214.93 | 1.47 | 1.63 | 793.38 | 474.50 |

TABLE 6-continued

Pharmacokinetic parameters of ICR mice after intravenous and oral administration of compound S-9

| | | | | | | | | | |
|---|---|---|---|---|---|---|---|---|---|
| Mean | 1.27 | 0.083 | 1440.61 | 3697.23 | 3832.46 | 1.51 | 1.73 | 967.64 | 525.33 |
| SD | 0.12 | 0.000 | 187.52 | 388.44 | 381.29 | 0.06 | 0.13 | 150.91 | 52.48 |

PO- 5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 801 | 1.57 | 2.00 | 1366.47 | 6319.30 | 6555.06 | 2.65 | 2.92 | |
| 802 | 1.44 | 1.00 | 2009.05 | 8692.39 | 8911.44 | 2.60 | 2.78 | |
| 803 | 1.22 | 1.00 | 1914.07 | 6976.33 | 7048.92 | 2.68 | 2.75 | |
| Mean | 1.41 | 1.33 | 1763.20 | 7329.34 | 7505.14 | 2.64 | 2.82 | 79.30 |
| SD | 0.18 | 0.58 | 346.84 | 1225.29 | 1242.67 | 0.04 | 0.09 | |

$$^*F = \frac{AUC_{(0-t)(PO)} \times Dose_{(IV)}}{AUC_{(0-t)(IV)} \times Dose_{(PO)}} \times 100\%$$

TABLE 7

Pharmacokinetic parameters of ICR mice after intravenous and oral administration of compound S-11

IV- 2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | $V_Z$ L/kg | CL mL/min/kg |
|---|---|---|---|---|---|---|---|---|---|
| 101 | 1.15 | 0.50 | 1376.51 | 3578.38 | 3680.24 | 1.43 | 1.61 | 0.91 | 9.06 |
| 102 | 2.09 | 0.50 | 1519.69 | 4225.58 | 4820.40 | 1.81 | 2.70 | 1.25 | 6.92 |
| 103 | 1.15 | 0.50 | 1302.60 | 3169.84 | 3250.24 | 1.40 | 1.55 | 1.02 | 10.26 |
| Mean | 1.46 | 0.500 | 1399.60 | 3657.93 | 3916.96 | 1.55 | 1.95 | 1.06 | 8.74 |
| SD | 0.54 | 0.000 | 110.37 | 532.35 | 811.41 | 0.23 | 0.65 | 0.17 | 1.69 |

PO-5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 201 | 2.18 | 1.00 | 1645.73 | 8018.78 | 8771.68 | 2.96 | 3.66 | |
| 202 | 1.55 | 1.00 | 1573.02 | 8536.56 | 8816.41 | 2.87 | 3.11 | |
| 203 | 1.33 | 2.00 | 2144.69 | 11568.40 | 11784.98 | 2.92 | 3.05 | |
| Mean | 1.69 | 1.33 | 1787.81 | 9374.58 | 9791.02 | 2.92 | 3.27 | 102.51 |
| SD | 0.44 | 0.58 | 311.20 | 1917.46 | 1726.96 | 0.04 | 0.34 | |

TABLE 8

Some pharmacokinetic parameters of ICR mice after intravenous and oral administration of S-23

IV- 2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
|---|---|---|---|---|---|---|---|---|---|
| 101 | 1.57 | 0.08 | 3640.21 | 6625.30 | 7084.65 | 1.55 | 1.99 | 0.64 | 4.71 |
| 102 | 1.86 | 0.08 | 3779.72 | 9462.95 | 10504.31 | 1.78 | 2.46 | 0.51 | 3.17 |
| 103 | 1.33 | 0.08 | 3040.32 | 6172.76 | 6427.71 | 1.50 | 1.75 | 0.60 | 5.19 |
| Mean | 1.59 | 0.083 | 3486.75 | 7420.34 | 8005.55 | 1.61 | 2.07 | 0.58 | 4.35 |
| SD | 0.26 | 0.000 | 392.86 | 1783.37 | 2188.77 | 0.15 | 0.36 | 0.07 | 1.05 |

PO- 5 mg/kg

| 动物号 | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 201 | 1.15 | 1.00 | 2050.29 | 7235.20 | 7315.60 | 2.35 | 2.43 | |
| 202 | 0.98 | 1.00 | 3316.65 | 9122.66 | 9163.57 | 2.02 | 2.05 | |

TABLE 8-continued

Some pharmacokinetic parameters of ICR mice after intravenous and oral administration of S-23

| 203 | 1.52 | 0.50 | 2730.39 | 7675.41 | 7881.03 | 2.08 | 2.29 | |
| Animal | 1.22 | 0.83 | 2699.11 | 8011.09 | 8120.07 | 2.15 | 2.26 | 43.18 |
| number | 0.27 | 0.79 | 633.76 | 987.49 | 946.89 | 0.18 | 0.19 | |

$$^*F = \frac{AUC_{(0-t)(PO)} \times Dose_{(IV)}}{AUC_{(0-t)(IV)} \times Dose_{(PO)}} \times 100\%$$

TABLE 9

Pharmacokinetic parameters of ICR mice after intravenous and oral administration of S-32

| | | | | IV- 2 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz mL/kg | CL mL/h/kg |
| 901 | 1.23 | 0.25 | 2766.01 | 4699.29 | 4854.66 | 1.32 | 1.53 | 730.20 | 411.98 |
| 902 | 1.44 | 0.50 | 2451.28 | 7199.84 | 7627.51 | 1.61 | 1.97 | 542.87 | 262.21 |
| 903 | 1.26 | 0.08 | 1902.13 | 3859.04 | 4004.98 | 1.29 | 1.53 | 908.33 | 499.38 |
| Mean | 1.31 | 0.278 | 2373.14 | 5252.72 | 5495.32 | 1.41 | 1.68 | 727.14 | 391.19 |
| SD | 0.11 | 0.210 | 437.21 | 1737.80 | 1894.44 | 0.17 | 0.25 | 182.75 | 119.94 |

| | | | | PO- 5 mg/kg | | | | |
|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
| 1001 | 2.89 | 1.00 | 1578.70 | 6017.39 | 7102.68 | 2.79 | 4.22 | |
| 1002 | 1.51 | 1.00 | 3356.31 | 10704.89 | 11027.74 | 2.24 | 2.48 | |
| 1003 | 2.07 | 1.00 | 2518.33 | 8458.06 | 9168.53 | 2.48 | 3.14 | |
| Mean | 2.16 | 1.00 | 2484.45 | 8393.45 | 9099.65 | 2.50 | 3.28 | 63.92 |
| SD | 0.69 | 0.00 | 889.29 | 2344.42 | 1963.44 | 0.27 | 0.88 | |

$$^*F = \frac{AUC_{(0-t)(PO)} \times Dose_{(IV)}}{AUC_{(0-t)(IV)} \times Dose_{(PO)}} \times 100\%$$

TABLE 10

Some pharmacokinetic parameters of ICR mice after intravenous and oral administration of S-44

| | | | | IV- 2 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
| 301 | 1.91 | 0.08 | 951.21 | 2987.84 | 3364.67 | 1.77 | 2.56 | 1.64 | 9.91 |
| 302 | 1.79 | 0.08 | 872.25 | 2506.41 | 2766.34 | 1.71 | 2.35 | 1.86 | 12.05 |
| 303 | 1.92 | 0.08 | 826.58 | 2703.63 | 3052.47 | 1.82 | 2.61 | 1.82 | 10.92 |
| Mean | 1.87 | 0.083 | 883.35 | 2732.63 | 3061.16 | 1.77 | 2.51 | 1.77 | 10.96 |
| SD | 0.08 | 0.000 | 63.05 | 242.03 | 299.26 | 0.05 | 0.14 | 0.12 | 1.07 |

| | | | | PO- 5 mg/kg | | | | |
|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
| 401 | 2.56 | 1.00 | 1357.96 | 7904.41 | 8959.71 | 3.17 | 4.17 | |
| 402 | 1.77 | 1.00 | 1097.85 | 5161.46 | 5447.83 | 2.81 | 3.22 | |
| 403 | 1.65 | 2.00 | 1204.30 | 6287.89 | 6556.64 | 3.08 | 3.38 | |
| Mean | 2.00 | 1.33 | 1220.04 | 6451.26 | 6988.07 | 3.02 | 3.59 | 94.43 |
| SD | 0.49 | 0.58 | 130.77 | 1378.76 | 1795.24 | 0.19 | 0.51 | |

$$^*F = \frac{AUC_{(0-t)(PO)} \times Dose_{(IV)}}{AUC_{(0-t)(IV)} \times Dose_{(PO)}} \times 100\%$$

TABLE 11

Some pharmacokinetic parameters of ICR mice after intravenous and oral administration of S-45

IV-2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | $V_Z$ L/kg | CL mL/min/kg |
|---|---|---|---|---|---|---|---|---|---|
| 301 | 1.01 | 0.25 | 779.74 | 1865.23 | 1895.22 | 1.36 | 1.45 | 1.54 | 17.59 |
| 302 | 1.00 | 0.08 | 882.75 | 2072.07 | 2103.04 | 1.35 | 1.44 | 1.37 | 15.85 |
| 303 | 1.05 | 0.08 | 765.75 | 1793.27 | 1825.35 | 1.34 | 1.45 | 1.65 | 18.26 |
| Mean | 1.02 | 0.139 | 809.41 | 19110.19 | 1941.20 | 1.35 | 1.45 | 1.52 | 17.23 |
| SD | 0.02 | 0.096 | 63.90 | 144.74 | 144.44 | 0.01 | 0.01 | 0.14 | 1.24 |

PO-5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 2.17 | 0.50 | 1590.61 | 5862.67 | 6346.49 | 2.56 | 3.21 | |
| 402 | 1.54 | 1.00 | 1355.63 | 5315.63 | 5471.40 | 2.53 | 2.75 | |
| 403 | 1.87 | 1.00 | 1169.32 | 4196.04 | 4431.71 | 2.56 | 2.99 | |
| Mean | 1.86 | 0.83 | 1371.85 | 5124.78 | 5416.53 | 2.55 | 2.99 | 107.31 |
| SD | 0.32 | 0.29 | 211.11 | 849.55 | 958.57 | 0.02 | 0.23 | |

TABLE 12

Some pharmacokinetic parameters of ICR mice after intravenous and oral administration of S-61

IV- 2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
|---|---|---|---|---|---|---|---|---|---|
| 301 | 1.09 | 0.08 | 2994.43 | 4640.74 | 4724.28 | 1.21 | 1.32 | 0.67 | 7.06 |
| 302 | 1.00 | 0.08 | 3249.64 | 3583.88 | 3626.86 | 0.99 | 1.07 | 0.80 | 9.19 |
| 303 | 1.15 | 0.08 | 3244.96 | 5346.76 | 5483.62 | 1.26 | 1.42 | 0.60 | 6.08 |
| Mean | 1.08 | 0.083 | 3163.00 | 4523.79 | 4611.59 | 1.15 | 1.27 | 0.69 | 7.44 |
| SD | 0.07 | 0.000 | 146.02 | 887.24 | 933.50 | 0.14 | 0.18 | 0.10 | 1.59 |

PO- 5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 3.58 | 0.25 | 2434.93 | 2462.65 | 2768.24 | 1.57 | 2.85 | |
| 402 | 2.71 | 0.50 | 2489.40 | 4960.30 | 5500.70 | 2.03 | 3.00 | |
| 403 | 2.98 | 0.25 | 1772.67 | 3162.34 | 3530.81 | 1.91 | 3.00 | |
| Mean | 3.09 | 0.33 | 2232.33 | 3528.43 | 3933.25 | 1.84 | 2.95 | 31.20 |
| SD | 0.44 | 0.14 | 399.01 | 1288.44 | 1409.98 | 0.24 | 0.09 | |

$$^*F = \frac{AUC_{(0-t)(PO)} \times Dose_{(IV)}}{AUC_{(0-t)(IV)} \times Dose_{(PO)}} \times 100\%$$

TABLE 13

Some pharmacokinetic parameters of ICR mice after intravenous and oral administration of S-69

IV-2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
|---|---|---|---|---|---|---|---|---|---|
| 301 | 2.83 | 0.08 | 6038.43 | 52203.96 | 52314.11 | 4.30 | 4.35 | 0.16 | 0.64 |
| 302 | 2.88 | 0.50 | 5977.53 | 53093.43 | 53217.23 | 4.38 | 4.44 | 0.16 | 0.63 |
| 303 | 4.02 | 0.08 | 5141.60 | 50006.21 | 50659.35 | 4.62 | 4.95 | 0.23 | 0.66 |
| Mean | 3.24 | 0.222 | 5719.19 | 51767.87 | 52061.56 | 4.43 | 4.58 | 0.18 | 0.64 |
| SD | 0.67 | 0.241 | 501.13 | 1589.14 | 1297.22 | 0.17 | 0.32 | 0.04 | 0.02 |

TABLE 13-continued

| | PO-5 mg/kg | | | | | | | |
|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
| 401 | 2.24 | 2.00 | 7627.20 | 69211.96 | 69264.13 | 4.92 | 4.94 | |
| 402 | 2.28 | 2.00 | 10867.97 | 106563.84 | 106654.00 | 5.03 | 5.04 | |
| 403 | 2.03 | 2.00 | 11828.43 | 85266.27 | 85298.58 | 4.46 | 4.47 | |
| Mean | 2.18 | 2.00 | 10107.87 | 87014.02 | 87072.23 | 4.80 | 4.82 | 67.23 |
| SD | 0.13 | 0.00 | 2201.34 | 18737.18 | 18757.93 | 0.30 | 0.31 | |

TABLE 14

Some pharmacokinetic parameters of ICR mice after intravenous and oral administration of S-72

| | IV-2 mg/kg | | | | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
| 301 | 2.16 | 1.00 | 3686.88 | 14847.37 | 17305.95 | 1.96 | 2.98 | 0.36 | 1.93 |
| 302 | 1.39 | 0.08 | 4634.53 | 11456.75 | 11918.88 | 1.53 | 1.78 | 0.34 | 2.80 |
| 303 | 1.23 | 0.08 | 4839.23 | 11802.83 | 12174.58 | 1.52 | 1.71 | 0.29 | 2.74 |
| Mean | 1.59 | 0.389 | 4386.88 | 12702.32 | 13799.80 | 1.67 | 2.16 | 0.33 | 2.49 |
| SD | 0.50 | 0.529 | 614.80 | 1865.71 | 3039.10 | 0.25 | 0.71 | 0.03 | 0.49 |

| | PO-5 mg/kg | | | | | | | |
|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
| 401 | 2.54 | 0.50 | 7867.58 | 51286.19 | 51351.03 | 3.95 | 3.98 | |
| 402 | 1.13 | 0.50 | 7160.86 | 23996.12 | 24161.28 | 2.18 | 2.23 | |
| 403 | 1.47 | 1.00 | 6289.71 | 26941.23 | 27586.31 | 2.66 | 2.84 | |
| Mean | 1.72 | 0.67 | 7106.05 | 34074.52 | 34366.20 | 2.93 | 3.01 | 107.30 |
| SD | 0.73 | 0.29 | 790.36 | 14978.31 | 14808.64 | 0.91 | 0.89 | |

TABLE 15

Some pharmacokinetic parameters of ICR mice after intravenous and oral administration of S-96

| | IV-2 mg/kg | | | | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
| 301 | 3.36 | 0.08 | 3438.41 | 6719.85 | 6815.93 | 2.62 | 2.99 | 1.42 | 4.89 |
| 302 | 0.93 | 0.08 | 2982.34 | 3109.78 | 3157.25 | 0.90 | 1.00 | 0.85 | 10.56 |
| 303 | 1.07 | 0.08 | 3353.43 | 3206.41 | 3250.65 | 0.90 | 0.99 | 0.95 | 10.25 |
| Mean | 1.79 | 0.083 | 3258.06 | 4345.35 | 4407.95 | 1.47 | 1.66 | 1.07 | 8.57 |
| SD | 1.37 | 0.000 | 242.53 | 2056.95 | 2085.90 | 1.00 | 1.16 | 0.31 | 3.19 |

| | PO-5 mg/kg | | | | | | | |
|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
| 401 | 1.69 | 0.25 | 3921.65 | 6327.28 | 6705.00 | 1.66 | 2.15 | |
| 402 | 2.06 | 0.50 | 2400.19 | 6993.90 | 7471.54 | 2.42 | 2.97 | |
| 403 | 2.58 | 0.50 | 5236.64 | 13010.63 | 15115.19 | 2.30 | 3.61 | |
| Mean | 2.11 | 0.42 | 3852.83 | 8777.27 | 9763.91 | 2.13 | 2.91 | 80.80 |
| SD | 0.44 | 0.14 | 1419.48 | 3681.32 | 4650.17 | 0.41 | 0.73 | |

TABLE 16

Some pharmacokinetic parameters of ICR mice after intravenous and oral administration of S-98

| | | | | IV-2 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
| 301 | 1.93 | 0.08 | 3405.07 | 11177.15 | 12596.27 | 1.82 | 2.60 | 0.44 | 2.65 |
| 302 | 1.43 | 0.08 | 3672.74 | 10025.81 | 10533.19 | 1.55 | 1.86 | 0.39 | 3.16 |
| 303 | 1.17 | 0.08 | 3789.06 | 8869.53 | 9108.92 | 1.43 | 1.60 | 0.37 | 3.66 |
| Mean | 1.51 | 0.083 | 3622.29 | 10024.16 | 10746.13 | 1.60 | 2.02 | 0.40 | 3.16 |
| SD | 0.39 | 0.000 | 196.90 | 1153.81 | 1753.40 | 0.20 | 0.52 | 0.04 | 0.51 |

| | | | | PO-5 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | | F* % |
| 401 | 2.31 | 4.00 | 3835.13 | 37288.31 | 37324.50 | 5.36 | 5.38 | | |
| 402 | 2.12 | 2.00 | 3420.72 | 18064.52 | 19691.36 | 3.17 | 3.82 | | |
| 403 | 2.30 | 2.00 | 2943.86 | 23330.62 | 23352.18 | 4.72 | 4.74 | | |
| Mean | 2.24 | 2.67 | 3399.90 | 26227.82 | 26789.35 | 4.41 | 4.65 | | 104.66 |
| SD | 0.11 | 1.15 | 446.00 | 9933.98 | 9305.51 | 1.12 | 0.78 | | |

TABLE 17

Some pharmacokinetic parameters of ICR mice after intravenous and oral administration of S-103

| | | | | IV-2 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
| 301 | 4.11 | 1.00 | 1333.49 | 5508.40 | 8771.81 | 2.33 | 5.91 | 1.35 | 3.80 |
| 302 | 2.89 | 1.00 | 1332.61 | 10460.62 | 10483.52 | 4.16 | 4.21 | 0.79 | 3.18 |
| 303 | 2.71 | 1.00 | 1045.99 | 4009.87 | 5119.53 | 2.05 | 3.75 | 1.53 | 6.51 |
| Mean | 3.24 | 1.000 | 1237.36 | 6659.63 | 8124.95 | 2.85 | 4.62 | 1.22 | 4.50 |
| SD | 0.77 | 0.000 | 165.73 | 3375.95 | 2739.88 | 1.15 | 1.13 | 0.38 | 1.77 |

| | | | | PO-5 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | | F* % |
| 401 | 1.84 | 2.00 | 2382.42 | 10967.55 | 11688.42 | 3.08 | 3.54 | | |
| 402 | 1.72 | 4.00 | 2344.01 | 13078.28 | 14231.55 | 3.36 | 3.93 | | |
| 403 | 2.23 | 4.00 | 3008.06 | 19872.62 | 19888.79 | 4.45 | 4.47 | | |
| Mean | 1.93 | 3.33 | 2578.16 | 14639.49 | 15269.59 | 3.63 | 3.98 | | 87.93 |
| SD | 0.27 | 1.15 | 372.80 | 4653.29 | 4197.58 | 0.73 | 0.46 | | |

TABLE 18

Some pharmacokinetic parameters of ICR mice after intravenous and oral administration of S-115

| | | | | IV-2 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
| 301 | 0.90 | 0.08 | 4136.98 | 2987.42 | 3011.30 | 0.82 | 0.87 | 0.87 | 11.07 |
| 302 | 0.90 | 0.08 | 2997.99 | 2575.46 | 2591.81 | 0.90 | 0.94 | 1.00 | 12.86 |
| 303 | 0.80 | 0.08 | 2549.96 | 2278.66 | 2289.66 | 0.79 | 0.82 | 1.01 | 14.56 |
| Mean | 0.87 | 0.083 | 3228.31 | 2613.85 | 2630.92 | 0.84 | 0.88 | 0.96 | 12.83 |
| SD | 0.06 | 0.000 | 818.20 | 355.93 | 362.40 | 0.05 | 0.06 | 0.08 | 1.74 |

TABLE 18-continued

PO-5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 1.07 | 0.50 | 2135.46 | 3655.37 | 3672.50 | 1.37 | 1.41 | |
| 402 | 1.19 | 1.00 | 834.66 | 2355.30 | 2377.88 | 2.13 | 2.20 | |
| 403 | 1.12 | 4.00 | 601.29 | 2985.59 | 3066.25 | 3.22 | 3.39 | |
| Mean | 1.12 | 1.83 | 1190.47 | 2998.75 | 3038.87 | 2.24 | 2.33 | 45.89 |
| SD | 0.06 | 1.89 | 826.66 | 650.14 | 647.74 | 0.93 | 1.00 | |

TABLE 19

Some pharmacokinetic parameters of ICR mice after intravenous and oral administration of S-121

IV-2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
|---|---|---|---|---|---|---|---|---|---|
| 301 | 5.50 | 0.08 | 3887.60 | 24572.30 | 25488.79 | 5.26 | 6.22 | 0.62 | 1.31 |
| 302 | 5.25 | 0.08 | 3346.18 | 28379.48 | 29352.82 | 5.15 | 6.03 | 0.52 | 1.14 |
| 303 | 5.09 | 0.08 | 3576.94 | 26953.62 | 27749.72 | 5.04 | 5.79 | 0.53 | 1.20 |
| Mean | 5.28 | 0.083 | 3603.57 | 26635.14 | 27530.44 | 5.15 | 6.01 | 0.56 | 1.21 |
| SD | 0.21 | 0.000 | 271.69 | 1923.47 | 1941.33 | 0.11 | 0.21 | 0.06 | 0.09 |

PO-5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 3.09 | 2.00 | 4920.31 | 40051.63 | 40259.72 | 4.96 | 5.08 | |
| 402 | 3.34 | 4.00 | 4835.52 | 43063.09 | 43407.01 | 5.27 | 5.45 | |
| 403 | 3.14 | 4.00 | 4714.57 | 40782.54 | 41032.91 | 5.40 | 5.54 | |
| Mean | 3.19 | 3.33 | 4823.47 | 41299.09 | 41566.55 | 5.21 | 5.36 | 62.02 |
| SD | 0.13 | 1.15 | 103.40 | 1570.77 | 1640.10 | 0.23 | 0.24 | |

TABLE 20

Some pharmacokinetic parameters of ICR mice after intravenous and oral administration of S-131

IV-2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
|---|---|---|---|---|---|---|---|---|---|
| 301 | 0.90 | 0.08 | 1997.01 | 1776.79 | 1788.59 | 0.94 | 0.98 | 1.45 | 18.64 |
| 302 | 0.76 | 0.08 | 1776.22 | 1261.09 | 1264.23 | 0.71 | 0.73 | 1.73 | 26.37 |
| 303 | 0.98 | 0.08 | 2021.33 | 1579.23 | 1594.10 | 0.90 | 0.96 | 1.78 | 20.91 |
| Mean | 0.88 | 0.083 | 1931.52 | 1539.04 | 1548.98 | 0.85 | 0.89 | 1.65 | 21.97 |
| SD | 0.11 | 0.000 | 135.04 | 260.19 | 265.08 | 0.12 | 0.14 | 0.18 | 3.97 |

PO-5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 1.03 | 1.00 | 1438.00 | 3743.48 | 3765.68 | 1.90 | 1.95 | |
| 402 | 1.28 | 1.00 | 1853.01 | 5902.77 | 6003.28 | 2.27 | 2.40 | |
| 403 | 1.47 | 1.00 | 1794.96 | 6839.45 | 7052.50 | 2.45 | 2.68 | |
| Mean | 1.26 | 1.00 | 1695.32 | 5495.23 | 5607.15 | 2.21 | 2.34 | 142.82 |
| SD | 0.22 | 0.00 | 224.73 | 1587.71 | 1678.83 | 0.28 | 0.37 | |

TABLE 21

Some pharmacokinetic parameters of ICR mice
after intravenous and oral administration of S-133

| | | | | IV-2 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
| 301 | 1.22 | 0.08 | 2055.95 | 2904.29 | 3022.24 | 1.20 | 1.45 | 1.16 | 11.03 |
| 302 | 1.07 | 0.08 | 2980.85 | 4602.71 | 4699.55 | 1.18 | 1.31 | 0.66 | 7.09 |
| 303 | 1.13 | 0.08 | 2521.09 | 3187.22 | 3247.82 | 1.05 | 1.17 | 1.01 | 10.26 |
| Mean | 1.14 | 0.083 | 2519.30 | 3564.74 | 3656.54 | 1.14 | 1.31 | 0.94 | 9.46 |
| SD | 0.08 | 0.000 | 462.45 | 909.97 | 910.29 | 0.08 | 0.14 | 0.26 | 2.09 |

| | | | | PO-5 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | | F* % |
| 401 | 1.15 | 1.00 | 1569.92 | 6074.68 | 6148.80 | 2.34 | 2.43 | | |
| 402 | 1.05 | 1.00 | 1489.30 | 4282.62 | 4314.80 | 2.17 | 2.22 | | |
| 403 | 1.04 | 1.00 | 2195.02 | 5953.82 | 5994.87 | 2.05 | 2.10 | | |
| Mean | 1.08 | 1.00 | 1751.41 | 5437.04 | 5486.16 | 2.19 | 2.25 | | 61.01 |
| SD | 0.06 | 0.00 | 386.28 | 1001.58 | 1017.34 | 0.15 | 0.17 | | |

TABLE 22

Some pharmacokinetic parameters of ICR mice
after intravenous and oral administration of S-134

| | | | | IV-2 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
| 301 | 1.47 | 0.08 | 3408.57 | 6534.27 | 6880.52 | 1.50 | 1.83 | 0.61 | 4.84 |
| 302 | 0.93 | 0.08 | 3518.10 | 5015.80 | 5060.18 | 1.17 | 1.23 | 0.53 | 6.59 |
| 303 | 1.07 | 0.25 | 4224.01 | 7289.25 | 7419.12 | 1.28 | 1.39 | 0.42 | 4.49 |
| Mean | 1.15 | 0.14 | 3716.89 | 6279.77 | 6453.27 | 1.32 | 1.48 | 0.52 | 5.31 |
| SD | 0.28 | 0.10 | 442.58 | 1159.90 | 1236.14 | 0.17 | 0.31 | 0.10 | 1.12 |

| | | | | PO-5 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | | F* % |
| 401 | 1.38 | 0.50 | 3905.15 | 9716.82 | 9926.06 | 2.04 | 2.21 | | |
| 402 | 1.54 | 0.25 | 3059.53 | 7889.97 | 8123.13 | 2.04 | 2.28 | | |
| 403 | 1.43 | 0.50 | 1591.65 | 4859.23 | 4978.41 | 2.21 | 2.40 | | |
| Mean | 1.45 | 0.42 | 2852.11 | 7488.67 | 7675.87 | 2.10 | 2.29 | | 47.70 |
| SD | 0.08 | 0.14 | 1170.61 | 2453.53 | 2503.96 | 0.10 | 0.10 | | |

TABLE 23

Some pharmacokinetic parameters of ICR mice
after intravenous and oral administration of S-135

| | | | | IV-2 mg/kg | | | | | |
|---|---|---|---|---|---|---|---|---|---|
| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
| 301 | 2.03 | 0.08 | 3314.60 | 6495.01 | 7378.29 | 1.70 | 2.57 | 0.80 | 4.52 |
| 302 | 1.65 | 0.08 | 3896.05 | 7270.82 | 7835.48 | 1.60 | 2.09 | 0.61 | 4.25 |
| 303 | 1.78 | 0.08 | 3518.53 | 7341.09 | 7977.92 | 1.66 | 2.21 | 0.64 | 4.18 |
| Mean | 1.82 | 0.083 | 3576.39 | 7035.64 | 7730.56 | 1.65 | 2.29 | 0.68 | 4.32 |
| SD | 0.19 | 0.000 | 295.01 | 469.51 | 313.28 | 0.05 | 0.25 | 0.10 | 0.18 |

TABLE 23-continued

PO-5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 1.87 | 1.00 | 2159.84 | 9385.38 | 9974.62 | 2.64 | 3.12 | |
| 402 | 1.27 | 1.00 | 2014.04 | 7012.03 | 7126.47 | 2.19 | 2.32 | |
| 403 | 1.34 | 1.00 | 2249.28 | 9412.84 | 9616.11 | 2.43 | 2.59 | |
| Mean | 1.49 | 1.00 | 2141.05 | 8603.42 | 8905.73 | 2.42 | 2.67 | 48.91 |
| SD | 0.33 | 0.00 | 118.74 | 1378.25 | 1551.28 | 0.22 | 0.41 | |

TABLE 24

Some pharmacokinetic parameters of ICR mice after intravenous and oral administration of S-137

IV-2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
|---|---|---|---|---|---|---|---|---|---|
| 301 | 1.57 | 0.08 | 5653.28 | 10168.14 | 10938.18 | 1.50 | 1.97 | 0.41 | 3.05 |
| 302 | 1.68 | 0.08 | 5261.76 | 8963.80 | 9736.77 | 1.51 | 2.06 | 0.50 | 3.42 |
| 303 | 2.79 | 0.08 | 5945.51 | 15555.08 | 15581.80 | 2.84 | 2.88 | 0.52 | 2.14 |
| Mean | 2.01 | 0.083 | 5620.19 | 11562.34 | 12085.58 | 1.95 | 2.30 | 0.48 | 2.87 |
| SD | 0.67 | 0.000 | 343.08 | 3509.85 | 3086.83 | 0.77 | 0.50 | 0.05 | 0.66 |

PO-5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 1.85 | 0.50 | 5883.71 | 15390.44 | 16193.31 | 2.28 | 2.70 | |
| 402 | 1.98 | 0.50 | 5542.83 | 16097.34 | 17159.38 | 2.31 | 2.84 | |
| 403 | 1.69 | 0.50 | 6791.01 | 14779.57 | 15367.65 | 2.03 | 2.35 | |
| Mean | 1.84 | 0.50 | 6072.52 | 15422.45 | 16240.12 | 2.21 | 2.63 | 53.35 |
| SD | 0.15 | 0.00 | 645.15 | 659.47 | 896.78 | 0.16 | 0.25 | |

TABLE 25

Some pharmacokinetic parameters of ICR mice after intravenous and oral administration of S-138

IV-2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
|---|---|---|---|---|---|---|---|---|---|
| 301 | 3.81 | 0.08 | 1828.27 | 6387.52 | 6445.45 | 4.19 | 4.42 | 1.70 | 5.17 |
| 302 | 4.03 | 0.08 | 2169.08 | 6061.48 | 6126.90 | 4.04 | 4.32 | 1.90 | 5.44 |
| 303 | 4.29 | 0.08 | 2002.99 | 3427.99 | 5237.36 | 2.03 | 5.54 | 2.37 | 6.36 |
| Mean | 4.04 | 0.083 | 2000.11 | 5292.33 | 5936.57 | 3.42 | 4.76 | 1.99 | 5.66 |
| SD | 0.24 | 0.000 | 170.42 | 1622.77 | 626.13 | 1.21 | 0.68 | 0.34 | 0.63 |

PO-5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 2.69 | 4.00 | 1239.88 | 7428.81 | 9151.03 | 3.56 | 5.12 | |
| 402 | 2.74 | 2.00 | 1475.55 | 7494.57 | 8818.35 | 3.19 | 4.51 | |
| 403 | 2.74 | 1.00 | 1466.48 | 8147.05 | 9514.89 | 3.27 | 4.52 | |
| Mean | 2.72 | 2.33 | 1393.97 | 7690.15 | 9161.42 | 3.34 | 4.72 | 58.12 |
| SD | 0.02 | 1.53 | 133.53 | 397.06 | 348.38 | 0.19 | 0.35 | |

TABLE 26

Some pharmacokinetic parameters of ICR mice after intravenous and oral administration of S-140

IV-2 mg/kg

| Animal number | $t_{1/2}$ h | $T_{max}$ h | $C_{max}$ ng/mL | $AUC_{(0-t)}$ h*ng/mL | $AUC_{(0-t)}$ h*ng/mL | $MRT_{(0-t)}$ h | $MRT_{(0-t)}$ h | Vz L/kg | CL mL/min/kg |
|---|---|---|---|---|---|---|---|---|---|
| 301 | 2.67 | 0.08 | 5215.16 | 11628.12 | 14758.73 | 1.94 | 3.62 | 0.52 | 2.26 |
| 302 | 1.70 | 0.08 | 4542.99 | 9144.58 | 9903.12 | 1.58 | 2.11 | 0.50 | 3.37 |
| 303 | 4.19 | 0.08 | 6627.89 | 19456.40 | 19918.23 | 3.73 | 4.34 | 0.61 | 1.67 |
| Mean | 2.86 | 0.083 | 5462.01 | 13409.70 | 14860.03 | 2.42 | 3.36 | 0.54 | 2.43 |
| SD | 1.25 | 0.000 | 1064.14 | 5381.82 | 5008.33 | 1.15 | 1.14 | 0.06 | 0.86 |

PO-5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 2.19 | 2.00 | 4254.74 | 22556.48 | 24737.64 | 2.97 | 3.69 | |
| 402 | 1.54 | 2.00 | 5947.01 | 26053.96 | 26994.24 | 2.67 | 2.93 | |
| 403 | 2.38 | 1.00 | 4972.85 | 23914.34 | 26699.24 | 2.97 | 3.85 | |
| Mean | 2.04 | 1.67 | 5058.20 | 24174.92 | 26143.71 | 2.87 | 3.49 | 72.11 |
| SD | 0.44 | 0.58 | 849.36 | 1763.24 | 1226.59 | 0.18 | 0.49 | |

TABLE 27

Some pharmacokinetic parameters of ICR mice after intravenous and oral administration of S-159

IV-2 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | Vz L/kg | CL mL/min/kg |
|---|---|---|---|---|---|---|---|---|---|
| 301 | 1.86 | 0.08 | 2457.53 | 4501.92 | 4960.27 | 1.52 | 2.19 | 1.08 | 13.44 |
| 302 | 1.22 | 0.08 | 2540.90 | 3595.54 | 3718.50 | 1.23 | 1.45 | 0.95 | 17.93 |
| 303 | 1.75 | 0.08 | 2591.90 | 4456.51 | 4834.16 | 1.45 | 2.00 | 1.05 | 13.79 |
| Mean | 1.61 | 0.083 | 2530.11 | 4184.66 | 4504.31 | 1.40 | 1.88 | 1.02 | 15.05 |
| SD | 0.34 | 0.000 | 67.83 | 510.70 | 683.45 | 0.15 | 0.38 | 0.07 | 2.50 |

PO-5 mg/kg

| Animal number | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(0-\infty)}$ h | F* % |
|---|---|---|---|---|---|---|---|---|
| 401 | 1.03 | 1.00 | 1438.00 | 3743.48 | 3765.68 | 1.90 | 1.95 | |
| 402 | 1.28 | 1.00 | 1853.01 | 5902.77 | 6003.28 | 2.27 | 2.40 | |
| 403 | 1.47 | 1.00 | 1794.96 | 6839.45 | 7052.50 | 2.45 | 2.68 | |
| Mean | 1.26 | 1.00 | 1695.32 | 5495.23 | 5607.15 | 2.21 | 2.34 | 52.53 |
| SD | 0.22 | 0.00 | 224.73 | 1587.71 | 1678.83 | 0.28 | 0.37 | |

Experimental results: the experimental results in tables 3 to 27 above show that: after oral intragastric administration at a dose of 5 mg/kg, the bioavailability of HDM201 is 78.76%, and the $AUC_{0-t}$ is 1126.24 h*ng/ml; after oral intragastric administration at a dose of 5 mg/kg, the representative compound S-1 of the present invention has an $AUC_{0-t}$ of 1336.16 h*ng/mL, and a half-life of 1.64 hr, which are better than the corresponding parameters of HDM201; the compound S-2 has a bioavailability of 101.81%, an $AUC_{0-t}$ of 3728.38 h*ng/mL, and a half-life of 1.59 hr, which are better than the corresponding parameters of HDM201; the compound S-9 has an $AUC_{0-t}$ of 7329.34 h*ng/mL, which is better than the corresponding parameter of HDM201; the compound S-11 has a bioavailability of 102.51%, an $AUC_{0-t}$ of 9374.58 h*ng/mL, and a half-life of 1.69 hr, which are better than the corresponding parameters of HDM201; the compound S-23 has an $AUC_{0-t}$ of 8011.09 h*ng/mL, which is better than the corresponding parameter of HDM201; the compound S-32 has an $AUC_{0-t}$ of 8393.45 h*ng/mL, and a half-life of 2.16 hr, which are better than the corresponding parameters of HDM201; the compound S-44 has a bioavailability of 94.43%, an $AUC_{0-t}$ of 6451.26 h*ng/mL, and a half-life of 2.00 hr, which are better than the corresponding parameters of HDM201; the compound S-45 has a bioavailability of 107.31%, an $AUC_{0-t}$ of 5124.78 h*ng/mL, and a half-life of 1.86 hr, which are better than the corresponding parameters of HDM201; the compound S-61 has an $AUC_{0-t}$ of 3528.43 h*ng/mL, and a half-life of 3.09 hr, which are better than the corresponding parameters of HDM201; the compound S-69 has an $AUC_{0-t}$ of 87014.02 h*ng/mL, and a half-life of 2.18 hr, which are better than the corresponding parameters of HDM201; the compound S-72 has a bioavailability of 107.30%, an $AUC_{0-t}$ of 34074.52 h*ng/mL, and a half-life of 1.72 hr, which are better than the corresponding parameters of HDM201; the compound S-96 has an $AUC_{0-t}$ of 8777.27 h*ng/mL, and a half-life of 2.11 hr, which are better than the corresponding parameters of HDM201; the compound S-98 has a bioavailability of 104.66%, an $AUC_{0-t}$ of 26227.82 h*ng/mL, and a half-life of 2.24 hr, which are better than the corresponding parameters of HDM201; the compound S-103 has an $AUC_{0-t}$ of 14639.49 h*ng/mL, and a half-life of 1.93 hr, which is better than the corresponding parameters of HDM201; the compound S-115 has an $AUC_{0-t}$ of 2998.75 h*ng/mL, which is better than the corresponding parameter of HDM201; the compound S-121 has an $AUC_{0-t}$ of 41299.09 h*ng/mL, and a half-life of 3.19 hr, which are better than the corresponding parameters of HDM201; the compound S-131 has an $AUC_{0-t}$ of 5495.23 h*ng/mL, and a half-life of 1.26 hr, which are significantly better than the corresponding parameters of HDM201; the compound S-133 has an $AUC_{0-t}$ of 5437.04 h*ng/mL, which is better than the corresponding parameter of HDM201; the compound S-134 has an $AUC_{0-t}$ of 7488.67 h*ng/mL, and a half-life of 1.45 hr, which are better than the corresponding parameters of HDM201; the compound S-135 has an $AUC_{0-t}$ of 8603.42 h*ng/mL, which is better than the corresponding parameter of HDM201; the compound S-137 has an $AUC_{0-t}$ of 15422.45 h*ng/mL, and a half-life of 1.84 hr, which are better than the corresponding parameters of HDM201; the compound S-138 has an $AUC_{0-t}$ of 7690.15 h*ng/mL, and a half-life of 2.72 hr, which are better than the corresponding parameters of HDM201; the compound S-140 has an $AUC_{0-t}$ of 24174.92 h*ng/mL, and a half-life of 2.04 hr, which are better than the corresponding parameters of HDM201; and the compound S-159 has an $AUC_{0-t}$ of 5495.23 h*ng/mL, which is better than the corresponding parameter of HDM201.

The above contents show and describe the basic principles, main features and advantages of the present invention. A person skilled in the art should understand that the present invention is not limited by the above-mentioned Examples. The above-mentioned Examples and the description only describe the principles of the present invention. It is obvious to a person skilled in the art that there will be various variations and improvements in the present invention, without departing from the spirit and scope of the present invention, and these variations and improvements fall within the claimed protection scope of the present invention. The claimed protection scope of the present invention is defined by the appended claims and their equivalents.

What is claimed is:

1. A compound of structural formula I:

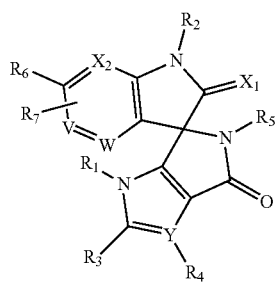

(I)

wherein, $R_1$ is linear or branched $C_1$-$C_5$ alkyl, $C_3$-$C_5$ cycloalkyl or

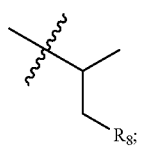

$R_2$ is H or ($C_1$-$C_6$ alkyl), wherein the alkyl is optionally substituted with 0 to 3 substituents independently selected from alkoxy having 1 to 4 carbon atoms, hydroxyl, sulfhydryl, halogen, —C(O)OH, —C(O)O—($C_1$-$C_4$)alkyl, —C(O)$NR_9R_{10}$, —$NR_9R_{10}$ and methanesulfonyl;

$R_3$ is a 5- or 6-membered aromatic ring or aromatic heterocycle comprising 1 or 2 heteroatoms independently selected from N, S, and O, which is unsubstituted or substituted by 1 to 3 substituents independently selected from H, ($C_1$-$C_6$)alkyl, ($C_3$-$C_6$)cycloalkyl, —O—($C_1$-$C_6$)alkyl, —O—($C_3$-$C_6$)cycloalkyl, —S—($C_1$-$C_6$)alkyl, halogen, haloalkyl, haloalkoxy, hydroxyalkoxy, —CN, —C(O)$NR_9R_{10}$, —C(O)-morpholin-4-yl, hydroxy-azetidin-1-yl-carbonyl, —$CH_2NR_9R_{10}$, —$CH_2NR_9$—C(O)$R_{10}$, methyl-imidazolyl-, —$CH_2$C(O)$NR_9R_{10}$, —$CH_2$C(O)OH, —C(O)OH, —$CH_2$C(O)O—($C_1$-$C_4$)alkyl, —N($R_9$)—C(O)—($C_1$-$C_4$)alkyl, —$NR_9R_{10}$, —C(O)O—($C_1$-$C_4$)alkyl, —$CH_2$CN, tetrahydropyrrol-1-yl, azetidin-1-yl and azetidin-1-yl substituted with one or more —OH, or with —$CH_3$ and —OH; wherein the alkyl or cycloalkyl is optionally substituted with 0 to 3 substituents independently selected from alkoxy having 1 to 4 carbon atoms, hydroxyl, sulfhydryl, halogen, —C(O)OH, —C(O)O—($C_1$-$C_4$)alkyl, —C(O)$NR_9R_{10}$, —$NR_9R_{10}$ and methanesulfonyl; or $R_3$ is selected from:

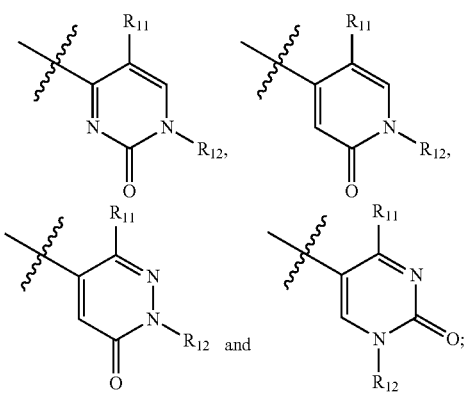

$R_5$ is a 5- or 6-membered aromatic ring or aromatic heterocycle comprising 1 or 2 heteroatoms independently selected from N, S, and O, which is unsubstituted or substituted with 1 to 3 substituents independently selected from H, ($C_1$-$C_6$)alkyl, ($C_3$-$C_6$)cycloalkyl, —O—($C_1$-$C_6$)alkyl, —O—($C_3$-$C_6$)cycloalkyl, —S—($C_1$-$C_6$)alkyl, halogen, haloalkyl, haloalkoxy, hydroxyalkoxy, —CN, —C(O)$NR_9R_{10}$, —C(O)-morpholin-4-yl, hydroxy-azetidin-1-yl-carbonyl, —$CH_2NR_9R_{10}$, —$CH_2NR_9$—C(O)$R_{10}$, methyl-imidazolyl-, —$CH_2$C(O)$NR_9R_{10}$, —$CH_2$C(O)OH, —C(O)OH, —$CH_2$C(O)O—($C_1$-$C_4$)alkyl, —N($R_9$)—C(O)—($C_1$-$C_4$)alkyl, —$NR_9R_{10}$, —C(O)O$CH_3$, —$CH_2$CN, tetrahydropyrrol-1-yl, azetidin-1-yl, and azetidin-1-yl substituted with one or more —OH, or with —$CH_3$ and —OH; wherein the alkyl or cycloalkyl is optionally substituted with 0 to 3 substituents independently selected from alkoxy having 1 to 4 carbon atoms, hydroxyl, sulfhydryl, halogen, —C(O)OH, —C(O)O—($C_1$-$C_4$)alkyl, —C(O)$NR_9R_{10}$, —$NR_9R_{10}$ and methanesulfonyl; or $R_5$ is selected from:

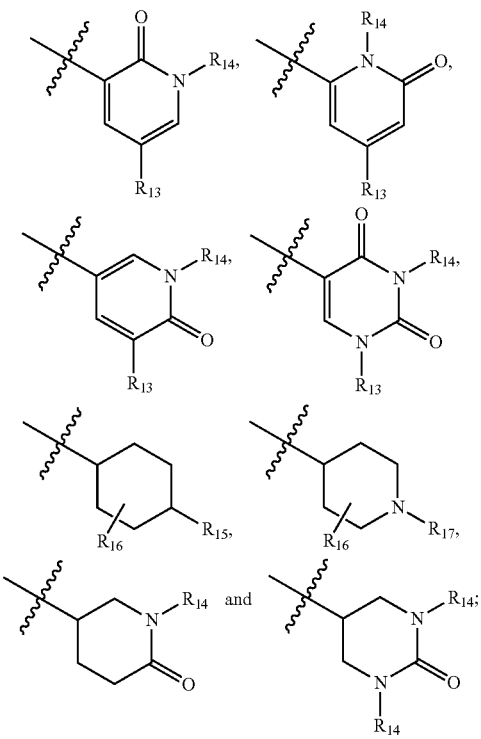

$R_6$ is selected from halogen, halomethyl, methyl and cyano;

$R_7$ is selected from H, $(C_1-C_6)$ alkyl and halogen; wherein the alkyl is optionally substituted with 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)$NR_9R_{10}$, —$NR_9R_{10}$ and methanesulfonyl;

wherein:

$R_8$ is selected from —OH, —$OCH_3$, —$NH_2$, —NHMe, —$NMe_2$, —NHCOMe, —NHCOH and methanesulfonyl;

$R_9$ is H or alkyl having 1 to 4 carbon atoms;

$R_{10}$ is H or $(C_1-C_6)$ alkyl, wherein the alkyl is optionally substituted with 0 to 3 substituents independently selected from alkoxy having 1 to 4 carbon atoms, hydroxyl, sulfhydryl, halogen, —C(O)OH, —C(O)O—$(C_1-C_4)$alkyl and methanesulfonyl;

wherein $R_{11}$ is selected from —$OCH_3$, —$CH_2CH_3$, —OH, halomethoxy and H;

$R_{12}$ is H or $(C_1-C_6)$ alkyl, wherein the alkyl is optionally substituted with 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)$NR_9R_{10}$, —$NR_9R_{10}$ and methanesulfonyl;

$R_{13}$ is halogen or alkyl having 1 to 4 carbon atoms;

$R_{14}$ is H or $(C_1-C_6)$ alkyl, wherein the alkyl is optionally substituted with 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)$NR_9R_{10}$, —$NR_9R_{10}$ and methanesulfonyl;

$R_{15}$ is selected from $NH_2$, —C(O)OH, —NH(C(O)—$CH_3$) and —C(O)—NH($CH_3$);

$R_{16}$ is selected from H, $(C_1-C_6)$ alkyl and halogen; wherein the alkyl is optionally substituted by 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)$NR_9R_{10}$, —$NR_9R_{10}$ and methanesulfonyl; and $R_{17}$ is selected from —C(O)—$NR_9(R_{10})$, $(C_1-C_6)$alkyl, —C(O)($C_1-C_6$)alkyl, and —C(O)O($C_1-C_6$)alkyl; wherein the alkyl is optionally substituted with 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)$NR_9R_{10}$, —$NR_9R_{10}$ and methanesulfonyl; and $X_1$ is oxygen or sulfur; Y, $X_2$, V and W are each independently carbon or nitrogen;

wherein when Y is carbon, $R_4$ is selected from H, hydroxyl, —O—$(C_1-C_6)$alkyl, —CN, halogen, $(C_1-C_6)$ alkyl, —C(O)OH, —$CH_2$C(O)OH, —$CH_2$C(O)$NR_9R_{10}$, and —C(O)O—$(C_1-C_6)$alkyl, wherein the alkyl is optionally substituted with 0 to 3 substituents independently selected from alkoxy having 1 to 4 carbon atoms, hydroxyl, sulfhydryl, halogen, —C(O)OH, —C(O)O—$(C_1-C_4)$alkyl and methanesulfonyl; or a stereoisomer, an enantiomer, a diastereomer, a racemate, a mesomer, a cis/trans isomer, a tautomer, an isotopic variant of the compound of structural formula I, or any combination thereof; or a pharmaceutical salt thereof.

2. The compound according to claim 1, wherein $R_3$ is a 5- or 6-membered aromatic ring or aromatic heterocycle comprising 1 or 2 heteroatoms independently selected from N, S, and O, which is unsubstituted or substituted with 1 to 3 substituents independently selected from H, $(C_1-C_6)$alkyl, —O—$(C_1-C_6)$alkyl, —S—$(C_1-C_6)$alkyl, halogen, haloalkyl, haloalkoxy, —CN, —C(O)$NR_9R_{10}$, —C(O)-morpholin-4-yl, hydroxy-azetidin-1-yl-carbonyl, —$CH_2NR_9R_{10}$, —$CH_2NR_9$—C(O)$R_{10}$, methyl-imidazolyl-, —$CH_2$C(O)$NR_9R_{10}$, —$CH_2$C(O)OH, —C(O)OH, —$CH_2$C(O)O—$(C_1-C_4)$alkyl, —N($R_9$)—C(O)—$(C_1-C_4)$alkyl, —$NR_9R_{10}$, —C(O)O—$(C_1-C_4)$alkyl, —$CH_2$CN, azetidin-1-yl and azetidin-1-yl substituted with one or more —OH, or with —$CH_3$ and —OH; wherein the alkyl is optionally substituted with 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)$NR_9R_{10}$, —$NR_9R_{10}$ and methanesulfonyl; and $R_5$ is a 5- or 6-membered aromatic ring or aromatic heterocycle comprising 1 or 2 heteroatoms independently selected from N, S, and O, which is unsubstituted or substituted by 1 to 3 substituents independently selected from H, $(C_1-C_6)$alkyl, —O—$(C_1-C_6)$alkyl, —S—$(C_1-C_6)$alkyl, halogen, haloalkyl, haloalkoxy, —CN, —C(O)$NR_9R_{10}$, —C(O)-morpholin-4-yl, hydroxy-azetidin-1-yl-carbonyl, —$CH_2NR_9R_{10}$, —$CH_2NR_9$—C(O)$R_{10}$, —$CH_2$CN, methyl-imidazolyl-, —$CH_2$C(O)$NR_9R_{10}$, —$CH_2$C(O)OH, —C(O)OH, —$CH_2$C(O)O—$(C_1-C_4)$alkyl, —N($R_9$)—C(O)—$(C_1-C_4)$alkyl, —$NR_9R_{10}$, —C(O)$OCH_3$, azetidin-1-yl and azetidin-1-yl substituted with one or more —OH or with —$CH_3$ and —OH; wherein the alkyl is optionally substituted by 0 to 3 substituents independently selected from alkoxy having 1 to 4 carbon atoms, hydroxyl, sulfhydryl, halogen, —C(O)OH, —C(O)O—$(C_1-C_4)$alkyl, —C(O)$NR_9R_{10}$, —$NR_9R_{10}$ and methanesulfonyl.

3. The compound according to claim 2, wherein

R$_1$ is selected from methyl, ethyl, isopropyl, cyclopropyl, isobutyl, cyclobutyl, cyclopentyl, and

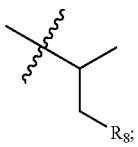

R$_2$ is H or (C$_1$-C$_6$ alkyl), wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl;

R$_3$ is a 5- or 6-membered aromatic ring or aromatic heterocycle comprising 1 or 2 heteroatoms independently selected from N, S, and O, which is unsubstituted or substituted with 1 to 3 substituents independently selected from H, (C$_1$-C$_6$)alkyl, —O—(C$_1$-C$_6$)alkyl, —S—(C$_1$-C$_6$)alkyl, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, —CN, —C(O)NR$_9$R$_{10}$, —C(O)-morpholin-4-yl, hydroxy-azetidin-1-yl-carbonyl, —CH$_2$NR$_9$R$_{10}$, —CH$_2$NR$_9$—C(O)R$_{10}$, methyl-imidazolyl-, —CH$_2$C(O)NR$_9$R$_{10}$, —CH$_2$C(O)OH, —C(O)OH, —CH$_2$C(O)O—(C$_1$-C$_4$)alkyl, —N(R$_9$)—C(O)—(C$_1$-C$_4$)alkyl, —NR$_9$R$_{10}$, —CH$_2$NR$_9$R$_{10}$, —C(O)O—(C$_1$-C$_4$)alkyl, —CH$_2$CN, azetidin-1-yl and azetidin-1-yl substituted with one or more —OH, or with —CH$_3$ and —OH; wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl; or R$_3$ is selected from:

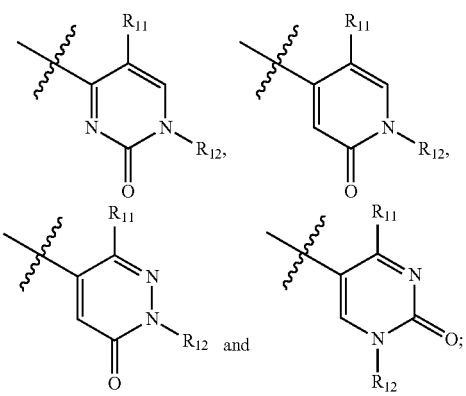

R$_5$ is a 5- or 6-membered aromatic ring or aromatic heterocycle comprising 1 or 2 heteroatoms independently selected from N, S, and O, which is unsubstituted or substituted by 1 to 3 substituents independently selected from H, (C$_1$-C$_6$)alkyl, —O—(C$_1$-C$_6$)alkyl, —S—(C$_1$-C$_6$)alkyl, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, —CN, —C(O)NR$_9$R$_{10}$, —C(O)-morpholin-4-yl, hydroxy-azetidin-1-yl-carbonyl, —CH$_2$NR$_9$R$_{10}$, —CH$_2$NR$_9$—C(O)R$_{10}$, —CH$_2$CN, methyl-imidazolyl-, —CH$_2$C(O)NR$_9$R$_{10}$, —CH$_2$C(O)OH, —C(O)OH, —CH$_2$C(O)O—(C$_1$-C$_4$) alkyl, —N(R$_9$)—C(O)—(C$_1$-C$_4$)alkyl, —NR$_9$R$_{10}$, —CH$_2$NR$_9$R$_{10}$, —C(O)OCH$_3$, —CH$_2$CN, azetidin-1-yl and azetidin-1-yl substituted with one or more —OH or with —CH$_3$ and —OH; wherein the alkyl is optionally substituted by 0 to 3 substituents independently selected from methoxy and ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl; or R$_5$ is selected from:

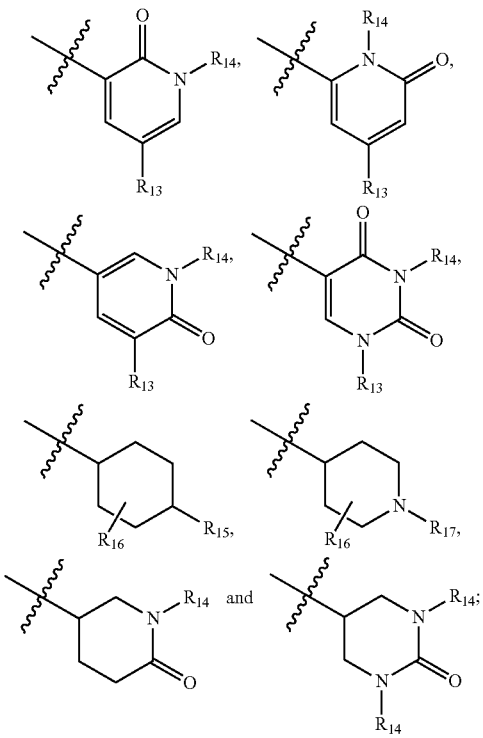

R$_6$ is selected from chlorine, fluorine, bromine, trifluoromethyl, difluoromethyl, monofluoromethyl, methyl and cyano;

R$_7$ is selected from H, (C$_1$-C$_6$) alkyl and halogen; wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl;

R$_8$ is selected from —OH, —OCH$_3$, —NH$_2$, —NHMe, —NMe$_2$, —NHCOMe, —NHCOH or methanesulfonyl;

R$_9$ is H, methyl or ethyl;

R$_{10}$ is H or (C$_1$-C$_6$) alkyl, wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl and methanesulfonyl;

R$_{11}$ is selected from —OCH$_3$, —CH$_2$CH$_3$, —OH, —OCF$_3$, —OCHF$_2$, —OCH$_2$F and H;

R$_{12}$ is H or (C$_1$-C$_6$) alkyl, wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl;

R$_{13}$ is selected from halogen, methyl and ethyl;

R$_{14}$ is H or (C$_1$-C$_6$) alkyl, wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O) NR$_9$R$_{10}$, —NR$_9$R$_{10}$ and methanesulfonyl;

R$_{16}$ is selected from H, (C$_1$-C$_6$) alkyl and halogen; wherein the alkyl is optionally substituted by 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl; and R$_{17}$ is selected from —C(O)—NR$_9$(R$_{10}$), (C$_1$-C$_6$)alkyl, —C(O)(C$_1$-C$_6$)alkyl, and —C(O)O(C$_1$-C$_6$)alkyl; wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl, and when present, R$_4$ is selected from H, hydroxyl, —O—(C$_1$-C$_6$)alkyl, —CN, halogen, (C$_1$-C$_6$)alkyl, —C(O)OH, —CH$_2$C(O)OH, —CH$_2$C(O)NR$_9$R$_{10}$, or —C(O)O—(C$_1$-C$_6$)alkyl, wherein the alkyl is optionally substituted by 0 to 3 substituents independently selected from methoxy, ethoxy, hydroxyl, sulfhydryl, halogen, —C(O)OH, —C(O)O—(C$_1$-C$_4$)alkyl or methanesulfonyl.

4. The compound according to claim 1, wherein R$_1$ is selected from methyl, ethyl, isopropyl, cyclopropyl, isobutyl, cyclobutyl, cyclopentyl,

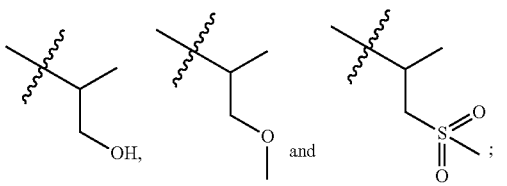

R$_2$ is H or methyl;

R$_3$ is a 6-membered aromatic ring or aromatic heterocycle comprising 1 or 2 heteroatoms independently selected from N, S, and O, substituted with 1 to 3 substituents independently selected from H, (C$_1$-C$_6$)alkyl, (C$_3$-C$_6$) cycloalkyl, —O—(C$_1$-C$_6$)alkyl, —S—(C$_1$-C$_6$)alkyl, —O—(C$_3$-C$_6$)cycloalkyl, halogen, —CF$_3$, —CHF$_2$, —OCHF$_2$, —OCH$_2$F, —OCH$_2$CF$_3$, —OCH$_2$CHF$_2$, —OCH$_2$CH$_2$F, hydroxyalkoxy, —CN, —C(O)NR$_9$R$_{10}$, —CH$_2$NR$_9$R$_{10}$, —CH$_2$NR$_9$—C(O)R$_{10}$, —CH$_2$CN, —CH$_2$C(O)NR$_9$R$_{10}$, —CH$_2$C(O)OH, —C(O)OH, —CH$_2$C(O)O—(C$_1$-C$_4$)alkyl, —N(R$_9$)—C(O)—(C$_1$-C$_4$)alkyl, —NR$_9$R$_{10}$, —CH$_2$NR$_9$R$_{10}$, —C(O)O—(C$_1$-C$_4$)alkyl, —CH$_2$CN and tetrahydropyrrol-1-yl, wherein the alkyl or cycloalkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O) NR$_9$R$_{10}$, —NR$_9$R$_{10}$ and methanesulfonyl;

R$_5$ is a 6-membered aromatic ring or aromatic heterocycle comprising 1 or 2 heteroatoms independently selected from N, S, and O, substituted with 1 to 3 substituents independently selected from H, (C$_1$-C$_6$)alkyl, (C$_3$-C$_6$) cycloalkyl, —O—(C$_1$-C$_6$)alkyl, —S—(C$_1$-C$_6$)alkyl, —O—(C$_3$-C$_6$)cycloalkyl, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, hydroxyalkoxy, —CN, —C(O)NR$_9$R$_{10}$, —CH$_2$NR$_9$R$_{10}$, —CH$_2$NR$_9$—C(O)R$_{10}$, —CH$_2$CN, —CH$_2$C(O)NR$_9$R$_{10}$, —CH$_2$C(O)OH, —C(O)OH, —CH$_2$C(O)O—(C$_1$-C$_4$)alkyl, —N(R$_9$)—C(O)—(C$_1$-C$_4$)alkyl, —NR$_9$R$_{10}$, —CH$_2$NR$_9$R$_{10}$, —C(O)OCH$_3$, —CH$_2$CN and tetrahydropyrrol-1-yl, wherein the alkyl or cycloalkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl;

R$_6$ is chlorine or cyano;

R$_7$ is hydrogen;

X$_1$ is oxygen;

X$_2$, V and W are each carbon; and

Y is nitrogen or carbon; wherein when Y is carbon, R$_4$ is selected from H, hydroxyl, —O—(C$_1$-C$_6$)alkyl, —C(O)OH, —CH$_2$C(O)OH, —CH$_2$C(O)NR$_9$R$_{10}$ and —C(O)O—(C$_1$-C$_6$)alkyl, wherein the alkyl is optionally substituted with 0 to 3 substituents independently selected from methoxy, ethoxy, hydroxyl, sulfhydryl, halogen, —C(O)OH, —C(O)O—(C$_1$-C$_4$) alkyl, —C(O)NR$_9$R$_{10}$, —NR$_9$R$_{10}$ and methanesulfonyl;

wherein R$_9$ is selected from H, methyl and ethyl; and

R$_{10}$ is H or (C$_1$-C$_6$)alkyl, wherein the alkyl is optionally substituted with 0 to 3 substituents independently selected from methoxy, ethoxy, hydroxyl, sulfhydryl, halogen, —C(O)OH, —C(O)O—(C$_1$-C$_4$) alkyl and methanesulfonyl.

5. The compound according to claim 4, wherein

R$_3$ is a 6-membered aromatic ring or aromatic heterocycle comprising 1 or 2 heteroatoms independently selected from N, S, and O, substituted with 1 to 3 substituents independently selected from H, (C$_1$-C$_6$)alkyl, —O—(C$_1$-C$_6$)alkyl, halogen, —CF$_3$, —CHF$_2$, —CH$_2$F, —OCF$_3$, —OCHF$_2$, —OCH$_2$F, —CN, —C(O)NR$_9$R$_{10}$, —CH$_2$NR$_9$R$_{10}$, —CH$_2$NR$_9$—C(O)R$_{10}$, —CH$_2$CN, —CH$_2$C(O)NR$_9$R$_{10}$, —CH$_2$C(O)OH, —C(O)OH, —CH$_2$C(O)O—(C$_1$-C$_4$)alkyl, —N(R$_9$)—C(O)—(C$_1$-C$_4$)alkyl, —NR$_9$R$_{10}$, —CH$_2$NR$_9$R$_{10}$, —C(O)O—(C$_1$-C$_4$)alkyl and —CH$_2$CN, wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl; and R$_5$ is a 6-membered aromatic ring or aromatic heterocycle comprising 1 or 2 heteroatoms independently selected from N, S, and O, substituted with 1 to 3 substituents independently selected from H, (C$_1$-C$_6$)alkyl, —O—(C$_1$-C$_6$)alkyl, halogen, —CF$_3$, —CHF$_2$, —CH$_2$F, —OCF$_3$, —OCHF$_2$, —OCH$_2$F, —CN, —C(O)NR$_9$R$_{10}$, —CH$_2$NR$_9$R$_{10}$, —CH$_2$NR$_9$—C(O)R$_{10}$, —CH$_2$CN, —CH$_2$C(O)NR$_9$R$_{10}$, —CH$_2$C(O)OH, —C(O)OH, —CH$_2$C(O)O—(C$_1$-C$_4$)alkyl, —N(R$_9$)—C(O)—(C$_1$-C$_4$)alkyl, —NR$_9$R$_{10}$, —CH$_2$NR$_9$R$_{10}$, —C(O)OCH$_3$ and —CH$_2$CN, wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl.

6. The compound according to claim 5, wherein

R$_3$ is a 6-membered aromatic ring or aromatic heterocycle comprising 1 or 2 heteroatoms independently selected from N, S, and O, substituted with 1 to 3 substituents independently selected from H, methyl, ethyl, isopropyl, tert-butyl, cyclopropyl, methoxy, ethoxy, isopropoxy, —O-cyclopropyl, hydroxyethoxy, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, —CN, —C(O)NR$_9$R$_{10}$, —CH$_2$NR$_9$R$_{10}$, —CH$_2$NR$_9$—C(O)R$_{10}$, —CH$_2$CN, —CH$_2$C(O)NR$_9$R$_{10}$, —CH$_2$C(O)OH, —C(O)OH, —CH$_2$C(O)O—(C$_1$-C$_4$)alkyl, —N(R$_9$)—C(O)—(C$_1$-C$_4$)alkyl, —NR$_9$R$_{10}$, —CH$_2$NR$_9$R$_{10}$, —C(O)O—(C$_1$-C$_4$)alkyl and tetrahydropyrrol-1-yl; and R$_5$ is a 6-membered aromatic ring or aromatic heterocycle comprising 1 or 2 heteroatoms independently selected from N, S, and O, substituted with 1 to 3 substituents independently selected from H, methyl, ethyl, isopropyl, tert-butyl, cyclopropyl, methoxy, ethoxy, isopropoxy, —O-cyclopropyl, hydroxyethoxy, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, —CN, —C(O)NR$_9$R$_{10}$, —CH$_2$NR$_9$R$_{10}$, —CH$_2$NR$_9$—C(O)R$_{10}$, —CH$_2$CN, —CH$_2$C(O)NR$_9$R$_{10}$, —CH$_2$C(O)OH, —C(O)OH, —CH$_2$C(O)O—(C$_1$-C$_4$)alkyl, —N(R$_9$)—C(O)—(C$_1$-C$_4$)alkyl, —NR$_9$R$_{10}$, —CH$_2$NR$_9$R$_{10}$, —C(O)OCH$_3$ and tetrahydropyrrol-1-yl.

7. The compound according to claim 4, wherein

Y is carbon or nitrogen; wherein when Y is nitrogen, R$_4$ is absent; and wherein when Y is carbon, R$_4$ is selected from H, hydroxyl, —O—(C$_1$-C$_6$)alkyl, —C(O)OH, —CH$_2$C(O)OH, —CH$_2$C(O)NR$_9$R$_{10}$ and —C(O)O—(C$_1$-C$_6$)alkyl, wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl;

R$_1$ is selected from methyl, ethyl, isopropyl, cyclopropyl, cyclobutyl and cyclopentyl;

R$_2$ is H;

R$_3$ is a pyridine, pyridone, pyrimidine, pyrazine or pyridazine ring each substituted with 1 to 3 substituents independently selected from H, (C$_1$-C$_6$)alkyl, (C$_3$-C$_6$)cycloalkyl, —S—(C$_1$-C$_6$)alkyl, —O—(C$_3$-C$_6$)cycloalkyl, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, hydroxyalkoxy, —CN, —C(O)NR$_9$R$_{10}$, —CH$_2$NR$_9$R$_{10}$, —CH$_2$NR$_9$—C(O)R$_{10}$, —C(O)OH, —CH$_2$NR$_9$R$_{10}$, tetrahydropyrrol-1-yl and —NR$_9$R$_{10}$; wherein the alkyl or cycloalkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl;

R$_5$ is a pyridine, pyridone, pyrimidine, pyrazine or pyridazine ring each substituted with 1 to 3 substituents independently selected from H, (C$_1$-C$_6$)alkyl, (C$_3$-C$_6$)cycloalkyl, —S—(C$_1$-C$_6$)alkyl, —O—(C$_3$-C$_6$)cycloalkyl, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, hydroxyalkoxy, —CN, —C(O)NR$_9$R$_{10}$, —CH$_2$NR$_9$R$_{10}$, —CH$_2$NR$_9$—C(O)R$_{10}$, —C(O)OH, —CH$_2$NR$_9$R$_{10}$, tetrahydropyrrol-1-yl and —NR$_9$R$_{10}$; wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl;

R$_6$ is chlorine;

R$_7$ is hydrogen;

X$_1$ is oxygen; and

X$_2$, V and W are each carbon;

wherein R$_9$ is selected from H, methyl and ethyl; and R$_{10}$ is H or (C$_1$-C$_6$)alkyl, wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl and methanesulfonyl.

8. The compound according to claim 7, wherein

R$_3$ is a pyridine, pyridone, pyrimidine, pyrazine or pyridazine ring each substituted with 1 to 3 substituents, the substituent independently selected from H, (C$_1$-C$_6$)alkyl, —S—(C$_1$-C$_6$)alkyl, halogen, —CF$_3$, —CHF$_2$, —CH$_2$F, —OCF$_3$, —OCHF$_2$, —OCH$_2$F, —CN, —C(O)NR$_9$R$_{10}$, —CH$_2$NR$_9$R$_{10}$, —CH$_2$NR$_9$—C(O)R$_{10}$, —C(O)OH, —CH$_2$NR$_9$R$_{10}$ and —NR$_9$R$_{10}$; wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$ and methanesulfonyl;

R$_5$ is a pyridine, pyridone, pyrimidine, pyrazine or pyridazine ring each substituted with 1 to 3 substituents independently selected from H, (C$_1$-C$_6$)alkyl, —O—(C$_1$-C$_6$)alkyl, —S—(C$_1$-C$_6$)alkyl, halogen, —CF$_3$, —CHF$_2$, —CH$_2$F, —OCF$_3$, —OCHF$_2$, —OCH$_2$F, —CN, —C(O)NR$_9$R$_{10}$, —CH$_2$NR$_9$R$_{10}$, —CH$_2$NR$_9$—C(O)R$_{10}$, —C(O)OH, —CH$_2$NR$_9$R$_{10}$ and —NR$_9$R$_{10}$; wherein the alkyl is optionally substituted with 0 to 3 substituents independently selected from methoxy, ethoxy, hydroxyl, sulfhydryl, halogen, —C(O)OH, —C(O)O—(C$_1$-C$_4$)alkyl, —C(O)NR$_9$R$_{10}$, —NR$_9$R$_{10}$, and methanesulfonyl; and R$_{10}$ is selected from H, methyl, ethyl and 1-hydroxyethyl.

9. The compound according to claim 8, wherein

R$_3$ is a pyridine, pyridone, pyrimidine, pyrazine or pyridazine ring each substituted by 1 to 3 substituents independently selected from H, methyl, ethyl, isopropyl, tert-butyl, cyclopropyl, methoxy, ethoxy, isopropoxy, —O-cyclopropyl, hydroxyethoxy, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, —CN, —C(O)NR$_9$R$_{10}$, —CH$_2$NR$_9$R$_{10}$, —CH$_2$NR$_9$—C(O)R$_{10}$, —C(O)OH, —CH$_2$NR$_9$R$_{10}$, tetrahydropyrrol-1-yl and —NR$_9$R$_{10}$;

R$_5$ is a pyridine, pyridone, pyrimidine, pyrazine or pyridazine ring each substituted with 1 to 3 substituents independently selected from H, methyl, ethyl, isopropyl, tert-butyl, cyclopropyl, methoxy, ethoxy, isopropoxy, —O-cyclopropyl, hydroxyethoxy, halogen, —CF$_3$, —CHF$_2$, —CH$_2$F, —OCF$_3$, —OCHF$_2$, —OCH$_2$F, —OCH$_2$CF$_3$, —OCH$_2$CHF$_2$, —OCH$_2$CH$_2$F, —CN, —C(O)NR$_9$R$_{10}$, —CH$_2$NR$_9$R$_{10}$, —CH$_2$NR$_9$—C(O)R$_{10}$, —C(O)OH, —CH$_2$NR$_9$R$_{10}$, tetrahydropyrrol-1-yl and —NR$_9$R$_{10}$; and R$_{10}$ is H, methyl or ethyl.

10. The compound according to claim 1, selected from:
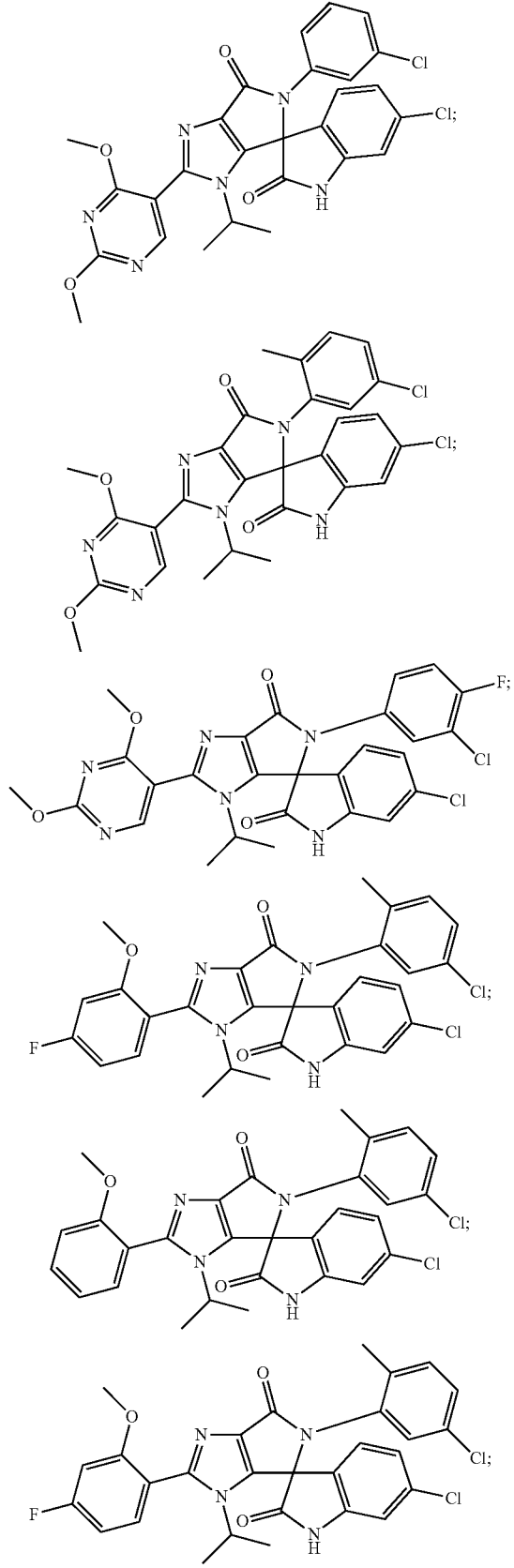
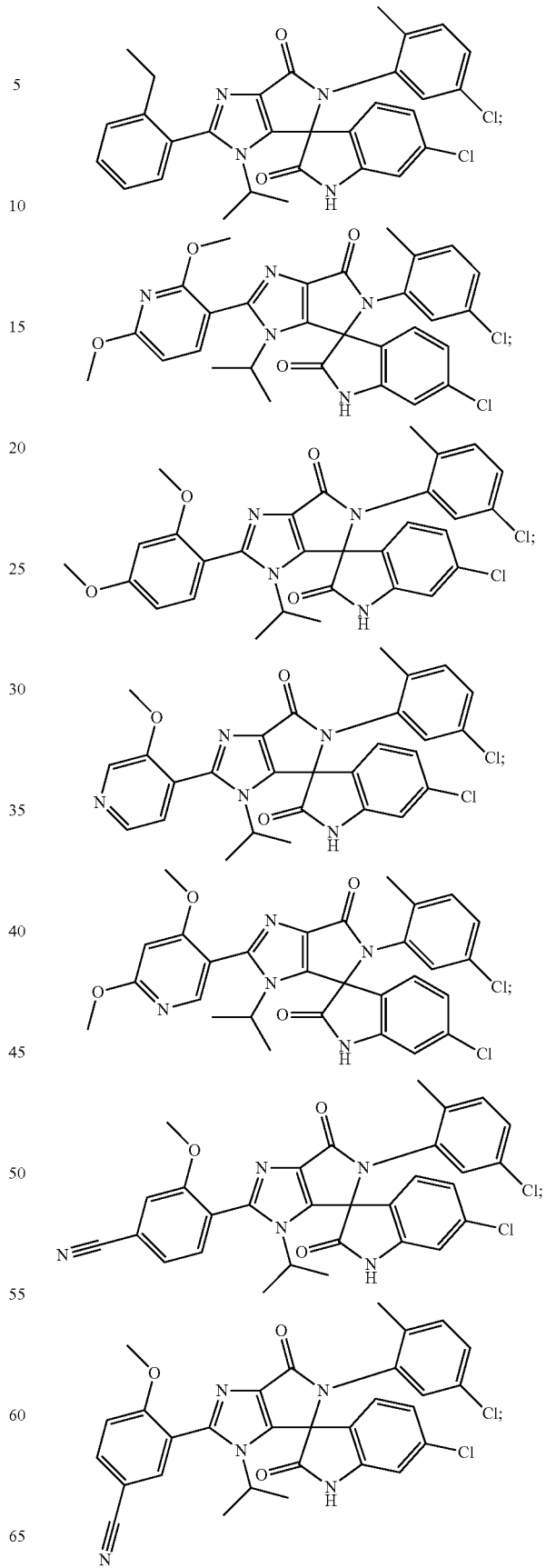

219
-continued
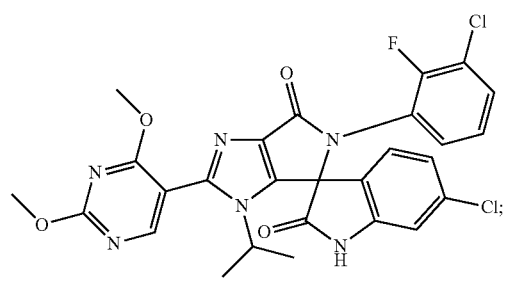
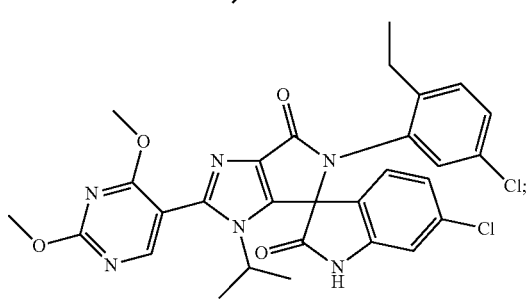
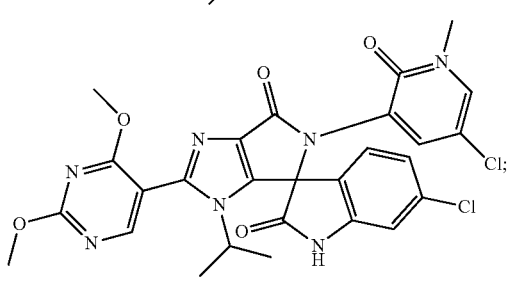
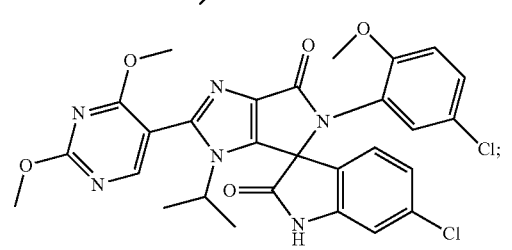
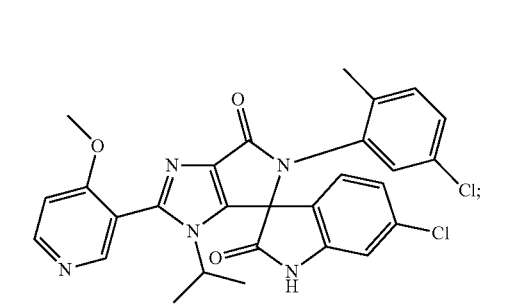
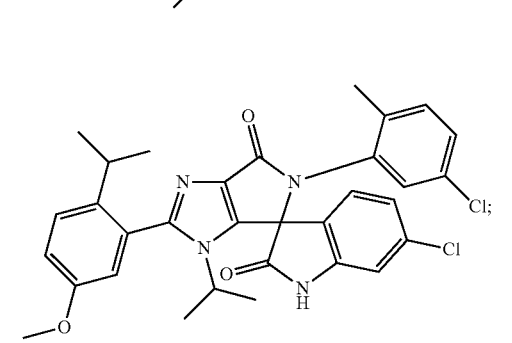
220
-continued
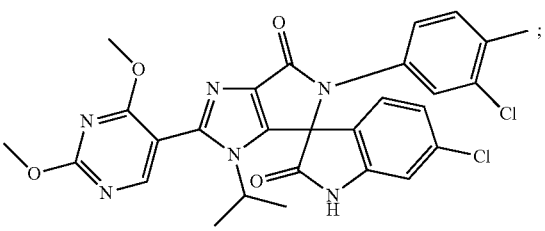
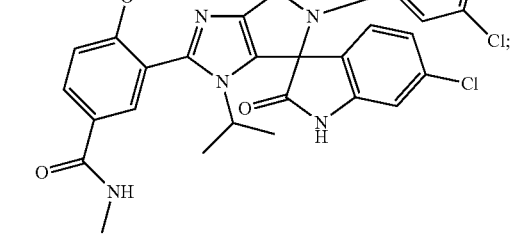
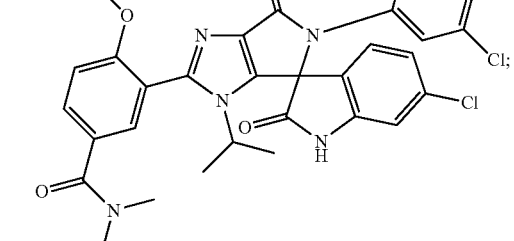
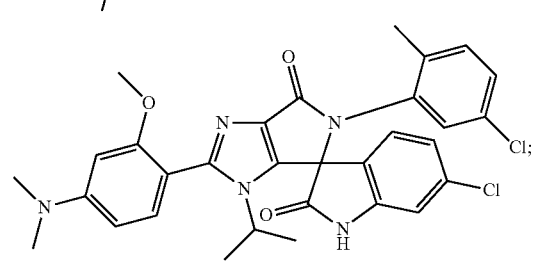
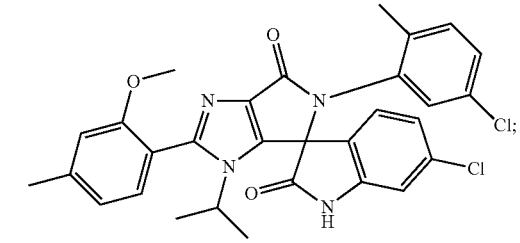
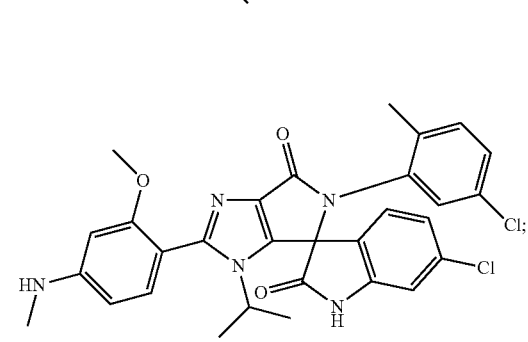

-continued
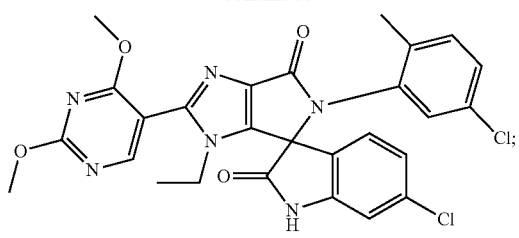
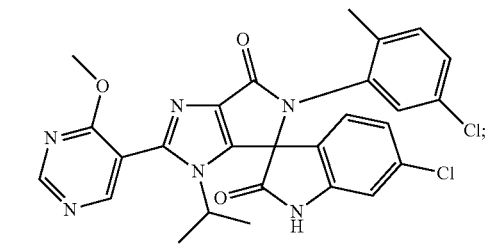
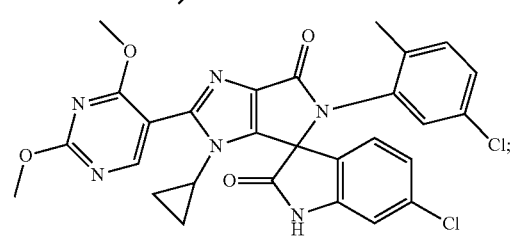
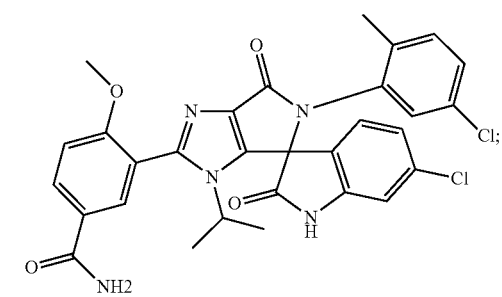
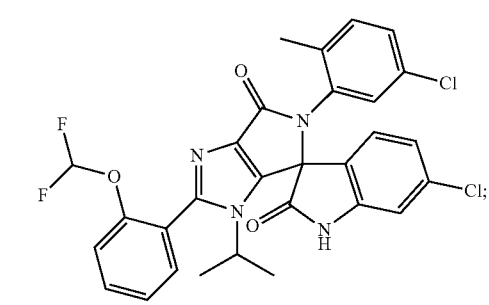
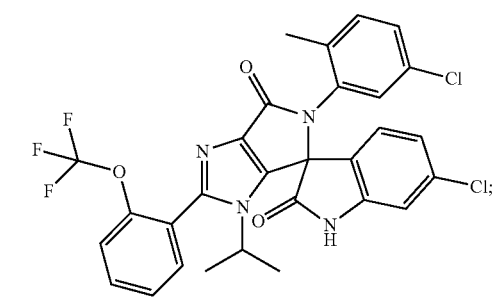
-continued
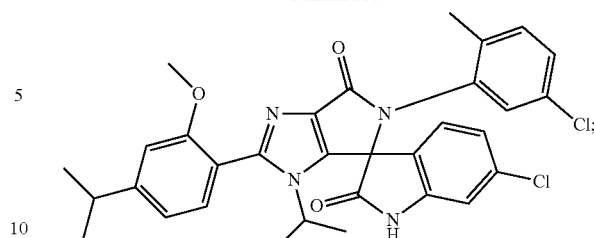
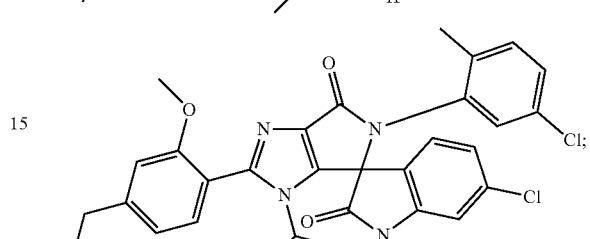
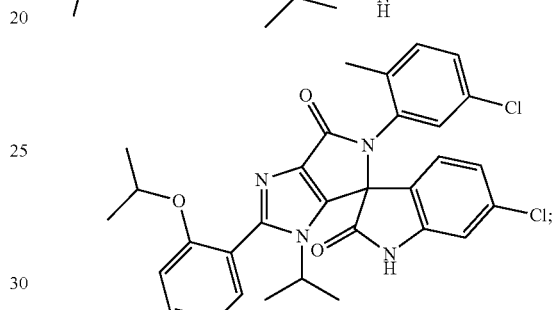
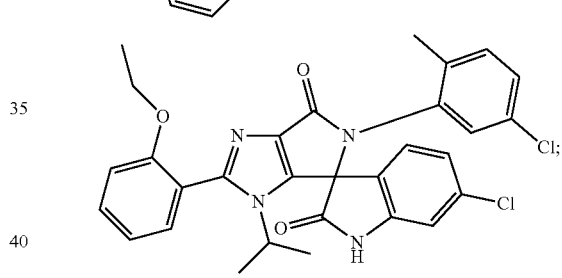
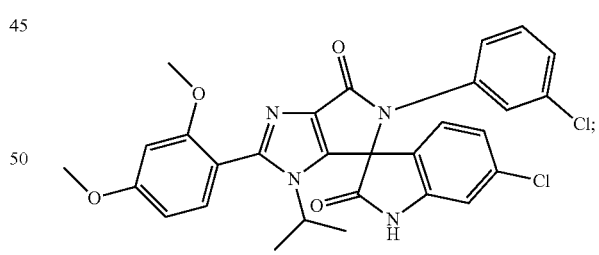
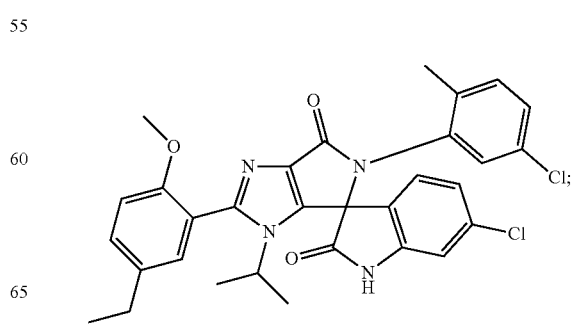

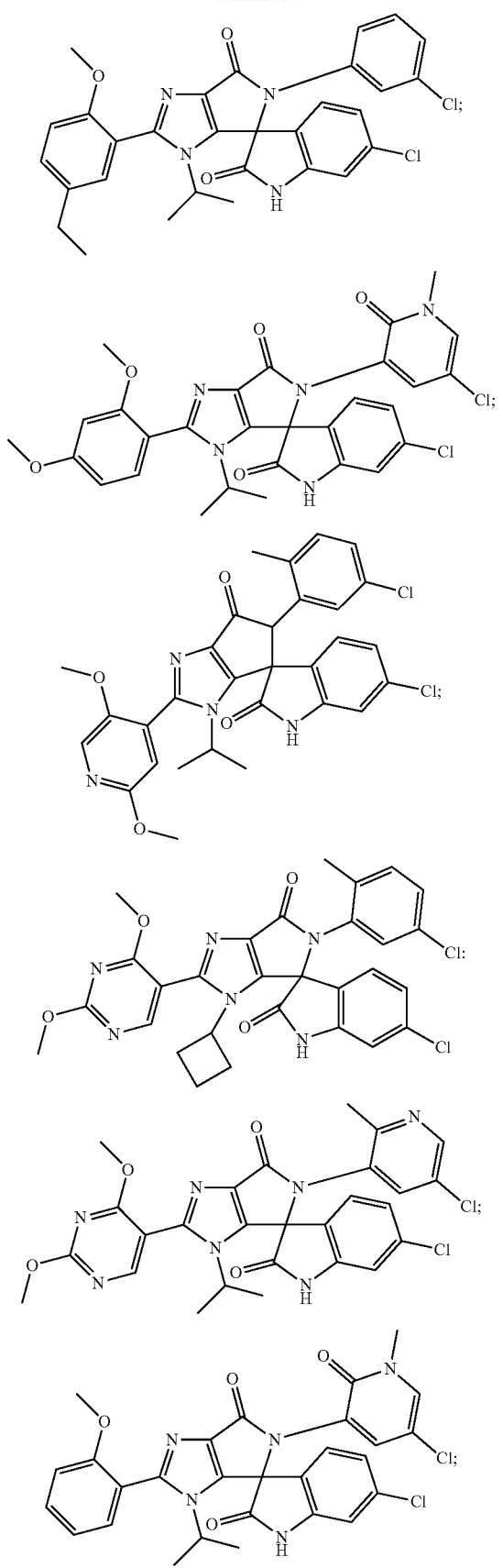
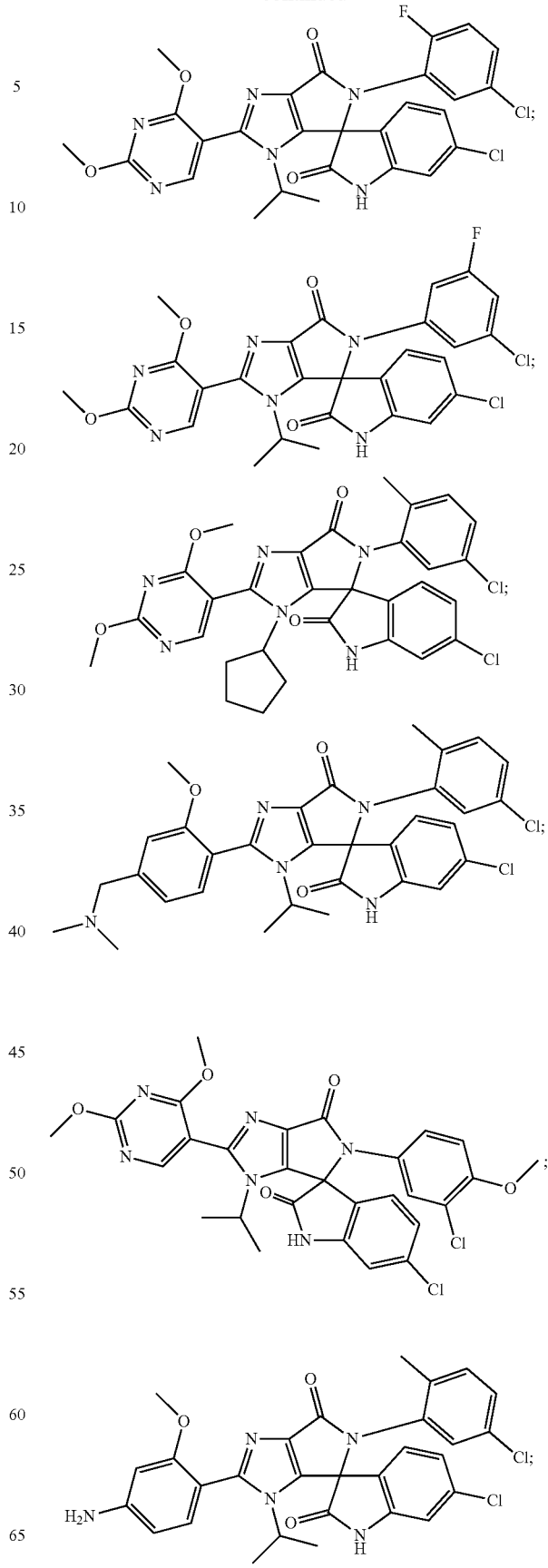

225
-continued
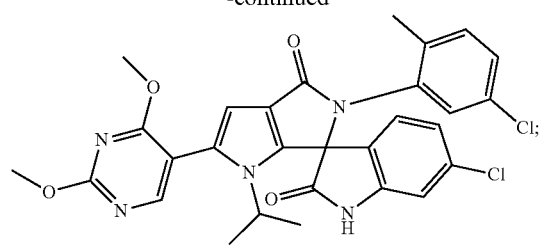
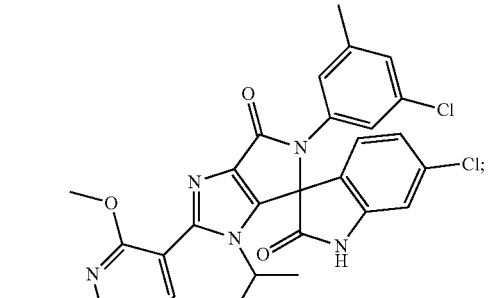
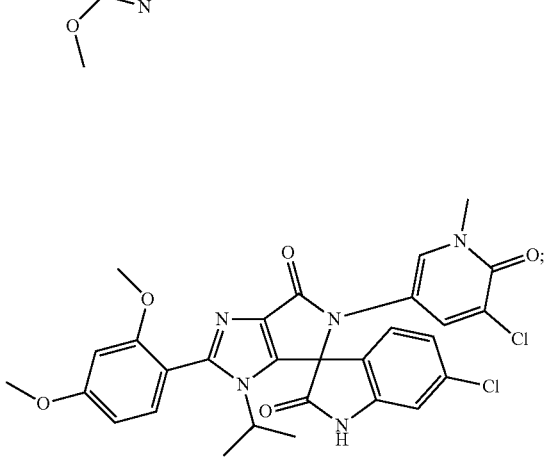
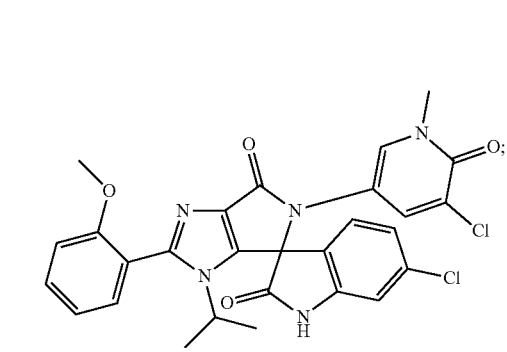
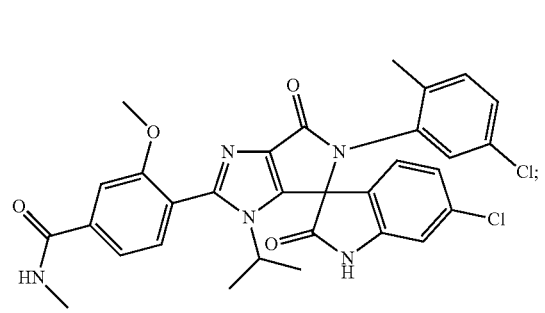
226
-continued
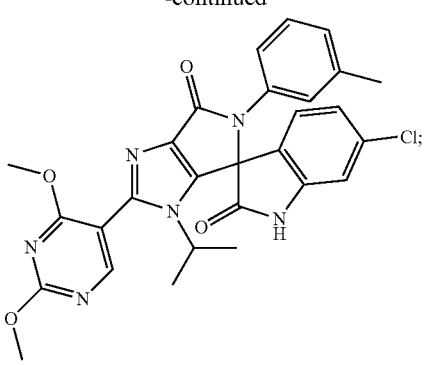
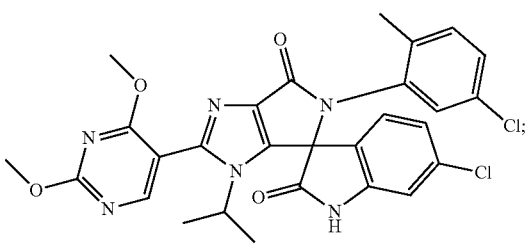
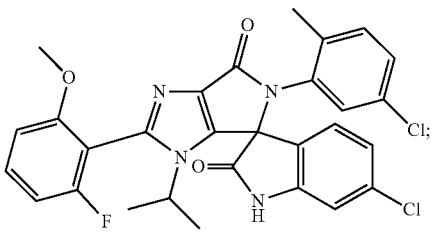
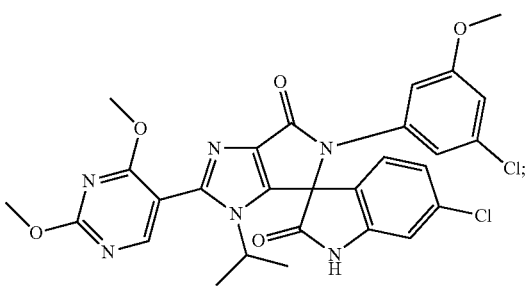
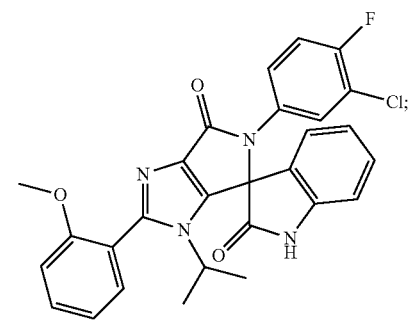
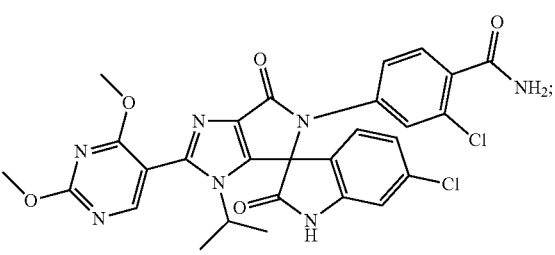

227
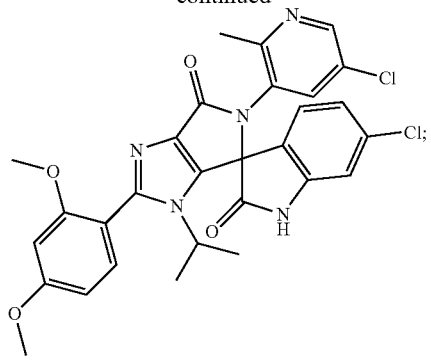
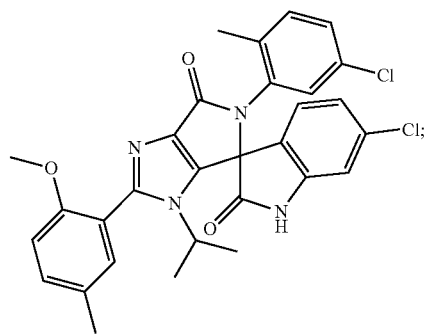
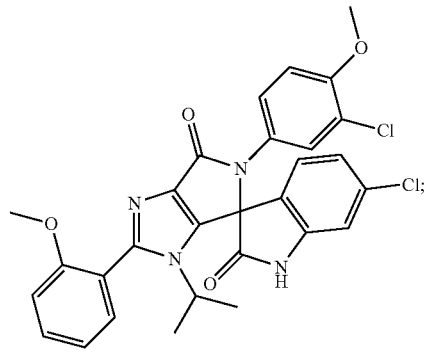
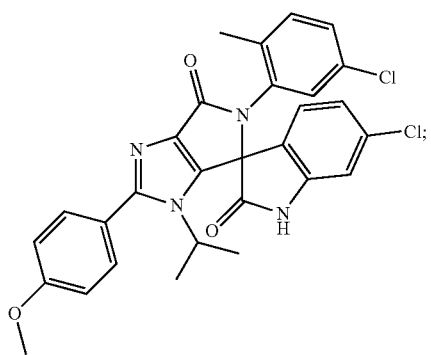
228
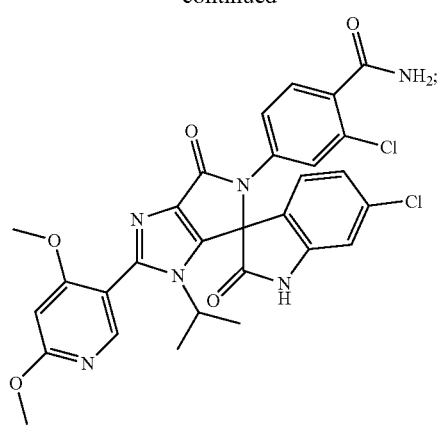
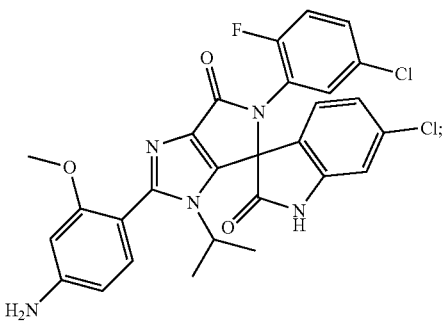
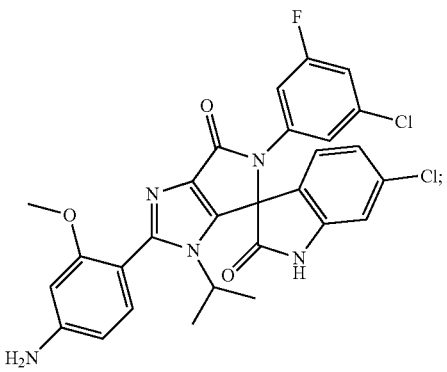
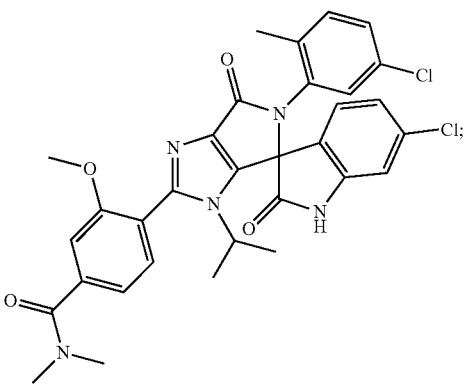

229
-continued
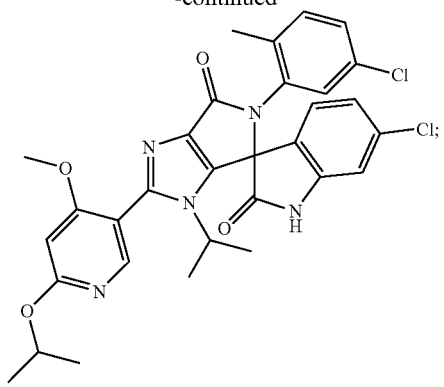
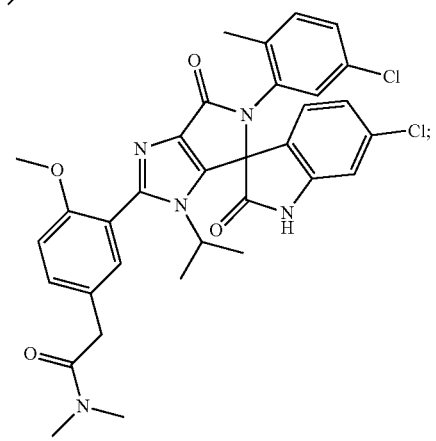
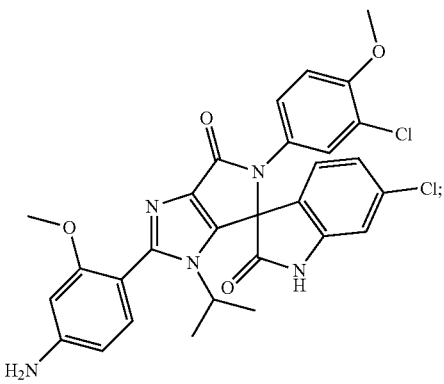
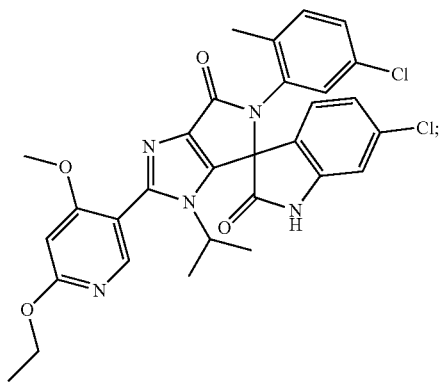
230
-continued
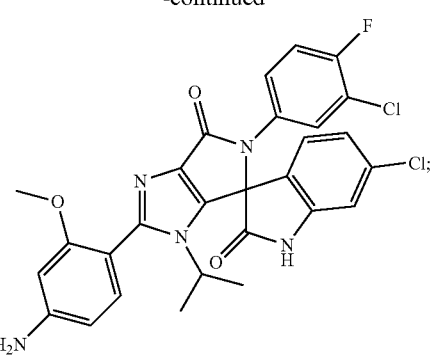
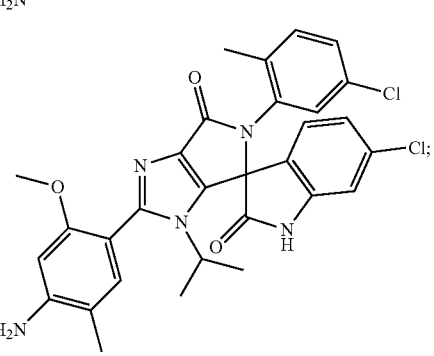
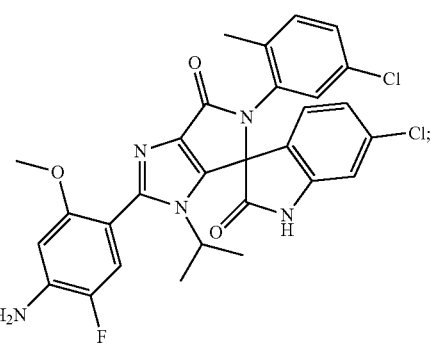
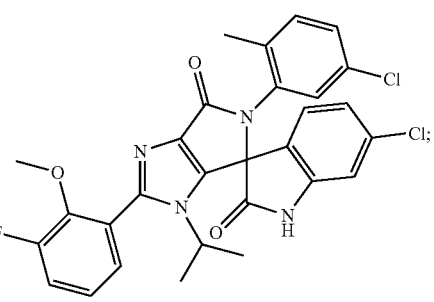
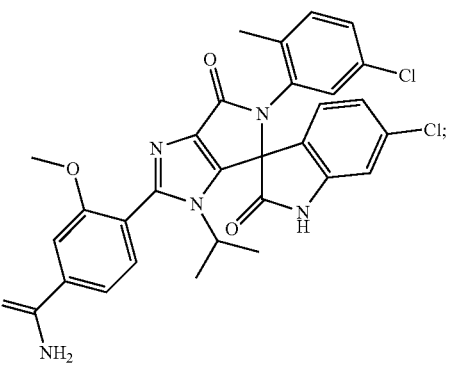

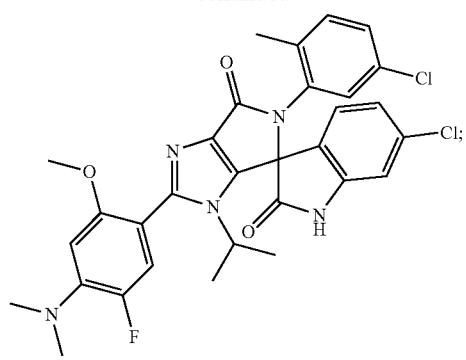
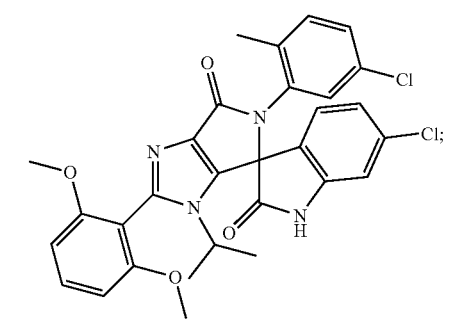
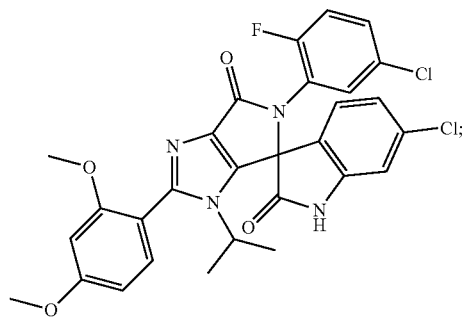
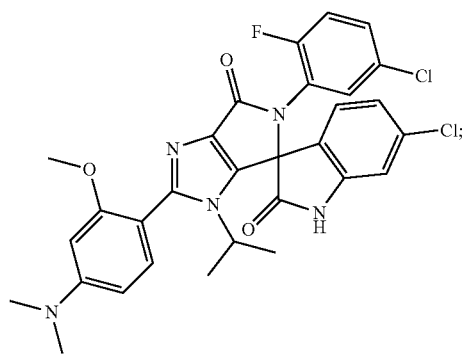
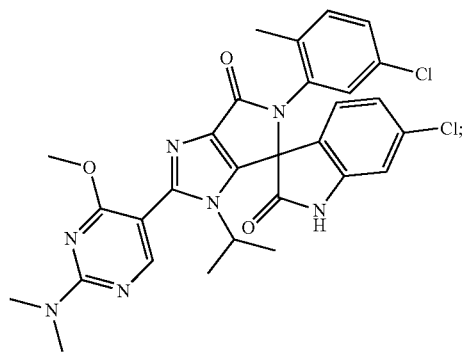
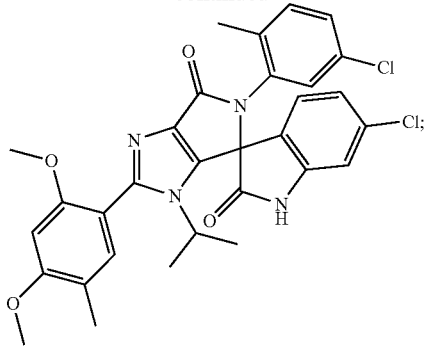
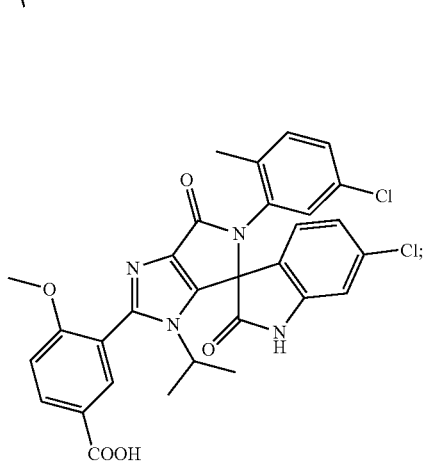
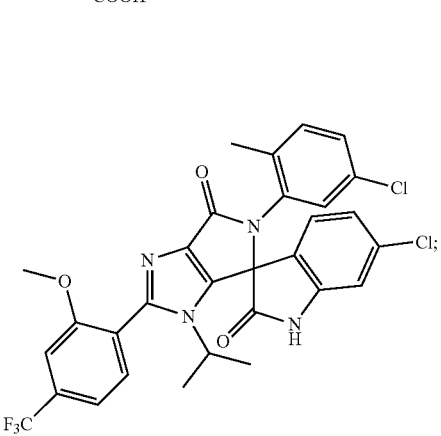

233
-continued
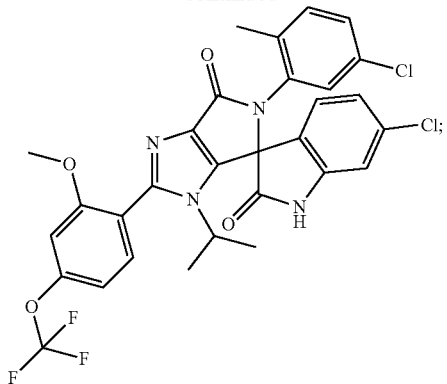
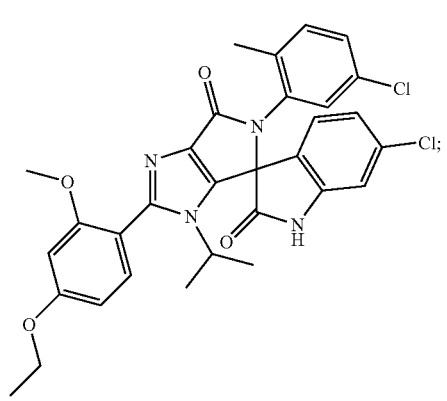
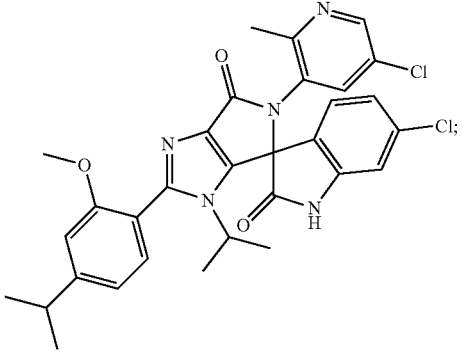
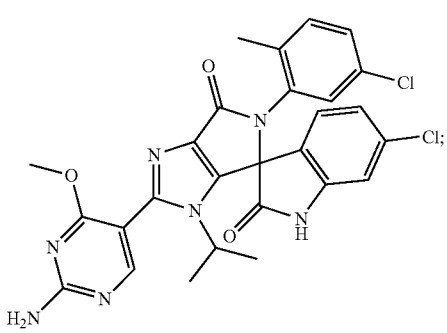
234
-continued
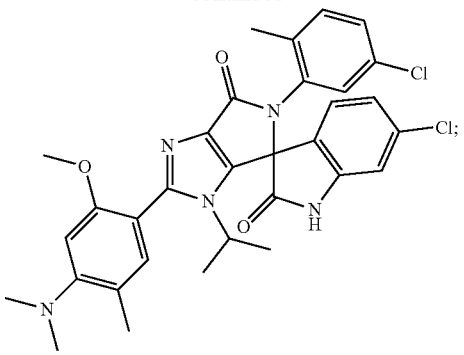
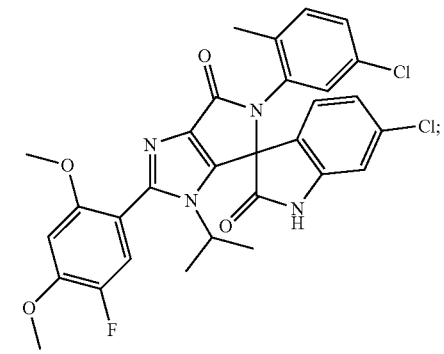
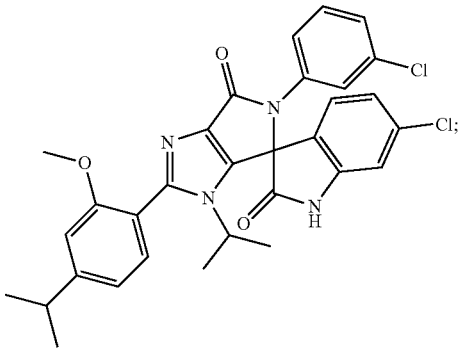
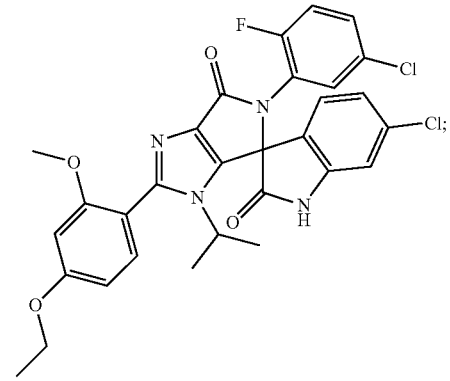

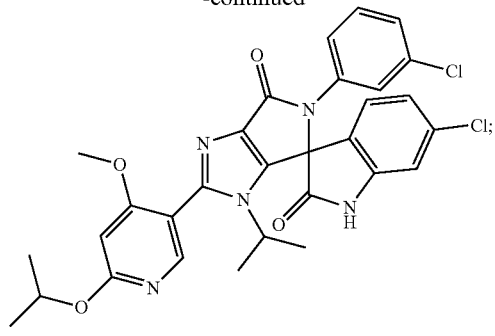
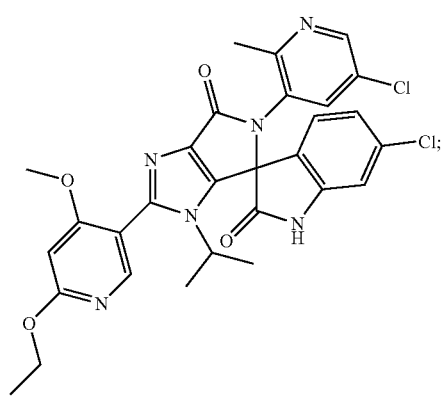
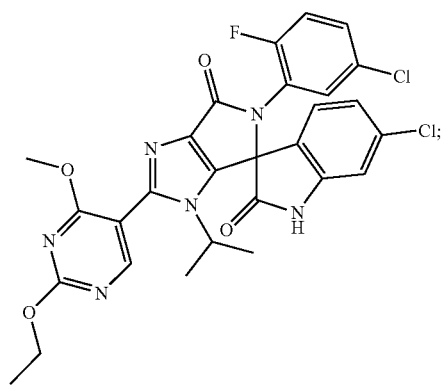
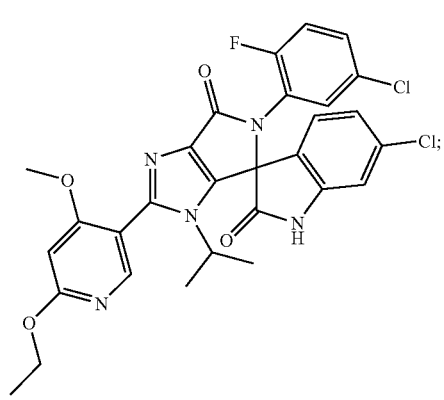
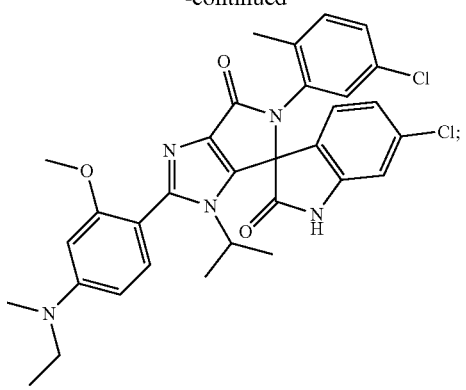
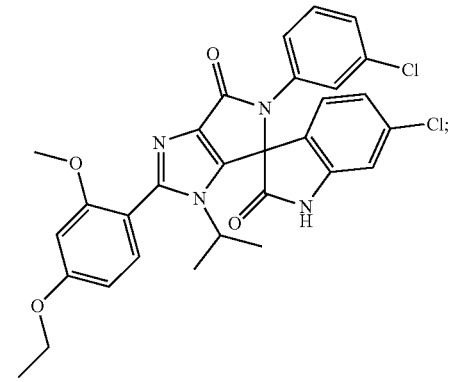
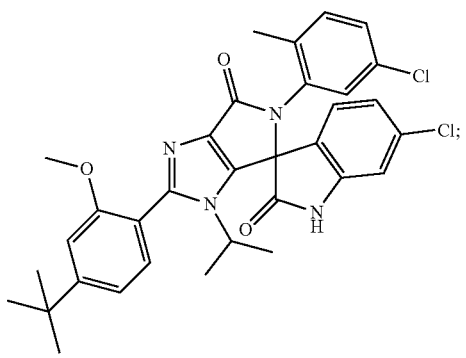
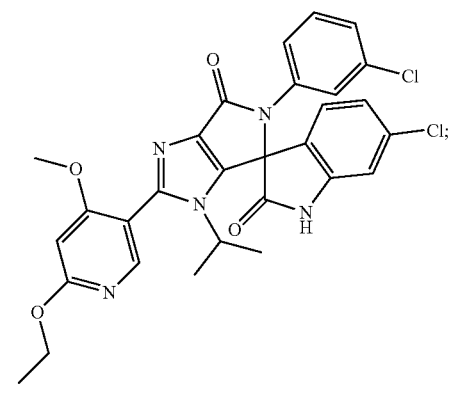

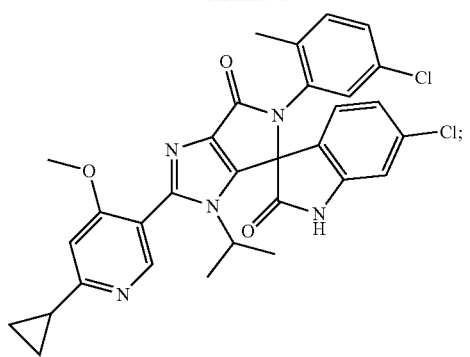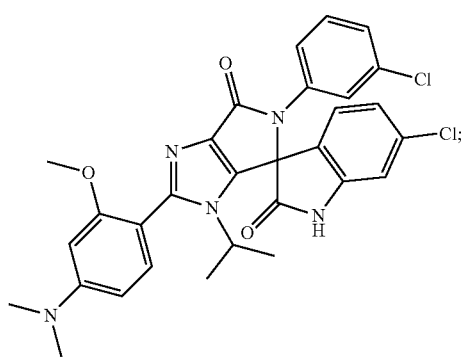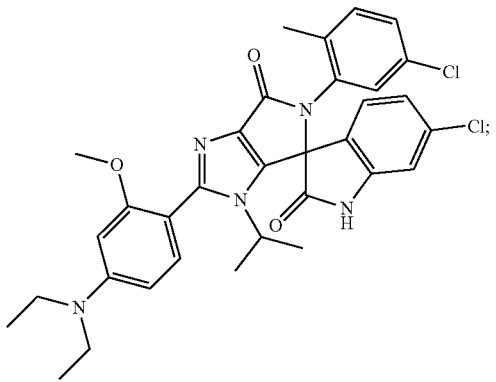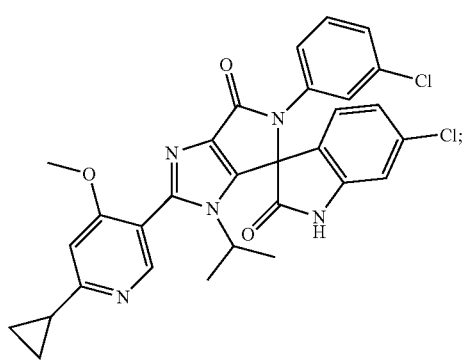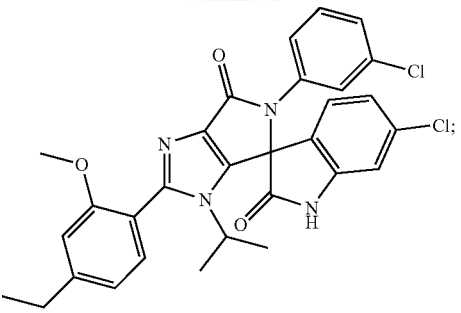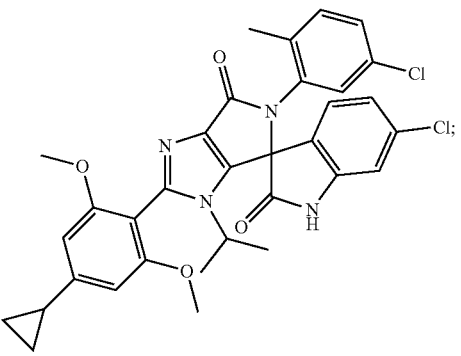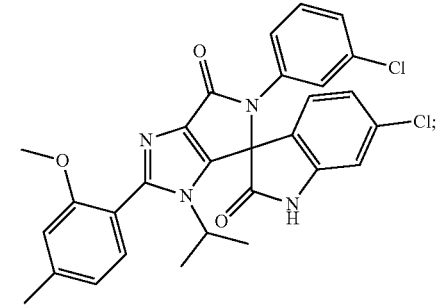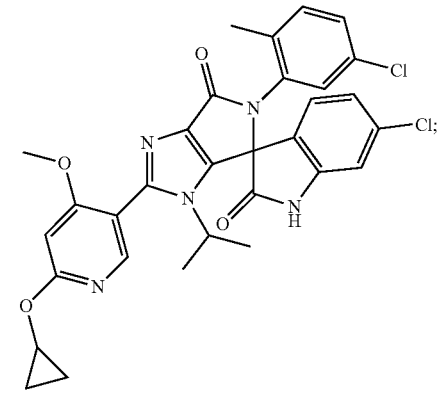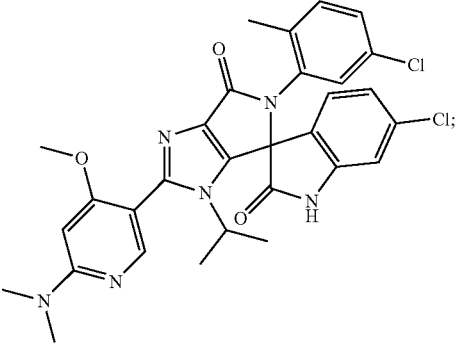

-continued
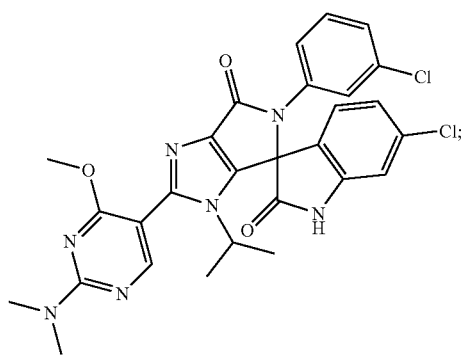
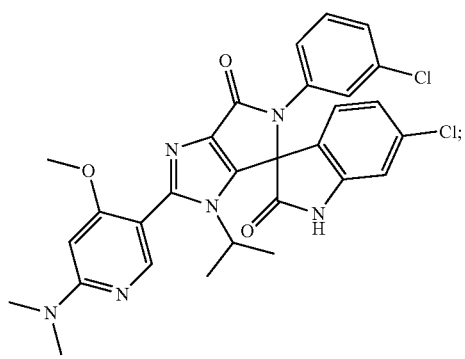
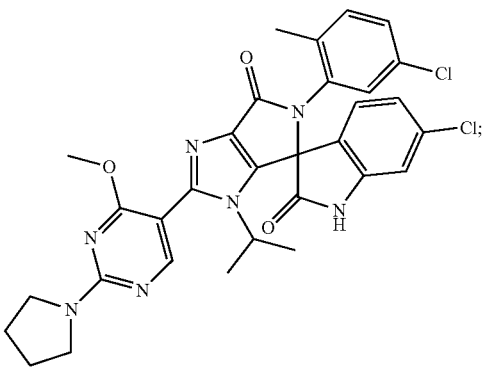
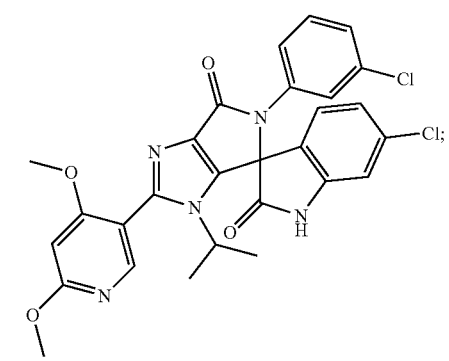
-continued
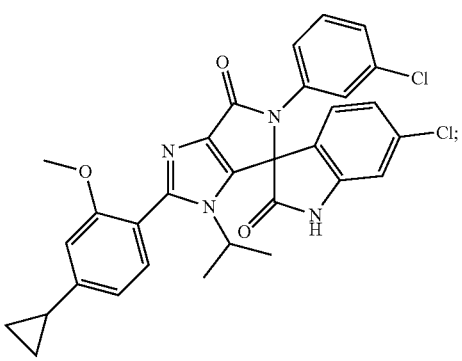
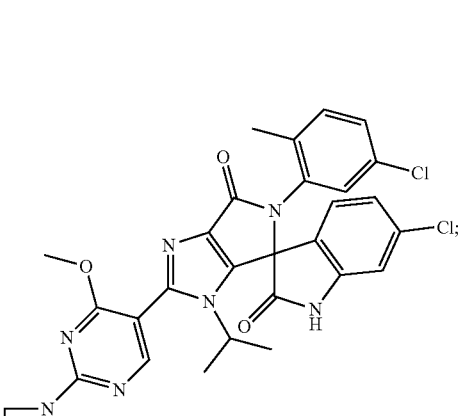
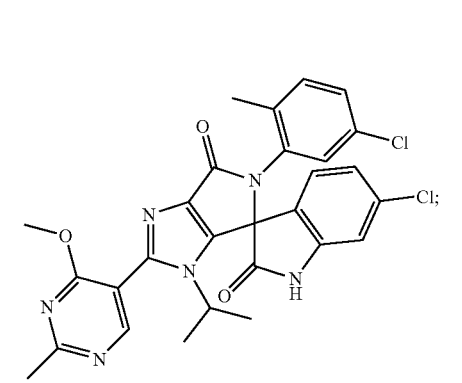
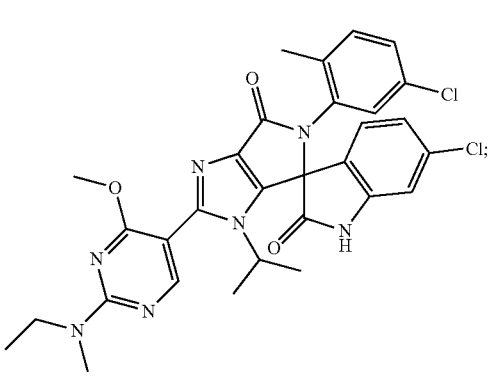

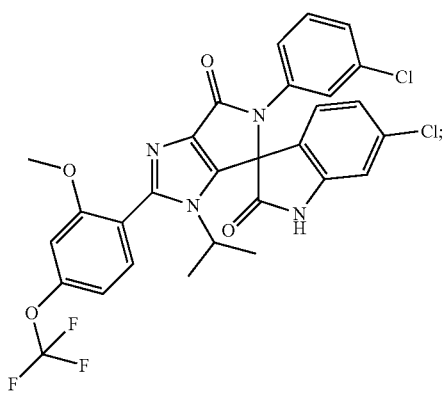
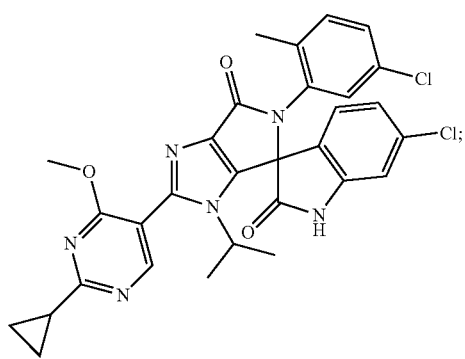
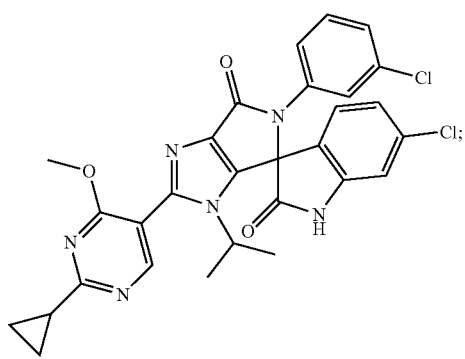
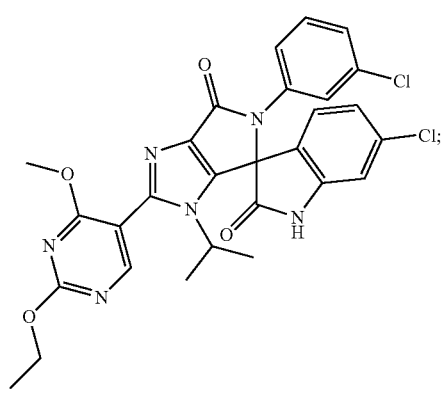
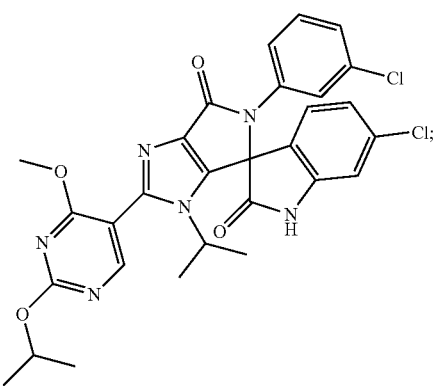
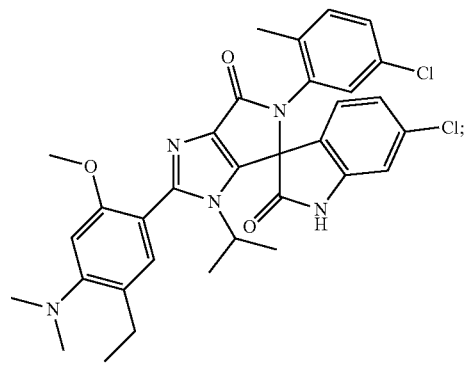
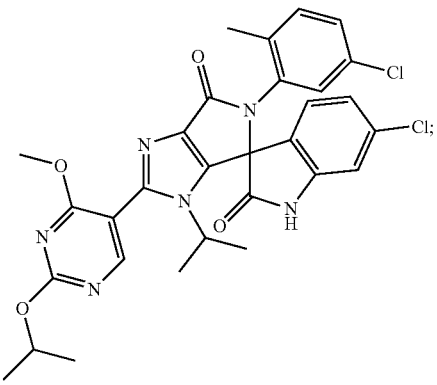
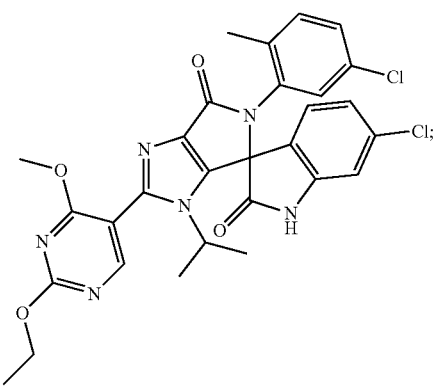

243
-continued
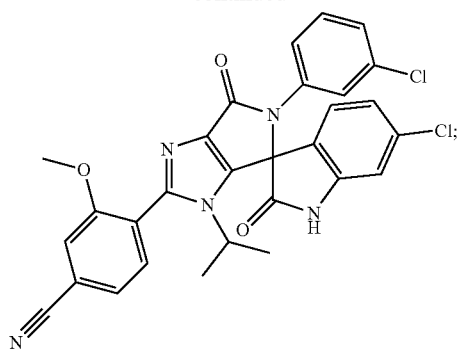
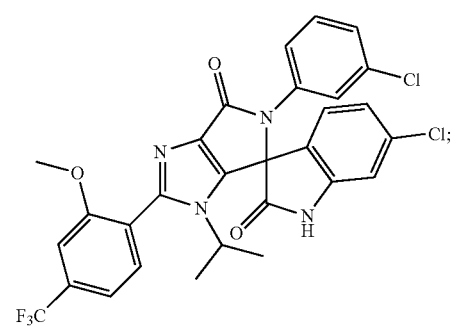
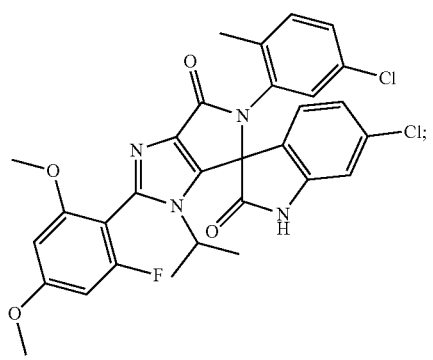
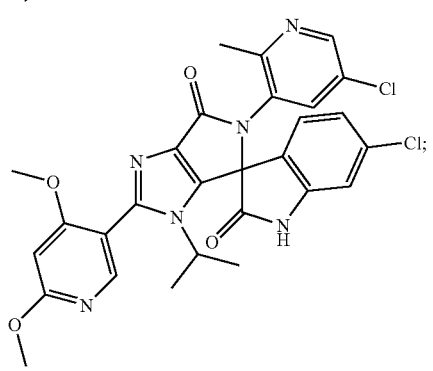
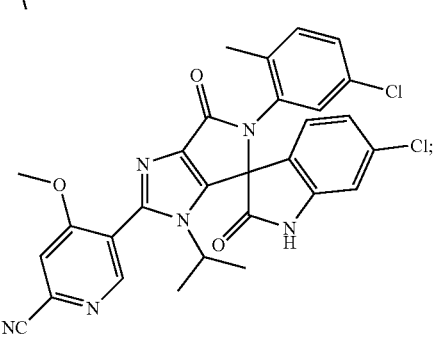
244
-continued
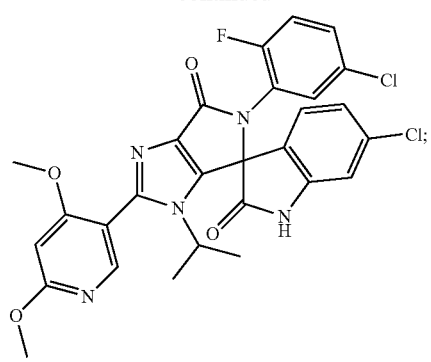
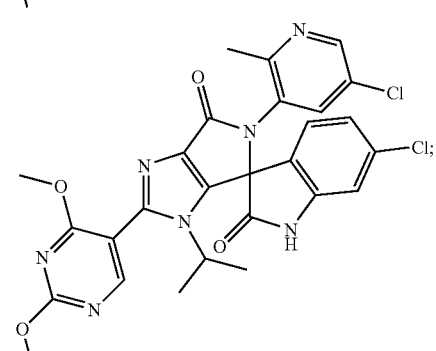
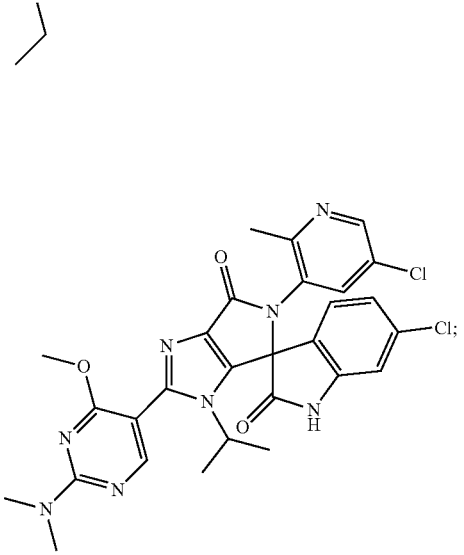
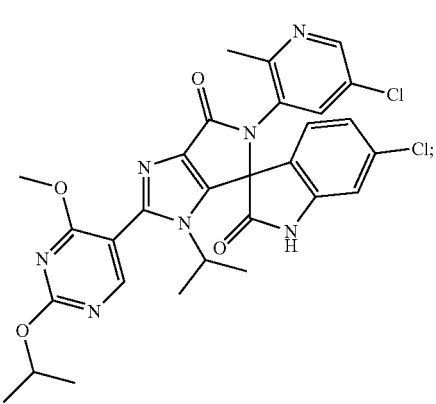

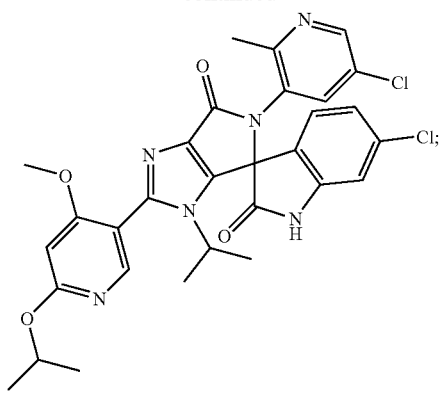
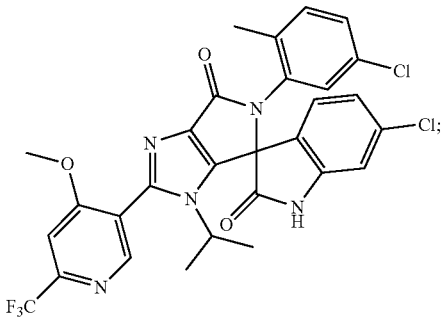
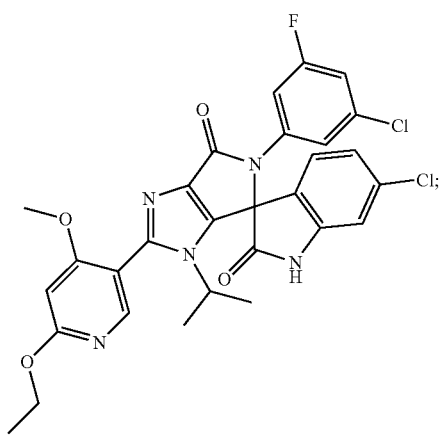
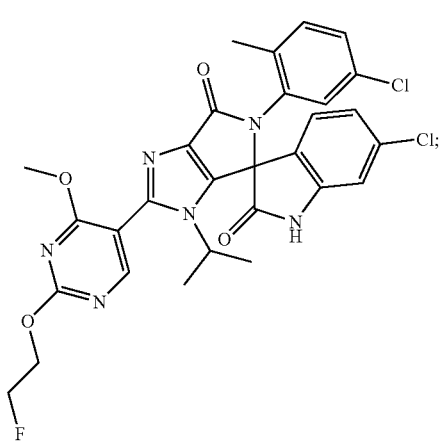
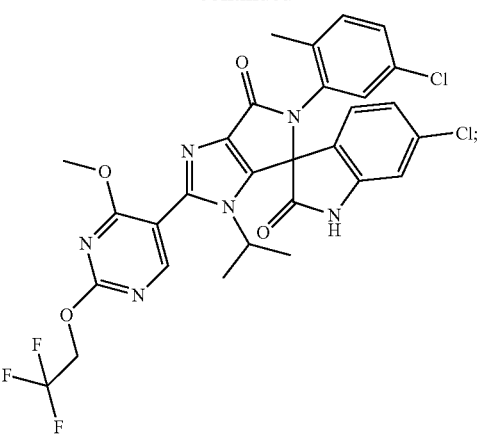
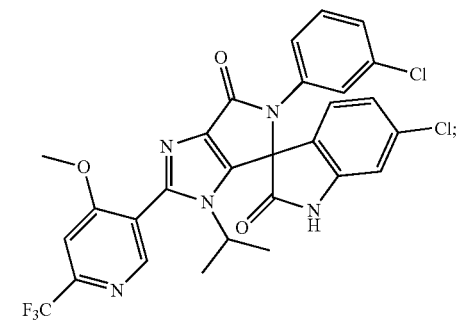
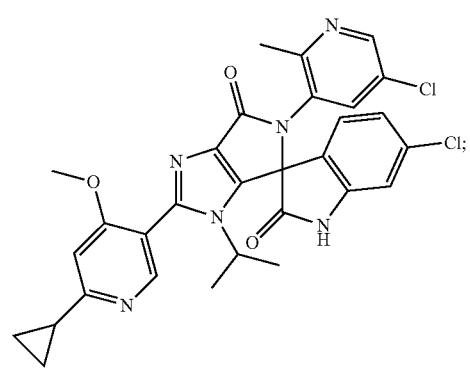
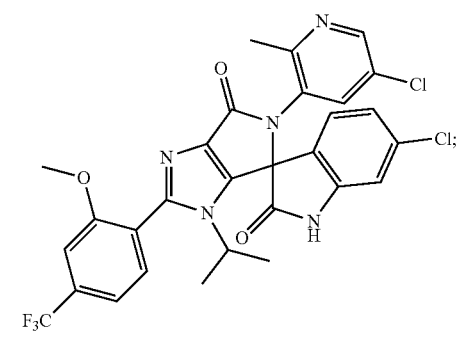

-continued
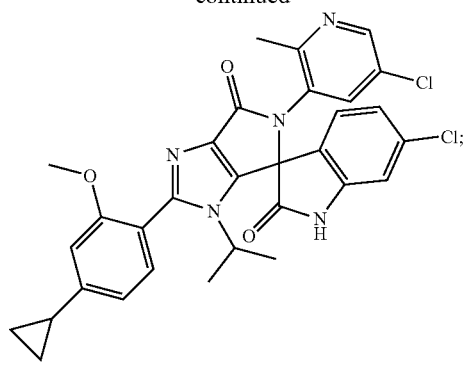
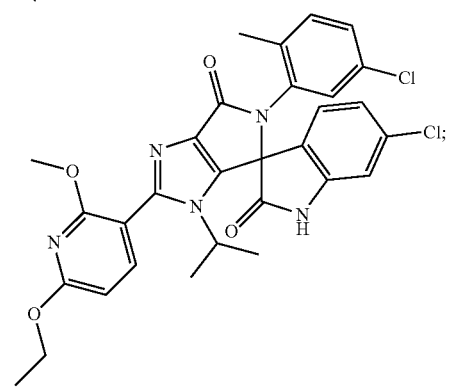
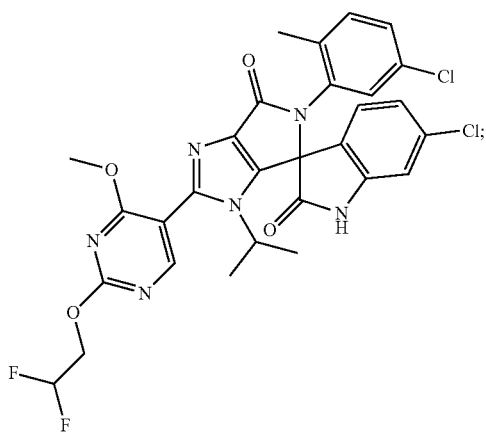
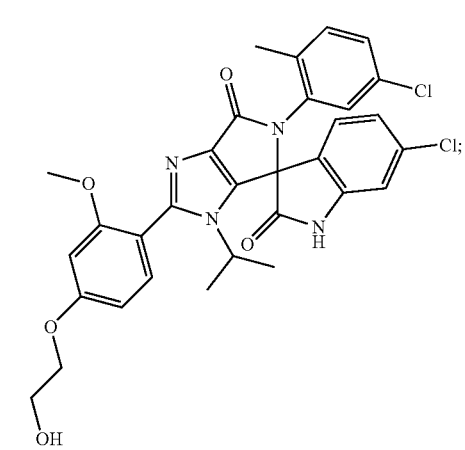
-continued
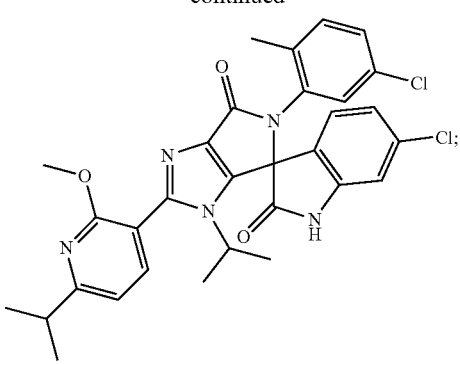
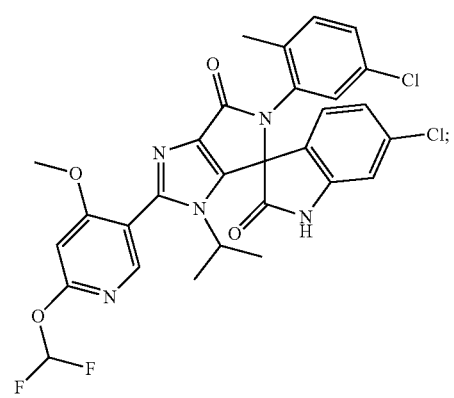
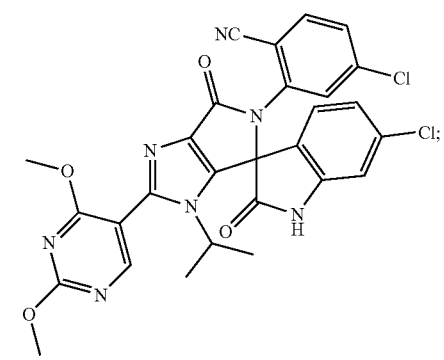
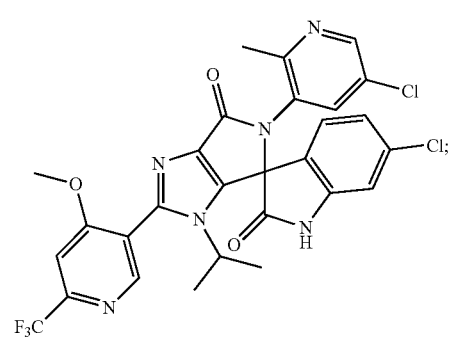

249
-continued
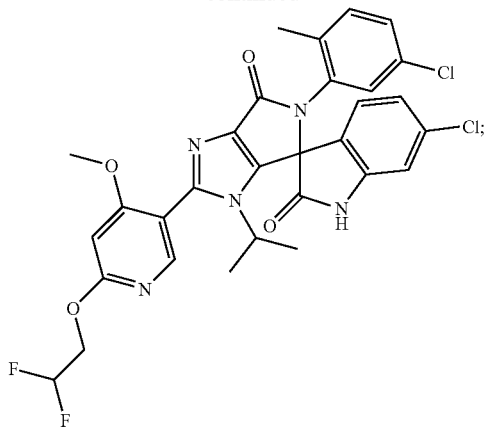
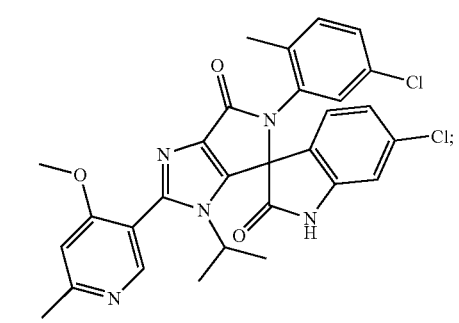
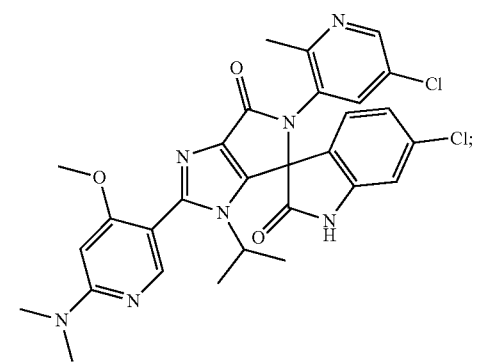
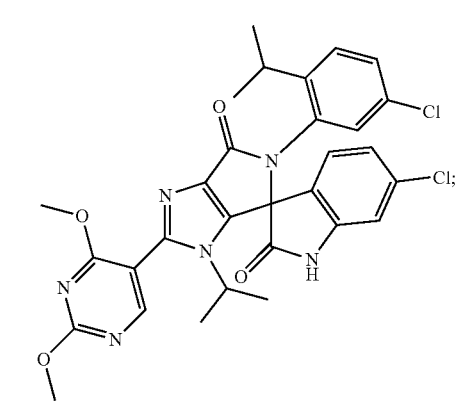
250
-continued
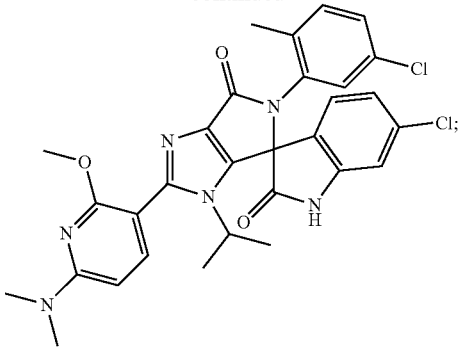
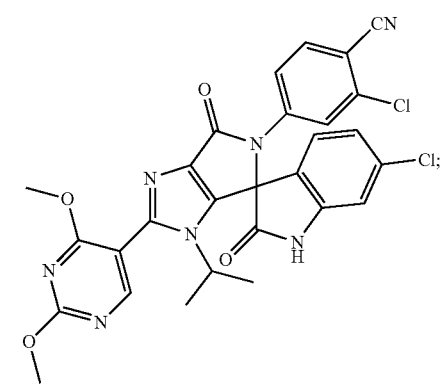
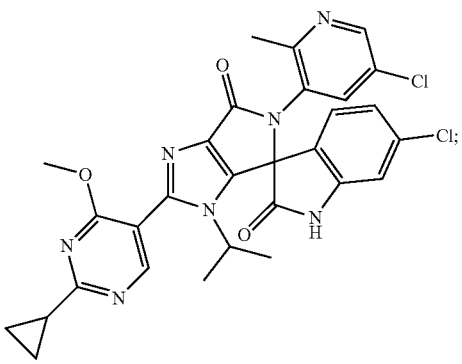
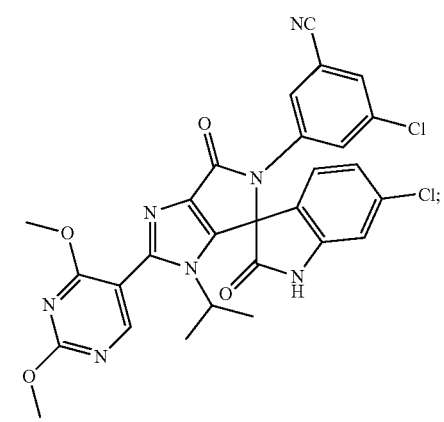

251
-continued
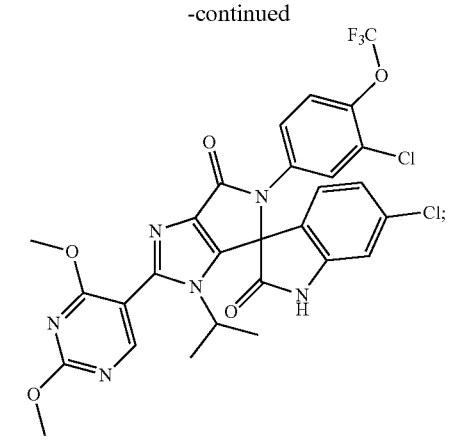
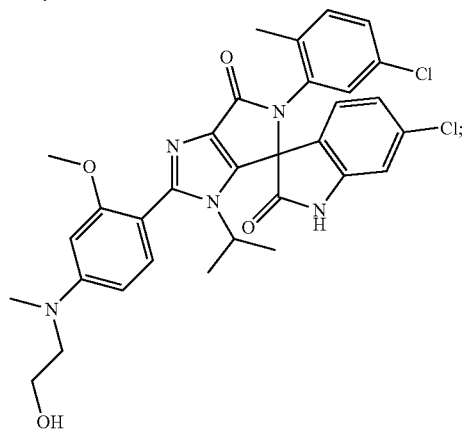
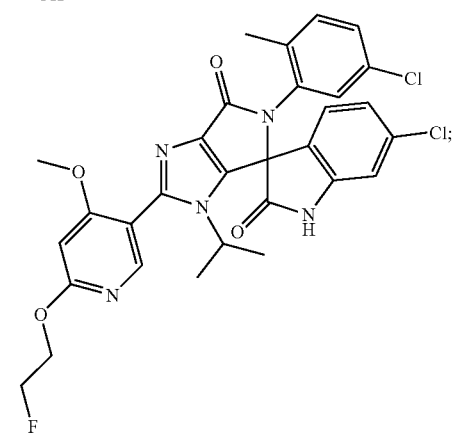
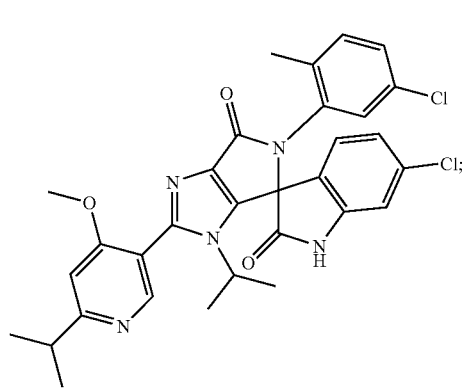
252
-continued
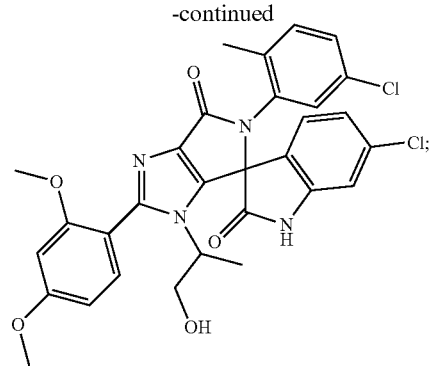
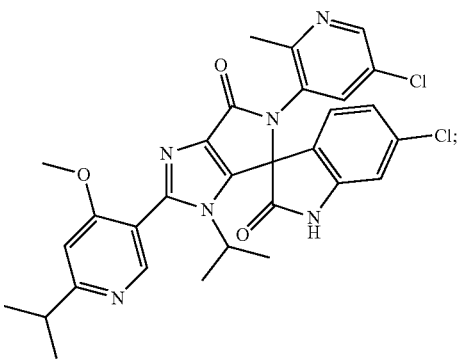
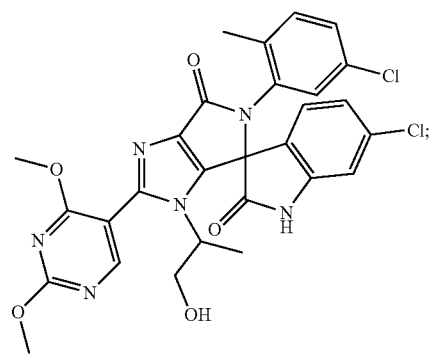
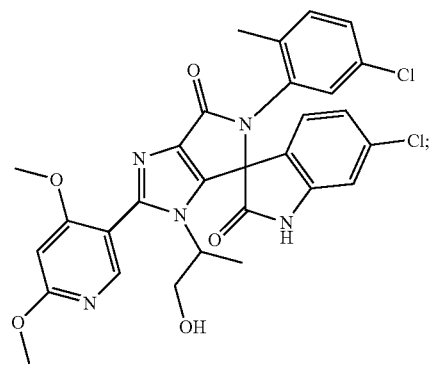

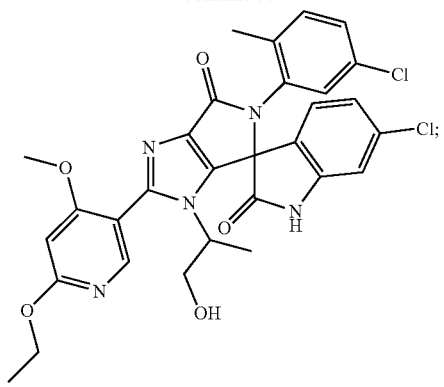
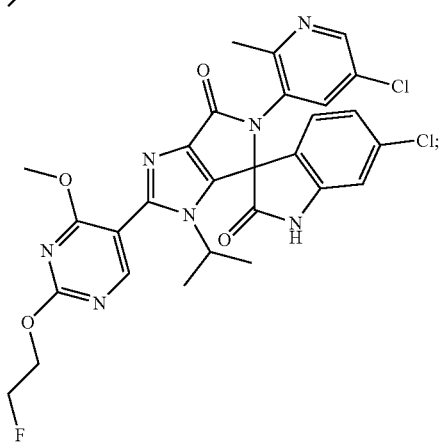
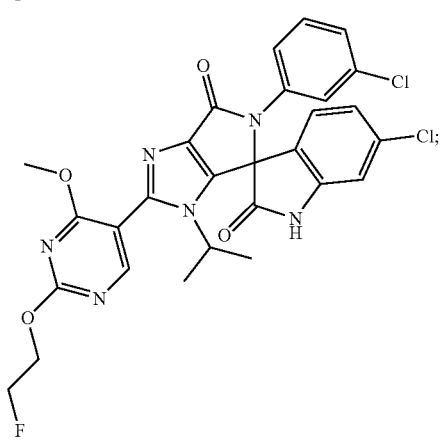
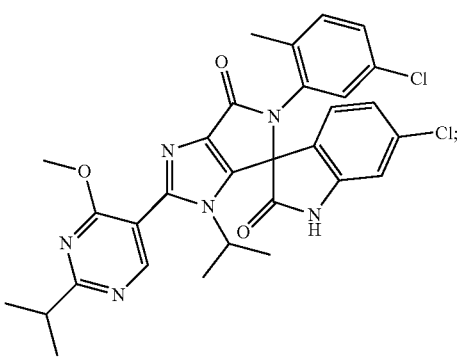
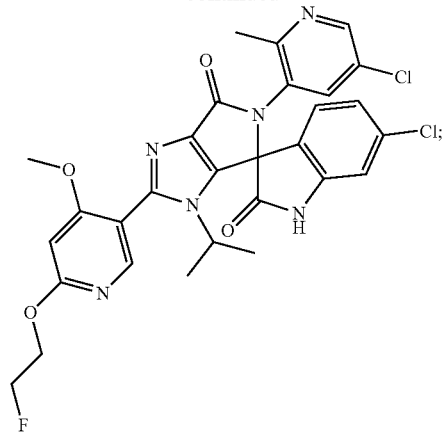
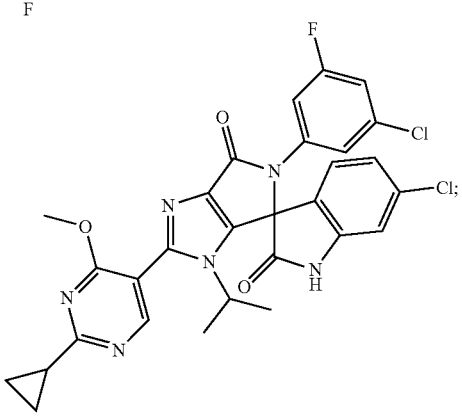
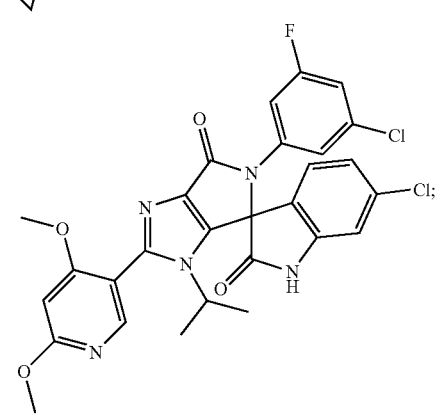
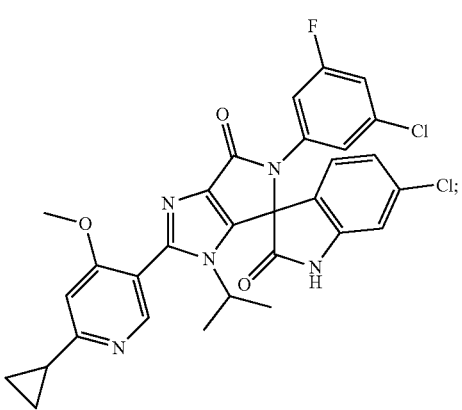

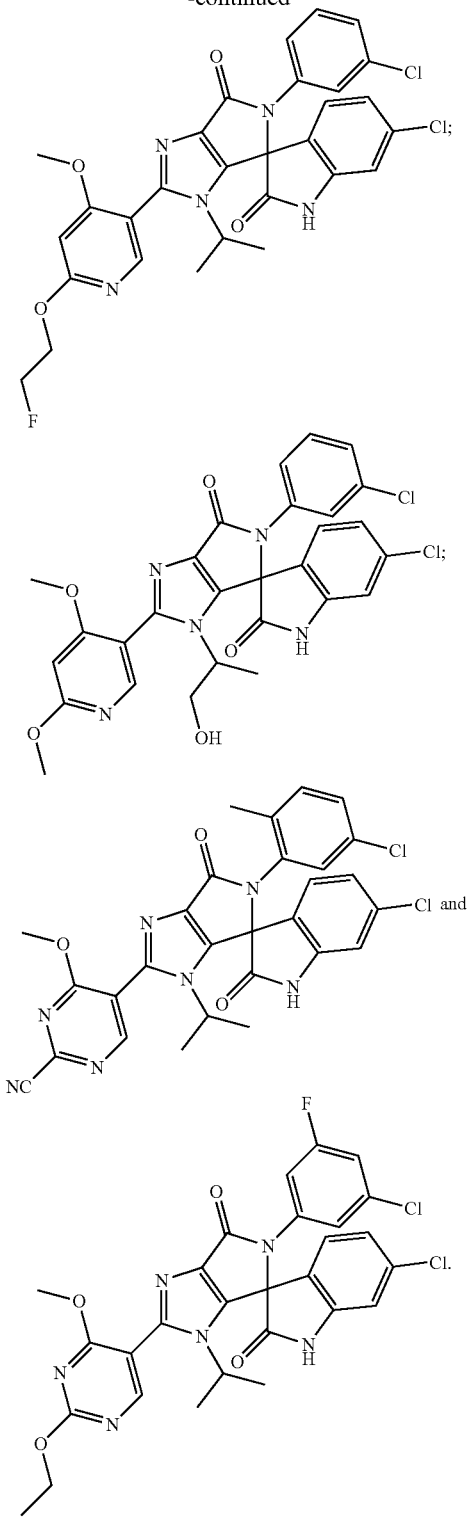

11. The compound according to claim 1, selected from:

6-chloro-5'-(3-chlorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione;

6-chloro-5'-(5-chloro-2-methylphenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione 6-chloro-5'-(5-chloro-2-methylphenyl)-2'-(2,4-dimethoxyphenyl)-3'-isopropyl-3'H-spiro[dihydroindole-3,4'-pyrrolo[3,4-d]imidazole]-2,6'(5'H)-dione;

6-chloro-5'-(5-chloro-2-methylphenyl)-2'-(4,6-dimethoxypyridin-3-yl)-3'-isopropyl-3'H-spiro[dihydroindole-3,4'-pyrrolo[3,4-d]imidazole]-2,6'(5'H)-dione;

6-chloro-5'-(5-chloro-2-methylphenyl)-2'-(4-(dimethylamino)-2-methoxyphenyl)-3'-isopropyl-3'H-spiro[dihydroindole-3,4'-pyrrolo[3,4-d]imidazole]-2,6'(5'H)-dione;

6-chloro-5'-(5-chloro-2-methylphenyl)-3'-isopropyl-2'-(4-isopropyl-2-methoxyphenyl)-3'H-spiro[dihydroindole-3,4'-pyrrolo[3,4-d]imidazole]-2,6'(5'H)-dione;

6-chloro-5'-(5-chloro-2-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione;

6-chloro-5'-(3-chloro-5-fluorophenyl)-2'-(2,4-dimethoxypyrimidin-5-yl)-3'-isopropyl-3'H-spiro[dihydroindole-3,4'-pyrrolo[3,4-d]imidazole]-2,6'(5'H)-dione;

6-chloro-5'-(5-chloro-2-methylphenyl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione;

6-chloro-5'-(5-chloro-2-methylphenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione;

6-chloro-5'-(5-chloro-2-methylpyridin-3-yl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione;

6-chloro-5'-(5-chloro-2-fluorophenyl)-2'-(6-ethoxy-4-methoxypyridin-3-yl)-3'-isopropyl-3'H-spiro[dihydroindole-3,4'-pyrrolo[3,4-d]imidazole]-2,6'(5'H)-dione;

6-chloro-5'-(5-chloro-2-methylphenyl)-2'-(6-cyclopropyl-4-methoxypyridin-3-yl)-3'-isopropyl-3'H-spiro[dihydroindole-3,4'-pyrrolo[3,4-d]imidazole]-2,6'(5'H)-dione;

6-chloro-5'-(3-chlorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione;

6-chloro-5'-(5-chloro-2-methylpyridin-3-yl)-2'-(4,6-dimethoxypyridin-3-yl)-3'-isopropyl-3'H-spiro[dihydroindole-3,4'-pyrrolo[3,4-d]imidazole]-2,6'(5'H)-dione;

6-chloro-5'-(5-chloro-2-fluorophenyl)-2'-(4,6-dimethoxypyridin-3-yl)-3'-isopropyl-3'H-spiro[dihydroindole-3,4'-pyrrolo[3,4-d]imidazole]-2,6'(5'H)-dione;

6-chloro-5'-(5-chloro-2-methylpyridin-3-yl)-2'-(2-ethoxy-4-methoxypyrimidin-5-yl)-3'-isopropyl-3'H-spiro[dihydroindole-3,4'-pyrrolo[3,4-d]imidazole]-2,6'(5'H)-dione;

6-chloro-5'-(5-chloro-2-methylpyridin-3-yl)-2'-(2-(dimethylamino)-4-methoxypyrimidin-5-yl)-3'-isopropyl-3'H-spiro[dihydroindole-3,4'-pyrrolo[3,4-d]imidazole]-2,6'(5'H)-dione;

6-chloro-5'-(5-chloro-2-methylpyridin-3-yl)-2'-(6-isopropoxy-4-methoxypyridin-3-yl)-3'-isopropyl-3'H-spiro[dihydroindole-3,4'-pyrrolo[3,4-d]imidazole]-2,6'(5'H)-dione;

6-chloro-5'-(5-chloro-2-methylphenyl)-2'-(2-(2-fluoroethoxy)-4-methoxypyrimidin-5-yl)-3'-isopropyl-3'H-spiro[dihydroindole-3,4'-pyrrolo[3,4-d]imidazole]-2,6'(5'H)-dione; and 6-chloro-5'-(5-chloro-2-methylpyridin-3-yl)-2'-(2-cyclo-propyl-4-methoxypyrimidin-5-yl)-3'-isopropyl-3'H-spiro[dihydroindole-3,4'-pyrrolo[3,4-d]imidazole]-2,6'(5'H)-dione.

12. The compound according to claim 1, wherein the compound is in the S configuration.

13. A method of synthesizing a compound according to claim 1, wherein Y is N, the method comprising:

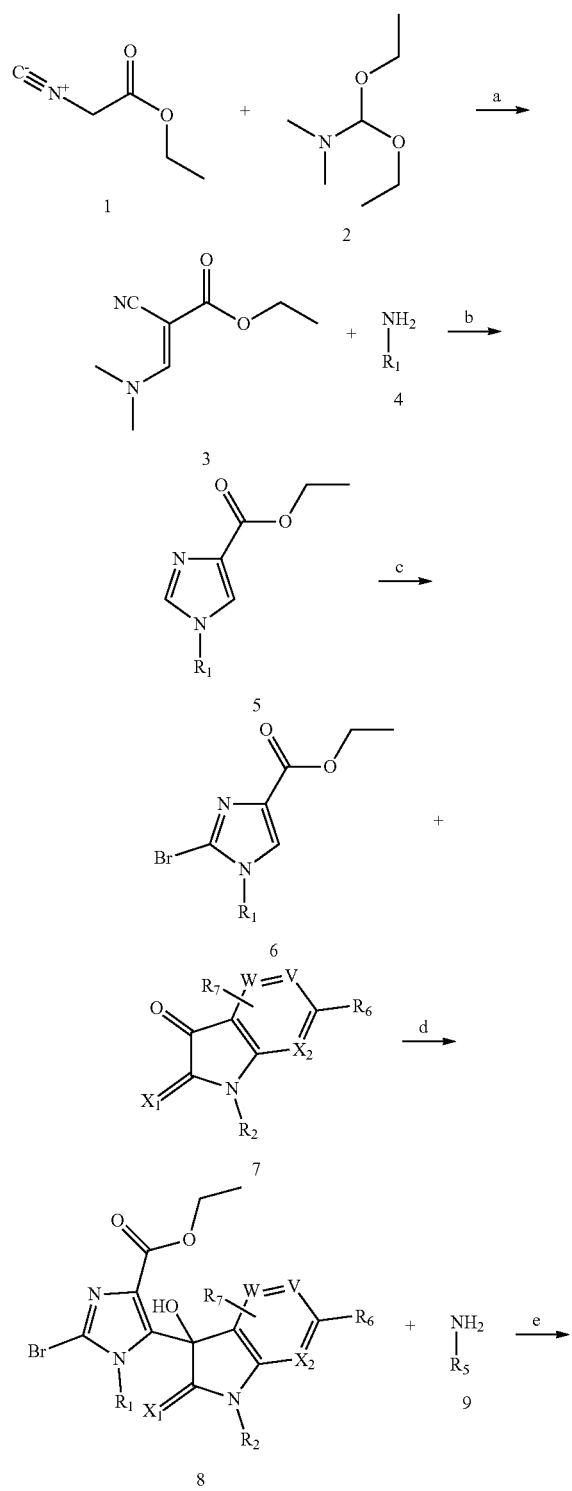

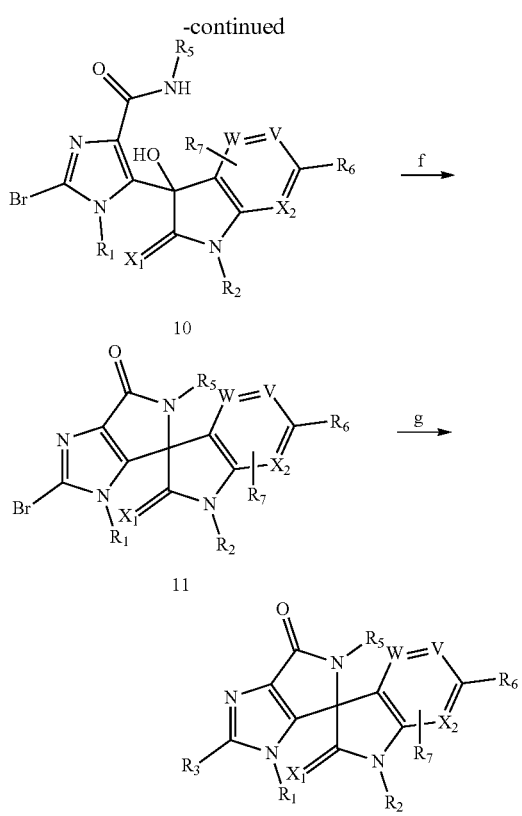

(1) subjecting compound 1 and compound 2 to a substitution and rearrangement reaction to synthesize compound 3;
(2) subjecting compound 3 and compound 4 to a cyclization reaction to construct an imidazole ring to obtain compound 5;
(3) brominating compound 5 with N-bromosuccinimide to obtain compound 6;
(4) subjecting compound 6 and compound 7 to low-temperature lithiation with lithium diisopropylamide to obtain compound 8;
(5) subjecting compound 8 and compound 9 to an ammonolysis reaction to obtain compound 10;
(6) subjecting compound 10 to an acidification and dehydration reaction to obtain compound 11; and
(7) subjecting compound 11 and an aryl or heteroaryl borate or boronic acid to a Suzuki coupling reaction to obtain a compound according to claim 1, wherein Y is N.

14. A method of synthesizing a compound according to claim 1, wherein Y is C, the method comprising:

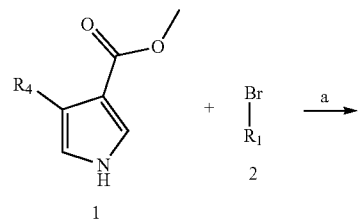

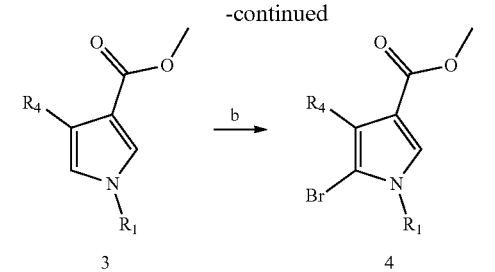
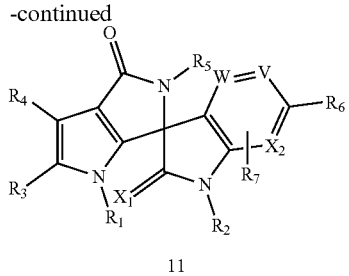
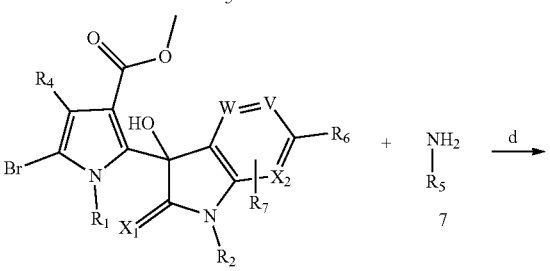
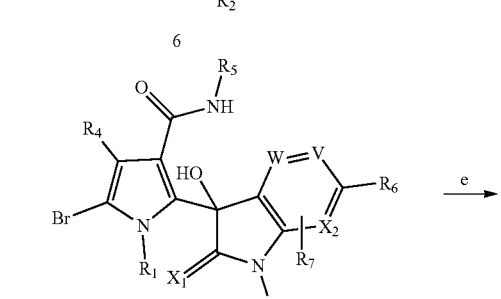
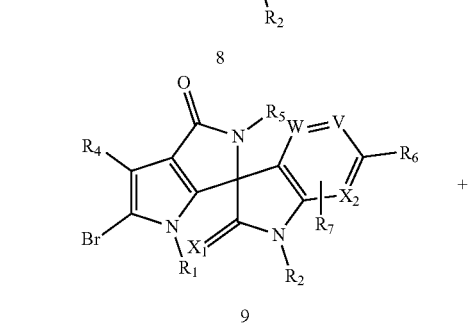

(1) subjecting compound 1 and compound 2 to a substitution reaction to synthesize compound 3;
(2) brominating compound 3 with N-bromosuccinimide to obtain compound 4;
(3) subjecting compound 4 and compound 5 to low-temperature lithiation with lithium diisopropylamide to obtain compound 6;
(4) subjecting compound 6 and compound 7 to an ammonolysis reaction to obtain compound 8;
(5) subjecting compound 8 to an acidification and dehydration reaction to obtain compound 9; and
(6) subjecting compound 9 and an aryl or heteroaryl boronic acid to a Suzuki coupling reaction to obtain a compound according to claim 1, wherein Y is C.

15. A pharmaceutical composition comprising a compound according to claim 1 and a pharmaceutically acceptable excipient.

16. The pharmaceutical composition of claim 15, further comprising one or more therapeutically active agents.

17. The pharmaceutical composition of claim 16, wherein the therapeutically active agent is an anti-proliferative agent.

18. A method for inducing apoptosis in tumor cells in a subject in need of treatment thereof, the method comprising administering to such subject an effective amount of an MDM2 inhibitor selected from a compound according to claim 1.

19. A method for inhibiting tumor cell growth in a subject in need of treatment thereof, the method comprising administering to such subject an effective amount of an MDM2 inhibitor selected from a compound according to claim 1.

* * * * *